US007261876B2

(12) United States Patent
Arbogast et al.

(10) Patent No.: US 7,261,876 B2
(45) Date of Patent: Aug. 28, 2007

(54) MULTIVALENT CONSTRUCTS FOR THERAPEUTIC AND DIAGNOSTIC APPLICATIONS

(75) Inventors: Christophe Arbogast, Viuz-En-Sallaz (FR); Philippe Bussat, Feigers (FR); Hong Fan, Plainsboro, NJ (US); Karen E. Linder, Kingston, NJ (US); Edmund R. Marinelli, Lawrenceville, NJ (US); Palaniappa Nanjappan, Dayton, NJ (US); Adrian Nunn, Lamberville, NJ (US); Radhakrishna Pillai, Cranbury, NJ (US); Sibylle Pochon, Troinex (CH); Kondareddiar Ramalingam, Dayton, NJ (US); Ajay Shrivastava, Plainsboro, NJ (US); Bo Song, Princeton, NJ (US); Rolf E. Swenson, Princeton, NJ (US); Mathew A. Von Wronski, Moorestown, NJ (US); Aaron Sato, Somerville, MA (US); Sharon Michele Walker, Boston, MA (US); Daniel T. Dransfield, Hanson, MA (US)

(73) Assignees: Bracco International BV, Amsterdam (NL); Dyax Corp., Cambridge, MA (US)

( * ) Notice: Subject to any disclaimer, the term of this patent is extended or adjusted under 35 U.S.C. 154(b) by 84 days.

(21) Appl. No.: 10/661,032

(22) Filed: Sep. 11, 2003

(65) Prior Publication Data
US 2004/0210041 A1 Oct. 21, 2004
US 2005/0027105 A9 Feb. 3, 2005

Related U.S. Application Data

(63) Continuation-in-part of application No. 10/379,287, filed on Mar. 3, 2003.

(60) Provisional application No. 60/440,201, filed on Jan. 15, 2003, provisional application No. 60/360,821, filed on Mar. 1, 2002.

(51) Int. Cl.
*A61K 49/00* (2006.01)

(52) U.S. Cl. ............. 424/9.1; 424/1.11; 424/1.65; 424/9.3; 424/9.4; 424/9.5; 424/9.6

(58) Field of Classification Search .......... 424/1.11, 424/1.65, 1.37, 1.69, 9.1, 9.2, 9.3, 9.4, 9.5, 424/9.6, 9.7, 9.8; 534/7, 10–16; 530/300, 530/326, 333
See application file for complete search history.

(56) References Cited

U.S. PATENT DOCUMENTS

| | | | |
|---|---|---|---|
| 2,913,451 A | 11/1959 | De La Mater et al. | |
| 5,547,656 A | 8/1996 | Unger | |
| 5,766,860 A | 6/1998 | Terman et al. | |
| 5,769,080 A | 6/1998 | Unger et al. | |
| 5,773,024 A | 6/1998 | Unger et al. | |
| 5,855,866 A | 1/1999 | Thorpe et al. | |
| 5,861,301 A | 1/1999 | Terman et al. | |
| 5,935,820 A | 8/1999 | Hu et al. | |
| 6,025,331 A | * 2/2000 | Moses et al. | 514/12 |
| 6,033,645 A | 3/2000 | Unger et al. | |
| 6,051,230 A | 4/2000 | Thorpe et al. | |
| 6,071,495 A | 6/2000 | Unger et al. | |
| 6,130,071 A | 10/2000 | Alitalo et al. | |
| 6,146,657 A | 11/2000 | Unger et al. | |
| 6,204,011 B1 | 3/2001 | Kendall et al. | |
| 6,221,839 B1 | 4/2001 | Alitalo et al. | |
| 6,231,834 B1 | 5/2001 | Unger et al. | |
| 6,245,318 B1 | 6/2001 | Klibanov et al. | |
| 6,245,530 B1 | 6/2001 | Alitalo et al. | |
| 6,261,535 B1 | 7/2001 | Thorpe et al. | |
| 6,261,537 B1 | 7/2001 | Klaveness et al. | |
| 6,264,917 B1 | 7/2001 | Klaveness et al. | |
| 6,322,770 B1 | 11/2001 | Rajopadhye et al. | |
| 6,331,289 B1 | 12/2001 | Klaveness et al. | |
| 6,359,115 B1 | 3/2002 | Kendall et al. | |
| 6,361,946 B1 | 3/2002 | Alitalo et al. | |
| 6,403,088 B1 | 6/2002 | Alitalo et al. | |
| 6,451,764 B1 | 9/2002 | Lee et al. | |
| 6,521,211 B1 | 2/2003 | Unger et al. | |
| 6,524,553 B1 | 2/2003 | Harris | |
| 6,528,039 B2 | 3/2003 | Unger | |
| 6,537,520 B1 | 3/2003 | Rajopadhye et al. | |
| 6,548,048 B1 | 4/2003 | Cuthbertson et al. | |
| 6,548,663 B1 | 4/2003 | Cheesman et al. | |
| 6,576,608 B1 | 6/2003 | Lee et al. | |
| 6,610,269 B1 | 8/2003 | Klaveness et al. | |
| 6,645,933 B1 | 11/2003 | Alitalo et al. | |
| 6,680,047 B2 | 1/2004 | Klaveness et al. | |

(Continued)

FOREIGN PATENT DOCUMENTS

EP 0580726 2/1994

(Continued)

OTHER PUBLICATIONS

International Search Report for PCT/US03/28838, mailed Oct. 12, 2004.

(Continued)

*Primary Examiner*—Dameron L. Jones
(74) *Attorney, Agent, or Firm*—Kramer Levin Naftalis & Frankel LLP

(57) ABSTRACT

The invention provides compositions and methods for therapeutic and diagnostic applications.

33 Claims, 59 Drawing Sheets

U.S. PATENT DOCUMENTS

| | | |
|---|---|---|
| 6,689,352 B2 | 2/2004 | Achen et al. |
| 6,730,658 B1 | 5/2004 | Alitalo et al. |
| 6,733,755 B2 | 5/2004 | Tchistiakova et al. |
| 6,773,696 B2 | 8/2004 | Unger |
| 6,777,534 B1 | 8/2004 | Klagsbrun et al. |
| 6,800,273 B2 | 10/2004 | Rajopadhye et al. |
| 6,841,367 B2 | 1/2005 | Kendall et al. |
| 6,841,382 B2 | 1/2005 | Kendall et al. |
| 6,875,741 B2 | 4/2005 | Pillutla et al. |
| 7,034,105 B2 | 4/2006 | Alitalo et al. |
| 2001/0031485 A1 | 10/2001 | Backer et al. |
| 2001/0038842 A1 | 11/2001 | Achen et al. |
| 2002/0001566 A1 | 1/2002 | Rajopadhye et al. |
| 2002/0010137 A1 | 1/2002 | Ashkenazi et al. |
| 2002/0015680 A1 | 2/2002 | Harris |
| 2002/0037289 A1 | 3/2002 | Thorpe et al. |
| 2002/0058619 A1 | 5/2002 | Tohisitiakova et al. |
| 2002/0065218 A1 | 5/2002 | Achen et al. |
| 2002/0068697 A1 | 6/2002 | Tournaire |
| 2002/0086013 A1 | 7/2002 | King |
| 2002/0091082 A1 | 7/2002 | Aiello |
| 2002/0098187 A1 | 7/2002 | Ferrara et al. |
| 2002/0102215 A1 | 8/2002 | Klaveness et al. |
| 2002/0102217 A1 | 8/2002 | Klaveness et al. |
| 2002/0102260 A1 | 8/2002 | Achen et al. |
| 2002/0164667 A1 | 11/2002 | Alitalo et al. |
| 2003/0023046 A1 | 1/2003 | Ferrara et al. |
| 2003/0055006 A1 | 3/2003 | Siemeister et al. |
| 2003/0082103 A1 | 5/2003 | Wartchow et al. |
| 2003/0091567 A1 | 5/2003 | Alitalo et al. |
| 2003/0124120 A1 | 7/2003 | Harris et al. |
| 2003/0149262 A1 | 8/2003 | Cheesman et al. |
| 2003/0157025 A1 | 8/2003 | Unger et al. |
| 2003/0166523 A1 | 9/2003 | Achen et al. |
| 2003/0166873 A1 | 9/2003 | Lee et al. |
| 2003/0176674 A1 | 9/2003 | Rosen et al. |
| 2003/0180305 A1 | 9/2003 | Rajopadhye et al. |
| 2003/0180718 A1 | 9/2003 | Pillutla et al. |
| 2003/0195147 A1 | 10/2003 | Pillutla et al. |
| 2003/0236190 A1 | 12/2003 | Pillutla et al. |
| 2004/0009122 A1 | 1/2004 | Klaveness et al. |
| 2004/0023887 A1 | 2/2004 | Pillutla et al. |
| 2004/0033949 A1 | 2/2004 | Bunting |
| 2004/0037820 A1 | 2/2004 | Alitalo et al. |
| 2004/0141922 A1 | 7/2004 | Klaveness et al. |
| 2004/0147448 A1 | 7/2004 | Alitalo et al. |
| 2004/0147449 A1 | 7/2004 | Siemeister et al. |
| 2004/0147726 A1 | 7/2004 | Alitalo et al. |
| 2004/0213790 A1 | 10/2004 | Lee et al. |
| 2004/0223911 A1 | 11/2004 | Bednarski et al. |
| 2004/0224398 A1 | 11/2004 | Anand-Apte |
| 2004/0248781 A1 | 12/2004 | Kerbel |
| 2004/0266694 A1 | 12/2004 | Tohisitiakova et al. |
| 2005/0002865 A1 | 1/2005 | Klaveness et al. |
| 2005/0037967 A1 | 2/2005 | Rosenblum |
| 2006/0003926 A1 | 1/2006 | Rajopdhye et al. |
| 2006/0089307 A1 | 4/2006 | Kulseth |

FOREIGN PATENT DOCUMENTS

| | | |
|---|---|---|
| EP | 0627940 | 12/1994 |
| EP | 0711127 | 5/1996 |
| EP | 0804932 | 11/1997 |
| EP | 1081913 | 3/2001 |
| EP | 1166798 | 1/2002 |
| EP | 1166799 | 1/2002 |
| EP | 0666868 | 4/2002 |
| EP | 1238986 | 9/2002 |
| EP | 1306095 | 5/2003 |
| EP | 0848755 | 6/2003 |
| EP | 0831932 | 5/2004 |
| EP | 0977600 | 6/2004 |
| EP | 1444991 | 8/2004 |
| EP | 1259248 | 12/2004 |
| EP | 0842273 | 3/2005 |
| EP | 1519193 | 3/2005 |
| EP | 1574518 | 9/2005 |
| EP | 1586333 | 10/2005 |
| EP | 1007101 | 5/2006 |
| JP | 3398382 | 2/2003 |
| WO | WO92/14748 | 9/1992 |
| WO | WO94/10202 | 5/1994 |
| WO | WO96/40285 | 12/1996 |
| WO | 97/05250 | 2/1997 |
| WO | WO97/09427 | 3/1997 |
| WO | WO97/17422 | 5/1997 |
| WO | 98/18495 | 5/1998 |
| WO | 98/18500 | 5/1998 |
| WO | WO98/18498 | 5/1998 |
| WO | WO98/18501 | 5/1998 |
| WO | 98/33917 | 8/1998 |
| WO | WO98/47541 | 10/1998 |
| WO | 98/58053 | 12/1998 |
| WO | WO99/29861 | 6/1999 |
| WO | WO99/40947 | 8/1999 |
| WO | 99/55383 | 11/1999 |
| WO | WO99/58162 | 11/1999 |
| WO | WO 00/27414 | 5/2000 |
| WO | WO 00/45856 | 8/2000 |
| WO | WO 01/42284 | 6/2001 |
| WO | 01/057067 | 8/2001 |
| WO | WO 01/54723 | 8/2001 |
| WO | WO 01/62942 | 8/2001 |
| WO | WO 01/64235 | 9/2001 |
| WO | WO 01/70268 | 9/2001 |
| WO | WO 01/70681 | 9/2001 |
| WO | WO 01/70945 | 9/2001 |
| WO | WO 01/82870 | 11/2001 |
| WO | WO 01/83693 | 11/2001 |
| WO | WO 01/97850 | 12/2001 |
| WO | WO 02/06789 | 1/2002 |
| WO | WO 02/07747 | 1/2002 |
| WO | WO 02/028895 | 4/2002 |
| WO | WO 02/057299 | 7/2002 |
| WO | WO 02/060950 | 8/2002 |
| WO | 02/72011 | 9/2002 |
| WO | WO 02/083849 | 10/2002 |
| WO | 02/96367 | 12/2002 |
| WO | WO 03/080653 | 2/2003 |
| WO | 2003027246 | 4/2003 |
| WO | WO 03/028643 | 4/2003 |
| WO | 03/035839 | 5/2003 |
| WO | WO 03/018797 | 6/2003 |
| WO | 03/070747 | 8/2003 |
| WO | WO 03/094617 | 11/2003 |
| WO | 03/103581 | 12/2003 |
| WO | 2004/033949 | 4/2004 |
| WO | 2004/058802 | 7/2004 |
| WO | 2004/058803 | 7/2004 |
| WO | 2004/085617 | 10/2004 |
| WO | 2005/011722 | 2/2005 |
| WO | 2005/016963 | 2/2005 |
| WO | 2005/070472 | 8/2005 |
| WO | 2005/072417 | 8/2005 |
| WO | 2006/015385 | 2/2006 |

OTHER PUBLICATIONS

Lu, D. et al. "Identification of the Residues in the Extracellular Region of KDR Important for Interaction with Vascular Endothelial Growth Factor and Neutralizing Anti-KDR Antibodies", *J. Biol. Chem.*, May 2000, vol. 275, No. 19, pp. 14321-14330.

Tamura, S. et al. "Expression and Function of c-Met, a Receptor for Hepatocyte Growth Factor, During T-Cell Development", *Scand. J. Immunol.* 1998, vol. 47, pp. 296-301.

Wei, K. et al. "Quantification of Renal Blood Flow With Contrast-Enhanced Ultrasound" *J. Am. Coll. Cardiol.* 2001, vol. 37, No. 4., pp. 1135-1140.

Gestwicki, J.E.; Cairo, C.W.; Strong, L.E.; Oetjen, K.A. and Kiessling, L. L. Influencing Receptor-Ligand Binding Mechanisms with Multivalent Ligand Architecture. J. Am. Chem. Soc. 2002, 124, 14922-14933.

Jackson, D. C. ; Fitzmaurice, C. J.; Brown, L. E.; Zeng, W. Preparation and properties of totally synthetic immunogens. Vaccine 1999, 18, 355-361.

Ben-Yedidia, T.; Arnon, R. Design of peptide and polypeptide vaccines. Current Opinion in Biotechnology 1997, 8, 442-448.

Mammen, M.; Choi, S-K; and Whitesides, G.M. Polyvalent interactions in biological systems: Implications for design and use of multivalent ligands and inhibitors. Angew. Chem. Int. Edn. Engl. 1998, 37, 2754-2794.

Pillai et al., "A novel and flexible method for preparation of peptide homo- and heterodimers functionalized with affinity probes, reported molecules and chelating ligands".

Pillai et al, "A Flexible Method for Preparation of Peptide Homo- and Heterodimers Functionalized with Affinity Probes, Chelating Ligands and Latent Conjugating Groups".

O'Brien-Simpson, N. M.; Ede, N. J.; Brown, L. E.; Swan, J.; Jackson, D. C. Polymerization of Unprotected Synthetic Peptides: A View toward Synthetic Peptide Vaccines. Journal of the American Chemical Society 1997, 119, 1183-1188.

A general review : Sadler, Kristen; Tam, James P. Peptide dendrimers: applications and synthesis. Reviews in Molecular Biotechnology 2002, 90(3-4), 195-229.

Futaki, S. Creation of ion channel function using synthetic peptides. (1998) *Yuki Gosei Kagaku Kyokaishi* 56, 125-133.

Loffet, A. Q. Peptides as drugs: is there a market? In: *Peptides: The Wave of the Future*, Proceedings of the Second International and the Seventeenth American Peptide Symposium, San Diego, CA, United States, Jun. 9-14, 2001; Lebl, M., and Houghten, R. A. Eds.; American Peptide Society: San Diego, Calif. 2001; pp. 214-216.

De Villiers, M. M., Liebenberg, W., Malan, S. F., and Gerber, J. J. (2000) Solubilization of poorly water soluble non-steroidal anti-inflammatory drugs at low pH with N-methylglucamine. *S. Afr. Pharmazie*, 55, 544-546.

Bajusz, S. (2003) Peptide related drug research. *J. Pept. Sci. 9*, 321-332.

Souriau, C., and Hudson, P. J. (2001) Recombinant antibodies for cancer diagnosis and therapy. *Expert Opin. Biol. Ther. 1*, 845-855.

Mammen, M., Choi, S-K, and Whitesides, G. M. (1998) Polyvalent interactions in biological systems: Implications for design and use of multivalent ligands and inhibitors. *Angew. Chem. Int. Edn. 37*, 2754-2794.

Gestwicki, J. E., Cairo, C. W., Strong, L. E., Oetjen, K. A., and Kiessling, L. L. (2002) Influencing Receptor-Ligand Binding Mechanisms with Multivalent Ligand Architecture. *J. Am. Chem., Soc. 124*, 14922-14933.

Tam, J. P., Lu, Y-A., and Yang, J-L. (2002) Antimicrobial Dendrimeric Peptides. *Eur. J. Biochem. 269*, 923-932.

Liu, S., Edwards, D. S., Ziegler, M. C., Harris, A. R., Hemingway, s. J., and Barret, J. A. (2001) [99m]Tc-Labeling of Hydrazinonicotiniamide-Conjugated Vitronection Receptor Antagonist Useful for Imaging Tumors. *Bioconjugate Chem. 12*, 624-629.

Hillairet de Boisferon, M., Raguin, O., Dussaillant, M., Rostène, W., Barbet, J., and Gruaz-Guyon, A. (2000) Enhanced Targeting Specificity to Tumor Cells by Simultaneous Recognition of Two Antigens. *Bioconjugate Chem. 11*, 452-460.

Schaffer, L., Brissette, R. E., Spetzler, J. C., Pillutla, R. C., Østergaard, S., Lennick, M., Brandt, J., Fletcher, P. W., Danielsen, G. M., Hsaio, K-C., Andersen, A. S., Dedova, O., Ribel, U., Hoeg-Jensen, T., Hansen, P.H., Blume, A.J., Markussen, J., and Goldstein, N.I. (2003) Assembly of High Affinity Insulin Receptor Agonists and Antagonists from Peptide Building Blocks. *Proc. Natl. Acad. Sci. U.S.A. 100*, 4435-4439.

Jackson, D. C., Fitzmaurice, C. J., Brown, L. E., and Zeng, W. (1999) Preparation and properties of totally synthetic immunogens. *Vaccine 18*, 355-361.

Ben-Yedidia, T., and Arnon, R. (1997) Design of peptide and polypeptide vaccines. *Curr. Opin. Biotechnol. 8*, 442-448.

O'Brien-Simpson, N. M., Ede, N. J., Brown, L. E., Swan, J., and Jackson, D. C. (1997) Polymerization of Unprotected Synthetic Peptides: A View toward Synthetic Peptide Vaccines. *J. Am. Chem. Soc. 119*, 1183-1188.

Chen, H., Holl, M-B., Orr, B. G., Majoros, I., and Clarkson, B. H. (2003) Interaction of dendrimers (artificial proteins) with biological hydroxyapatile crystals. *J. Dent. Res. 82*, 443-448.

Sal-Man, N., Oren, Z., and Shai, Y. (2002) Preassembly of membrane-active peptides is an important factor in their selectivity toward target cells. *Biochemistry 41*, 11921-11930.

Lucke, A. J., Tyndall, J. D. A., Singh, Y., and Fairlie, D. P. (2003) Designing supramolecular structures from models of cyclic peptide scaffolds with heterocyclic constraints. *J. Mol. Graphics Modell. 21*, 341-355.

Mutter, M. and Tuchscherer, G. (2000) Evolution versus design: template-directed self-assembly of peptides to artificial proteins (TASP). *Chimia 54*, 552-557.

Todorovska, A., Roovers, R.C., Dolezal, O., Kortt, A. A., Hoogenboom, H. R., and Hudson, P. J. (2001) Design and Application of Diabodies, Triabodies and Tetrabodies for Cancer Targeting. *J. Immunol. Methods 248*, 47-66.

Veprek, P. and Jezek, J. (1999) Peptide and glycopeptide dendrimers. Part I. *J. Pept. Sci. 5*, 5-23.

Veprek, P. and Jezek, J. (1999) Peptide and glycopeptide dendrimers. Part II. *J. Pept. Sci. 5*, 203-220.

A general review: Sadler, K. and Tam, J. P. (2002) Peptide dendrimers: applications and synthesis. *Rev. Mol. Biotechnol. 90*, 195-229.

Hunter, C. L., and Kochendoerfer, G. G. (2004) Native Chemical Ligation of Hydrophobic Peptides in Lipid Bilayer Systems *Bioconjugate Chem. 15*, 437-440.

Thumshirn, G., Hersel, U., Goodman, S. L., and Kessler, H. (2003) Multimeric cyclic RGD peptides as potential tools for tumor targeting: Solid-phase peptide synthesis and chemoselective oxime ligation. *Chem.—Eur. J. 9*, 2717-2725.

Merkx, R., Rijkers, D. T. S., Kemmink, J., and Liskamp, R. M. J. (2003) Chemoselective coupling of peptide fragments using the Staudinger ligation. *Tetrahedron Lett. 44*, 4515-4518.

Tam, J.P., Yu, Q., and Yang, J-L. (2001) Tandem Ligation of Unprotected Peptides through Thiaprolyl and Cysteinyl Bonds in Water. *J. Am. Chem. Soc. 123*, 2487-2494.

Offer, J., Boddy, C. N. C., and Dawson, P. E. (2002) Extending Synthetic Access to Proteins with a Removable Acyl Transfer Auxiliary. *J. Am. Chem. Soc. 124*, 4642-4646.

Dawson, P.E. and Kent, S.B.H. (2000) Synthesis of Native Proteins by Chemical Ligation. *Ann. Rev. Biochem. 69*, 923-960.

Sole, N. A., and Barany, G. (1992) Optimization of solid-phase synthesis of [Ala$^8$]-Dynorphin A. *J. Org. Chem. 57*, 5399-5403.

Melkko et al. "Encoded self-assembling chemical libraries" *Nature Biotechnology*, vol. 22, No. 5, May 2004, pp. 568-574.

Pillai et al., "A Novel and Flexible Method for Preparation of Peptide Homo and Heterodimers Functionalized with Affinity Probes, Peporter Molecules and Chelating Ligands" Poster Presentation the at Third International and Twenty-Eight European Peptide Symposium, Prague, Czech Republic, Sep. 5-10, 2004.

\* cited by examiner

FIG. 40A

| Isolate | Initial Name | Elution | Library | Groups | Target OD | Background OD | SEQ ID NO | Trimmed AA |
|---|---|---|---|---|---|---|---|---|
| 365b-R0041-H11 | 365b-M0153-E03 | D6 | TN11_1 | 56 | 2.0933 | 0.0651 | 505 | GSNMVCMDDSYGGTTCYSMAP |
| 365b-R0041-G08 | 365b-M0153-G05 | D6 | TN11_1 | 56 | 1.8216 | 0.0783 | 505 | GSNMVCMDDSYGGTTCYSMAP |
| 365b-R0042-G09 | 365b-M0154-H04 | D6 | TN11_1 | 56 | 2.2305 | 0.072 | 505 | GSNMVCMDDSYGGTTCYSMAP |
| 365b-R0035-F10 | 365b-M0143-B10 | VEGF | TN11_1 | 56 | 1.4936 | 0.3746 | 505 | GSNMVCMDDSYGGTTCYSMAP |
| 365b-R0035-F09 | 365b-M0143-D09 | VEGF | TN11_1 | 56 | 1.2807 | 0.3825 | 505 | GSNMVCMDDSYGGTTCYSMAP |
| 365b-R0035-E08 | 365b-M0143-G01 | VEGF | TN11_1 | 56 | 1.6558 | 0.4609 | 505 | GSNMVCMDDSYGGTTCYSMAP |
| 365b-R0035-H08 | 365b-M0143-H04 | VEGF | TN11_1 | 56 | 1.4681 | 0.3838 | 505 | GSNMVCMDDSYGGTTCYSMAP |
| 365b-R0035-E07 | 365b-M0144-A08 | VEGF | TN11_1 | 56 | 1.1095 | 0.059 | 505 | GSNMVCMDDSYGGTTCYSMAP |
| 365b-R0035-G07 | 365b-M0144-A12 | VEGF | TN11_1 | 56 | 1.2127 | 0.0706 | 505 | GSNMVCMDDSYGGTTCYSMAP |
| 365b-R0035-B06 | 365b-M0144-B05 | VEGF | TN11_1 | 56 | 1.6427 | 0.0657 | 505 | GSNMVCMDDSYGGTTCYSMAP |
| 365b-R0035-C06 | 365b-M0144-B06 | VEGF | TN11_1 | 56 | 1.7453 | 0.0654 | 505 | GSNMVCMDDSYGGTTCYSMAP |
| 365b-R0035-D06 | 365b-M0144-B09 | VEGF | TN11_1 | 56 | 1.8068 | 0.061 | 505 | GSNMVCMDDSYGGTTCYSMAP |
| 365b-R0035-E06 | 365b-M0144-B10 | VEGF | TN11_1 | 56 | 1.6318 | 0.0643 | 505 | GSNMVCMDDSYGGTTCYSMAP |
| 365b-R0035-F06 | 365b-M0144-B12 | VEGF | TN11_1 | 56 | 1.6116 | 0.0687 | 505 | GSNMVCMDDSYGGTTCYSMAP |
| 365b-R0035-H06 | 365b-M0144-C05 | VEGF | TN11_1 | 56 | 1.6786 | 0.0631 | 505 | GSNMVCMDDSYGGTTCYSMAP |
| 365b-R0035-B05 | 365b-M0144-C08 | VEGF | TN11_1 | 56 | 1.5119 | 0.0615 | 505 | GSNMVCMDDSYGGTTCYSMAP |
| 365b-R0035-C05 | 365b-M0144-C11 | VEGF | TN11_1 | 56 | 1.6498 | 0.0668 | 505 | GSNMVCMDDSYGGTTCYSMAP |
| 365b-R0035-G05 | 365b-M0144-D05 | VEGF | TN11_1 | 56 | 1.8483 | 0.0701 | 505 | GSNMVCMDDSYGGTTCYSMAP |
| 365b-R0035-B04 | 365b-M0144-D10 | VEGF | TN11_1 | 56 | 1.6392 | 0.0664 | 505 | GSNMVCMDDSYGGTTCYSMAP |
| 365b-R0035-C04 | 365b-M0144-E01 | VEGF | TN11_1 | 56 | 1.7831 | 0.075 | 505 | GSNMVCMDDSYGGTTCYSMAP |
| 365b-R0035-D04 | 365b-M0144-E02 | VEGF | TN11_1 | 56 | 2.3208 | 0.1052 | 505 | GSNMVCMDDSYGGTTCYSMAP |
| 365b-R0035-E04 | 365b-M0144-E05 | VEGF | TN11_1 | 56 | 1.9583 | 0.0695 | 505 | GSNMVCMDDSYGGTTCYSMAP |
| 365b-R0035-F04 | 365b-M0144-E12 | VEGF | TN11_1 | 56 | 1.7604 | 0.0802 | 505 | GSNMVCMDDSYGGTTCYSMAP |
| 365b-R0035-A03 | 365b-M0144-F04 | VEGF | TN11_1 | 56 | 2.0114 | 0.0793 | 505 | GSNMVCMDDSYGGTTCYSMAP |
| 365b-R0035-C03 | 365b-M0144-F07 | VEGF | TN11_1 | 56 | 2.1028 | 0.0841 | 505 | GSNMVCMDDSYGGTTCYSMAP |
| 365b-R0035-D03 | 365b-M0144-F03 | VEGF | TN11_1 | 56 | 1.7666 | 0.0872 | 505 | GSNMVCMDDSYGGTTCYSMAP |
| 365b-R0035-E01 | 365b-M0145-A05 | VEGF | TN11_1 | 56 | 1.8146 | 0.0702 | 505 | GSNMVCMDDSYGGTTCYSMAP |
| 365b-R0035-F01 | 365b-M0145-A06 | VEGF | TN11_1 | 56 | 1.8092 | 0.0692 | 505 | GSNMVCMDDSYGGTTCYSMAP |
| 365b-R0035-B02 | 365b-M0145-A08 | VEGF | TN11_1 | 56 | 1.4711 | 0.0986 | 505 | GSNMVCMDDSYGGTTCYSMAP |
| 365b-R0035-C02 | 365b-M0145-A09 | VEGF | TN11_1 | 56 | 2.3898 | 0.0795 | 505 | GSNMVCMDDSYGGTTCYSMAP |
| 365b-R0035-F02 | 365b-M0145-B01 | VEGF | TN11_1 | 56 | 1.7058 | 0.0753 | 505 | GSNMVCMDDSYGGTTCYSMAP |
| 365b-R0035-H01 | 365b-M0145-B03 | VEGF | TN11_1 | 56 | 1.81 | 0.1338 | 505 | GSNMVCMDDSYGGTTCYSMAP |
| 365b-R0035-G01 | 365b-M0145-B06 | VEGF | TN11_1 | 56 | 1.2331 | 0.0652 | 505 | GSNMVCMDDSYGGTTCYSMAP |
| 365b-R0036-A12 | 365b-M0145-B08 | VEGF | TN11_1 | 56 | 1.1611 | 0.0635 | 505 | GSNMVCMDDSYGGTTCYSMAP |
| 365b-R0036-B12 | 365b-M0145-C01 | VEGF | TN11_1 | 56 | 1.4894 | 0.0807 | 505 | GSNMVCMDDSYGGTTCYSMAP |
| 365b-R0036-D12 | 365b-M0145-D01 | VEGF | TN11_1 | 56 | 1.8554 | 0.0958 | 505 | GSNMVCMDDSYGGTTCYSMAP |
| 365b-R0036-F12 | 365b-M0145-E01 | VEGF | TN11_1 | 56 | 2.0003 | 0.0677 | 505 | GSNMVCMDDSYGGTTCYSMAP |
| 365b-R0036-B11 | 365b-M0145-C04 | VEGF | TN11_1 | 56 | 1.9329 | 0.0615 | 505 | GSNMVCMDDSYGGTTCYSMAP |
| 365b-R0036-B11 | 365b-M0145-C04 | VEGF | TN11_1 | 56 | 2.3501 | 0.1338 | 505 | GSNMVCMDDSYGGTTCYSMAP |

FIG. 40B

| Isolate | Initial Name | Elution | Library | Groups | Target OD | Background OD | SEQ ID NO | Trimmed AA |
|---|---|---|---|---|---|---|---|---|
| 365b-R0036-C11 | 365b-M0145-C05 | VEGF | TN11_1 | 56 | 2.1168 | 0.1115 | 505 | GSNMVCMDDSYGGTTCYSMAP |
| 365b-R0036-F11 | 365b-M0145-D01 | VEGF | TN11_1 | 56 | 1.8932 | 0.0783 | 505 | GSNMVCMDDSYGGTTCYSMAP |
| 365b-R0036-H11 | 365b-M0145-D09 | VEGF | TN11_1 | 56 | 2.0577 | 0.0721 | 505 | GSNMVCMDDSYGGTTCYSMAP |
| 365b-R0036-A10 | 365b-M0145-D10 | VEGF | TN11_1 | 56 | 1.8547 | 0.0687 | 505 | GSNMVCMDDSYGGTTCYSMAP |
| 365b-R0036-B10 | 365b-M0145-D11 | VEGF | TN11_1 | 56 | 1.7683 | 0.0744 | 505 | GSNMVCMDDSYGGTTCYSMAP |
| 365b-R0036-D10 | 365b-M0145-E04 | VEGF | TN11_1 | 56 | 2.4185 | 0.078 | 505 | GSNMVCMDDSYGGTTCYSMAP |
| 365b-R0036-F10 | 365b-M0145-E09 | VEGF | TN11_1 | 56 | 1.7433 | 0.0736 | 505 | GSNMVCMDDSYGGTTCYSMAP |
| 365b-R0036-A09 | 365b-M0145-F01 | VEGF | TN11_1 | 56 | 2.1888 | 0.0811 | 505 | GSNMVCMDDSYGGTTCYSMAP |
| 365b-R0036-C09 | 365b-M0145-F04 | VEGF | TN11_1 | 56 | 2.072 | 0.0761 | 505 | GSNMVCMDDSYGGTTCYSMAP |
| 365b-R0036-F09 | 365b-M0145-F10 | VEGF | TN11_1 | 56 | 1.6636 | 0.074 | 505 | GSNMVCMDDSYGGTTCYSMAP |
| 365b-R0036-B08 | 365b-M0145-G06 | VEGF | TN11_1 | 56 | 2.3362 | 0.085 | 505 | GSNMVCMDDSYGGTTCYSMAP |
| 365b-R0036-E08 | 365b-M0145-G11 | VEGF | TN11_1 | 56 | 1.8104 | 0.0786 | 505 | GSNMVCMDDSYGGTTCYSMAP |
| 365b-R0036-G08 | 365b-M0145-H01 | VEGF | TN11_1 | 56 | 2.5832 | 0.0827 | 505 | GSNMVCMDDSYGGTTCYSMAP |
| 365b-R0036-C07 | 365b-M0145-H07 | VEGF | TN11_1 | 56 | 2.1164 | 0.079 | 505 | GSNMVCMDDSYGGTTCYSMAP |
| 365b-R0036-E07 | 365b-M0145-H10 | VEGF | TN11_1 | 56 | 2.0299 | 0.0775 | 505 | GSNMVCMDDSYGGTTCYSMAP |
| 365b-R0036-G07 | 365b-M0146-A04 | VEGF | TN11_1 | 56 | 1.5759 | 0.0685 | 505 | GSNMVCMDDSYGGTTCYSMAP |
| 365b-R0036-B06 | 365b-M0146-A07 | VEGF | TN11_1 | 56 | 1.2674 | 0.0703 | 505 | GSNMVCMDDSYGGTTCYSMAP |
| 365b-R0036-F06 | 365b-M0146-B04 | VEGF | TN11_1 | 56 | 1.951 | 0.0712 | 505 | GSNMVCMDDSYGGTTCYSMAP |
| 365b-R0036-H06 | 365b-M0146-B06 | VEGF | TN11_1 | 56 | 1.8714 | 0.0625 | 505 | GSNMVCMDDSYGGTTCYSMAP |
| 365b-R0036-B05 | 365b-M0146-B09 | VEGF | TN11_1 | 56 | 1.989 | 0.061 | 505 | GSNMVCMDDSYGGTTCYSMAP |
| 365b-R0036-C05 | 365b-M0146-B11 | VEGF | TN11_1 | 56 | 1.6568 | 0.0639 | 505 | GSNMVCMDDSYGGTTCYSMAP |
| 365b-R0036-H05 | 365b-M0146-C09 | VEGF | TN11_1 | 56 | 1.7486 | 0.0652 | 505 | GSNMVCMDDSYGGTTCYSMAP |
| 365b-R0036-C04 | 365b-M0146-D03 | VEGF | TN11_1 | 56 | 2.1767 | 0.0647 | 505 | GSNMVCMDDSYGGTTCYSMAP |
| 365b-R0036-E03 | 365b-M0146-E06 | VEGF | TN11_1 | 56 | 1.9461 | 0.0697 | 505 | GSNMVCMDDSYGGTTCYSMAP |
| 365b-R0036-D02 | 365b-M0146-F08 | VEGF | TN11_1 | 56 | 1.6111 | 0.0742 | 505 | GSNMVCMDDSYGGTTCYSMAP |
| 365b-R0036-H02 | 365b-M0146-G02 | VEGF | TN11_1 | 56 | 2.1987 | 0.0789 | 505 | GSNMVCMDDSYGGTTCYSMAP |
| 365b-R0036-D04 | 365b-M0146-G06 | VEGF | TN11_1 | 56 | 1.7793 | 0.0749 | 505 | GSNMVCMDDSYGGTTCYSMAP |
| 365b-R0036-H04 | 365b-M0146-D12 | VEGF | TN11_1 | 56 | 1.765 | 0.0797 | 505 | GSNMVCMDDSYGGTTCYSMAP |
| 365b-R0036-A03 | 365b-M0146-E01 | VEGF | TN11_1 | 56 | 1.4439 | 0.0677 | 505 | GSNMVCMDDSYGGTTCYSMAP |
| 365b-R0036-B03 | 365b-M0146-E02 | VEGF | TN11_1 | 56 | 2.2531 | 0.0775 | 505 | GSNMVCMDDSYGGTTCYSMAP |
| 365b-R0036-F01 | 365b-M0146-H01 | VEGF | TN11_1 | 56 | 1.5328 | 0.0812 | 505 | GSNMVCMDDSYGGTTCYSMAP |
| 365b-R0036-G01 | 365b-M0146-H02 | VEGF | TN11_1 | 56 | 1.8568 | 0.0746 | 505 | GSNMVCMDDSYGGTTCYSMAP |
| 365b-R0036-H08 | 365b-M0146-H07 | VEGF | TN11_1 | 56 | 1.9864 | 0.0768 | 505 | GSNMVCMDDSYGGTTCYSMAP |
| 365b-R0037-C12 | 365b-M0146-H08 | VEGF | TN11_1 | 56 | 1.9049 | 0.0736 | 505 | GSNMVCMDDSYGGTTCYSMAP |
| 365b-R0037-D12 | 365b-M0146-H12 | VEGF | TN11_1 | 56 | 2.1298 | 0.1011 | 505 | GSNMVCMDDSYGGTTCYSMAP |
| 365b-R0037-F12 | 365b-M0147-A01 | VEGF | TN11_1 | 56 | 1.337 | 0.0649 | 505 | GSNMVCMDDSYGGTTCYSMAP |
| 365b-R0037-G12 | 365b-M0147-A08 | VEGF | TN11_1 | 56 | 1.4345 | 0.0648 | 505 | GSNMVCMDDSYGGTTCYSMAP |
| 365b-R0037-A11 | 365b-M0147-A10 | VEGF | TN11_1 | 56 | 2.0773 | 0.0648 | 505 | GSNMVCMDDSYGGTTCYSMAP |
| 365b-R0037-C11 | | | | | | | | |

FIG. 40C

| Isolate | Initial Name | Elution | Library | Groups | Target OD | Background OD | SEQ ID NO | Trimmed AA |
|---|---|---|---|---|---|---|---|---|
| 365b-R0037-G11 | 365b-M0147-B12 | VEGF | TN11_1 | 56 | 2.1013 | 0.1125 | 505 | GSNMVCMDDSYGGTTCYSMAP |
| 365b-R0037-A10 | 365b-M0147-C02 | VEGF | TN11_1 | 56 | 2.2433 | 0.0626 | 505 | GSNMVCMDDSYGGTTCYSMAP |
| 365b-R0037-D10 | 365b-M0147-C11 | VEGF | TN11_1 | 56 | 1.7404 | 0.0619 | 505 | GSNMVCMDDSYGGTTCYSMAP |
| 365b-R0037-E10 | 365b-M0147-C12 | VEGF | TN11_1 | 56 | 2.3397 | 0.1106 | 505 | GSNMVCMDDSYGGTTCYSMAP |
| 365b-R0037-B09 | 365b-M0147-D12 | VEGF | TN11_1 | 56 | 2.1546 | 0.1078 | 505 | GSNMVCMDDSYGGTTCYSMAP |
| 365b-R0037-F08 | 365b-M0147-F04 | VEGF | TN11_1 | 56 | 2.0243 | 0.0788 | 505 | GSNMVCMDDSYGGTTCYSMAP |
| 365b-R0037-G08 | 365b-M0147-F05 | VEGF | TN11_1 | 56 | 2.3835 | 0.0635 | 505 | GSNMVCMDDSYGGTTCYSMAP |
| 365b-R0037-B07 | 365b-M0147-F09 | VEGF | TN11_1 | 56 | 1.6595 | 0.0727 | 505 | GSNMVCMDDSYGGTTCYSMAP |
| 365b-R0037-D07 | 365b-M0147-G02 | VEGF | TN11_1 | 56 | 2.514 | 0.0747 | 505 | GSNMVCMDDSYGGTTCYSMAP |
| 365b-R0037-E07 | 365b-M0147-G04 | VEGF | TN11_1 | 56 | 2.4482 | 0.0727 | 505 | GSNMVCMDDSYGGTTCYSMAP |
| 365b-R0037-G07 | 365b-M0147-G06 | VEGF | TN11_1 | 56 | 2.3408 | 0.0795 | 505 | GSNMVCMDDSYGGTTCYSMAP |
| 365b-R0037-H06 | 365b-M0147-H06 | VEGF | TN11_1 | 56 | 2.4723 | 0.0686 | 505 | GSNMVCMDDSYGGTTCYSMAP |
| 365b-R0037-H10 | 365b-M0147-H10 | VEGF | TN11_1 | 56 | 2.3901 | 0.068 | 505 | GSNMVCMDDSYGGTTCYSMAP |
| 365b-R0037-C05 | 365b-M0148-A02 | VEGF | TN11_1 | 56 | 1.3504 | 0.0594 | 505 | GSNMVCMDDSYGGTTCYSMAP |
| 365b-R0037-B03 | 365b-M0148-B11 | VEGF | TN11_1 | 56 | 1.7443 | 0.0571 | 505 | GSNMVCMDDSYGGTTCYSMAP |
| 365b-R0037-C03 | 365b-M0148-B12 | VEGF | TN11_1 | 56 | 1.9696 | 0.1511 | 505 | GSNMVCMDDSYGGTTCYSMAP |
| 365b-R0037-E03 | 365b-M0148-C04 | VEGF | TN11_1 | 56 | 2.1486 | 0.0578 | 505 | GSNMVCMDDSYGGTTCYSMAP |
| 365b-R0037-G03 | 365b-M0148-C06 | VEGF | TN11_1 | 56 | 1.8688 | 0.0595 | 505 | GSNMVCMDDSYGGTTCYSMAP |
| 365b-R0037-B02 | 365b-M0148-C12 | VEGF | TN11_1 | 56 | 2.0771 | 0.0776 | 505 | GSNMVCMDDSYGGTTCYSMAP |
| 365b-R0037-H02 | 365b-M0148-D10 | VEGF | TN11_1 | 56 | 1.5815 | 0.0683 | 505 | GSNMVCMDDSYGGTTCYSMAP |
| 365b-R0037-B01 | 365b-M0148-D12 | VEGF | TN11_1 | 56 | 2.1104 | 0.0871 | 505 | GSNMVCMDDSYGGTTCYSMAP |
| 365b-R0037-D01 | 365b-M0148-E03 | VEGF | TN11_1 | 56 | 2.2617 | 0.0607 | 505 | GSNMVCMDDSYGGTTCYSMAP |
| 365b-R0037-F01 | 365b-M0148-E06 | VEGF | TN11_1 | 56 | 1.8064 | 0.057 | 505 | GSNMVCMDDSYGGTTCYSMAP |
| 365b-R0038-A11 | 365b-M0148-E07 | VEGF | TN11_1 | 56 | 1.6833 | 0.0624 | 505 | GSNMVCMDDSYGGTTCYSMAP |
| 365b-R0038-B11 | 365b-M0148-F11 | VEGF | TN11_1 | 56 | 2.1956 | 0.0883 | 505 | GSNMVCMDDSYGGTTCYSMAP |
| 365b-R0038-C11 | 365b-M0148-F12 | VEGF | TN11_1 | 56 | 1.7961 | 0.0661 | 505 | GSNMVCMDDSYGGTTCYSMAP |
| 365b-R0038-D11 | 365b-M0148-G01 | VEGF | TN11_1 | 56 | 2.1389 | 0.0681 | 505 | GSNMVCMDDSYGGTTCYSMAP |
| 365b-R0038-C10 | 365b-M0148-G03 | VEGF | TN11_1 | 56 | 2.2304 | 0.0719 | 505 | GSNMVCMDDSYGGTTCYSMAP |
| 365b-R0038-G10 | 365b-M0148-H01 | VEGF | TN11_1 | 56 | 2.3756 | 0.1056 | 505 | GSNMVCMDDSYGGTTCYSMAP |
| 365b-R0035-A11 | 365b-M0148-H07 | BEAD | TN11_1 | 108 | 1.5109 | 0.1282 | 506 | GSYNQCYGDYWGETCYLIAP |
| 365b-R0035-H11 | 365b-M0139-H11 | D6 | TN11_1 | 108 | 2.4218 | 0.4915 | 506 | GSYNQCYGDYWGETCYLIAP |
| 365b-R0038-G09 | 365b-M0149-B02 | D6 | TN11_1 | 108 | 1.9571 | 0.4891 | 506 | GSYNQCYGDYWGETCYLIAP |
| 365b-R0038-C08 | 365b-M0149-C09 | D6 | TN11_1 | 108 | 2.6639 | 0.543 | 506 | GSYNQCYGDYWGETCYLIAP |
| 365b-R0038-C07 | 365b-M0149-E02 | D6 | TN11_1 | 108 | 2.2313 | 0.4666 | 506 | GSYNQCYGDYWGETCYLIAP |
| 365b-R0038-E07 | 365b-M0149-E06 | D6 | TN11_1 | 108 | 1.8612 | 0.4252 | 506 | GSYNQCYGDYWGETCYLIAP |
| 365b-R0038-F07 | 365b-M0149-E12 | D6 | TN11_1 | 108 | 2.4657 | 0.487 | 506 | GSYNQCYGDYWGETCYLIAP |
| 365b-R0038-E05 | 365b-M0149-H03 | D6 | TN11_1 | 108 | 2.4751 | 0.5198 | 506 | GSYNQCYGDYWGETCYLIAP |
| 365b-R0038-F05 | 365b-M0149-H04 | D6 | TN11_1 | 108 | 2.0215 | 0.5437 | 506 | GSYNQCYGDYWGETCYLIAP |
| 365b-R0038-G05 | 365b-M0149-H11 | D6 | TN11_1 | 108 | 2.0215 | 0.5437 | 506 | GSYNQCYGDYWGETCYLIAP |
| 365b-R0038-C04 | 365b-M0150-A04 | D6 | TN11_1 | 108 | 0.7779 | 0.1201 | 506 | GSYNQCYGDYWGETCYLIAP |

| Isolate | Initial Name | Elution | Library | Groups | Target OD | Background OD | SEQ ID NO | Trimmed AA |
|---|---|---|---|---|---|---|---|---|
| 365b-R0038-E04 | 365b-M0150-A06 | D6 | TN11_1 | 108 | 0.9415 | 0.1344 | 506 | GSYNQCYGDYWGGETCYLIAP |
| 365b-R0038-G04 | 365b-M0150-A09 | D6 | TN11_1 | 108 | 0.6491 | 0.1151 | 506 | GSYNQCYGDYWGGETCYLIAP |
| 365b-R0038-E03 | 365b-M0150-B10 | D6 | TN11_1 | 108 | 0.7843 | 0.1227 | 506 | GSYNQCYGDYWGGETCYLIAP |
| 365b-R0038-C02 | 365b-M0150-C06 | D6 | TN11_1 | 108 | 0.6503 | 0.1133 | 506 | GSYNQCYGDYWGGETCYLIAP |
| 365b-R0038-H02 | 365b-M0150-D02 | D6 | TN11_1 | 108 | 0.9275 | 0.1248 | 506 | GSYNQCYGDYWGGETCYLIAP |
| 365b-R0038-B01 | 365b-M0150-D04 | D6 | TN11_1 | 108 | 0.7195 | 0.1405 | 506 | GSYNQCYGDYWGGETCYLIAP |
| 365b-R0038-E01 | 365b-M0150-D09 | D6 | TN11_1 | 108 | 0.6338 | 0.1151 | 506 | GSYNQCYGDYWGGETCYLIAP |
| 365b-R0038-G01 | 365b-M0150-D12 | D6 | TN11_1 | 108 | 1.0842 | 0.1905 | 506 | GSYNQCYGDYWGGETCYLIAP |
| 365b-R0039-D12 | 365b-M0150-E09 | D6 | TN11_1 | 108 | 0.577 | 0.1083 | 506 | GSYNQCYGDYWGGETCYLIAP |
| 365b-R0039-F12 | 365b-M0150-F02 | D6 | TN11_1 | 108 | 0.8116 | 0.1157 | 506 | GSYNQCYGDYWGGETCYLIAP |
| 365b-R0039-G12 | 365b-M0150-F03 | D6 | TN11_1 | 108 | 0.8147 | 0.1245 | 506 | GSYNQCYGDYWGGETCYLIAP |
| 365b-R0039-D11 | 365b-M0150-G03 | D6 | TN11_1 | 108 | 0.7427 | 0.1382 | 506 | GSYNQCYGDYWGGETCYLIAP |
| 365b-R0039-B10 | 365b-M0150-G12 | D6 | TN11_1 | 108 | 1.0725 | 0.2625 | 506 | GSYNQCYGDYWGGETCYLIAP |
| 365b-R0039-C09 | 365b-M0151-A01 | D6 | TN11_1 | 108 | 0.5609 | 0.0972 | 506 | GSYNQCYGDYWGGETCYLIAP |
| 365b-R0039-F09 | 365b-M0151-A04 | D6 | TN11_1 | 108 | 0.7301 | 0.1073 | 506 | GSYNQCYGDYWGGETCYLIAP |
| 365b-R0039-G09 | 365b-M0151-A05 | D6 | TN11_1 | 108 | 0.8841 | 0.1089 | 506 | GSYNQCYGDYWGGETCYLIAP |
| 365b-R0039-H09 | 365b-M0151-A06 | D6 | TN11_1 | 108 | 0.7865 | 0.102 | 506 | GSYNQCYGDYWGGETCYLIAP |
| 365b-R0039-C08 | 365b-M0151-A10 | D6 | TN11_1 | 108 | 0.6065 | 0.116 | 506 | GSYNQCYGDYWGGETCYLIAP |
| 365b-R0039-C07 | 365b-M0151-B10 | D6 | TN11_1 | 108 | 0.701 | 0.0946 | 506 | GSYNQCYGDYWGGETCYLIAP |
| 365b-R0039-E06 | 365b-M0151-D06 | D6 | TN11_1 | 108 | 0.6977 | 0.1366 | 506 | GSYNQCYGDYWGGETCYLIAP |
| 365b-R0039-F06 | 365b-M0151-D07 | D6 | TN11_1 | 108 | 0.6537 | 0.1041 | 506 | GSYNQCYGDYWGGETCYLIAP |
| 365b-R0039-E05 | 365b-M0151-E07 | D6 | TN11_1 | 108 | 0.5556 | 0.0893 | 506 | GSYNQCYGDYWGGETCYLIAP |
| 365b-R0039-F05 | 365b-M0151-E09 | D6 | TN11_1 | 108 | 0.5836 | 0.1025 | 506 | GSYNQCYGDYWGGETCYLIAP |
| 365b-R0039-C04 | 365b-M0151-F03 | D6 | TN11_1 | 108 | 0.7685 | 0.1237 | 506 | GSYNQCYGDYWGGETCYLIAP |
| 365b-R0039-A03 | 365b-M0151-F10 | D6 | TN11_1 | 108 | 0.7138 | 0.1044 | 506 | GSYNQCYGDYWGGETCYLIAP |
| 365b-R0039-C03 | 365b-M0151-G01 | D6 | TN11_1 | 108 | 0.6251 | 0.1115 | 506 | GSYNQCYGDYWGGETCYLIAP |
| 365b-R0039-E03 | 365b-M0151-G03 | D6 | TN11_1 | 108 | 0.809 | 0.129 | 506 | GSYNQCYGDYWGGETCYLIAP |
| 365b-R0039-H03 | 365b-M0151-G06 | D6 | TN11_1 | 108 | 0.7398 | 0.1653 | 506 | GSYNQCYGDYWGGETCYLIAP |
| 365b-R0039-A02 | 365b-M0151-G08 | D6 | TN11_1 | 108 | 0.6397 | 0.1151 | 506 | GSYNQCYGDYWGGETCYLIAP |
| 365b-R0039-D02 | 365b-M0151-G12 | D6 | TN11_1 | 108 | 1.1096 | 0.2457 | 506 | GSYNQCYGDYWGGETCYLIAP |
| 365b-R0039-E02 | 365b-M0151-H02 | D6 | TN11_1 | 108 | 0.7822 | 0.0977 | 506 | GSYNQCYGDYWGGETCYLIAP |
| 365b-R0039-G02 | 365b-M0151-H03 | D6 | TN11_1 | 108 | 0.8631 | 0.1002 | 506 | GSYNQCYGDYWGGETCYLIAP |
| 365b-R0039-H04 | 365b-M0151-H04 | D6 | TN11_1 | 108 | 0.8218 | 0.1129 | 506 | GSYNQCYGDYWGGETCYLIAP |
| 365b-R0039-F01 | 365b-M0151-H11 | D6 | TN11_1 | 108 | 0.873 | 0.1035 | 506 | GSYNQCYGDYWGGETCYLIAP |
| 365b-R0040-A12 | 365b-M0152-A04 | D6 | TN11_1 | 108 | 0.939 | 0.1041 | 506 | GSYNQCYGDYWGGETCYLIAP |
| 365b-R0040-C12 | 365b-M0152-A06 | D6 | TN11_1 | 108 | 1.462 | 0.0954 | 506 | GSYNQCYGDYWGGETCYLIAP |
| 365b-R0040-A11 | 365b-M0152-B01 | D6 | TN11_1 | 108 | 0.7894 | 0.0819 | 506 | GSYNQCYGDYWGGETCYLIAP |
| 365b-R0040-B11 | 365b-M0152-B02 | D6 | TN11_1 | 108 | 1.3078 | 0.0941 | 506 | GSYNQCYGDYWGGETCYLIAP |
| 365b-R0040-A10 | 365b-M0152-B11 | D6 | TN11_1 | 108 | 1.3612 | 0.0889 | 506 | GSYNQCYGDYWGGETCYLIAP |

FIG. 40D

| Isolate | Initial Name | Elution | Library | Groups | Target OD | Background OD | SEQ ID NO | Trimmed AA |
|---|---|---|---|---|---|---|---|---|
| 365b-R0040-B10 | 365b-M0152-B12 | D6 | TN11_1 | 108 | 1.7873 | 0.1135 | 506 | GSYNQCYGDYWGGETCYLIAP |
| 365b-R0040-G10 | 365b-M0152-C05 | D6 | TN11_1 | 108 | 1.3721 | 0.094 | 506 | GSYNQCYGDYWGGETCYLIAP |
| 365b-R0040-F09 | 365b-M0152-D04 | D6 | TN11_1 | 108 | 1.4476 | 0.1023 | 506 | GSYNQCYGDYWGGETCYLIAP |
| 365b-R0040-C08 | 365b-M0152-D11 | D6 | TN11_1 | 108 | 1.2676 | 0.0926 | 506 | GSYNQCYGDYWGGETCYLIAP |
| 365b-R0040-C07 | 365b-M0152-E08 | D6 | TN11_1 | 108 | 1.1603 | 0.0931 | 506 | GSYNQCYGDYWGGETCYLIAP |
| 365b-R0040-E07 | 365b-M0152-E10 | D6 | TN11_1 | 108 | 1.248 | 0.0867 | 506 | GSYNQCYGDYWGGETCYLIAP |
| 365b-R0040-F07 | 365b-M0152-F01 | D6 | TN11_1 | 108 | 1.2199 | 0.0899 | 506 | GSYNQCYGDYWGGETCYLIAP |
| 365b-R0040-E06 | 365b-M0152-F10 | D6 | TN11_1 | 108 | 1.2302 | 0.0911 | 506 | GSYNQCYGDYWGGETCYLIAP |
| 365b-R0040-H06 | 365b-M0152-G01 | D6 | TN11_1 | 108 | 0.9249 | 0.0797 | 506 | GSYNQCYGDYWGGETCYLIAP |
| 365b-R0040-A04 | 365b-M0152-H02 | D6 | TN11_1 | 108 | 1.5889 | 0.0925 | 506 | GSYNQCYGDYWGGETCYLIAP |
| 365b-R0040-D04 | 365b-M0152-H05 | D6 | TN11_1 | 108 | 1.831 | 0.1062 | 506 | GSYNQCYGDYWGGETCYLIAP |
| 365b-R0040-F04 | 365b-M0152-H07 | D6 | TN11_1 | 108 | 1.8048 | 0.114 | 506 | GSYNQCYGDYWGGETCYLIAP |
| 365b-R0040-H04 | 365b-M0152-H10 | D6 | TN11_1 | 108 | 1.7804 | 0.0956 | 506 | GSYNQCYGDYWGGETCYLIAP |
| 365b-R0040-B02 | 365b-M0153-B01 | D6 | TN11_1 | 108 | 1.3845 | 0.0848 | 506 | GSYNQCYGDYWGGETCYLIAP |
| 365b-R0040-B01 | 365b-M0153-B10 | D6 | TN11_1 | 108 | 1.24 | 0.0781 | 506 | GSYNQCYGDYWGGETCYLIAP |
| 365b-R0040-G01 | 365b-M0153-C03 | D6 | TN11_1 | 108 | 1.6074 | 0.0853 | 506 | GSYNQCYGDYWGGETCYLIAP |
| 365b-R0041-F12 | 365b-M0153-C11 | D6 | TN11_1 | 108 | 1.2196 | 0.08 | 506 | GSYNQCYGDYWGGETCYLIAP |
| 365b-R0041-H12 | 365b-M0153-D03 | D6 | TN11_1 | 108 | 1.6923 | 0.0909 | 506 | GSYNQCYGDYWGGETCYLIAP |
| 365b-R0041-C11 | 365b-M0153-D09 | D6 | TN11_1 | 108 | 1.586 | 0.0829 | 506 | GSYNQCYGDYWGGETCYLIAP |
| 365b-R0041-D10 | 365b-M0153-E07 | D6 | TN11_1 | 108 | 1.2619 | 0.0827 | 506 | GSYNQCYGDYWGGETCYLIAP |
| 365b-R0041-E09 | 365b-M0153-F05 | D6 | TN11_1 | 108 | 1.5307 | 0.0903 | 506 | GSYNQCYGDYWGGETCYLIAP |
| 365b-R0041-F09 | 365b-M0153-F06 | D6 | TN11_1 | 108 | 1.5206 | 0.0904 | 506 | GSYNQCYGDYWGGETCYLIAP |
| 365b-R0041-H08 | 365b-M0153-G06 | D6 | TN11_1 | 108 | 1.8126 | 0.1136 | 506 | GSYNQCYGDYWGGETCYLIAP |
| 365b-R0041-E07 | 365b-M0153-H01 | D6 | TN11_1 | 108 | 1.2867 | 0.0891 | 506 | GSYNQCYGDYWGGETCYLIAP |
| 365b-R0041-F07 | 365b-M0153-H02 | D6 | TN11_1 | 108 | 1.6853 | 0.087 | 506 | GSYNQCYGDYWGGETCYLIAP |
| 365b-R0041-B05 | 365b-M0154-A08 | D6 | TN11_1 | 108 | 1.091 | 0.0963 | 506 | GSYNQCYGDYWGGETCYLIAP |
| 365b-R0041-B04 | 365b-M0154-B04 | D6 | TN11_1 | 108 | 1.2637 | 0.1048 | 506 | GSYNQCYGDYWGGETCYLIAP |
| 365b-R0041-H03 | 365b-M0154-C08 | D6 | TN11_1 | 108 | 1.0433 | 0.1111 | 506 | GSYNQCYGDYWGGETCYLIAP |
| 365b-R0041-A02 | 365b-M0154-C09 | D6 | TN11_1 | 108 | 1.0429 | 0.0954 | 506 | GSYNQCYGDYWGGETCYLIAP |
| 365b-R0041-E02 | 365b-M0154-D01 | D6 | TN11_1 | 108 | 1.5327 | 0.1155 | 506 | GSYNQCYGDYWGGETCYLIAP |
| 365b-R0041-F02 | 365b-M0154-D03 | D6 | TN11_1 | 108 | 1.3788 | 0.1047 | 506 | GSYNQCYGDYWGGETCYLIAP |
| 365b-R0042-C12 | 365b-M0154-E05 | D6 | TN11_1 | 108 | 1.2854 | 0.1057 | 506 | GSYNQCYGDYWGGETCYLIAP |
| 365b-R0042-E12 | 365b-M0154-E08 | D6 | TN11_1 | 108 | 0.7958 | 0.1016 | 506 | GSYNQCYGDYWGGETCYLIAP |
| 365b-R0042-C11 | 365b-M0154-F03 | D6 | TN11_1 | 108 | 1.538 | 0.1437 | 506 | GSYNQCYGDYWGGETCYLIAP |
| 365b-R0042-D11 | 365b-M0154-F04 | D6 | TN11_1 | 108 | 1.0934 | 0.1149 | 506 | GSYNQCYGDYWGGETCYLIAP |
| 365b-R0042-G10 | 365b-M0154-G02 | D6 | TN11_1 | 108 | 1.5584 | 0.1248 | 506 | GSYNQCYGDYWGGETCYLIAP |
| 365b-R0042-D10 | 365b-M0154-G03 | D6 | TN11_1 | 108 | 1.2629 | 0.1204 | 506 | GSYNQCYGDYWGGETCYLIAP |
| 365b-R0042-E10 | 365b-M0154-G07 | D6 | TN11_1 | 108 | 1.0574 | 0.0999 | 506 | GSYNQCYGDYWGGETCYLIAP |
| 365b-R0042-D09 | 365b-M0154-H01 | D6 | TN11_1 | 108 | 0.8517 | 0.0868 | 506 | GSYNQCYGDYWGGETCYLIAP |

| Isolate | Initial Name | Elution | Library | Groups | Target OD | Background OD | SEQ ID NO | Trimmed AA |
|---|---|---|---|---|---|---|---|---|
| 365b-R0042-F09 | 365b-M0154-H03 | D6 | TN11_1 | 108 | 1.6117 | 0.1027 | 506 | GSYNQCYGDYWGGETCYLIAP |
| 365b-R0042-B08 | 365b-M0154-H07 | D6 | TN11_1 | 108 | 1.3945 | 0.0923 | 506 | GSYNQCYGDYWGGETCYLIAP |
| 365b-R0042-D08 | 365b-M0154-H09 | D6 | TN11_1 | 108 | 0.8929 | 0.1491 | 506 | GSYNQCYGDYWGGETCYLIAP |
| 365b-R0035-F04 | 365b-M0144-E06 | VEGF | TN11_1 | 108 | 1.1299 | 0.0869 | 506 | GSYNQCYGDYWGGETCYLIAP |
| 365b-R0035-D03 | 365b-M0144-F05 | VEGF | TN11_1 | 108 | 1.2744 | 0.0928 | 506 | GSYNQCYGDYWGGETCYLIAP |
| 365b-R0035-G11 | 365b-M0141-C01 | BEAD | TN11_1 | 108 | 0.7345 | 0.0742 | 507 | GSRVNCGAEDGLSFLCMMDAP |
| 365b-R0035-D10 | 365b-M0143-B06 | VEGF | TN11_1 | 79 | 1.2166 | 0.3889 | 507 | GSRVNCGAEDGLSFLCMMDAP |
| 365b-R0035-E10 | 365b-M0143-B09 | VEGF | TN11_1 | 79 | 1.1555 | 0.3697 | 507 | GSRVNCGAEDGLSFLCMMDAP |
| 365b-R0035-G10 | 365b-M0143-C01 | VEGF | TN11_1 | 79 | 1.1283 | 0.3727 | 507 | GSRVNCGAEDGLSFLCMMDAP |
| 365b-R0035-H10 | 365b-M0143-C03 | VEGF | TN11_1 | 79 | 1.3144 | 0.371 | 507 | GSRVNCGAEDGLSFLCMMDAP |
| 365b-R0035-A09 | 365b-M0143-C05 | VEGF | TN11_1 | 79 | 1.2601 | 0.4075 | 507 | GSRVNCGAEDGLSFLCMMDAP |
| 365b-R0035-B09 | 365b-M0143-C06 | VEGF | TN11_1 | 79 | 1.3289 | 0.33 | 507 | GSRVNCGAEDGLSFLCMMDAP |
| 365b-R0035-C09 | 365b-M0143-C09 | VEGF | TN11_1 | 79 | 1.1007 | 0.3639 | 507 | GSRVNCGAEDGLSFLCMMDAP |
| 365b-R0035-E09 | 365b-M0143-D08 | VEGF | TN11_1 | 79 | 1.0239 | 0.3353 | 507 | GSRVNCGAEDGLSFLCMMDAP |
| 365b-R0035-G09 | 365b-M0143-E02 | VEGF | TN11_1 | 79 | 1.5319 | 0.4308 | 507 | GSRVNCGAEDGLSFLCMMDAP |
| 365b-R0035-H09 | 365b-M0143-E03 | VEGF | TN11_1 | 79 | 1.3567 | 0.3826 | 507 | GSRVNCGAEDGLSFLCMMDAP |
| 365b-R0035-A08 | 365b-M0143-E05 | VEGF | TN11_1 | 79 | 1.4667 | 0.3864 | 507 | GSRVNCGAEDGLSFLCMMDAP |
| 365b-R0035-B08 | 365b-M0143-E07 | VEGF | TN11_1 | 79 | 1.2165 | 0.3718 | 507 | GSRVNCGAEDGLSFLCMMDAP |
| 365b-R0035-C08 | 365b-M0143-F02 | VEGF | TN11_1 | 79 | 1.4336 | 0.4348 | 507 | GSRVNCGAEDGLSFLCMMDAP |
| 365b-R0035-D08 | 365b-M0143-F04 | VEGF | TN11_1 | 79 | 1.2934 | 0.4065 | 507 | GSRVNCGAEDGLSFLCMMDAP |
| 365b-R0035-F08 | 365b-M0143-G04 | VEGF | TN11_1 | 79 | 1.3589 | 0.4454 | 507 | GSRVNCGAEDGLSFLCMMDAP |
| 365b-R0035-G08 | 365b-M0143-H03 | VEGF | TN11_1 | 79 | 1.3421 | 0.3736 | 507 | GSRVNCGAEDGLSFLCMMDAP |
| 365b-R0035-A07 | 365b-M0143-H06 | VEGF | TN11_1 | 79 | 1.1833 | 0.3753 | 507 | GSRVNCGAEDGLSFLCMMDAP |
| 365b-R0035-H07 | 365b-M0144-B01 | VEGF | TN11_1 | 79 | 0.4672 | 0.0662 | 507 | GSRVNCGAEDGLSFLCMMDAP |
| 365b-R0036-E10 | 365b-M0145-E07 | VEGF | TN11_1 | 79 | 0.614 | 0.0753 | 507 | GSRVNCGAEDGLSFLCMMDAP |
| 365b-R0035-H05 | 365b-M0144-D06 | VEGF | TN11_1 | 79 | 0.4068 | 0.0682 | 507 | GSRVNCGAEDGLSFLCMMDAP |
| 365b-R0035-A04 | 365b-M0144-D09 | VEGF | TN11_1 | 79 | 0.3866 | 0.073 | 507 | GSRVNCGAEDGLSFLCMMDAP |
| 365b-R0035-G04 | 365b-M0144-E08 | VEGF | TN11_1 | 79 | 0.3714 | 0.0682 | 507 | GSRVNCGAEDGLSFLCMMDAP |
| 365b-R0036-D11 | 365b-M0145-C08 | VEGF | TN11_1 | 79 | 0.487 | 0.0683 | 507 | GSRVNCGAEDGLSFLCMMDAP |
| 365b-R0036-E10 | 365b-M0145-E07 | VEGF | TN11_1 | 79 | 0.614 | 0.0753 | 507 | GSRVNCGAEDGLSFLCMMDAP |
| 365b-R0036-F08 | 365b-M0145-F11 | VEGF | TN11_1 | 79 | 0.5203 | 0.0735 | 507 | GSRVNCGAEDGLSFLCMMDAP |
| 365b-R0036-G09 | 365b-M0146-A11 | VEGF | TN11_1 | 79 | 0.4988 | 0.0592 | 507 | GSRVNCGAEDGLSFLCMMDAP |
| 365b-R0036-C06 | 365b-M0146-B03 | VEGF | TN11_1 | 79 | 0.5454 | 0.0968 | 507 | GSRVNCGAEDGLSFLCMMDAP |
| 365b-R0036-E06 | 365b-M0146-G11 | VEGF | TN11_1 | 79 | 0.4965 | 0.0788 | 507 | GSRVNCGAEDGLSFLCMMDAP |
| 365b-R0037-E11 | 365b-M0147-B09 | VEGF | TN11_1 | 79 | 0.7309 | 0.0824 | 507 | GSRVNCGAEDGLSFLCMMDAP |
| 365b-R0037-A07 | 365b-M0147-F08 | VEGF | TN11_1 | 79 | 0.4608 | 0.0791 | 507 | GSRVNCGAEDGLSFLCMMDAP |
| 365b-R0037-C07 | 365b-M0147-F10 | VEGF | TN11_1 | 79 | 0.5636 | 0.0682 | 507 | GSRVNCGAEDGLSFLCMMDAP |
| 365b-R0037-H07 | 365b-M0147-G09 | VEGF | TN11_1 | 79 | 0.6262 | 0.0756 | 507 | GSRVNCGAEDGLSFLCMMDAP |
| 365b-R0037-D06 | 365b-M0147-H01 | VEGF | TN11_1 | 79 | 0.4735 | 0.0816 | 507 | GSRVNCGAEDGLSFLCMMDAP |
| 365b-R0037-F05 | 365b-M0148-A06 | VEGF | TN11_1 | 79 | 0.4994 | 0.0652 | 507 | GSRVNCGAEDGLSFLCMMDAP |

FIG. 40G

| Isolate | Initial Name | Elution | Library | Groups | Target OD | Background OD | SEQ ID NO | Trimmed AA |
|---|---|---|---|---|---|---|---|---|
| 365b-R0037-C02 | 365b-M0148-D01 | VEGF | TN11_1 | 79 | 0.7838 | 0.0633 | 507 | GSRVNCGAEDGLSFLCMMDAP |
| 365b-R0037-F02 | 365b-M0148-D04 | VEGF | TN11_1 | 79 | 0.625 | 0.0593 | 507 | GSRVNCGAEDGLSFLCMMDAP |
| 365b-R0038-A12 | 365b-M0148-E10 | VEGF | TN11_1 | 79 | 0.437 | 0.0591 | 507 | GSRVNCGAEDGLSFLCMMDAP |
| 365b-R0038-E11 | 365b-M0148-G04 | VEGF | TN11_1 | 79 | 0.5606 | 0.0677 | 507 | GSRVNCGAEDGLSFLCMMDAP |
| 365b-R0038-A10 | 365b-M0148-G11 | VEGF | TN11_1 | 79 | 0.6155 | 0.0679 | 507 | GSRVNCGAEDGLSFLCMMDAP |
| 365b-R0038-F10 | 365b-M0148-H05 | VEGF | TN11_1 | 79 | 0.6749 | 0.0715 | 507 | GSRVNCGAEDGLSFLCMMDAP |
| 365b-R0038-A08 | 365b-M0149-B11 | D6 | TN11_1 | 43 | 2.0419 | 0.5295 | 508 | GSIWDCQISEYGGEDCYLVAP |
| 365b-R0038-D08 | 365b-M0149-C12 | D6 | TN11_1 | 43 | 1.5383 | 0.436 | 508 | GSIWDCQISEYGGEDCYLVAP |
| 365b-R0038-G07 | 365b-M0149-F01 | D6 | TN11_1 | 43 | 2.1116 | 0.4716 | 508 | GSIWDCQISEYGGEDCYLVAP |
| 365b-R0038-B06 | 365b-M0149-F07 | D6 | TN11_1 | 43 | 2.3101 | 0.4743 | 508 | GSIWDCQISEYGGEDCYLVAP |
| 365b-R0038-C06 | 365b-M0149-F10 | D6 | TN11_1 | 43 | 1.5905 | 0.4115 | 508 | GSIWDCQISEYGGEDCYLVAP |
| 365b-R0038-H06 | 365b-M0149-G06 | D6 | TN11_1 | 43 | 2.6437 | 0.6119 | 508 | GSIWDCQISEYGGEDCYLVAP |
| 365b-R0038-B04 | 365b-M0150-A03 | D6 | TN11_1 | 43 | 0.6808 | 0.0937 | 508 | GSIWDCQISEYGGEDCYLVAP |
| 365b-R0038-D01 | 365b-M0150-D08 | D6 | TN11_1 | 43 | 0.5882 | 0.0823 | 508 | GSIWDCQISEYGGEDCYLVAP |
| 365b-R0039-B12 | 365b-M0150-E05 | D6 | TN11_1 | 43 | 0.7005 | 0.0983 | 508 | GSIWDCQISEYGGEDCYLVAP |
| 365b-R0039-D08 | 365b-M0151-A11 | D6 | TN11_1 | 43 | 0.365 | 0.0924 | 508 | GSIWDCQISEYGGEDCYLVAP |
| 365b-R0040-E12 | 365b-M0152-A08 | D6 | TN11_1 | 43 | 0.983 | 0.0819 | 508 | GSIWDCQISEYGGEDCYLVAP |
| 365b-R0040-D09 | 365b-M0152-C11 | D6 | TN11_1 | 43 | 1.0764 | 0.0756 | 508 | GSIWDCQISEYGGEDCYLVAP |
| 365b-R0040-H09 | 365b-M0152-D06 | D6 | TN11_1 | 43 | 1.2021 | 0.0797 | 508 | GSIWDCQISEYGGEDCYLVAP |
| 365b-R0040-A08 | 365b-M0152-D08 | D6 | TN11_1 | 43 | 1.0779 | 0.0721 | 508 | GSIWDCQISEYGGEDCYLVAP |
| 365b-R0040-G05 | 365b-M0152-G12 | D6 | TN11_1 | 43 | 1.561 | 0.1663 | 508 | GSIWDCQISEYGGEDCYLVAP |
| 365b-R0040-H05 | 365b-M0152-H01 | D6 | TN11_1 | 43 | 0.7801 | 0.0854 | 508 | GSIWDCQISEYGGEDCYLVAP |
| 365b-R0040-C04 | 365b-M0152-H04 | D6 | TN11_1 | 43 | 1.5565 | 0.08 | 508 | GSIWDCQISEYGGEDCYLVAP |
| 365b-R0040-G02 | 365b-M0153-B07 | D6 | TN11_1 | 43 | 0.9987 | 0.0805 | 508 | GSIWDCQISEYGGEDCYLVAP |
| 365b-R0040-E01 | 365b-M0153-C01 | D6 | TN11_1 | 43 | 1.2912 | 0.072 | 508 | GSIWDCQISEYGGEDCYLVAP |
| 365b-R0040-F01 | 365b-M0153-C02 | D6 | TN11_1 | 43 | 1.2425 | 0.076 | 508 | GSIWDCQISEYGGEDCYLVAP |
| 365b-R0041-E10 | 365b-M0153-E09 | D6 | TN11_1 | 43 | 0.9415 | 0.0704 | 508 | GSIWDCQISEYGGEDCYLVAP |
| 365b-R0041-F10 | 365b-M0153-E10 | D6 | TN11_1 | 43 | 0.9284 | 0.0665 | 508 | GSIWDCQISEYGGEDCYLVAP |
| 365b-R0041-C08 | 365b-M0153-F12 | D6 | TN11_1 | 43 | 1.4044 | 0.1209 | 508 | GSIWDCQISEYGGEDCYLVAP |
| 365b-R0041-A06 | 365b-M0153-H06 | D6 | TN11_1 | 43 | 1.428 | 0.0763 | 508 | GSIWDCQISEYGGEDCYLVAP |
| 365b-R0041-B06 | 365b-M0153-H07 | D6 | TN11_1 | 43 | 1.3097 | 0.08 | 508 | GSIWDCQISEYGGEDCYLVAP |
| 365b-R0041-H05 | 365b-M0154-B02 | D6 | TN11_1 | 43 | 1.1868 | 0.0883 | 508 | GSIWDCQISEYGGEDCYLVAP |
| 365b-R0041-A04 | 365b-M0154-B03 | D6 | TN11_1 | 43 | 0.9499 | 0.0884 | 508 | GSIWDCQISEYGGEDCYLVAP |
| 365b-R0042-H12 | 365b-M0154-E12 | D6 | TN11_1 | 43 | 1.2489 | 0.1536 | 508 | GSIWDCQISEYGGEDCYLVAP |
| 365b-R0042-A11 | 365b-M0154-F01 | D6 | TN11_1 | 43 | 1.1863 | 0.0979 | 508 | GSIWDCQISEYGGEDCYLVAP |
| 365b-R0038-H09 | 365b-M0149-B07 | D6 | TN11_1 | 111 | 4 | 0.5739 | 509 | GSYWHCMDDFFGGETCFATAP |
| 365b-R0038-A04 | 365b-M0150-A01 | D6 | TN11_1 | 111 | 1.1419 | 0.1288 | 509 | GSYWHCMDDFFGGETCFATAP |
| 365b-R0039-E12 | 365b-M0150-F01 | D6 | TN11_1 | 111 | 1.676 | 0.1496 | 509 | GSYWHCMDDFFGGETCFATAP |
| 365b-R0039-F11 | 365b-M0150-G05 | D6 | TN11_1 | 111 | 1.2592 | 0.1442 | 509 | GSYWHCMDDFFGGETCFATAP |

| Isolate | Initial Name | Elution | Library | Groups | Target OD | Background OD | SEQ ID NO | Trimmed AA |
|---|---|---|---|---|---|---|---|---|
| 365b-R0039-G11 | 365b-M0150-G08 | D6 | TN11_1 | 111 | 1.2749 | 0.1385 | 509 | GSYWHCMDFFGGETCFATAP |
| 365b-R0039-C10 | 365b-M0150-H01 | D6 | TN11_1 | 111 | 1.1529 | 0.1197 | 509 | GSYWHCMDFFGGETCFATAP |
| 365b-R0039-H06 | 365b-M0151-E01 | D6 | TN11_1 | 111 | 1.507 | 0.1199 | 509 | GSYWHCMDFFGGETCFATAP |
| 365b-R0039-A05 | 365b-M0151-E02 | D6 | TN11_1 | 111 | 1.7557 | 0.1303 | 509 | GSYWHCMDFFGGETCFATAP |
| 365b-R0039-A04 | 365b-M0151-F01 | D6 | TN11_1 | 111 | 1.9634 | 0.1403 | 509 | GSYWHCMDFFGGETCFATAP |
| 365b-R0039-C02 | 365b-M0151-G11 | D6 | TN11_1 | 111 | 1.6072 | 0.1492 | 509 | GSYWHCMDFFGGETCFATAP |
| 365b-R0040-H10 | 365b-M0152-C06 | D6 | TN11_1 | 111 | 2.4674 | 0.1103 | 509 | GSYWHCMDFFGGETCFATAP |
| 365b-R0040-B08 | 365b-M0152-D09 | D6 | TN11_1 | 111 | 2.7702 | 0.1294 | 509 | GSYWHCMDFFGGETCFATAP |
| 365b-R0040-A07 | 365b-M0152-E05 | D6 | TN11_1 | 111 | 2.6951 | 0.1053 | 509 | GSYWHCMDFFGGETCFATAP |
| 365b-R0040-C06 | 365b-M0152-F08 | D6 | TN11_1 | 111 | 2.1454 | 0.1114 | 509 | GSYWHCMDFFGGETCFATAP |
| 365b-R0040-G06 | 365b-M0152-F12 | D6 | TN11_1 | 111 | 2.728 | 0.245 | 509 | GSYWHCMDFFGGETCFATAP |
| 365b-R0040-A05 | 365b-M0152-G02 | D6 | TN11_1 | 111 | 2.7657 | 0.1262 | 509 | GSYWHCMDFFGGETCFATAP |
| 365b-R0040-B03 | 365b-M0152-H12 | D6 | TN11_1 | 111 | 2.9163 | 0.1563 | 509 | GSYWHCMDFFGGETCFATAP |
| 365b-R0040-C02 | 365b-M0153-B02 | D6 | TN11_1 | 111 | 2.6862 | 0.1018 | 509 | GSYWHCMDFFGGETCFATAP |
| 365b-R0040-D02 | 365b-M0153-B03 | D6 | TN11_1 | 111 | 2.4014 | 0.0993 | 509 | GSYWHCMDFFGGETCFATAP |
| 365b-R0041-C12 | 365b-M0153-C08 | D6 | TN11_1 | 111 | 2.4439 | 0.0976 | 509 | GSYWHCMDFFGGETCFATAP |
| 365b-R0041-D12 | 365b-M0153-C09 | D6 | TN11_1 | 111 | 2.2474 | 0.0903 | 509 | GSYWHCMDFFGGETCFATAP |
| 365b-R0041-F11 | 365b-M0153-D12 | D6 | TN11_1 | 111 | 2.8165 | 0.1229 | 509 | GSYWHCMDFFGGETCFATAP |
| 365b-R0041-B10 | 365b-M0153-E05 | D6 | TN11_1 | 111 | 2.8272 | 0.1043 | 509 | GSYWHCMDFFGGETCFATAP |
| 365b-R0041-D09 | 365b-M0153-F04 | D6 | TN11_1 | 111 | 2.5974 | 0.1115 | 509 | GSYWHCMDFFGGETCFATAP |
| 365b-R0041-E06 | 365b-M0149-D10 | D6 | TN11_1 | 31 | 1.6239 | 0.132 | 510 | GSGEYCFPSIYGGETCYAHAP |
| 365b-R0041-A01 | 365b-M0149-G10 | D6 | TN11_1 | 31 | 2.5151 | 0.1237 | 510 | GSGEYCFPSIYGGETCYAHAP |
| 365b-R0041-B03 | 365b-M0150-C08 | D6 | TN11_1 | 31 | 1.6268 | 0.0913 | 510 | GSGEYCFPSIYGGETCYAHAP |
| 365b-R0041-C01 | 365b-M0150-D11 | D6 | TN11_1 | 31 | 1.9768 | 0.1203 | 510 | GSGEYCFPSIYGGETCYAHAP |
| 365b-R0041-F03 | 365b-M0150-G01 | D6 | TN11_1 | 31 | 1.5058 | 0.0894 | 510 | GSGEYCFPSIYGGETCYAHAP |
| 365b-R0042-A12 | 365b-M0150-G04 | D6 | TN11_1 | 31 | 1.8336 | 0.0825 | 510 | GSGEYCFPSIYGGETCYAHAP |
| 365b-R0038-A07 | 365b-M0150-H11 | D6 | TN11_1 | 31 | 2.0997 | 0.1 | 510 | GSGEYCFPSIYGGETCYAHAP |
| 365b-R0038-A05 | 365b-M0150-H12 | D6 | TN11_1 | 31 | 2.2131 | 0.0854 | 510 | GSGEYCFPSIYGGETCYAHAP |
| 365b-R0038-D02 | 365b-M0151-A07 | D6 | TN11_1 | 31 | 2.2237 | 0.1137 | 510 | GSGEYCFPSIYGGETCYAHAP |
| 365b-R0038-F01 | 365b-M0151-A12 | D6 | TN11_1 | 31 | 2.1761 | 0.0808 | 510 | GSGEYCFPSIYGGETCYAHAP |
| 365b-R0039-C11 | 365b-M0151-B05 | D6 | TN11_1 | 31 | 1.6938 | 0.0911 | 510 | GSGEYCFPSIYGGETCYAHAP |
| 365b-R0039-E08 | 365b-M0151-B08 | D6 | TN11_1 | 31 | 1.8393 | 0.0822 | 510 | GSGEYCFPSIYGGETCYAHAP |
| 365b-R0039-H08 | 365b-M0151-C10 | D6 | TN11_1 | 31 | 1.838 | 0.0904 | 510 | GSGEYCFPSIYGGETCYAHAP |
| 365b-R0039-B07 | 365b-M0152-C04 | D6 | TN11_1 | 31 | 1.4918 | 0.0777 | 510 | GSGEYCFPSIYGGETCYAHAP |
| 365b-R0039-G07 | 365b-M0153-B12 | D6 | TN11_1 | 31 | 3 | 0.0764 | 510 | GSGEYCFPSIYGGETCYAHAP |
| 365b-R0040-F10 | | D6 | TN11_1 | 31 | 2.7311 | 0.0631 | 510 | GSGEYCFPSIYGGETCYAHAP |

| Isolate | Initial Name | Elution | Library | Groups | Target OD | Background OD | SEQ ID NO | Trimmed AA |
|---|---|---|---|---|---|---|---|---|
| 365b-R0041-A08 | 365b-M0153-F10 | D6 | TN11_1 | 31 | 2.5077 | 0.0752 | 510 | GSGEYCFPSIYGGETCYAHAP |
| 365b-R0041-H06 | 365b-M0154-A04 | D6 | TN11_1 | 31 | 2.5667 | 0.0956 | 510 | GSGEYCFPSIYGGETCYAHAP |
| 365b-R0041-E05 | 365b-M0154-A11 | D6 | TN11_1 | 31 | 2.0621 | 0.0864 | 510 | GSGEYCFPSIYGGETCYAHAP |
| 365b-R0041-E04 | 365b-M0154-B07 | D6 | TN11_1 | 31 | 2.1282 | 0.0785 | 510 | GSGEYCFPSIYGGETCYAHAP |
| 365b-R0041-E03 | 365b-M0154-C05 | D6 | TN11_1 | 31 | 2.4869 | 0.085 | 510 | GSGEYCFPSIYGGETCYAHAP |
| 365b-R0041-C02 | 365b-M0154-C11 | D6 | TN11_1 | 31 | 1.9893 | 0.0709 | 510 | GSGEYCFPSIYGGETCYAHAP |
| 365b-R0042-B12 | 365b-M0154-E03 | D6 | TN11_1 | 31 | 2.8076 | 0.0831 | 510 | GSGEYCFPSIYGGETCYAHAP |
| 365b-R0042-F12 | 365b-M0154-E09 | D6 | TN11_1 | 31 | 2.0439 | 0.0793 | 510 | GSGEYCFPSIYGGETCYAHAP |
| 365b-R0042-C08 | 365b-M0154-H08 | D6 | TN11_1 | 31 | 2.5615 | 0.1115 | 510 | GSGEYCFPSIYGGETCYAHAP |
| 365b-R0038-E02 | 365b-M0150-C10 | D6 | TN11_1 | 21 | 0.5866 | 0.1044 | 511 | GSEQLCFEYQYGGVECFGPAP |
| 365b-R0038-C01 | 365b-M0150-D06 | D6 | TN11_1 | 21 | 0.5888 | 0.0878 | 511 | GSEQLCFEYQYGGVECFGPAP |
| 365b-R0038-H01 | 365b-M0150-E01 | D6 | TN11_1 | 21 | 0.5976 | 0.083 | 511 | GSEQLCFEYQYGGVECFGPAP |
| 365b-R0039-G05 | 365b-M0151-E11 | D6 | TN11_1 | 21 | 0.531 | 0.0805 | 511 | GSEQLCFEYQYGGVECFGPAP |
| 365b-R0039-F04 | 365b-M0151-F07 | D6 | TN11_1 | 21 | 0.5238 | 0.0841 | 511 | GSEQLCFEYQYGGVECFGPAP |
| 365b-R0039-G03 | 365b-M0151-G05 | D6 | TN11_1 | 21 | 0.5075 | 0.0865 | 511 | GSEQLCFEYQYGGVECFGPAP |
| 365b-R0039-B01 | 365b-M0151-H07 | D6 | TN11_1 | 21 | 0.8078 | 0.0896 | 511 | GSEQLCFEYQYGGVECFGPAP |
| 365b-R0040-D11 | 365b-M0152-B04 | D6 | TN11_1 | 21 | 1.1873 | 0.0799 | 511 | GSEQLCFEYQYGGVECFGPAP |
| 365b-R0040-G11 | 365b-M0152-B08 | D6 | TN11_1 | 21 | 1.1131 | 0.0816 | 511 | GSEQLCFEYQYGGVECFGPAP |
| 365b-R0040-A09 | 365b-M0152-C07 | D6 | TN11_1 | 21 | 1.2876 | 0.0631 | 511 | GSEQLCFEYQYGGVECFGPAP |
| 365b-R0040-G07 | 365b-M0152-F03 | D6 | TN11_1 | 21 | 1.3527 | 0.0821 | 511 | GSEQLCFEYQYGGVECFGPAP |
| 365b-R0040-C03 | 365b-M0153-A01 | D6 | TN11_1 | 21 | 0.7142 | 0.0759 | 511 | GSEQLCFEYQYGGVECFGPAP |
| 365b-R0040-H03 | 365b-M0153-A10 | D6 | TN11_1 | 21 | 0.9649 | 0.0686 | 511 | GSEQLCFEYQYGGVECFGPAP |
| 365b-R0040-E02 | 365b-M0153-B04 | D6 | TN11_1 | 21 | 1.1747 | 0.0703 | 511 | GSEQLCFEYQYGGVECFGPAP |
| 365b-R0041-G12 | 365b-M0153-C12 | D6 | TN11_1 | 21 | 1.4529 | 0.0773 | 511 | GSEQLCFEYQYGGVECFGPAP |
| 365b-R0041-C10 | 365b-M0153-E06 | D6 | TN11_1 | 21 | 0.948 | 0.0669 | 511 | GSEQLCFEYQYGGVECFGPAP |
| 365b-R0041-D08 | 365b-M0153-G02 | D6 | TN11_1 | 21 | 1.4348 | 0.0824 | 511 | GSEQLCFEYQYGGVECFGPAP |
| 365b-R0041-D07 | 365b-M0153-G11 | D6 | TN11_1 | 21 | 1.0631 | 0.0759 | 511 | GSEQLCFEYQYGGVECFGPAP |
| 365b-R0041-C04 | 365b-M0154-B05 | D6 | TN11_1 | 21 | 0.9363 | 0.0786 | 511 | GSEQLCFEYQYGGVECFGPAP |
| 365b-R0041-C01 | 365b-M0154-D08 | D6 | TN11_1 | 21 | 0.8975 | 0.0707 | 511 | GSEQLCFEYQYGGVECFGPAP |
| 365b-R0042-D12 | 365b-M0154-E07 | D6 | TN11_1 | 21 | 0.811 | 0.0759 | 511 | GSEQLCFEYQYGGVECFGPAP |
| 365b-R0038-G08 | 365b-M0149-D06 | D6 | TN11_1 | 89 | 3.0154 | 0.4493 | 512 | GSTGVCSPAPYGGEVCYHFAP |
| 365b-R0039-A12 | 365b-M0150-E04 | D6 | TN11_1 | 89 | 1.1513 | 0.0925 | 512 | GSTGVCSPAPYGGEVCYHFAP |
| 365b-R0039-H11 | 365b-M0150-G09 | D6 | TN11_1 | 89 | 0.8518 | 0.114 | 512 | GSTGVCSPAPYGGEVCYHFAP |
| 365b-R0039-E10 | 365b-M0150-H06 | D6 | TN11_1 | 89 | 1.1328 | 0.0852 | 512 | GSTGVCSPAPYGGEVCYHFAP |
| 365b-R0039-D09 | 365b-M0151-A02 | D6 | TN11_1 | 89 | 0.7824 | 0.0722 | 512 | GSTGVCSPAPYGGEVCYHFAP |
| 365b-R0039-F08 | 365b-M0151-B01 | D6 | TN11_1 | 89 | 0.995 | 0.0666 | 512 | GSTGVCSPAPYGGEVCYHFAP |
| 365b-R0039-C06 | 365b-M0151-D02 | D6 | TN11_1 | 89 | 1.2588 | 0.0716 | 512 | GSTGVCSPAPYGGEVCYHFAP |
| 365b-R0039-H05 | 365b-M0151-E12 | D6 | TN11_1 | 89 | 1.6778 | 0.1395 | 512 | GSTGVCSPAPYGGEVCYHFAP |
| 365b-R0039-F03 | 365b-M0151-G04 | D6 | TN11_1 | 89 | 0.8997 | 0.0855 | 512 | GSTGVCSPAPYGGEVCYHFAP |

FIG. 40J

| Isolate | Initial Name | Elution | Library | Groups | Target OD | Background OD | SEQ ID NO | Trimmed AA |
|---|---|---|---|---|---|---|---|---|
| 365b-R0040-F08 | 365b-M0152-E02 | D6 | TN11_1 | 89 | 1.9751 | 0.0708 | 512 | GSTGVCSPAPYGGEVCYHFAP |
| 365b-R0040-F06 | 365b-M0152-F11 | D6 | TN11_1 | 89 | 1.6171 | 0.0776 | 512 | GSTGVCSPAPYGGEVCYHFAP |
| 365b-R0041-A12 | 365b-M0153-C06 | D6 | TN11_1 | 89 | 1.6131 | 0.0623 | 512 | GSTGVCSPAPYGGEVCYHFAP |
| 365b-R0041-C09 | 365b-M0153-F03 | D6 | TN11_1 | 89 | 1.9526 | 0.073 | 512 | GSTGVCSPAPYGGEVCYHFAP |
| 365b-R0041-F08 | 365b-M0153-G04 | D6 | TN11_1 | 89 | 1.9254 | 0.0742 | 512 | GSTGVCSPAPYGGEVCYHFAP |
| 365b-R0041-A07 | 365b-M0153-G07 | D6 | TN11_1 | 89 | 1.5484 | 0.0842 | 512 | GSTGVCSPAPYGGEVCYHFAP |
| 365b-R0041-B07 | 365b-M0153-G08 | D6 | TN11_1 | 89 | 1.6544 | 0.0765 | 512 | GSTGVCSPAPYGGEVCYHFAP |
| 365b-R0041-G04 | 365b-M0154-B10 | D6 | TN11_1 | 89 | 1.3059 | 0.0673 | 512 | GSTGVCSPAPYGGEVCYHFAP |
| 365b-R0041-A01 | 365b-M0154-D06 | D6 | TN11_1 | 89 | 1.5102 | 0.0762 | 512 | GSTGVCSPAPYGGEVCYHFAP |
| 365b-R0042-C09 | 365b-M0154-G11 | D6 | TN11_1 | 89 | 1.4167 | 0.0808 | 512 | GSTGVCSPAPYGGEVCYHFAP |
| 365b-R0042-G08 | 365b-M0154-H12 | D6 | TN11_1 | 89 | 2.5633 | 0.1158 | 512 | GSTGVCSPAPYGGEVCYHFAP |
| 365b-R0039-D07 | 365b-M0151-B11 | D6 | TN11_1 | 35 | 0.3793 | 0.1155 | 513 | GSHDECWEDIYGGFTCMLMAP |
| 365b-R0039-E04 | 365b-M0151-F06 | D6 | TN11_1 | 35 | 0.3604 | 0.109 | 513 | GSHDECWEDIYGGFTCMLMAP |
| 365b-R0039-D03 | 365b-M0151-G02 | D6 | TN11_1 | 35 | 0.4063 | 0.1305 | 513 | GSHDECWEDIYGGFTCMLMAP |
| 365b-R0039-H01 | 365b-M0152-A03 | D6 | TN11_1 | 35 | 0.3844 | 0.0984 | 513 | GSHDECWEDIYGGFTCMLMAP |
| 365b-R0040-G12 | 365b-M0152-A10 | D6 | TN11_1 | 35 | 0.5678 | 0.0885 | 513 | GSHDECWEDIYGGFTCMLMAP |
| 365b-R0040-D07 | 365b-M0152-E09 | D6 | TN11_1 | 35 | 0.4932 | 0.0924 | 513 | GSHDECWEDIYGGFTCMLMAP |
| 365b-R0041-E12 | 365b-M0153-C10 | D6 | TN11_1 | 35 | 0.5638 | 0.0743 | 513 | GSHDECWEDIYGGFTCMLMAP |
| 365b-R0041-G11 | 365b-M0153-E02 | D6 | TN11_1 | 35 | 0.6335 | 0.0818 | 513 | GSHDECWEDIYGGFTCMLMAP |
| 365b-R0041-B09 | 365b-M0153-F02 | D6 | TN11_1 | 35 | 0.6639 | 0.0904 | 513 | GSHDECWEDIYGGFTCMLMAP |
| 365b-R0041-H07 | 365b-M0153-H05 | D6 | TN11_1 | 35 | 0.6628 | 0.0875 | 513 | GSHDECWEDIYGGFTCMLMAP |
| 365b-R0041-C06 | 365b-M0153-H10 | D6 | TN11_1 | 35 | 0.6876 | 0.0913 | 513 | GSHDECWEDIYGGFTCMLMAP |
| 365b-R0041-D06 | 365b-M0153-H11 | D6 | TN11_1 | 35 | 0.6591 | 0.0813 | 513 | GSHDECWEDIYGGFTCMLMAP |
| 365b-R0041-D05 | 365b-M0154-A10 | D6 | TN11_1 | 35 | 0.4842 | 0.0977 | 513 | GSHDECWEDIYGGFTCMLMAP |
| 365b-R0041-A03 | 365b-M0154-B12 | D6 | TN11_1 | 35 | 0.6564 | 0.1336 | 513 | GSHDECWEDIYGGFTCMLMAP |
| 365b-R0041-B02 | 365b-M0154-C10 | D6 | TN11_1 | 35 | 0.4368 | 0.0856 | 513 | GSHDECWEDIYGGFTCMLMAP |
| 365b-R0042-B11 | 365b-M0154-F02 | D6 | TN11_1 | 35 | 0.5976 | 0.1014 | 513 | GSHDECWEDIYGGFTCMLMAP |
| 365b-R0042-E11 | 365b-M0154-F05 | D6 | TN11_1 | 35 | 0.4479 | 0.1031 | 513 | GSHDECWEDIYGGFTCMLMAP |
| 365b-R0042-G11 | 365b-M0154-F07 | D6 | TN11_1 | 35 | 0.419 | 0.0963 | 513 | GSHDECWEDIYGGFTCMLMAP |
| 365b-R0042-A09 | 365b-M0154-G09 | D6 | TN11_1 | 35 | 0.4759 | 0.1094 | 513 | GSHDECWEDIYGGFTCMLMAP |
| 365b-R0038-A01 | 365b-M0150-D03 | D6 | TN11_1 | 71 | 0.2353 | 0.0745 | 514 | GSQHTCFSDPYGGEVCYADAP |
| 365b-R0040-D12 | 365b-M0152-A07 | D6 | TN11_1 | 71 | 0.3006 | 0.0729 | 514 | GSQHTCFSDPYGGEVCYADAP |
| 365b-R0040-H12 | 365b-M0152-A12 | D6 | TN11_1 | 71 | 0.3519 | 0.0779 | 514 | GSQHTCFSDPYGGEVCYADAP |
| 365b-R0040-C10 | 365b-M0152-C01 | D6 | TN11_1 | 71 | 0.302 | 0.0817 | 514 | GSQHTCFSDPYGGEVCYADAP |
| 365b-R0040-E05 | 365b-M0152-G07 | D6 | TN11_1 | 71 | 0.343 | 0.0769 | 514 | GSQHTCFSDPYGGEVCYADAP |
| 365b-R0041-A11 | 365b-M0153-D04 | D6 | TN11_1 | 71 | 0.3026 | 0.0662 | 514 | GSQHTCFSDPYGGEVCYADAP |
| 365b-R0041-E11 | 365b-M0153-D11 | D6 | TN11_1 | 71 | 0.232 | 0.0576 | 514 | GSQHTCFSDPYGGEVCYADAP |
| 365b-R0041-G06 | 365b-M0154-A03 | D6 | TN11_1 | 71 | 0.3326 | 0.0747 | 514 | GSQHTCFSDPYGGEVCYADAP |
| 365b-R0041-F05 | 365b-M0154-A12 | D6 | TN11_1 | 71 | 0.2065 | 0.0676 | 514 | GSQHTCFSDPYGGEVCYADAP |

| Isolate | Initial Name | Elution | Library | Groups | Target OD | Background OD | SEQ ID NO | Trimmed AA |
|---|---|---|---|---|---|---|---|---|
| 365b-R0041-D04 | 365b-M0154-B06 | D6 | TN11_1 | 71 | 0.3142 | 0.0684 | 514 | GSQHTCFSDPYGGEVCYADAP |
| 365b-R0041-H04 | 365b-M0154-B11 | D6 | TN11_1 | 71 | 0.2721 | 0.0647 | 514 | GSQHTCFSDPYGGEVCYADAP |
| 365b-R0041-G03 | 365b-M0154-C07 | D6 | TN11_1 | 71 | 0.3162 | 0.0633 | 514 | GSQHTCFSDPYGGEVCYADAP |
| 365b-R0041-D02 | 365b-M0154-C12 | D6 | TN11_1 | 71 | 1.462 | 0.0983 | 514 | GSQHTCFSDPYGGEVCYADAP |
| 365b-R0041-B01 | 365b-M0154-D07 | D6 | TN11_1 | 71 | 0.3042 | 0.0745 | 514 | GSQHTCFSDPYGGEVCYADAP |
| 365b-R0041-G01 | 365b-M0154-D12 | D6 | TN11_1 | 71 | 0.6479 | 0.1262 | 514 | GSQHTCFSDPYGGEVCYADAP |
| 365b-R0042-A08 | 365b-M0154-H06 | D6 | TN11_1 | 71 | 0.3838 | 0.0836 | 514 | GSQHTCFSDPYGGEVCYADAP |
| 365b-R0042-E08 | 365b-M0154-H10 | D6 | TN11_1 | 71 | 0.3738 | 0.081 | 514 | GSQHTCFSDPYGGEVCYADAP |
| 365b-R0042-F08 | 365b-M0154-H11 | D6 | TN11_1 | 71 | 0.3994 | 0.0769 | 514 | GSQHTCFSDPYGGEVCYADAP |
| 365b-R0038-D09 | 365b-M0149-A01 | D6 | TN11_1 | 101 | 1.8491 | 0.6126 | 515 | GSWEVCENSNYGGQICYWFAP |
| 365b-R0038-E09 | 365b-M0149-A03 | D6 | TN11_1 | 101 | 1.5976 | 0.4832 | 515 | GSWEVCENSNYGGQICYWFAP |
| 365b-R0038-F09 | 365b-M0149-A05 | D6 | TN11_1 | 101 | 1.8468 | 0.5075 | 515 | GSWEVCENSNYGGQICYWFAP |
| 365b-R0038-E08 | 365b-M0149-D03 | D6 | TN11_1 | 101 | 1.9946 | 0.5704 | 515 | GSWEVCENSNYGGQICYWFAP |
| 365b-R0038-F08 | 365b-M0149-D04 | D6 | TN11_1 | 101 | 1.836 | 0.5544 | 515 | GSWEVCENSNYGGQICYWFAP |
| 365b-R0038-H08 | 365b-M0149-D08 | D6 | TN11_1 | 101 | 2.1181 | 0.5426 | 515 | GSWEVCENSNYGGQICYWFAP |
| 365b-R0038-B07 | 365b-M0149-E01 | D6 | TN11_1 | 101 | 1.9735 | 0.5446 | 515 | GSWEVCENSNYGGQICYWFAP |
| 365b-R0038-D07 | 365b-M0149-E05 | D6 | TN11_1 | 101 | 2.5131 | 0.6138 | 515 | GSWEVCENSNYGGQICYWFAP |
| 365b-R0038-H07 | 365b-M0149-F02 | D6 | TN11_1 | 101 | 2.2534 | 0.5999 | 515 | GSWEVCENSNYGGQICYWFAP |
| 365b-R0038-A06 | 365b-M0149-F03 | D6 | TN11_1 | 101 | 2.209 | 0.5862 | 515 | GSWEVCENSNYGGQICYWFAP |
| 365b-R0038-D06 | 365b-M0149-F12 | D6 | TN11_1 | 101 | 1.5909 | 0.4574 | 515 | GSWEVCENSNYGGQICYWFAP |
| 365b-R0038-E06 | 365b-M0149-G01 | D6 | TN11_1 | 101 | 1.995 | 0.5119 | 515 | GSWEVCENSNYGGQICYWFAP |
| 365b-R0038-G06 | 365b-M0149-G04 | D6 | TN11_1 | 101 | 2.0748 | 0.6731 | 515 | GSWEVCENSNYGGQICYWFAP |
| 365b-R0038-B05 | 365b-M0149-G12 | D6 | TN11_1 | 101 | 1.7593 | 0.527 | 515 | GSWEVCENSNYGGQICYWFAP |
| 365b-R0038-C05 | 365b-M0149-H01 | D6 | TN11_1 | 101 | 1.8654 | 0.596 | 515 | GSWEVCENSNYGGQICYWFAP |
| 365b-R0038-D05 | 365b-M0149-H02 | D6 | TN11_1 | 101 | 2.0427 | 0.495 | 515 | GSWEVCENSNYGGQICYWFAP |
| 365b-R0038-H05 | 365b-M0149-H12 | D6 | TN11_1 | 101 | 1.3774 | 0.4206 | 515 | GSWEVCENSNYGGQICYWFAP |
| 365b-R0039-H07 | 365b-M0151-C11 | D6 | TN11_1 | 101 | 0.7023 | 0.1273 | 515 | GSWEVCENSNYGGQICYWFAP |
| 365b-R0038-D04 | 365b-M0150-A05 | D6 | TN11_1 | 38 | 1.1997 | 0.1663 | 516 | GSHEMCWSDVWGGLTCMTMAP |
| 365b-R0038-D03 | 365b-M0150-B09 | D6 | TN11_1 | 38 | 1.1861 | 0.1611 | 516 | GSHEMCWSDVWGGLTCMTMAP |
| 365b-R0038-H03 | 365b-M0150-C02 | D6 | TN11_1 | 38 | 1.1904 | 0.1652 | 516 | GSHEMCWSDVWGGLTCMTMAP |
| 365b-R0038-A02 | 365b-M0150-C03 | D6 | TN11_1 | 38 | 1.245 | 0.1621 | 516 | GSHEMCWSDVWGGLTCMTMAP |
| 365b-R0038-G02 | 365b-M0150-D01 | D6 | TN11_1 | 38 | 1.0877 | 0.1439 | 516 | GSHEMCWSDVWGGLTCMTMAP |
| 365b-R0039-C12 | 365b-M0150-E08 | D6 | TN11_1 | 38 | 0.7125 | 0.1752 | 516 | GSHEMCWSDVWGGLTCMTMAP |
| 365b-R0039-F10 | 365b-M0150-H07 | D6 | TN11_1 | 38 | 1.1403 | 0.1406 | 516 | GSHEMCWSDVWGGLTCMTMAP |
| 365b-R0039-A07 | 365b-M0151-B06 | D6 | TN11_1 | 38 | 1.3122 | 0.1395 | 516 | GSHEMCWSDVWGGLTCMTMAP |
| 365b-R0039-H02 | 365b-M0151-H05 | D6 | TN11_1 | 38 | 1.4814 | 0.1522 | 516 | GSHEMCWSDVWGGLTCMTMAP |
| 365b-R0039-C01 | 365b-M0151-H08 | D6 | TN11_1 | 38 | 1.5302 | 0.1464 | 516 | GSHEMCWSDVWGGLTCMTMAP |
| 365b-R0040-B04 | 365b-M0152-H03 | D6 | TN11_1 | 38 | 2.372 | 0.1233 | 516 | GSHEMCWSDVWGGLTCMTMAP |
| 365b-R0040-G03 | 365b-M0153-A09 | D6 | TN11_1 | 38 | 1.9306 | 0.1071 | 516 | GSHEMCWSDVWGGLTCMTMAP |

FIG. 40K

| Isolate | Initial Name | Elution | Library | Groups | Target OD | Background OD | SEQ ID NO | Trimmed AA |
|---|---|---|---|---|---|---|---|---|
| 365b-R0040-C01 | 365b-M0153-B11 | D6 | TN11_1 | 38 | 2.1487 | 0.0973 | 516 | GSHEMCWSDVWGGLTCMTMAP |
| 365b-R0041-G02 | 365b-M0154-D04 | D6 | TN11_1 | 38 | 1.6258 | 0.1382 | 516 | GSHEMCWSDVWGGLTCMTMAP |
| 365b-R0042-H10 | 365b-M0154-G08 | D6 | TN11_1 | 38 | 1.4378 | 0.1229 | 516 | GSHEMCWSDVWGGLTCMTMAP |
| 365b-R0038-F03 | 365b-M0150-B12 | D6 | TN11_1 | 46 | 0.4959 | 0.0725 | 517 | GSLSLCKFFGDGSYYCEPPAP |
| 365b-R0039-B11 | 365b-M0150-F10 | D6 | TN11_1 | 46 | 0.4515 | 0.0906 | 517 | GSLSLCKFFGDGSYYCEPPAP |
| 365b-R0039-B08 | 365b-M0151-A08 | D6 | TN11_1 | 46 | 0.678 | 0.0802 | 517 | GSLSLCKFFGDGSYYCEPPAP |
| 365b-R0039-A06 | 365b-M0151-C12 | D6 | TN11_1 | 46 | 0.7294 | 0.1096 | 517 | GSLSLCKFFGDGSYYCEPPAP |
| 365b-R0039-H04 | 365b-M0151-F09 | D6 | TN11_1 | 46 | 0.4237 | 0.0844 | 517 | GSLSLCKFFGDGSYYCEPPAP |
| 365b-R0039-B03 | 365b-M0151-F12 | D6 | TN11_1 | 46 | 0.8396 | 0.1244 | 517 | GSLSLCKFFGDGSYYCEPPAP |
| 365b-R0040-H11 | 365b-M0152-B10 | D6 | TN11_1 | 46 | 1.1946 | 0.0658 | 517 | GSLSLCKFFGDGSYYCEPPAP |
| 365b-R0040-B09 | 365b-M0152-C08 | D6 | TN11_1 | 46 | 1.2395 | 0.0698 | 517 | GSLSLCKFFGDGSYYCEPPAP |
| 365b-R0040-C09 | 365b-M0152-C10 | D6 | TN11_1 | 46 | 1.192 | 0.0719 | 517 | GSLSLCKFFGDGSYYCEPPAP |
| 365b-R0040-E08 | 365b-M0152-E01 | D6 | TN11_1 | 46 | 1.025 | 0.0748 | 517 | GSLSLCKFFGDGSYYCEPPAP |
| 365b-R0041-G07 | 365b-M0153-H04 | D6 | TN11_1 | 46 | 1.6178 | 0.0789 | 517 | GSLSLCKFFGDGSYYCEPPAP |
| 365b-R0041-F06 | 365b-M0154-A02 | D6 | TN11_1 | 46 | 0.9957 | 0.0916 | 517 | GSLSLCKFFGDGSYYCEPPAP |
| 365b-R0041-C03 | 365b-M0154-C02 | D6 | TN11_1 | 46 | 1.473 | 0.0871 | 517 | GSLSLCKFFGDGSYYCEPPAP |
| 365b-R0041-E01 | 365b-M0154-D10 | D6 | TN11_1 | 46 | 1.0247 | 0.0746 | 517 | GSLSLCKFFGDGSYYCEPPAP |
| 365b-R0039-D10 | 365b-M0150-H04 | D6 | TN11_1 | 94 | 0.3049 | 0.0938 | 518 | GSTRFCEPYQWGGEVCYWKAP |
| 365b-R0039-H10 | 365b-M0150-H09 | D6 | TN11_1 | 94 | 0.2777 | 0.0869 | 518 | GSTRFCEPYQWGGEVCYWKAP |
| 365b-R0039-D06 | 365b-M0151-D05 | D6 | TN11_1 | 94 | 0.2509 | 0.0733 | 518 | GSTRFCEPYQWGGEVCYWKAP |
| 365b-R0039-G06 | 365b-M0151-D08 | D6 | TN11_1 | 94 | 0.2476 | 0.0781 | 518 | GSTRFCEPYQWGGEVCYWKAP |
| 365b-R0039-B05 | 365b-M0151-E03 | D6 | TN11_1 | 94 | 0.2506 | 0.0829 | 518 | GSTRFCEPYQWGGEVCYWKAP |
| 365b-R0039-D05 | 365b-M0151-E06 | D6 | TN11_1 | 94 | 0.2639 | 0.0824 | 518 | GSTRFCEPYQWGGEVCYWKAP |
| 365b-R0040-D10 | 365b-M0152-C02 | D6 | TN11_1 | 94 | 0.5991 | 0.088 | 518 | GSTRFCEPYQWGGEVCYWKAP |
| 365b-R0040-H01 | 365b-M0153-C05 | D6 | TN11_1 | 94 | 0.5008 | 0.0714 | 518 | GSTRFCEPYQWGGEVCYWKAP |
| 365b-R0041-D11 | 365b-M0153-D10 | D6 | TN11_1 | 94 | 0.4261 | 0.0673 | 518 | GSTRFCEPYQWGGEVCYWKAP |
| 365b-R0041-H02 | 365b-M0154-D05 | D6 | TN11_1 | 94 | 0.4419 | 0.0878 | 518 | GSTRFCEPYQWGGEVCYWKAP |
| 365b-R0042-A10 | 365b-M0154-F10 | D6 | TN11_1 | 94 | 0.4133 | 0.0881 | 518 | GSTRFCEPYQWGGEVCYWKAP |
| 365b-R0042-B10 | 365b-M0154-F11 | D6 | TN11_1 | 94 | 0.4647 | 0.0943 | 518 | GSTRFCEPYQWGGEVCYWKAP |
| 365b-R0042-C10 | 365b-M0154-F12 | D6 | TN11_1 | 94 | 1.0342 | 0.1771 | 518 | GSTRFCEPYQWGGEVCYWKAP |
| 365b-R0042-B09 | 365b-M0154-G10 | D6 | TN11_1 | 94 | 0.4678 | 0.0806 | 518 | GSTRFCEPYQWGGEVCYWKAP |
| 365b-R0035-B07 | 365b-M0144-A02 | VEGF | TN11_1 | 29 | 0.361 | 0.0863 | 519 | GSFSTCATFPWTTKFCSNMAP |
| 365b-R0035-E05 | 365b-M0144-D02 | VEGF | TN11_1 | 29 | 0.6453 | 0.1524 | 519 | GSFSTCATFPWTTKFCSNMAP |
| 365b-R0036-C10 | 365b-M0145-D12 | VEGF | TN11_1 | 29 | 0.2781 | 0.0843 | 519 | GSFSTCATFPWTTKFCSNMAP |
| 365b-R0036-B07 | 365b-M0145-H05 | VEGF | TN11_1 | 29 | 0.4571 | 0.0953 | 519 | GSFSTCATFPWTTKFCSNMAP |
| 365b-R0036-H03 | 365b-M0146-F02 | VEGF | TN11_1 | 29 | 0.4041 | 0.0894 | 519 | GSFSTCATFPWTTKFCSNMAP |
| 365b-R0036-G02 | 365b-M0146-F12 | VEGF | TN11_1 | 29 | 0.4657 | 0.1055 | 519 | GSFSTCATFPWTTKFCSNMAP |
| 365b-R0037-B11 | 365b-M0147-A09 | VEGF | TN11_1 | 29 | 0.34 | 0.0773 | 519 | GSFSTCATFPWTTKFCSNMAP |
| 365b-R0037-B10 | 365b-M0147-C05 | VEGF | TN11_1 | 29 | 0.3593 | 0.073 | 519 | GSFSTCATFPWTTKFCSNMAP |

| Isolate | Initial Name | Elution | Library | Groups | Target OD | Background OD | SEQ ID NO | Trimmed AA |
|---|---|---|---|---|---|---|---|---|
| 365b-R0037-E08 | 3655b-M0147-F03 | VEGF | TN11_1 | 29 | 0.5011 | 0.0889 | 519 | GSFSTCATFPWTKFCSNMAP |
| 365b-R0037-B05 | 3655b-M0147-H12 | VEGF | TN11_1 | 29 | 0.6314 | 0.1435 | 519 | GSFSTCATFPWTKFCSNMAP |
| 365b-R0037-G04 | 3655b-M0148-B08 | VEGF | TN11_1 | 29 | 0.3203 | 0.066 | 519 | GSFSTCATFPWTKFCSNMAP |
| 365b-R0037-G02 | 3655b-M0148-D07 | VEGF | TN11_1 | 29 | 0.3418 | 0.0738 | 519 | GSFSTCATFPWTKFCSNMAP |
| 365b-R0038-F04 | 3655b-M0150-A08 | D6 | TN11_1 | 37 | 1.9756 | 0.1127 | 520 | GSHELCFEGTYGGEVCFSMAP |
| 365b-R0039-E07 | 3655b-M0151-C02 | D6 | TN11_1 | 37 | 2.3831 | 0.0896 | 520 | GSHELCFEGTYGGEVCFSMAP |
| 365b-R0039-C05 | 3655b-M0151-E04 | D6 | TN11_1 | 37 | 2.3037 | 0.0976 | 520 | GSHELCFEGTYGGEVCFSMAP |
| 365b-R0039-G04 | 3655b-M0151-F08 | D6 | TN11_1 | 37 | 1.6606 | 0.0878 | 520 | GSHELCFEGTYGGEVCFSMAP |
| 365b-R0040-F12 | 3655b-M0152-A09 | D6 | TN11_1 | 37 | 2.3067 | 0.0859 | 520 | GSHELCFEGTYGGEVCFSMAP |
| 365b-R0040-E10 | 3655b-M0152-C03 | D6 | TN11_1 | 37 | 2.9164 | 0.0769 | 520 | GSHELCFEGTYGGEVCFSMAP |
| 365b-R0040-G09 | 3655b-M0152-D05 | D6 | TN11_1 | 37 | 2.7444 | 0.0832 | 520 | GSHELCFEGTYGGEVCFSMAP |
| 365b-R0040-H02 | 3655b-M0153-B08 | D6 | TN11_1 | 37 | 2.5788 | 0.0724 | 520 | GSHELCFEGTYGGEVCFSMAP |
| 365b-R0041-G10 | 3655b-M0153-E11 | D6 | TN11_1 | 37 | 2.4376 | 0.0691 | 520 | GSHELCFEGTYGGEVCFSMAP |
| 365b-R0041-C05 | 3655b-M0154-A09 | D6 | TN11_1 | 37 | 1.9559 | 0.0773 | 520 | GSHELCFEGTYGGEVCFSMAP |
| 365b-R0041-F01 | 3655b-M0154-D11 | D6 | TN11_1 | 37 | 1.8989 | 0.079 | 520 | GSHELCFEGTYGGEVCFSMAP |
| 365b-R0042-F10 | 3655b-M0154-G06 | D6 | TN11_1 | 37 | 2.7201 | 0.095 | 520 | GSHELCFEGTYGGEVCFSMAP |
| 365b-R0035-D09 | 3655b-M0143-D01 | VEGF | TN11_1 | 50 | 1.733 | 0.5358 | 521 | GSLWHCFNDVYGGENCIPFAP |
| 365b-R0035-F07 | 3655b-M0144-A09 | VEGF | TN11_1 | 50 | 0.8158 | 0.0684 | 521 | GSLWHCFNDVYGGENCIPFAP |
| 365b-R0035-B03 | 3655b-M0144-F02 | VEGF | TN11_1 | 50 | 2.2239 | 0.1728 | 521 | GSLWHCFNDVYGGENCIPFAP |
| 365b-R0035-H03 | 3655b-M0144-F12 | VEGF | TN11_1 | 50 | 1.5655 | 0.1083 | 521 | GSLWHCFNDVYGGENCIPFAP |
| 365b-R0036-F08 | 3655b-M0145-G12 | VEGF | TN11_1 | 50 | 1.8613 | 0.1377 | 521 | GSLWHCFNDVYGGENCIPFAP |
| 365b-R0036-G05 | 3655b-M0146-C08 | VEGF | TN11_1 | 50 | 1.3691 | 0.0703 | 521 | GSLWHCFNDVYGGENCIPFAP |
| 365b-R0037-H12 | 3655b-M0147-A02 | VEGF | TN11_1 | 50 | 1.0434 | 0.0709 | 521 | GSLWHCFNDVYGGENCIPFAP |
| 365b-R0037-F10 | 3655b-M0147-D03 | VEGF | TN11_1 | 50 | 2.016 | 0.0703 | 521 | GSLWHCFNDVYGGENCIPFAP |
| 365b-R0037-G10 | 3655b-M0147-D04 | VEGF | TN11_1 | 50 | 1.8402 | 0.0789 | 521 | GSLWHCFNDVYGGENCIPFAP |
| 365b-R0037-F03 | 3655b-M0148-C05 | VEGF | TN11_1 | 50 | 1.5701 | 0.0641 | 521 | GSLWHCFNDVYGGENCIPFAP |
| 365b-R0037-H03 | 3655b-M0148-C07 | VEGF | TN11_1 | 50 | 1.5274 | 0.0583 | 521 | GSLWHCFNDVYGGENCIPFAP |
| 365b-R0038-B12 | 3655b-M0148-E11 | VEGF | TN11_1 | 50 | 1.3707 | 0.0721 | 521 | GSLWHCFNDVYGGENCIPFAP |
| 365b-R0035-C12 | 3655b-M0138-C11 | BEAD | TN11_1 | 74 | 0.5174 | 0.0736 | 522 | GSQQYCIPAEYGGMECYPFAP |
| 365b-R0035-F12 | 3655b-M0139-A08 | BEAD | TN11_1 | 74 | 0.4199 | 0.0686 | 522 | GSQQYCIPAEYGGMECYPFAP |
| 365b-R0038-B02 | 3655b-M0150-C05 | D6 | TN11_1 | 74 | 0.3112 | 0.0811 | 522 | GSQQYCIPAEYGGMECYPFAP |
| 365b-R0036-E12 | 3655b-M0145-B07 | VEGF | TN11_1 | 74 | 0.4441 | 0.0732 | 522 | GSQQYCIPAEYGGMECYPFAP |
| 365b-R0036-A07 | 3655b-M0145-D04 | VEGF | TN11_1 | 74 | 0.6027 | 0.0806 | 522 | GSQQYCIPAEYGGMECYPFAP |
| 365b-R0036-D07 | 3655b-M0145-H04 | VEGF | TN11_1 | 74 | 0.3694 | 0.0787 | 522 | GSQQYCIPAEYGGMECYPFAP |
| 365b-R0036-D06 | 3655b-M0145-H08 | VEGF | TN11_1 | 74 | 0.3704 | 0.0719 | 522 | GSQQYCIPAEYGGMECYPFAP |
| 365b-R0036-B01 | 3655b-M0146-A12 | VEGF | TN11_1 | 74 | 0.4217 | 0.0779 | 522 | GSQQYCIPAEYGGMECYPFAP |
| 365b-R0037-A09 | 3655b-M0146-G05 | VEGF | TN11_1 | 74 | 0.4864 | 0.0607 | 522 | GSQQYCIPAEYGGMECYPFAP |
| 365b-R0037-E02 | 3655b-M0147-D08 | VEGF | TN11_1 | 74 | 0.566 | 0.0585 | 522 | GSQQYCIPAEYGGMECYPFAP |

FIG. 40N

| Isolate | Initial Name | Elution | Library | Groups | Target OD | Background OD | SEQ ID NO | Trimmed AA |
|---|---|---|---|---|---|---|---|---|
| 365b-R0038-C12 | 3655-M0148-E12 | VEGF | TN11_1 | 74 | 0.5886 | 0.0915 | 522 | GSQQYCIPAEYGMECYPFAP |
| 365b-R0038-B03 | 3655-M0150-B06 | D6 | TN11_1 | 42 | 0.327 | 0.0874 | 523 | GSIQNCWKYEFGIVCMDMAP |
| 365b-R0038-F02 | 3655-M0150-C12 | D6 | TN11_1 | 42 | 0.5797 | 0.1641 | 523 | GSIQNCWKYEFGIVCMDMAP |
| 365b-R0039-H12 | 3655-M0150-F07 | D6 | TN11_1 | 42 | 0.289 | 0.0921 | 523 | GSIQNCWKYEFGIVCMDMAP |
| 365b-R0039-F07 | 3655-M0151-C07 | D6 | TN11_1 | 42 | 0.2353 | 0.068 | 523 | GSIQNCWKYEFGIVCMDMAP |
| 365b-R0040-D05 | 3655-M0152-G06 | D6 | TN11_1 | 42 | 0.5838 | 0.0913 | 523 | GSIQNCWKYEFGIVCMDMAP |
| 365b-R0040-E04 | 3655-M0152-H06 | D6 | TN11_1 | 42 | 0.7246 | 0.0865 | 523 | GSIQNCWKYEFGIVCMDMAP |
| 365b-R0041-H09 | 3655-M0153-F09 | D6 | TN11_1 | 42 | 0.5265 | 0.0703 | 523 | GSIQNCWKYEFGIVCMDMAP |
| 365b-R0041-C07 | 3655-M0153-G09 | D6 | TN11_1 | 42 | 0.5339 | 0.0785 | 523 | GSIQNCWKYEFGIVCMDMAP |
| 365b-R0042-G12 | 3655-M0154-E11 | D6 | TN11_1 | 42 | 0.4407 | 0.0815 | 523 | GSIQNCWKYEFGIVCMDMAP |
| 365b-R0038-B08 | 3655-M0149-C03 | D6 | TN11_1 | 99 | 1.756 | 0.4217 | 524 | GSVSGCKEFWNSSGRCFTHAP |
| 365b-R0038-G03 | 3655-M0150-C01 | D6 | TN11_1 | 99 | 0.6011 | 0.0813 | 524 | GSVSGCKEFWNSSGRCFTHAP |
| 365b-R0039-A10 | 3655-M0150-G10 | D6 | TN11_1 | 99 | 0.4631 | 0.0868 | 524 | GSVSGCKEFWNSSGRCFTHAP |
| 365b-R0039-B04 | 3655-M0151-F02 | D6 | TN11_1 | 99 | 0.623 | 0.0871 | 524 | GSVSGCKEFWNSSGRCFTHAP |
| 365b-R0039-D01 | 3655-M0151-H09 | D6 | TN11_1 | 99 | 0.5763 | 0.0834 | 524 | GSVSGCKEFWNSSGRCFTHAP |
| 365b-R0040-E09 | 3655-M0152-D01 | D6 | TN11_1 | 99 | 0.8589 | 0.077 | 524 | GSVSGCKEFWNSSGRCFTHAP |
| 365b-R0040-H08 | 3655-M0152-E04 | D6 | TN11_1 | 99 | 0.9011 | 0.0744 | 524 | GSVSGCKEFWNSSGRCFTHAP |
| 365b-R0040-B05 | 3655-M0152-G03 | D6 | TN11_1 | 99 | 0.817 | 0.0827 | 524 | GSVSGCKEFWNSSGRCFTHAP |
| 365b-R0040-A03 | 3655-M0152-H11 | D6 | TN11_1 | 99 | 0.9478 | 0.0765 | 524 | GSVSGCKEFWNSSGRCFTHAP |
| 365b-R0039-D04 | 3655-M0151-F05 | D6 | TN11_1 | 48 | 0.2971 | 0.0911 | 525 | GSLWECRGDFYGGEVCFNYAP |
| 365b-R0039-E01 | 3655-M0151-H10 | D6 | TN11_1 | 48 | 0.3412 | 0.0976 | 525 | GSLWECRGDFYGGEVCFNYAP |
| 365b-R0040-B12 | 3655-M0152-A05 | D6 | TN11_1 | 48 | 0.4593 | 0.0879 | 525 | GSLWECRGDFYGGEVCFNYAP |
| 365b-R0040-B07 | 3655-M0152-E06 | D6 | TN11_1 | 48 | 0.4377 | 0.0709 | 525 | GSLWECRGDFYGGEVCFNYAP |
| 365b-R0040-D06 | 3655-M0152-F09 | D6 | TN11_1 | 48 | 0.5121 | 0.0974 | 525 | GSLWECRGDFYGGEVCFNYAP |
| 365b-R0040-F05 | 3655-M0152-G08 | D6 | TN11_1 | 48 | 0.5093 | 0.0912 | 525 | GSLWECRGDFYGGEVCFNYAP |
| 365b-R0041-D01 | 3655-M0154-D09 | D6 | TN11_1 | 48 | 0.4302 | 0.0823 | 525 | GSLWECRGDFYGGEVCFNYAP |
| 365b-R0041-H01 | 3655-M0154-E01 | VEGF | TN11_1 | 48 | 0.4239 | 0.0908 | 525 | GSLWECRGDFYGGEVCFNYAP |
| 365b-R0042-H11 | 3655-M0154-F09 | VEGF | TN11_1 | 54 | 0.8834 | 0.1009 | 526 | GSLNLICYDYYGGQDCYHDAP |
| 365b-R0039-A11 | 3655-M0150-F08 | VEGF | TN11_1 | 54 | 1.3328 | 0.0974 | 526 | GSLNLICYDYYGGQDCYHDAP |
| 365b-R0039-E09 | 3655-M0151-A03 | D6 | TN11_1 | 54 | 1.6202 | 0.0872 | 526 | GSLNLICYDYYGGQDCYHDAP |
| 365b-R0041-G09 | 3655-M0153-F08 | D6 | TN11_1 | 54 | 1.5309 | 0.1028 | 526 | GSNLICYDYYGGQDCYHDAP |
| 365b-R0035-E03 | 3655-M0144-F06 | VEGF | TN11_1 | 54 | 1.5585 | 0.0884 | 526 | GSNLICYDYYGGQDCYHDAP |
| 365b-R0036-E09 | 3655-M0145-F09 | VEGF | TN11_1 | 54 | 1.5586 | 0.0877 | 526 | GSNLICYDYYGGQDCYHDAP |
| 365b-R0036-C01 | 3655-M0146-G07 | VEGF | TN11_1 | 54 | 1.6044 | 0.1008 | 526 | GSNLICYDYYGGQDCYHDAP |
| 365b-R0038-H12 | 3655-M0148-F10 | VEGF | TN11_1 | 54 | 1.5022 | 0.0732 | 526 | GSNLICYDYYGGQDCYHDAP |
| 365b-R0038-F06 | 3655-M0149-G03 | D6 | TN11_1 | 19 | 1.7445 | 0.5281 | 527 | GSEGTCEEYQYGGIVCWWGAP |
| 365b-R0040-D08 | 3655-M0152-D12 | D6 | TN11_1 | 19 | 0.9818 | 0.1252 | 527 | GSEGTCEEYQYGGIVCWWGAP |
| 365b-R0040-G08 | 3655-M0152-E03 | D6 | TN11_1 | 19 | 0.7051 | 0.0785 | 527 | GSEGTCEEYQYGGIVCWWGAP |
| 365b-R0040-H07 | 3655-M0152-F04 | D6 | TN11_1 | 19 | 0.6101 | 0.0803 | 527 | GSEGTCEEYQYGGIVCWWGAP |

FIG. 40O

| Isolate | Initial Name | Elution | Library | Groups | Target OD | Background OD | SEQ ID NO | Trimmed AA |
|---|---|---|---|---|---|---|---|---|
| 365b-R0040-G04 | 365b-M0152-H08 | D6 | TN11_1 | 19 | 0.7712 | 0.08 | 527 | GSEGTCEEYQYGGIVCWWGAP |
| 365b-R0041-D03 | 365b-M0154-C04 | D6 | TN11_1 | 19 | 0.6058 | 0.1002 | 527 | GSEGTCEEYQYGGIVCWWGAP |
| 365b-R0042-E09 | 365b-M0154-H02 | D6 | TN11_1 | 19 | 0.6837 | 0.0905 | 527 | GSEGTCEEYQYGGIVCWWGAP |
| 365b-R0036-A11 | 365b-M0145-C03 | VEGF | TN11_1 | 2 | 0.611 | 0.1548 | 528 | PGSGDCDWYEWLFDCPLNAP |
| 365b-R0036-E11 | 365b-M0145-C09 | VEGF | TN11_1 | 2 | 0.3465 | 0.0972 | 528 | PGSGDCDWYEWLFDCPLNAP |
| 365b-R0036-A05 | 365b-M0146-B07 | VEGF | TN11_1 | 2 | 0.3458 | 0.0885 | 528 | PGSGDCDWYEWLFDCPLNAP |
| 365b-R0037-F11 | 365b-M0147-B11 | VEGF | TN11_1 | 2 | 0.4386 | 0.0961 | 528 | PGSGDCDWYEWLFDCPLNAP |
| 365b-R0037-C09 | 365b-M0147-E01 | VEGF | TN11_1 | 2 | 0.3631 | 0.0863 | 528 | PGSGDCDWYEWLFDCPLNAP |
| 365b-R0037-D09 | 365b-M0147-E02 | VEGF | TN11_1 | 2 | 0.5282 | 0.1032 | 528 | PGSGDCDWYEWLFDCPLNAP |
| 365b-R0037-H04 | 365b-M0148-B09 | VEGF | TN11_1 | 2 | 0.405 | 0.0791 | 528 | PGSGDCDWYEWLFDCPLNAP |
| 365b-R0036-H08 | 365b-M0145-H03 | VEGF | TN11_1 | 16 | 0.3653 | 0.0933 | 529 | GSDQMCFNESFGGQICFYSAP |
| 365b-R0036-D05 | 365b-M0146-C02 | VEGF | TN11_1 | 16 | 0.3654 | 0.1159 | 529 | GSDQMCFNESFGGQICFYSAP |
| 365b-R0036-C03 | 365b-M0146-E03 | VEGF | TN11_1 | 16 | 0.3861 | 0.0733 | 529 | GSDQMCFNESFGGQICFYSAP |
| 365b-R0037-H11 | 365b-M0147-C01 | VEGF | TN11_1 | 16 | 0.3192 | 0.0789 | 529 | GSDQMCFNESFGGQICFYSAP |
| 365b-R0037-A08 | 365b-M0147-E11 | VEGF | TN11_1 | 16 | 0.3407 | -0.0832 | 529 | GSDQMCFNESFGGQICFYSAP |
| 365b-R0038-G12 | 365b-M0148-F07 | VEGF | TN11_1 | 16 | 0.2767 | 0.0678 | 529 | GSDQMCFNESFGGQICFYSAP |
| 365b-R0039-G10 | 365b-M0150-H08 | VEGF | TN11_1 | 32 | 1.7728 | 0.0824 | 530 | GSGMACMSDPYGGQVCYAIAP |
| 365b-R0040-F02 | 365b-M0153-B05 | D6 | TN11_1 | 32 | 2.9076 | 0.0665 | 530 | GSGMACMSDPYGGQVCYAIAP |
| 365b-R0041-A10 | 365b-M0153-E04 | D6 | TN11_1 | 32 | 3 | 0.0714 | 530 | GSGMACMSDPYGGQVCYAIAP |
| 365b-R0041-B08 | 365b-M0153-F11 | D6 | TN11_1 | 32 | 2.7626 | 0.0815 | 530 | GSGMACMSDPYGGQVCYAIAP |
| 365b-R0042-H09 | 365b-M0154-H05 | D6 | TN11_1 | 32 | 3 | 0.0943 | 530 | GSGMACMSDPYGGQVCYAIAP |
| 365b-R0035-D07 | 365b-M0144-A04 | VEGF | TN11_1 | 20 | 0.2226 | 0.066 | 531 | GSELTCWDSAYGGNECFFFAP |
| 365b-R0036-B09 | 365b-M0145-F03 | VEGF | TN11_1 | 39 | 0.6403 | 0.0933 | 532 | GSHFLCVKEMEGGETCYYSAP |
| 365b-R0036-B04 | 365b-M0146-D02 | VEGF | TN11_1 | 39 | 0.4706 | 0.0808 | 532 | GSHFLCVKEMEGGETCYYSAP |
| 365b-R0037-B12 | 365b-M0146-H06 | VEGF | TN11_1 | 39 | 0.4881 | 0.0833 | 532 | GSHFLCVKEMEGGETCYYSAP |
| 365b-R0037-E05 | 365b-M0148-A04 | VEGF | TN11_1 | 39 | 0.559 | 0.0741 | 532 | GSHFLCVKEMEGGETCYYSAP |
| 365b-R0035-D12 | 365b-M0138-D08 | BEAD | TN11_1 | 100 | 0.6286 | 0.1132 | 533 | GSWEICFAGFYGGSWCIPEAP |
| 365b-R0035-C11 | 365b-M0140-B05 | BEAD | TN11_1 | 100 | 0.6648 | 0.1347 | 533 | GSWEICFAGFYGGSWCIPEAP |
| 365b-R0035-F11 | 365b-M0141-A08 | BEAD | TN11_1 | 100 | 0.3904 | 0.0998 | 533 | GSWEICFAGFYGGSWCIPEAP |
| 365b-R0035-H11 | 365b-M0141-D03 | BEAD | TN11_1 | 100 | 0.7545 | 0.1166 | 533 | GSWEICFAGFYGGSWCIPEAP |
| 365b-R0035-E12 | 365b-M0138-F04 | BEAD | TN11_1 | 6 | 1.9751 | 0.118 | 534 | GSAQYCMESYYGGFTCVTLAP |
| 365b-R0039-G01 | 365b-M0151-H12 | D6 | TN11_1 | 6 | 1.463 | 0.1596 | 534 | GSAQYCMESYYGGFTCVTLAP |
| 365b-R0036-F04 | 365b-M0146-D08 | VEGF | TN11_1 | 6 | 2.1108 | 0.0817 | 534 | GSAQYCMESYYGGFTCVTLAP |
| 365b-R0036-D08 | 365b-M0145-G09 | VEGF | TN11_1 | 28 | 0.9584 | 0.0874 | 535 | GSFNACGFEEGLEWMCYRQAP |
| 365b-R0036-F02 | 365b-M0146-F11 | VEGF | TN11_1 | 28 | 0.9738 | 0.0787 | 535 | GSFNACGFEEGLEWMCYRQAP |
| 365b-R0037-E09 | 365b-M0147-E03 | VEGF | TN11_1 | 28 | 1.2937 | 0.0703 | 535 | GSFNACGFEEGLEWMCYRQAP |
| 365b-R0036-C08 | 365b-M0145-G07 | VEGF | TN11_1 | 44 | 0.755 | 0.1531 | 536 | GSKLLCQYWEHEWPCMNEAP |
| 365b-R0037-A12 | 365b-M0146-H05 | VEGF | TN11_1 | 44 | 0.7645 | 0.1577 | 536 | GSKLLCQYWEHEWPCMNEAP |
| 365b-R0037-H05 | 365b-M0148-A08 | VEGF | TN11_1 | 44 | 0.496 | 0.1162 | 536 | GSKLLCQYWEHEWPCMNEAP |

FIG. 40P

| Isolate | Initial Name | Elution | Library | Groups | Target OD | Background OD | SEQ ID NO | Trimmed AA |
|---|---|---|---|---|---|---|---|---|
| 365b-R0036-C12 | 365b-M0145-B04 | VEGF | TN11_1 | 55 | 0.4509 | 0.0959 | 537 | GSNMNCGAEQGLESLCGWRAP |
| 365b-R0036-G11 | 365b-M0145-D02 | VEGF | TN11_1 | 55 | 0.5252 | 0.0723 | 537 | GSNMNCGAEQGLESLCGWRAP |
| 365b-R0038-H11 | 365b-M0148-G09 | VEGF | TN11_1 | 55 | 0.3248 | 0.0729 | 537 | GSNMNCGAEQGLESLCGWRAP |
| 365b-R0035-A02 | 365b-M0144-G01 | VEGF | TN11_1 | 62 | 0.225 | 0.07 | 538 | GSNWVCLSEGYGGMTCYPSAP |
| 365b-R0036-B02 | 365b-M0146-F06 | VEGF | TN11_1 | 62 | 0.2585 | 0.0779 | 538 | GSNWVCLSEGYGGMTCYPSAP |
| 365b-R0038-G11 | 365b-M0148-G06 | VEGF | TN11_1 | 62 | 0.2367 | 0.0757 | 538 | GSNWVCLSEGYGGMTCYPSAP |
| 365b-R0037-G09 | 365b-M0147-E09 | VEGF | TN11_1 | 68 | 0.5271 | 0.0723 | 539 | GSPSTCIYSSGLIVDCGLLAP |
| 365b-R0037-C06 | 365b-M0147-G12 | VEGF | TN11_1 | 68 | 1.1897 | 0.152 | 539 | GSPSTCIYSSGLIVDCGLLAP |
| 365b-R0037-A01 | 365b-M0148-D11 | VEGF | TN11_1 | 68 | 0.5155 | 0.0755 | 539 | GSPSTCIYSSGLIVDCGLLAP |
| 365b-R0040-F03 | 365b-M0153-A07 | D6 | TN11_1 | 92 | 0.2871 | 0.0644 | 540 | GSTQHCWPSEYGGMTCVPAAP |
| 365b-R0035-E02 | 365b-M0144-G12 | VEGF | TN11_1 | 92 | 0.3927 | 0.0867 | 540 | GSTQHCWPSEYGGMTCVPAAP |
| 365b-R0036-A08 | 365b-M0145-G05 | VEGF | TN11_1 | 92 | 0.3092 | 0.0805 | 540 | GSTQHCWPSEYGGMTCVPAAP |
| 365b-R0035-B12 | 365b-M0138-C06 | BEAD | TN11_1 | 96 | 1.1917 | 0.0989 | 541 | GSTWACEEISAHHTKCTYQAP |
| 365b-R0035-D11 | 365b-M0140-B09 | BEAD | TN11_1 | 96 | 1.3917 | 0.0783 | 541 | GSTWACEEISAHHTKCTYQAP |
| 365b-R0037-C01 | 365b-M0148-E01 | VEGF | TN11_1 | 96 | 1.6726 | 0.0628 | 541 | GSTWACEEISAHHTKCTYQAP |
| 365b-R0035-A12 | 365b-M0138-A09 | BEAD | TN11_1 | 110 | 0.9799 | 0.0778 | 542 | GSYTECWEEDYGGVTCFNVAP |
| 365b-R0035-B11 | 365b-M0140-A04 | BEAD | TN11_1 | 110 | 1.334 | 0.1179 | 542 | GSYTECWEEDYGGVTCFNVAP |
| 365b-R0035-E11 | 365b-M0140-E06 | BEAD | TN11_1 | 110 | 1.232 | 0.1044 | 542 | GSYTECWEEDYGGVTCFNVAP |
| 365b-R0038-C03 | 365b-M0142-F03 | BEAD | TN11_1 | 12 | 1.2247 | 0.1099 | 543 | GSDKFCFKDPWGGVTCYHLAP |
| 365b-R0040-E11 | 365b-M0152-B06 | D6 | TN11_1 | 12 | 1.8704 | 0.0937 | 543 | GSDKFCFKDPWGGVTCYHLAP |
| 365b-R0041-H10 | 365b-M0153-E12 | D6 | TN11_1 | 14 | 0.6225 | 0.0981 | 544 | GSDLDCWTDPYGGEVCYWHAP |
| 365b-R0042-F11 | 365b-M0154-F06 | D6 | TN11_1 | 14 | 0.547 | 0.1087 | 544 | GSDLDCWTDPYGGEVCYWHAP |
| 365b-R0035-B10 | 365b-M0142-F03 | BEAD | TN11_1 | 18 | 0.4919 | 0.1192 | 545 | GSDYECYNAWFGYFDCPGDAP |
| 365b-R0037-B04 | 365b-M0148-A10 | VEGF | TN11_1 | 18 | 0.3521 | 0.0858 | 545 | GSDYECYNAWFGYFDCPGDAP |
| 365b-R0037-F04 | 365b-M0148-B07 | VEGF | TN11_1 | 47 | 0.1962 | 0.0611 | 546 | GSLSTCWKQAYGGVWCVDHAP |
| 365b-R0038-E10 | 365b-M0148-H04 | VEGF | TN11_1 | 47 | 0.3368 | 0.0737 | 546 | GSLSTCWKQAYGGVWCVDHAP |
| 365b-R0040-C11 | 365b-M0152-B03 | D6 | TN11_1 | 52 | 0.3635 | 0.1078 | 547 | GSMQLCRQWAYGGQTCYWYAP |
| 365b-R0040-A06 | 365b-M0152-F06 | D6 | TN11_1 | 52 | 0.4342 | 0.1046 | 547 | GSMQLCRQWAYGGQTCYWYAP |
| 365b-R0037-E12 | 365b-M0146-H10 | VEGF | TN11_1 | 57 | 0.314 | 0.081 | 548 | GSNQLCITAQFGGDCYPIAP |
| 365b-R0037-C04 | 365b-M0148-B01 | VEGF | TN11_1 | 57 | 0.4575 | 0.0632 | 548 | GSNQLCITAQFGGDCYPIAP |
| 365b-R0037-F05 | 365b-M0144-D03 | VEGF | TN11_1 | 66 | 0.5058 | 0.1038 | 549 | GSPMWCAPWGGEHCVGSAP |
| 365b-R0037-E04 | 365b-M0148-B05 | VEGF | TN11_1 | 66 | 0.4563 | 0.087 | 549 | GSPMWCAPWGGEHCVGSAP |
| 365b-R0037-A03 | 365b-M0148-B10 | VEGF | TN11_1 | 72 | 0.2712 | 0.0571 | 550 | GSQLLCGSEPELAWMCEQGAP |
| 365b-R0038-C09 | 365b-M0148-H12 | VEGF | TN11_1 | 72 | 0.3283 | 0.0999 | 550 | GSQLLCGSEPELAWMCEQGAP |
| 365b-R0036-H09 | 365b-M0145-F12 | VEGF | TN11_1 | 75 | 0.596 | 0.1475 | 551 | GSQRQCWDDYFGGIICYVIDA |
| 365b-R0036-F07 | 365b-M0145-H11 | VEGF | TN11_1 | 75 | 0.4555 | 0.1338 | 551 | GSQRQCWDDYFGGIICYVIDA |
| 365b-R0035-A10 | 365b-M0141-F09 | BEAD | TN11_1 | 77 | 0.9138 | 0.1193 | 552 | GSREVCWQDFFGGMVCVRDAP |
| 365b-R0037-A02 | 365b-M0148-C08 | VEGF | TN11_1 | 77 | 0.8702 | 0.0742 | 552 | GSREVCWQDFFGGMVCVRDAP |
| 365b-R0035-G06 | 365b-M0144-C04 | VEGF | TN11_1 | 81 | 0.8139 | 0.0915 | 553 | GSSQWCQRDFWGGDICINLAP |

FIG. 40Q

| Isolate | Initial Name | Elution | Library | Groups | Target OD | Background OD | SEQ ID NO | Trimmed AA |
|---|---|---|---|---|---|---|---|---|
| 365b-R0036-G10 | 365b-M0145-E11 | VEGF | TN11_1 | 81 | 0.7672 | 0.0836 | 553 | GSSQWCQRDFWGGDICINLAP |
| 365b-R0036-H01 | 365b-M0146-H03 | VEGF | TN11_1 | 86 | 1.4275 | 0.0872 | 554 | GSTDICWPGSYGGEICIPRAP |
| 365b-R0037-B06 | 365b-M0147-G11 | VEGF | TN11_1 | 86 | 1.3266 | 0.0796 | 554 | GSTDICWPGSYGGEICIPRAP |
| 365b-R0035-H01 | 365b-M0145-A12 | VEGF | TN11_1 | 88 | 0.4332 | 0.061 | 555 | GSTEYCWPEPHGGQACILLAP |
| 365b-R0038-H10 | 365b-M0148-H08 | VEGF | TN11_1 | 88 | 0.5378 | 0.0659 | 555 | GSTEYCWPEPHGGQACILLAP |
| 365b-R0036-D09 | 365b-M0145-F06 | VEGF | TN11_1 | 90 | 0.7089 | 0.0958 | 556 | GSTHFCIDYIWGGKHCIADAP |
| 365b-R0037-H10 | 365b-M0147-D05 | VEGF | TN11_1 | 90 | 0.6017 | 0.0943 | 556 | GSTHFCIDYIWGGKHCIADAP |
| 365b-R0036-H12 | 365b-M0145-C01 | VEGF | TN11_1 | 91 | 1.7304 | 0.0879 | 557 | GSTMMCWPAHYGGDECFALAP |
| 365b-R0036-F03 | 365b-M0146-E08 | VEGF | TN11_1 | 91 | 1.6849 | 0.0856 | 557 | GSTMMCWPAHYGGDECFALAP |
| 365b-R0038-D12 | 365b-M0148-F02 | VEGF | TN11_1 | 93 | 0.4764 | 0.0691 | 558 | GSTQMCFPHQYGGQSCYSFAP |
| 365b-R0038-E12 | 365b-M0148-F03 | VEGF | TN11_1 | 93 | 0.222 | 0.0601 | 558 | GSTQMCFPHQYGGQSCYSFAP |
| 365b-R0035-H02 | 365b-M0144-H04 | VEGF | TN11_1 | 98 | 0.6085 | 0.08 | 559 | GSVEGCWVEDQTSPFCWIDAP |
| 365b-R0037-H09 | 365b-M0147-E10 | VEGF | TN11_1 | 98 | 0.6242 | 0.0714 | 559 | GSVEGCWVEDQTSPFCWIDAP |
| 365b-R0037-D03 | 365b-M0148-C03 | VEGF | TN11_1 | 104 | 0.2375 | 0.0692 | 560 | GSWYTCWDEASGGQVCYQLAP |
| 365b-R0037-D02 | 365b-M0148-D02 | VEGF | TN11_1 | 104 | 0.2152 | 0.0675 | 560 | GSWYTCWDEASGGQVCYQLAP |
| 365b-R0039-G08 | 365b-M0151-B03 | D6 | TN11_1 | 107 | 1.1143 | 0.0857 | 561 | GSYNLCYPEIYGGQVCYRMAP |
| 365b-R0040-E03 | 365b-M0148-F03 | D6 | TN11_1 | 107 | 1.929 | 0.0807 | 561 | GSYNLCYPEIYGGQVCYRMAP |
| 365b-R0040-F11 | 365b-M0152-B07 | D6 | TN11_1 | 109 | 0.3468 | 0.0946 | 562 | GSYSQCFPDEFGGTTCFVSAP |
| 365b-R0041-G05 | 365b-M0154-B01 | D6 | TN11_1 | 109 | 0.3115 | 0.0953 | 562 | GSYSQCFPDEFGGTTCFVSAP |
| 365b-R0037-D08 | 365b-M0147-F02 | VEGF | Unknown | 114 | 2.3479 | 0.0831 | 563 | GSSMQCFNRVSQLVDCETAAP |
| 365b-R0037-G06 | 365b-M0147-H08 | VEGF | Unknown | 114 | 2.2969 | 0.0746 | 563 | GSSMQCFNRVSQLVDCETAAP |
| 365b-R0035-A01 | 365b-M0144-H06 | VEGF | TN11_1 | 117 | 2.0129 | 0.078 | 505 | GSNMVCMDDSYGGTTCYSMAP |
| 365b-R0036-H10 | 365b-M0145-E12 | VEGF | TN11_1 | 117 | 2.0751 | 0.0759 | 505 | GSNMVCMDDSYGGTTCYSMAP |
| 365b-R0038-A03 | 365b-M0150-A11 | D6 | TN11_1 | 4 | 0.39 | 0.093 | 564 | GSAKTCRSYWAQSGYCYEYAP |
| 365b-R0036-E04 | 365b-M0146-D06 | VEGF | TN11_1 | 5 | 1.3443 | 0.0896 | 565 | GSAQTCWDYVYGGFFCLNTAP |
| 365b-R0038-F12 | 365b-M0148-F05 | VEGF | TN11_1 | 7 | 2.7974 | 0.092 | 566 | GSAWDCFQQDTYSTHCHWRAP |
| 365b-R0036-G12 | 365b-M0148-D02 | VEGF | TN11_1 | 8 | 0.2393 | 0.075 | 567 | GSAWNCEMLDPWSTQCSWDAP |
| 365b-R0035-A05 | 365b-M0144-C06 | VEGF | TN11_1 | 9 | 0.7243 | 0.0673 | 568 | GSAWVCHPEQEGGTTCYWVAP |
| 365b-R0036-H10 | 365b-M0142-G03 | BEAD | TN11_1 | 10 | 1.061 | 0.0977 | 569 | GSDELCWPQEFGGWVCIQGAP |
| 365b-R0041-E08 | 365b-M0152-G04 | VEGF | TN11_1 | 11 | 2.5657 | 0.0849 | 570 | GSDFQCFNWECYPTNCYSNAP |
| 365b-R0036-B10 | 365b-M0153-G03 | D6 | TN11_1 | 13 | 0.4163 | 0.0896 | 571 | GSDKKCWPSPYGGQICWAVAP |
| 365b-R0038-B10 | 365b-M0148-G12 | VEGF | TN11_1 | 15 | 0.2183 | 0.0603 | 572 | GSDQLCFDQRWGGQVCVFGAP |
| 365b-R0037-G01 | 365b-M0146-E08 | VEGF | TN11_1 | 17 | 1.2634 | 0.079 | 573 | GSDSGCKEFWNSSDRCYTHAP |
| 365b-R0040-C05 | 365b-M0152-G04 | VEGF | TN11_1 | 22 | 0.4866 | 0.0895 | 574 | GSEWICWSSFFGGETCTPKAP |
| 365b-R0036-G04 | 365b-M0146-D11 | VEGF | TN11_1 | 23 | 0.494 | 0.0978 | 575 | GSEWNCLNNTPYQTTCSWRAP |
| 365b-R0035-G12 | 365b-M0139-D04 | BEAD | TN11_1 | 24 | 0.4888 | 0.1096 | 576 | GSEWRCWPDVFGGQMCFNMAP |
| 365b-R0037-A06 | 365b-M0147-G10 | VEGF | TN11_1 | 25 | 0.2435 | 0.1062 | 577 | GSEYECYPDWYGGEVCVQKAP |
| 365b-R0037-F07 | 365b-M0147-G05 | VEGF | TN11_1 | 26 | 0.6566 | 0.0776 | 578 | GSFEACWEEAYGGLTCWHDAP |
| 365b-R0041-B11 | 365b-M0153-D08 | D6 | TN11_1 | 27 | 0.722 | 0.0648 | 579 | GSFEECMPYRYGGQTCFMIAP |

FIG. 40R

| Isolate | Initial Name | Elution | Library | Groups | Target OD | Background OD | SEQ ID NO | Trimmed AA |
|---|---|---|---|---|---|---|---|---|
| 365b-R0036-C02 | 365b-M0146-F07 | VEGF | TN11_1 | 30 | 1.067 | 0.0902 | 580 | GSFWTCVDTNWHTTECFHSAP |
| 365b-R0037-G05 | 365b-M0148-A07 | VEGF | TN11_1 | 33 | 1.7984 | 0.1973 | 581 | GSGQMCWHGQYGGTICVAMAP |
| 365b-R0037-A05 | 365b-M0147-H11 | VEGF | TN11_1 | 34 | 1.1541 | 0.0944 | 582 | GSGWVCKQQGPHKTECLFMAP |
| 365b-R0040-A02 | 365b-M0153-A12 | D6 | TN11_1 | 36 | 0.2506 | 0.0648 | 583 | GSHDECWEDIYGGFTCMPYGS |
| 365b-R0035-G02 | 365b-M0144-H03 | VEGF | TN11_1 | 40 | 3 | 0.085 | 584 | GSHVVCWDDPYGGESCYNTAP |
| 365b-R0041-A09 | 365b-M0153-F01 | D6 | TN11_1 | 41 | 1.8781 | 0.1431 | 585 | GSIDICTDSYWGGITCYKFAP |
| 365b-R0036-G06 | 365b-M0146-B05 | VEGF | TN11_1 | 45 | 0.3069 | 0.0815 | 586 | GSKWICVDVKWGGSACYDIAP |
| 365b-R0040-D03 | 365b-M0153-A03 | D6 | TN11_1 | 49 | 0.6252 | 0.0746 | 587 | GSLWECRIDYYGGEVCFIDAP |
| 365b-R0035-D05 | 365b-M0144-D01 | VEGF | TN11_1 | 51 | 1.4799 | 0.0967 | 588 | GSLWTCVLSVYGGEDCYNLAP |
| 365b-R0037-H01 | 365b-M0148-E09 | VEGF | TN11_1 | 53 | 0.313 | 0.0698 | 589 | GSMTMCGAEEDLWYMCYGIAP |
| 365b-R0038-H04 | 365b-M0150-A10 | D6 | TN11_1 | 58 | 0.7672 | 0.1376 | 590 | GSNQYCMPYDWGGEMCFEVAP |
| 365b-R0037-E01 | 365b-M0148-E05 | VEGF | TN11_1 | 59 | 0.443 | 0.0654 | 591 | GSNVFCSEGPFGGEICYGIAP |
| 365b-R0037-D04 | 365b-M0148-B02 | VEGF | TN11_1 | 60 | 0.2309 | 0.0643 | 592 | GSNWACFIEAMGGWTCAPRPT |
| 365b-R0036-E02 | 365b-M0146-F09 | VEGF | TN11_1 | 61 | 0.3077 | 0.0756 | 593 | GSNWTCFIDSFQGETCYPFAP |
| 365b-R0036-D03- | 365b-M0146-E04 | VEGF | TN11_1 | 63 | 0.7171 | 0.0774 | 594 | GSNWWCHSEAFGGHTCYNAAP |
| 365b-R0037-F09 | 365b-M0147-E08 | VEGF | TN11_1 | 64 | 0.5968 | 0.119 | 595 | GSPCACNNSYGHSDDCDHLAP |
| 365b-R0037-D11 | 365b-M0147-B08 | VEGF | TN11_1 | 65 | 0.4696 | 0.1447 | 596 | GSPGNCKDFWAWSLQCFSFAP |
| 365b-R0037-C10 | 365b-M0147-C06 | VEGF | TN11_1 | 67 | 0.3577 | 0.0604 | 597 | GSPRMCYFSSGIMKDCDIIAP |
| 365b-R0035-D02 | 365b-M0144-G11 | VEGF | TN11_1 | 69 | 2.2025 | 0.0767 | 598 | GSPTYCQFHSGVVTLCSMFAP |
| 365b-R0040-B06 | 365b-M0152-F07 | D6 | TN11_1 | 70 | 1.7832 | 0.0699 | 599 | GSQEICFNSQYGGQVCFDSAP |
| 365b-R0035-H04 | 365b-M0144-E09 | VEGF | TN11_1 | 73 | 1.2428 | 0.078 | 600 | GSQMICYPHVFGGQDCFPGAP |
| 365b-R0035-C07 | 365b-M0144-A03 | VEGF | TN11_1 | 76 | 0.6981 | 0.0666 | 601 | GSQWTCTELSDVMTHCSYTAP |
| 365b-R0038-F11 | 365b-M0148-G05 | VEGF | TN11_1 | 78 | 1.1716 | 0.0773 | 602 | GSRVNCGAEDDLSFLCMTEAP |
| 365b-R0035-H12 | 365b-M0139-D09 | VEGF | TN11_1 | 80 | 0.9186 | 0.1256 | 603 | GSSGDCIEMYNDWYYCTILAP |
| 365b-R0037-D05 | 365b-M0148-A03 | VEGF | TN11_1 | 82 | 0.472 | 0.0649 | 604 | GSSWECGEFGDTTIQCNWVAP |
| 365b-R0037-C08 | 365b-M0147-F01 | VEGF | TN11_1 | 83 | 0.4466 | 0.0626 | 605 | GSSWQCFSEAPSGATCVFIAP |
| 365b-R0037-B08 | 365b-M0147-E12 | VEGF | TN11_1 | 84 | 2.89 | 0.125 | 606 | GSSWQCVQVDDFHTECSFMAP |
| 365b-R0039-A01 | 365b-M0151-H06 | VEGF | TN11_1 | 85 | 1.6824 | 0.1451 | 607 | GSSWTCVFYPYGGEVCIPDAP |
| 365b-R0041-A05 | 365b-M0154-A06 | D6 | TN11_1 | 87 | 2.2968 | 0.079 | 608 | GSTELCVPYQWGGEVCVAQAP |
| 365b-R0037-A04 | 365b-M0148-A09 | VEGF | TN11_1 | 95 | 0.2176 | 0.0645 | 609 | GSTVYCHNEYFGGQVCFTIAP |
| 365b-R0036-G03 | 365b-M0146-F01 | VEGF | TN11_1 | 97 | 1.3477 | 0.077 | 610 | GSTYGCEYYMPFQHKCSVEAP |
| 365b-R0036-F05 | 365b-M0151-D01 | VEGF | TN11_1 | 102 | 1.4691 | 0.4212 | 611 | GSWGCFPYSWGGEICTSIAP |
| 365b-R0039-B06 | 365b-M0148-H09 | VEGF | TN11_1 | 103 | 0.9874 | 0.0755 | 612 | GSWNNCVDTSFHTTQCKYAAP |
| 365b-R0038-B09 | 365b-M0148-H10 | VEGF | TN11_1 | 105 | 2.3946 | 0.0876 | 613 | GSYFMCQDGFWGGQDCFYIAP |
| 365b-R0036-H07 | 365b-M0146-A05 | VEGF | TN11_1 | 106 | 0.525 | 0.0716 | 614 | GSYMWCTESKFGGSTCFNLAP |
| 365b-R0036-F05 | 365b-M0146-C05 | VEGF | TN11_1 | 115 | 2.0082 | 0.0969 | 529 | GSDQMCFNESFGGQICFYSAP |
| 365b-R0036-E05 | 365b-M0146-C04 | VEGF | TN11_1 | 112 | 0.5384 | 0.1227 | 615 | GSGAYSHLLEYHAVCKNVAP |
| 365b-R0036-A01 | 365b-M0146-G04 | VEGF | TN11_1 | 116 | 2.1226 | 0.0756 | 526 | GSNLLCYDYYGGQDCYHDAP |
| 365b-R0035-A06 | 365b-M0144-B03 | VEGF | TN11_1 | 3 | 1.4371 | 0.0816 | 616 | PGSWTCQNYEPWATTCVDAP |

MULTIVALENT CONSTRUCTS FOR THERAPEUTIC AND DIAGNOSTIC APPLICATIONS

RELATED APPLICATIONS

This application is a continuation in part of U.S. application Ser. No. 10/379,287 filed Mar. 3, 2003, which claims the benefit of U.S. Provisional Application Ser. No. 60/440,201 filed Jan. 15, 2003 and U.S. Provisional Application Ser. No. 60/360,821 filed Mar. 1, 2002, all of which are incorporated by reference herein in their entirety.

FIELD OF THE INVENTION

The invention relates to compositions and methods for therapeutic and diagnostic applications.

BACKGROUND OF THE INVENTION

Researchers have long been attempting to exploit the ability of targeting moieties or ligands to bind to specific cells (via receptors or otherwise) to target compositions such as detectable labels or therapeutic agents to particular tissues of an animal (especially a human). In such situations, the ability of the targeting moiety to bind to the target (e.g., affinity, avidity, and/or specificity) significantly impacts the ability to successfully target the desired tissues.

Numerous attempts have been made to use natural (e.g. polyclonal) and monoclonal antibodies, as targeting moieties in vivo. However, use of such antibodies present certain disadvantages, such as unacceptable levels of antigenicity—even for humanized antibodies. In addition, natural antibodies are difficult to produce in recombinant form, due to the number of chains, disulfide bonds, and glycosylation. Natural antibodies also present pharmacokinetic problems. Antibodies pose significant problems in imaging and radiotherapeutic applications because, due to their large size, accumulation in extravascular target tissue and clearance from the vascular system are both slow. This problem is especially critical when dealing with solid tumors, which present additional barriers to the ingress of large blood born compounds. Similar problems occur with antibodies used for imaging using other modalities, such as magnetic resonance imaging (MRI), ultrasound and light. If the antibody is radiolabeled with a diagnostic or therapeutic radionuclide, lower target to background ratios result in the images. In addition, an undesirable distribution of radiation exposure between the tumor and normal tissues occurs.

In attempts to solve these problems, efforts have been directed towards the construction of smaller entities with similar binding affinities using the essential features of the natural antibody binding regions. The building blocks are typically single-chain Fv fragments (scFv) which are monovalent. Combining fragments of this type so that they have the bivalent or multivalent properties of the antibodies has been problematic. In order to dock to a surface it is an advantage that the two binding sites on the antibody are connected via a flexible hinge to the constant region. Thus, in order to imitate the binding efficacy of antibodies, not only must the binding site be recreated, but so also must the bivalency (or higher valency) and the flexibility. This flexibility is needed because the protein backbone that makes up the nonbinding region of the scFv is still bulky relative to the binding site. Once an appropriate method has been devised to join two scFv fragments together, different scFv fragments can be joined together as well as more than the customary two scFv moieties present in natural antibodies. Certain scFv fragments, depending both on the VH/VL interface and the linker length, can spontaneously dimerize or multimerize. These "diabodies" are smaller than the natural antibody and do not have the immunological properties of the Fc portion (which activates complement and/or binds to Fc receptors), which they lack. The two (or more) binding sites are rotated relative to each other, and thus the antigen must be correctly positioned to accommodate this presentation.

"Miniantibodies" have properties similar to those of diabodies, but rather than a short 5–20 amino acid linker they have a relatively more flexible linker that allows freer orientation of the binding sites relative to each other, similar to in a natural antibody. Like diabodies, miniantibodies do not have the high molecular weight, immunologically active Fc dimer fragment. They can also be made by bacterial systems. Although they have desired advantages over natural antibodies, miniantibodies still suffer from having a relatively large size, which affects their pharmacokinetics, and must be made using biological methods. The smallest miniantibody is about 120 kDa in size.

Attempts have been made to use bispecific antibodies (e.g. antibodies that bind to two separate targets) to overcome one of the major deficiencies of antibodies, namely, that the size of the antibodies slows accumulation in the extravascular target tissue and clearance from the blood. The bispecific approach taken has been referred to as "pretargeting." This approach uses a two-step protocol. A bispecific antibody with at least one arm that recognizes a tumor-associated antigen and at least one other arm that recognizes an epitope on a diagnostic or therapy agent is given as a first injection. After the unbound antibody has substantially cleared non-target tissues and has reached a maximum level in the tumor, the smaller, bispecific antibody-recognizable diagnostic or therapeutic agent is given. It is hoped that the latter agents distribute more rapidly throughout the body, and either bind to the bispecific antibody localized at the tumor, or are cleared via the kidneys.

An alternative to this approach attempts to use a mixed antibody avidin/biotin system in a two-step procedure. For example, a targeting antibody is conjugated with either avidin or biotin and then is injected whereupon it localizes in the tumor of interest. Thereafter, either biotin or avidin (depending on which was coupled to the targeting antibody), bearing an imaging or radiotherapeutic radionuclide, is injected and becomes localized at the site of the primary antibody by binding to avidin or biotin respectively.

Another approach to the use of antibodies as targeting moieties for radiopharmaceuticals or other diagnostic imaging agents has attempted to use a bivalent hapten to increase the avidity for the cell bound bispecific antibody over that of the circulating antibody. This approach relies on bidentate binding occurring with the cell bound antibodies, because the surface density on the cells is sufficiently high, but not occurring with the circulating antibodies, because the concentration is too low. In effect, the system makes use of the increase in avidity caused by the closer presentation of the antibodies/antigen on the cells.

Peptides have also been used as targeting moieties. In an attempt to improve the binding bi-specific peptide constructs have been prepared with two or more peptide based targeting agents selective for different targets. For example, a hybrid peptide having ligands to two targets selected from the somatostatin-, GRP-, CCK-, Substance P-, or VIP receptor and $\alpha_v\beta_3$ integrin was reportedly made and tested for the ability to bind to tumor cells. The initial evaluation showed no improved tumor uptake for the multiple ligand systems investigated. The investigators assumed that steric impairment leads to a reduction of the receptor affinities of the dimeric structures. Others have tested an RGD-DTPA-Octreotate hybrid peptide targeted towards both the $\alpha_v\beta_3$ integrin and the somatostatin-2 receptor for the ability to increase the tumor uptake over that of a peptide selective for one or the other targets. The different binding affinities of the two targeting moieties towards their targets, blood vessels and tumor cells, respectively, resulted in the avidity for tumors being dominated by the stronger (somatostatin mediated) interaction.

A variation of these approaches uses a bispecific diabody targeted to two different epitopes on the same antigen. This approach attempts to increase the avidity of the construct for the target, because, although the binding is monovalent for each epitope, the construct as a whole is bivalent to its target, as each of the binding epitopes is located within the same target molecule. In the case of the single molecule target, scFv fragments have been found to have insufficient affinity and an increase in avidity was required.

Two rationales underlie the approaches described above. The first rationale uses two different targeting moieties to overcome some of the pharmacokinetic problems associated with the delivery of antibodies to solid tumors. The second rationale uses two different targeting moieties to increase the avidity of the construct for a given target, such as a single molecule or a whole tumor. However, all of the approaches described suffer from various drawbacks. Thus, there remains a need for diagnostic and therapeutic agents with increased affinity and or avidity for a target of interest. There also remains a need for diagnostic and therapeutic agents that, when administered in vivo to a mammal, have acceptable pharmacokinetic properties.

Angiogenesis, the formation of new blood vessels, occurs not only during embryonic development and normal tissue growth and repair, but is also involved in the female reproductive cycle, establishment and maintenance of pregnancy, and repair of wounds and fractures. In addition to angiogenesis that occurs in the normal individual, angiogenic events are involved in a number of pathological processes, notably tumor growth and metastasis, and other conditions in which blood vessel proliferation is increased, such as diabetic retinopathy, psoriasis and arthropathies. Angiogenesis is so important in the transition of a tumor from hyperplastic to neoplastic growth, that inhibition of angiogenesis has become an active cancer therapy research field.

Tumor-induced angiogenesis is thought to depend on the production of pro-angiogenic growth factors by the tumor cells, which overcome other forces that tend to keep existing vessels quiescent and stable. The best characterized of these pro-angiogenic agents is vascular endothelial growth factor (VEGF) (Cohen et al., *FASEB J.*, 13: 9–22 (1999)). VEGF is produced naturally by a variety of cell types in response to hypoxia and some other stimuli. Many tumors also produce large amounts of VEGF, and/or induce nearby stromal cells to make VEGF (Fukumura et al., *Cell*, 94: 715–725 (1998)). VEGF, also referred to as VEGF-A, is synthesized as five different splice isoforms of 121, 145, 165, 189, and 206 amino acids. $VEGF_{121}$ and $VEGF_{165}$ are the main forms produced, particularly in tumors (see, Cohen et al. 1999, supra). $VEGF_{121}$ lacks a basic domain encoded by exons 6 and 7 of the VEGF gene and does not bind to heparin or extracellular matrix, unlike $VEGF_{165}$.

VEGF family members act primarily by binding to receptor tyrosine kinases. In general, receptor tyrosine kinases are glycoproteins having an extracellular domain capable of binding one or more specific growth factors, a transmembrane domain (usually an alpha helix), a juxtamembrane domain (where the receptor may be regulated, e.g., by phosphorylation), a tyrosine kinase domain (the catalytic component of the receptor), and a carboxy-terminal tail, which in many receptors is involved in recognition and binding of the substrates for the tyrosine kinase. There are three endothelial cell-specific receptor tyrosine kinases known to bind VEGF: VEGFR-1 (Flt-1), VEGFR-2 (KDR or Flk-1), and VEGFR-3 (Flt4). Flt-1 and KDR have been identified as the primary high affinity VEGF receptors. While Flt-1 has higher affinity for VEGF, KDR displays more abundant endothelial cell expression (Bikfalvi et al., *J. Cell. Physiol.*, 149: 50–59 (1991)). Moreover, KDR is thought to dominate the angiogenic response and is therefore of greater therapeutic and diagnostic interest (see, Cohen et al. 1999, supra). Expression of KDR is highly upregulated in angiogenic vessels, especially in tumors that induce a strong angiogenic response (Veikkola et al., *Cancer Res.*, 60: 203–212 (2000)). The critical role of KDR in angiogenesis is highlighted by the complete lack of vascular development in homozygous KDR knockout mouse embryos (Folkman et al., *Cancer Medicine*, $5^{th}$ Edition (B.C. Decker Inc.; Ontario, Canada, 2000) pp. 132–152).

KDR (kinase domain region) is made up of 1336 amino acids in its mature form. The glycosylated form of KDR migrates on an SDS-PAGE gel with an apparent molecular weight of about 205 kDa. KDR contains seven immunoglobulin-like domains in its extracellular domain, of which the first three are the most important in VEGF binding (Cohen et al. 1999, supra). VEGF itself is a homodimer capable of binding to two KDR molecules simultaneously. The result is that two KDR molecules become dimerized upon binding and autophosphorylate, becoming much more active. The increased kinase activity in turn initiates a signaling pathway that mediates the KDR-specific biological effects of VEGF.

Thus, not only is the VEGF binding activity of KDR in vivo critical to angiogenesis, but the ability to detect KDR upregulation on endothelial cells or to detect VEGF/KDR binding complexes would be extremely beneficial in detecting or monitoring angiogenesis. Diagnostic applications, such as detecting malignant tumor growth, and therapeutic applications, such as targeting tumoricidal agents or angiogenesis inhibitors to the tumor site, would be particularly beneficial.

Hepatocyte growth factor (also known as scatter factor) is a multi-functional growth factor involved in various physiological processes such as embryogenesis, wound healing and angiogenesis. It has become apparent that HGF, through interactions with its high affinity receptor (cMet), is involved in tumor growth, invasion and metastasis. In fact, dysregulated cMet expression (for example, the overexpression of cMet in neoplastic epithelium of colorectal adenomas and in other carcinomas as compared to normal mucosa) and/or activity, as well as hyperactivity of the cMet receptor through an autocrine stimulatory loop with HGF, has been demonstrated in a variety of tumor tissues and induces oncogenic transformation of specific cell lines.

In general, HGF is produced by the stromal cells, which form part of many epithelial tumors; however, it is believed that the production of HGF by tumor cells themselves comprises the main pathway leading to the hyperproliferation of specific tumors. HGF/cMet autocrine stimulatory loops have been detected in gliomas, osteosarcomas, and mammary, prostate, breast, lung and other carcinomas.

Interrupting the HGF interaction with the cMet receptor slows tumor progression in animal models. In addition to stimulating proliferation of certain cancer cells through activation of cMet, HGF also protects against DNA-damaging agent-induced cytotoxicity in a variety of cell lines susceptible to hyperproliferative phenotypes (e.g., breast cancer). Therefore, preventing HGF from binding to cMet could predispose certain cancer cells to the cytotoxicity of certain drugs.

In addition to hyperproliferative disorders, cMet also has been linked to angiogenesis. For example, stimulation of cMet leads to the production of vascular endothelial growth factor (VEGF), which, in turn, stimulates angiogenesis. Additionally, stimulation of cMet also has been implicated in promoting wound healing.

In addition to identifying the cMet receptor as a therapeutic target for hyperproliferative disorders, angiogenesis and wound healing, the large discrepancy between expression levels of neoplastic and corresponding normal tissues indicates that cMet is an attractive target for imaging applications directed to hyperproliferative disorders.

SUMMARY OF THE INVENTION

The present invention features multivalent constructs which bind to a target of interest, as well as various methods related to the use of these constructs. The present invention uses small targeting moieties which bind to different binding sites of the same target, allowing for improved localization to the desired target, and providing an improved means for detecting, imaging and/or treating the target site.

Preparation and use of multivalent (e.g., dimeric or multimeric) targeting constructs which include two or more targeting moieties, for example binding polypeptides, specific for different binding sites of the same target are described herein. These targeting constructs may be linked or conjugated to a detectable label and/or a therapeutic agent (as defined herein) and used to deliver the detectable label and/or therapeutic agent to the target of interest. Thus, in addition to the targeting constructs themselves, the invention includes diagnostic imaging agents and therapeutic agents useful in diagnostic imaging and treating various disease states. Furthermore, the invention includes use of the targeting constructs of the invention themselves to treat disease.

In one aspect, the present invention features a compound having a plurality of binding moieties, wherein at least two binding moieties have specificity for different binding sites on the same target. In preferred embodiments, the plurality of binding moieties includes a polypeptide. In other preferred embodiments, the targeting moieties are all binding polypeptides which bind to different sites on the desired target. In certain preferred emobidments, the target is a protein, a receptor, or a receptor/ligand complex and the binding polypeptides bind to different epitopes on the protein, the receptor, or the receptor/ligand complex. In one embodiment, the target is a receptor involved in angiogenesis, hyperproliferative disorders or wound healing. In another embodiment the target includes a family of receptors, such as, for example, protein-tyrosine kinase receptors. In a particularly preferred embodiment, the target is KDR or the KDR/VEGF complex, and the binding moieties, particularly binding peptides, bind to different epitopes on KDR or the KDR/VEGF complex.

In another preferred embodiment, the target is the hepatocyte growth factor (HGF) receptor (cMet) or the HGF/cMet complex, and the binding moieties (particularly binding polypeptides) bind to different epitopes on cMet or the HGF/cMet complex.

In further preferred embodiments, the affinity constant of a compound of the invention for its target is greater than the affinity constant of a constituent polypeptide for the target.

In another aspect, the compounds of the invention include a labelling group or a therapeutic agent. In certain embodiments, the compounds of the invention include a linker between a binding moiety and the labelling group. For example, the linker may include a substituted alkyl chain, an unsubstituted alkyl chain, a polyethylene glycol derivative, an amino acid spacer, a sugar, an aliphatic spacer, an aromatic spacer, a lipid molecule, or combination thereof. Preferred labelling groups include a radionuclide, a paramagnetic metal ion, an ultrasound contrast agent, and/or a photolabel. For example, preferred paramagnetic metal ions used in compounds of the invention include $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$, and $Eu^{2+}$.

Radionuclides are also preferred detectable labels and therapeutic agents. The choice of radionuclide will be determined based on the desired therapeutic or diagnostic application. In a preferred embodiment, where the detectable label is a paramagnetic metal or a radionuclide, the compounds of the invention include a chelator or chelating group. Preferable chelators inlcude DTPA, DOTA, DO3A, EDTA, TETA, EHPG, HBED, NOTA, DOTMA, TETMA, PDTA, TTHA, LICAM, or MECAM. For use as a PET agent, a peptide may be complexed with one of the various positron emitting metal ions, such as $^{51}Mn$, $^{52}Fe$, $^{60}Cu$, $^{68}Ga$, $^{72}As$, $^{94}mTc$, or $^{110}In$. The heteromultimeric constructs can also be labeled by halogenation using radionuclides, such as $^{18}F$, $^{124}I$, $^{125}I$, $^{131}I$, $^{123}I$, $^{77}Br$, and $^{76}Br$. Preferred metal radionuclides for scintigraphy or radiotherapy include $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $161Tb$, $^{177}Lu$, $^{198}Au$ and $^{199}Au$. The choice of metal or halogen will be determined based on the desired therapeutic or diagnostic application. For example, for diagnostic purposes the preferred radionuclides include $^{64}Cu$, $^{67}Ga$, $^{68}Ga$, $^{99m}Tc$, and $^{111}In$. For therapeutic purposes, the preferred radionuclides include $^{64}Cu$, $^{90}Y$, $^{105}Rh$, $^{111}In$, $^{117m}Sn$, $^{149}Pm$, $^{153}Sm$, $_{161}Tb$, $^{166}D$ $^{166}Ho$, $^{175}Yb$, $^{177}Lu$, $^{186/188}Re$, and $^{199}Au$. A most preferred chelator used in compounds of the invention is 1-substituted 4,7,10-tricarboxymethyl 1,4,7,10 tetraazacyclododecane triacetic acid (DO3A). Preferably, a radioactive lanthanide, such as, for example, $^{177}Lu$, $^{90}Y$, $^{153}Sm$, $^{111}In$, or $^{166}Ho$ is used with DOTA or DO3A in compounds of the invention.

Compounds of the invention include chelators having the following structure:

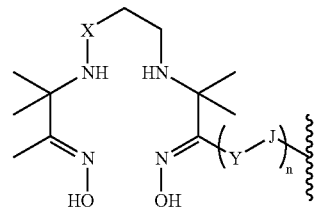

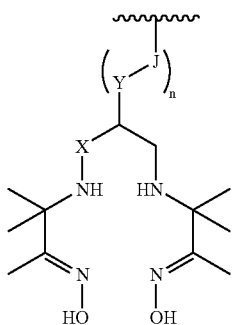

where X is CH$_2$ or O;
Y is C$_1$–C$_{10}$ branched or unbranched alkyl, aryl, aryloxy, arylamino, arylaminoacyl, or aralkyl comprising C$_1$–C$_{10}$ branched or unbranched alkyl groups, C$_1$–C$_{10}$ branched or unbranched hydroxy or polyhydroxyalkyl groups or polyalkoxyalkyl or polyhydroxy-polyalkoxyalkyl groups; J is C(=O)—, OC(=O)—, SO$_2$—, NC(=O)—, NC(=S)—, N(Y), NC(=NCH$_3$)—, NC(=NH)—, N=N—, a homopolyamide or a heteropolyamine derived from synthetic or naturally occurring amino acids; and n is 1–100. Most preferably, the compounds further include $^{99m}$Tc, $^{186}$Re, or $^{188}$Re.

In one embodiment, compounds of the the invention include a chelator having the following structure:

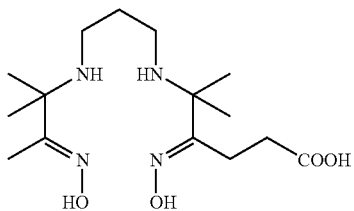

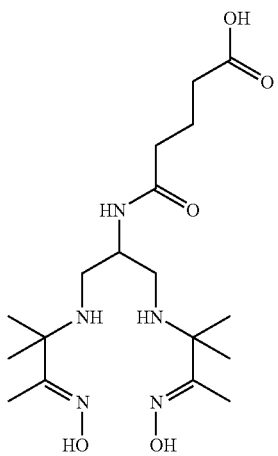

Most preferably, the compound further includes $^{99m}$Tc, $^{186}$Re, or $^{188}$Re.

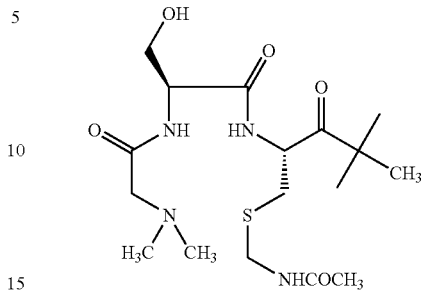

In another embodiment, the chelator comprises a compound having the following structure:Most preferably, the compound further includes $^{99m}$Tc.

In other embodiments, compounds of the invention include a chelator having the following structure:


where R is an alkyl group, such as CH$_3$. Most preferably, the compound further includes $^{177}$Lu, $^{90}$Y, $^{153}$Sm, $^{111}$In, or $^{166}$Ho.

In yet another embodiment, compounds of the invention include a chelator having the following structure:

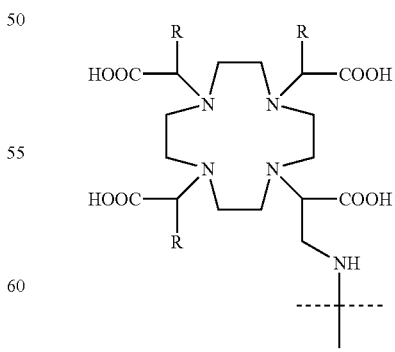

where R is an alkyl group, such as CH$_3$. Most preferably, the compound further includes $^{177}$Lu, $^{90}$Y, $^{153}$Sm, $^{111}$In, or $^{166}$Ho.

In other embodiments, the compound of the invention includes a chelator having the following structure:

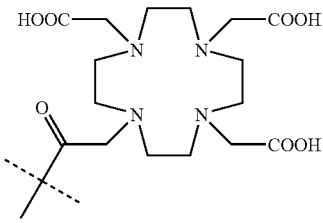

Most preferably, the compound further includes $^{177}$Lu, $^{90}$Y, $^{153}$Sm, $^{111}$In, or $^{166}$Ho.

Preferred ultrasound contrast agents for use in compounds of the invention include phospholipid stabilized microbubbles or microballoons comprising a fluorinated gas.

One preferred embodiment of the invention includes compounds comprising at least two binding moieties with specificity for different binding sites on a target. Preferably the target is a single receptor or receptor/ligand complex such as, for example, KDR or the KDR/VEGF complex or cMet of the cMet/VEGF complex. In further preferred embodiments, the binding moieties bind to different epitopes on the receptor or receptor/ligand complex. In a particularly preferred embodiment the binding moieties include a polypeptide. In other preferred embodiments, a compound of the invention includes a polypeptide having the amino acid sequence of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:26, SEQ ID NO:27, SEQ ID NO:28, or SEQ ID NO:29. The invention also provides a compound having one or more of the foregoing amino acid sequences that have been modified to include one or more amino acid substitutions, amide bond substitutions, D-amino acid substitutions, glycosylated amino acids, disulfide mimetic substitutions, amino acid translocations, or has been modified to include a retroinverso peptide, a peptoid, a retro-inverso peptoid, and/or a synthetic peptide. In preferred embodiments, the compound of the invention comprises SEQ ID NO:4, SEQ ID NO:5, SEQ ID NO:8, SEQ ID NO:9, SEQ ID NO:11, SEQ ID NO:12, SEQ ID NO:26, and/or SEQ ID NO:27. In a more preferred embodiment such compounds further include a labelling group or therapeutic agent as described herein.

In another aspect, the invention features diagnostic imaging methods using compounds of the invention that include a labelling group. Methods of the invention include the steps of administering to a patient a pharmaceutical preparation that includes a compound of the invention having a labelling group, and imaging the compound after administration to the patient. In preferred embodiments, the imaging step includes magnetic resonance imaging, ultrasound imaging, optical imaging, sonoluminescence imaging, photoacoustic imaging, or nuclear imaging. In these methods, the administering step may include inhaling, transdermal absorbing, intramuscular injecting, subcutaneous injecting, intravenous injecting, intraperitoneally injecting, intraarterial injecting or parenteral administration.

In another aspect, the compounds of the invention serve as therapeutic agents themselves and/or include a therapeutic agent. In certain embodiments, the compounds of the invention include a linker between a binding moiety and the therapeutic agent. For example, the linker may include a substituted alkyl chain, an unsubstituted alkyl chain, a polyethylene glycol derivative, an amino acid or peptide spacer, a sugar, an aliphatic spacer, an aromatic spacer, a lipid molecule, or combination thereof. Preferred therapeutic agents for use with compounds of the invention include a bioactive agent, a cytotoxic agent, a drug, a chemotherapeutic agent, or a radiotherapeutic agent.

In another aspect, the invention features a method of treating a disease by administering to a patient a pharmaceutical preparation including a compound of the invention. In one embodiment, where one or more binding moieties of the compound inhibits a biological process that contributes to a disease state, the compound may be administered to treat that disease state. For example, the binding moieties may inhibit the biological process by preventing or diminishing the activity of the receptor(e.g. by competition with the natural ligand for the receptor, by directly inhibiting the receptor activity whether or not the natural ligand is bound, or by a combination of the two). Thus, a heteromultimeric compound of the invention, may inhibit the activity of, for instance KDR or cMet, and thus inhibit angiogenesis and/or hyperproliferation and consequently the diseases these processes contribute to. Therefore, the invention features a method of treating a disease by administering to a patient a pharmaceutical preparation including a compound of the invention alone or attached or linked to a separate therapeutic agent. In preferred embodiments, the invention features a method of treating a disease associated with angiogenesis or hyperproliferation. In a most preferred embodiment, the disease is neoplastic tumor growth.

The invention also features a method of screening for heteromultimeric compounds having improved binding affinity. This method includes the steps of preparing a labeled heteromultimeric compound comprising a plurality of binding moieties, wherein at least two binding moieties bind to different binding sites of a target; contacting the labeled heteromultimeric compound with a target; determining a binding strength of the labeled heteromultimeric compound (for example, by determining the dissociation constant); and comparing the binding strength (e.g., dissociation constant) of the labeled heteromultimeric compound with the binding strength (e.g., dissociation constant) of one or more individual binding moieties. In preferred embodiments of this method one of the binding moieties includes a polypeptide. In another preferred embodiment, the target is KDR or KDR/VEGF complex. In a preferred embodiment, one of the polypeptides used in this method is SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. Preferably, the method includes the step of identifying a labeled heteromultimeric compound having a binding strength (for example, as measure by the dissociation constant) that is less than the binding strength of a constituent binding moiety.

In one preferred embodiment, the invention features dimeric or multimeric targeting constructs which include two or more KDR or VEGF/KDR complex binding polypeptides which bind to different binding sites of KDR or the VEGF/KDR complex. Such polypeptides are described in detail in U.S. Ser. No. 60/360,851 and U.S. Ser. No. 60/440,441, both of which are incorporated by reference herein in their entirety, and in copending application U.S. Ser. No. 10/382,082, entitled "KDR and VEGF/KDR binding peptides and their use in diagnosis and therapy," in the name of Aaron Sato, et al., filed on the same date as the instant application and incorporated by reference herein in its entirety. These constructs are referred to herein as "KDR-targeting constructs." The KDR targeting constructs exhibit improved binding to KDR (e.g. increased specificity and/or affinity and/or avidity) compared to monomeric KDR or VEGF/KDR complex binding polypeptides, and compared to dimeric or multimeric constructs of a single KDR-binding polypeptide. These preferred compounds may be linked or conjugated to a detectable moiety and used to target these compositions to KDR-expressing cells, permitting imaging of KDR-expressing tissue.

In another preferred embodiment, the invention features dimeric or multimeric targeting constructs which include two or more cMet or HGF/cMet complex binding polypeptides which bind to different binding sites of cMet or the HGF/cMet complex. Such polypeptides are described in detail in copending application U.S. Ser. No. 60/451,588, entitled "Peptides that specifically bind HGF receptor (cMet) and uses thereof," filed on the same date as the instant application and incorporated by reference herein in its entirety. These constructs are referred to herein as "cMet-targeting constructs." The cMet targeting constructs exhibit improved binding to cMet (e.g. increased specificity and/or affinity and/or avidity) compared to monomeric cMet or HGF/cMet complex binding polypeptides, and compared to dimeric or multimeric constructs of a single cMet-binding polypeptide.

The cMet and KDR targeting constructs of the invention may be linked or conjugated to a therapeutic agent and used to localize the therapeutic agent to cMet- or KDR-expressing tissue. Alternatively or additionally, the cMet or KDR targeting constructs of the invention may also be used as therapeutics themselves, as described herein.

In particularly preferred embodiments, the KDR targeting constructs of the invention include two or more of the following KDR and VEGF/KDR complex-binding polypeptides: SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

In other preferred embodiments, the cMet targeting constructs of the invention include two or more of the following binding polypeptides: SEQ ID NO:26, SEQ ID NO:27, SEQ ID NO:28, and/or SEQ ID NO:29.

In another embodiment, the invention provides a novel method for screening the KDR targeting constructs for the ability to bind the target, and thus, identify multimeric constructs of KDR binding polypeptides with improved binding (as determined, for example, by dissociation constants), as compared to binding of the constituent polypeptides. Additionally, the method of the invention allows for rapid determination of whether the multimeric targeting constructs will be stable in the presence of serum in vivo.

Constructs comprising two or more KDR or KDR/VEGF binding polypeptides show improved ability to bind the target molecule compared to the corresponding monomeric binding polypeptides. For instance, as shown in Example 6 below, tetrameric constructs of KDR binding polypeptides provided herein showed improved ability to bind KDR-transfected 293H cells. Combining two or more binding polypeptides in a single molecular construct appears to improve the avidity of the construct over the monomeric binding polypeptides a shown by a decrease in $K_D$.

In addition, as demonstrated herein, constructs comprising two or more binding polypeptides specific for different epitopes of KDR and/or KDR/VEGF (e.g., "heteromeric" constructs) were made. Constructs comprising two or more binding polypeptide provided herein are expected to block multiple sites on KDR or VEGF/KDR. The heteromeric constructs show superior binding ability over both the corresponding monomers, as well as tetrameric constructs comprising multiple copies of the same binding polypeptide. Furthermore, heteromeric constructs comprising two or more binding peptides specific for different epitopes were also able to efficiently bind KDR-transfected 293H cells. Thus, inclusion of two or more binding polypeptides that recognize different epitopes further improves the avidity of the construct for the target molecule, as demonstrated by a decrease in $K_D$.

Heteromeric constructs of the binding polypeptides provided herein show improved ability to inhibit receptor tyrosine kinase function. Based on experiments described herein, dimeric and other multimeric constructs of the present invention comprising at least two binding polypeptides specific for different epitopes of KDR and/or KDR/VEGF are expected to inhibit the function of receptor tyrosine kinases. In particular, such constructs are expected to inhibit the function of VEGFR-2/KDR, VEGFR-1/Flt-1 and VEGFR-3/Flt-4. Additionally, heteromultimeric constructs of the invention comprising two or more binding moieties specific for different epitopes of cMet and/or cMet/HGF are expected to inhibit the function of receptor tyrosine kinases and, in particular the function of cMet.

For the purposes of the present invention, receptor tyrosine kinase function can include any one of: oligomerization of the receptor, receptor phosphorylation, kinase activity of the receptor, recruitment of downstream signaling molecules, induction of genes induction of cell proliferation, induction of cell migration, or combination thereof. For example, heteromeric constructs of binding polypeptides provided herein inhibit VEGF-induced KDR receptor inactivation in human endothelial cells, demonstrated by the inhibition of VEGF-induced phosphorylation of the KDR receptor. In addition, heteromeric constructs of binding peptides provided herein inhibit VEGF-stimulated endothelial cell migration. As shown herein, targeting two or more distinct epitopes on KDR with a single binding construct greatly improves the ability of the construct to inhibit receptor function. Even binding peptides with weak ability to block receptor activity can be used to generate heteromeric constructs having improved ability to block VEGF-induced receptor function. Indeed, heteromultimers of this invention can also be useful for treating vascular permeability events that can result when VEGF binds KDR. See e.g. Example 30. In renal failure it has been shown that anti-VEGF antibodies can reverse damage and in a similar way the compounds of the invention can reverse renal permeability pathogenesis in, for example, diabetes.

Additionally, as further demonstrated herein, constructs comprising two or more binding polypeptides specific for different epitopes of cMet were made. Constructs containing two or more cMet binding polypeptide provided herein are expected to block multiple sites on cMet. These heteromeric cMet targeting constructs show superior binding ability over the corresponding monomers.

Therefore, the present invention is drawn to constructs comprising two or more binding polypeptides. The multimeric constructs of the present invention comprise two or more binding polypeptides, such that at least two of the binding polypeptides in the construct are specific for different epitopes of a target, for example, KDR and/or KDR/VEGF and cMet and/or cMet/HGF. These constructs are also referred to herein as "heteromeric constructs," "heteromultimers" and/or "heteromultimeric constructs." The constructs of the present invention can also include unrelated, or control peptide. The constructs can include two or more, three or more, or four or more binding polypeptides. Based on the teachings provided herein, one of ordinary skill in the art is able to assemble the binding polypeptides provided herein into multimeric constructs and to select multimeric constructs having improved properties, such as improved ability to bind the target molecule, or improved ability to inhibit receptor tyrosine kinase function. Such multimeric constructs having improved properties are included in the present invention. Furthermore, the methods and teachings provided herein have been shown to allow for the improved binding to a variety of different targets (e.g., KDR and cMet), thus demonstrating the wide applicability of the present invention.

BRIEF DESCRIPTION OF THE DRAWINGS

FIG. 8A shows the results obtained using P6-XB and P5-XB. FIG. 8B shows the results obtained using P12-XB and P13-XB. Calculated Kd values were: 10.00 nM (P6-XB), 14.87 nM (P5-XB), 4.03 nM (P12-XB) and 1.81 nM (P13-XB).

FIG. 40 is a list of KDR-binding peptides isolated from a TN11/1 library.

DETAILED DESCRIPTION

Figure 1:
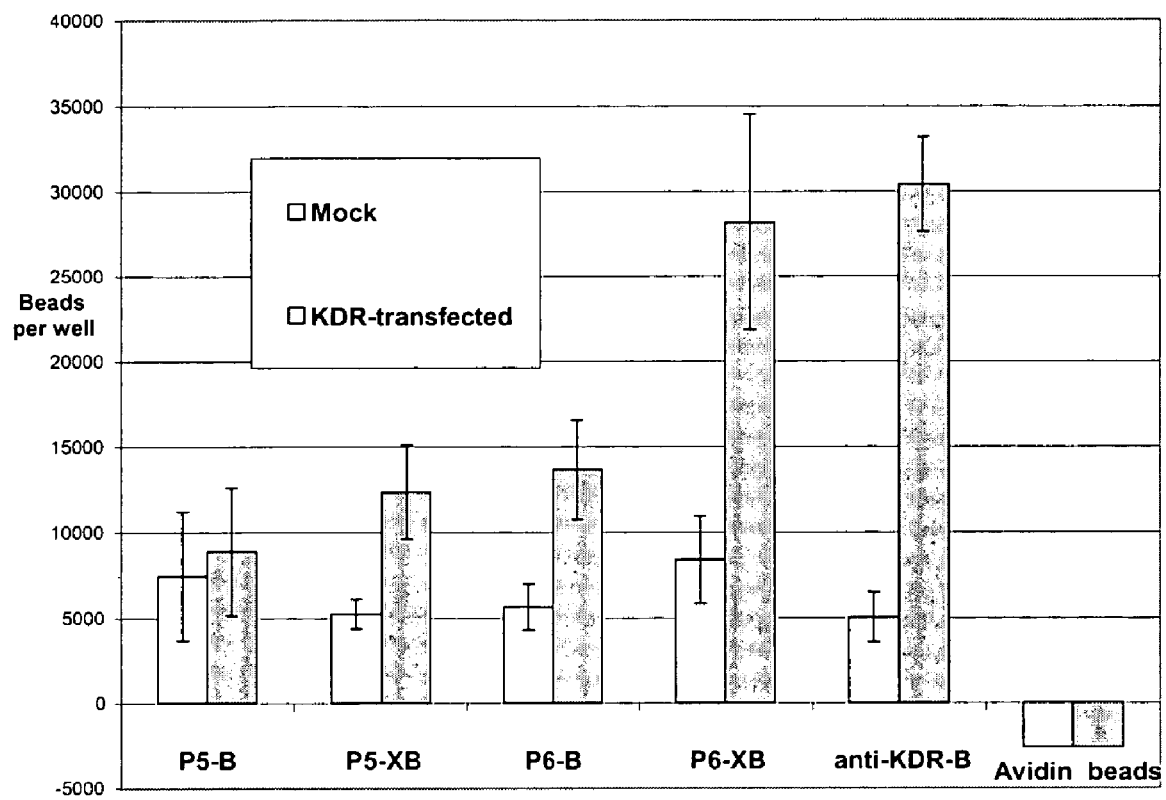
FIG. 1 shows the binding of fluorescent beads to KDR-transfected and mock-transfected cells. Neutravidin-coated beads with the indicated biotinylated ligands attached were tested for binding to KDR-expressing and non-expressing 293H cells. Specific binding to KDR was detected for both P5 (with hydrophilic spacer) and P6. Further details are provided in Example 2.

The present invention is based, in part, on the discovery that compounds having two or more binding moieties, wherein at least two of the binding moieties bind to different binding sites on the same target, have unexpected and significantly improved ability to bind the target. Preferably the target is a receptor or a receptor/ligand complex. The improved ability of compounds of the invention (variously referred to as "multivalent targeting constructs," "heterodimers," "heterotetramers," "heteromultimers" and/or "heteromultimeric constructs" herein) to bind a target may be demonstrated by comparison to the ability of an individual, constituent, binding moiety to bind the target. For example, the binding strength of a heteromultimer of the invention may be compared to the binding strength of one of its monomers. Preferably, a heteromultimer of the invention exhibits an increase in affinity (as determined, for example, by dissociation constants), compared to an individual, constituent monomer.

Definitions

As used herein, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompasses DNA molecules which have been constructed in vitro using genetic engineering techniques, and use of the term "recombinant" as an adjective to describe a molecule, construct, vector, transfected cell, polypeptide or polynucleotide specifically excludes naturally occurring such molecules, constructs, vectors, cells, polypeptides or polynucleotides.

The term "bacteriophage" is defined as a bacterial virus containing a DNA core and a protective shell built up by the aggregation of a number of different protein molecules. The terms "bacteriophage" and "phage" are used herein interchangeably.

The term "polypeptide" is used to refer to a compound of two or more amino acids joined through the main chain (as opposed to side chain) by a peptide amide bond (—C(:O) NH—). The term "peptide" is used interchangeably herein with "polypeptide" but is generally used to refer to polypeptides having fewer than 40, and preferably fewer than 25 amino acids.

The term "binding" refers to the determination by standard assays, including those described herein, that a binding polypeptide recognizes and binds reversibly to a given target. Such standard assays include, but are not limited to, equilibrium dialysis, gel filtration, and the monitoring of spectroscopic changes that result from binding.

The term "binding polypeptide" as used herein refers to any polypeptide capable of forming a binding complex with another molecule. Also included within the definition of "binding polypeptides" are polypeptides that are modified or optimized as disclosed herein. Specific examples of such modifications are discussed in detail infra, but include substitution of amino acids for those in the parent polypeptide sequence to optimize properties, obliterate an enzyme cleavage site, etc.; C- or N-terminal amino acid substitutions or elongations, e.g., for the purpose of linking the binding polypeptide to a detectable imaging label or other substrate, examples of which include, e.g., addition of a polyhistidine "tail" to assist in purification; truncations; amide bond changes; translocations; retroinverso peptides; peptoids; retroinversopeptoids; the use of N-terminal or C-terminal modifications or linkers, such as polyglycine or polylysine segments; alterations to include functional groups, notably hydrazide (—NH—NH$_2$) functionalities or the C-terminal linker -Gly-Gly-Gly-Lys, to assist in immobilization of binding peptides according to this invention on solid supports or for attachment of fluorescent dyes; modifications which effect pharmacokinetics; structural modifications to retain structural features; formation of salts to increase water solubility or ease of formulation, and the like. In addition to the detectable labels described further herein, the binding polypeptides may be linked or conjugated to a radiotherapeutic agent, a cytotoxic agent, a tumorcidal agent or enzyme, a liposome (e.g., loaded with a therapeutic agent, an ultrasound appropriate gas, or both). In addition, binding polypeptides of the invention may be bound or linked to a solid support, such as a well, plate, bead, tube, slide, filter, or dish. Moreover, dimers or multimers of one or more binding polypeptides may be formed. Such constructs may, for example, exhibit increased ability to bind to the target. All such modified polypeptides are also considered "binding polypeptides" so long as they retain the ability to bind the targets.

"Homologues" of the binding polypeptides described herein may be produced using any of the modification or optimization techniques described herein or known to those skilled in the art. Such homologous polypeptides will be understood to fall within the scope of the present invention and the definition of "binding polypeptides" so long as the substitution, addition, or deletion of amino acids or other such modification does not eliminate its ability to bind to the target. The term "homologous," as used herein, refers to the degree of sequence similarity between two polymers (i.e., polypeptide molecules or nucleic acid molecules). When the same nucleotide or amino acid residue or one with substantially similar properties (i.e. a conservative substitution) occupies a sequence position in the two polymers under comparison, then the polymers are homologous at that position. For example, if the amino acid residues at 60 of 100 amino acid positions in two polypeptide sequences match or are homologous then the two sequences are 60% homologous. The homology percentage figures referred to herein reflect the maximal homology possible between the two polymers, i.e., the percent homology when the two polymers are so aligned as to have the greatest number of matched (homologous) positions. Polypeptide homologues within the scope of the present invention will be at least 70% and preferably greater than 80% homologous to at least one of the binding sequences disclosed herein.

"KDR binding polypeptide" is a binding polypeptide that forms a complex in vitro or in vivo with vascular endothelial growth factor receptor-2 (or KDR, Flk-1);

"VEGF/KDR complex binding polypeptide" is a binding polypeptide that forms a complex in vitro or in vivo with a binding complex formed between vascular endothelial growth factor (VEGF) and KDR, in particular the complex of homodimeric VEUF and one or two KDR molecules that is believed to form at the surface of endothelial cells during angiogenesis. Specific examples of KDR and VEGF/KDR binding polypeptides include but are not limited to the peptides presented discussed herein, and in U.S. Ser. No. 60/360,851 and U.S. Ser. No. 60/440,441, both of which are incorporated by reference herein in their entirety, and in copending application U.S. Ser. No. 10/382,082, entitled "KDR and VEGF/KDR binding peptides and their use in diagnosis and therapy," and include hybrid and chimeric polypeptides incorporating such peptides as well as homologues.

"cMet binding polypeptide" is a binding polypeptide that forms a complex in vitro or in vivo with the HGF receptor, cMet;

"cMet/HGF complex binding polypeptide" is a binding polypeptide that forms a complex in vitro or in vivo with a binding complex formed between hepatocyte growth factor (HGF) and cMet. Specific examples of cMet and cMet/HGF binding polypeptides include but are not limited to the peptides presented discussed herein, and in U.S. Ser. No. copending provisional application U.S. Ser. No. 60/451,588, entitled "Peptides that Specifically Bind HGF Receptor (cMet) and Uses Thereof," and include hybrid and chimeric polypeptides incorporating such peptides as well as homologues.

A "labelling group" or "detectable label," as used herein, is a group or moiety capable of generating a signal for diagnostic imaging, such as magnetic resonance imaging, radioimaging, ultrasound imaging, x-ray imaging, light imaging, or carrying a moiety such as a radioactive metal or other entity that may be used in radiotherapy or other forms of therapy.

The term "specificity" refers to a binding polypeptide having a higher binding affinity for one target over another. Binding specificity may be characterized by a dissociation equilibrium constant ($K_D$) or an association equilibrium constant ($K_a$) for the two tested target materials. In a preferred embodiment, binding polypeptides of the invention have a dissociation constant for a desired target that is lower than about 10 µM, more preferably lower than about 1 µM, and most preferably less than about 0.5 µM or even lower. The term "KDR specificity" refers to a KDR binding moiety having a higher affinity for KDR than an irrelevant target. The term "VEGF/KDR specificity" refers to a VEGF/KDR complex binding moiety having a higher affinity for a VEGF/KDR complex than an irrelevant target. In a preferred embodiment, heteromultimers according to the present invention are specific for KDR or the VEGF/KDR complex, and preferably have a dissociation constant that is lower than about 10 µM, more preferably less than about 1 µM, most preferably less than about 0.5 µM or even lower. The term "cMet specificity" refers to a cMet binding moiety having a higher affinity for cMet than an irrelevant target. The term "cMet/HGF specificity" refers to a cMet/HGF complex binding moiety having a higher affinity for a cMet/HGF complex than an irrelevant target. In a preferred embodiment, binding heteromultimers according to the present invention are specific for cMet or the cMet/HGF complex, and preferably have a dissociation constant that is lower than about 10 μM, more preferably less than about 1 μM, most preferably less than about 0.5 μM or even lower.

The term "patient" as used herein refers to any mammal, especially humans.

The term "pharmaceutically acceptable" carrier or excipient refers to a non-toxic carrier or excipient that may be administered to a patient, together with a compound of this invention, and which does not destroy the pharmacological activity thereof.

The term "target" or "target molecule" refers to any substance that a binding moiety or binding polypeptide can bind to, such as proteins or polypeptides, cells, receptors, carbohydrates, lipids, etc. As used herein, "target" also includes a family of receptors, such as, for example, protein-tyrosine kinase receptors.

The terms "therapeutic agent" or "therapeutic" refer to a compound or an agent having a beneficial, therapeutic or cytotoxic effect in vivo. Therapeutic agents include those compositions referred to as, for example, bioactive agents, cytotoxic agents, drugs, chemotherapy agents, radiotherapeutic agents, genetic material, etc.

The following common abbreviations are used throughout this specification: 9-fluorenylmethyloxycarbonyl (fmoc or Fmoc), 1-hydroxybenozotriazole (HOBt), N,N'-diisopropylcarbodiimide (DIC), acetic anhydride (AC$_2$O), (4,4-dimethyl-2,6-dioxocyclohex-1-ylidene)-3-methylbutyl (ivDde), trifluoroacetic acid (TFA), Reagent B (TFA:H$_2$O:phenol:triisopropylsilane, 88:5:5:2), N,N-diisopropylethylamine (DIEA), O-(1H-benzotriazole-1-yl)-N,N,N',N'-tetramethyluronium hexafluorophosphate (HBTU),O-(7-azabenzotriazol-1-yl)-1,1,3,3-tetramethyluronium hexafluorphosphate (HATU), N-hydroxysuccinimide (NHS), solid phase peptide synthesis (SPPS), dimethyl sulfoxide (DMSO), dichloromethane (DCM), dimethylformamide (DMF), and N-methylpyrrolidinone (NMP).

(i) Dimeric and Multimeric Targeting Constructs of the Invention

The targeting constructs of the invention include two or more binding moieties which bind to different binding sites of a single target. The binding moieties are specific for different sites on the same target. They may be peptidic, peptidomimetic, etc and include binding polypeptides as ddefined herein. Additionally, binding moieties include small binding molecules. In a preferred embodiment the binding moieties comprise binding polypeptides. These targeting constructs are by definition dimeric or multimeric and may be referred to as "multivalent targeting constructs," "heterodimers," "heteromultimers," or "heteromers." These dimeric or multimeric constructs exhibit improved binding, as compared to a monomeric construct. Where the constructs comprise binding polypeptides, the polypeptide sequences may be attached at their N- or C-terminus or the N-epsilon nitrogen of a suitably placed lysine moiety (or another function bearing a selectively derivatizable group such as a pendant oxyamino or other nucleophilic group), or may be joined together via one or more linkers employing the appropriate attachment chemistry. This coupling chemistry may include amide, urea, thiourea, oxime, or aminoacetylamide (from chloro or bromo acetamide derivatives), but is not so limited.

Figure 37:
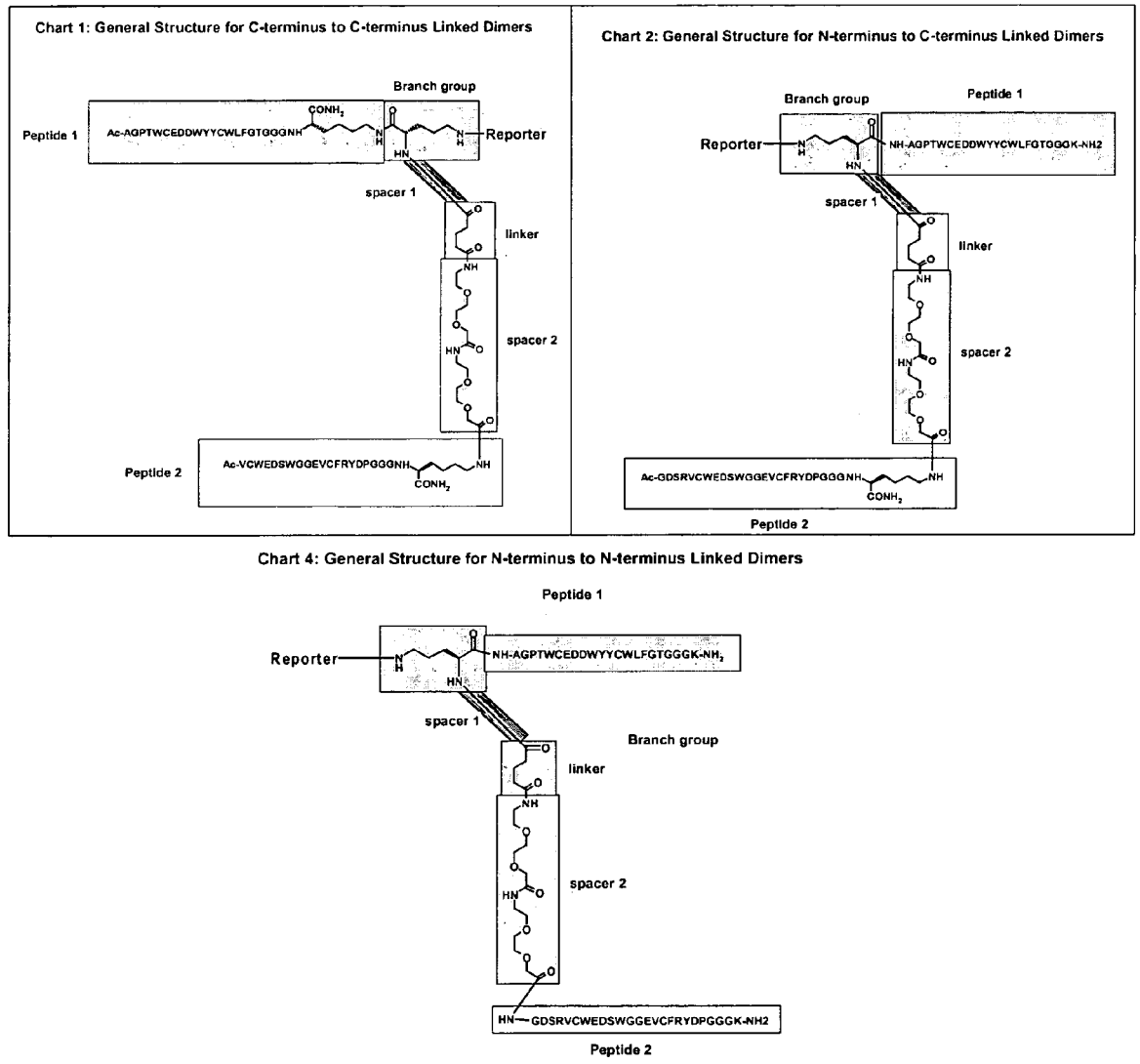
FIG. 37 shows examples of (A) a C-terminus to C-terminus linked dimer, (B) an N-terminus to C-terminus linked dimer, and (C) an N-terminus to N-terminus linked dimer.

Preferred dimers according to the invention can be constructed by connecting a first binding peptide to a branching group to a first spacer to a linker to second spacer and finally to the second binding peptide. This linking scheme for the dimers can be represented by the following general structure:

A-B-C-D-E-F where A and F are two different binding peptides which bind to different sites on the same target, B is a branch group, C and E are spacers, and D is a linker. Suitable spacers and linkers are known in the art and are also provided in the Examples below. In various embodiments, C, D and/or E may optionally be absent. A reporter moiety or similar group may optionally be attached to the dimer via the branch group. The exact arrangement of these components can vary depending, for example, on whether the peptides are linked from C-terminus to C-terminus, from N-terminus to C-terminus, or from N-terminus to N-terminus. Examples of these different attachment schemes are shown in FIG. 37.

The preparation of dimeric constructs bearing two different binding peptides (or two molecules of a particular peptide) and a labelling group may be accomplished as described herein, as well as by other methods known in the art. For example, fully protected binding peptides can be built up on Ellman-type safety catch resin using automated or manual Fmoc peptide synthesis protocols. See Backes, B. J., et al., *J. Am. Chem. Soc.* (1996), 118(12), 3055–6, which is hereby incorporated by reference in its entirety. Separately, using standard methods known in the art of peptide synthesis (see, e.g., Fields, G. B. et al., "Principles and Practice of Solid Phase Synthesis" in Synthetic Peptides, A Users Guide, Grant, G. A. ed., W.H. Freeman Co. NY. 1992, Chap. 3 pp 77–183, which is hereby incorporated by reference in its entirety), a di-lysine derivative can be constructed on 2-chlorotrityl resin. See Barlos, K. and Gatos, D. "Convergent Peptide Synthesis" in Fmoc Solid Phase Peptide Synthesis, Chan, W. C. and White, P. D. eds, Oxford University Press, New York, 2000, Chap 9: pp 215–228, which is hereby incorporated by reference in its entirety. Liberation of this derivative from the 2-chlorotrityl resin without removal of the side-chain protecting groups, activation of the carboxyl group, and coupling to any amine-functionalized labelling group provides a di-lysine derivative whose protected pendant nitrogen atoms may be unmasked to give two free amino groups. The aforementioned safety-catch resin is activated and the desired N-deprotected labelling group-functionalized di-lysine derivative is added to the activated safety-catch resin. The pendant amino groups are acylated by the carboxy-terminus of the safety-catch resin-bound peptide which is now detached from the resin and an integral part of the di-lysine structure. An excess of the safety-catch resin-bound peptide can be employed to insure complete reaction of the amino groups of the di-lysine construct. Optimization of the ratio of the reacting partners in this scheme optimizes the yield. The protecting groups on the binding peptides are removed employing trifluoroacetic acid based cleavage protocols.

For example, the synthesis of dimeric and multimeric constructs wherein two or more binding peptides are present in one construct is easily accomplished. Orthogonal protection schemes (such as an allyloxycarbonyl group on one nitrogen and an Fmoc group on the other, or employing the Fmoc group in conjunction with the iV-Dde protecting group on the other, for example) can be employed to distinguish the pendant nitrogen atoms of the di-lysine derivatives described above. Unmasking of one of the amino groups, followed by reaction of the resulting product with an activated safety-catch resin-bound binding peptide as described above, provides a di-lysine construct having a single binding peptide attached. Removal of the second protecting group unmasks the remaining nitrogen. See, e.g., Mellor, S. L. et al. "Synthesis of Modified Peptides" in Fmoc Solid Phase Peptide Synthesis, Chan, W. C. and White, P. D. eds, Oxford University Press, New York, 2000, Chap 6: pp 169–176, which is hereby incorporated by reference in its entirety. The resulting product may be reacted with a second safety-catch resin bearing a different binding peptide to provide a fully-protected heterodimeric construct, which after removal of protecting groups with trifluoroacetic acid, provides the desired material.

Alternatively, a binding peptide is first assembled on a Rink-amide resin by automated or manual peptide coupling methods, usually employing Fmoc peptide synthesis protocols. The peptide may possess a C-terminus or N-terminus functionalized with a linker or a linker-labelling group construct that may possess an additional nucleophilic group such as the $N^\epsilon$-amino group of a lysine moiety, for example. Cleavage of the protecting groups is accomplished by employing trifluoroacetic acid with appropriate modifiers, depending on the nature of the peptide. The fully deprotected peptide is then reacted with a large excess of a bifunctional electrophile such as glutaric acid bis-N-hydroxysuccinimide ester (commercially available from Tyger Scientific Inc., 324 Stokes Avenue, Ewing, N.J., 08638). The resulting monoamidated, mono-N-hydroxysuccinimidyl ester of glutaric acid is then treated with an additional equivalent of the same peptide, or an equivalent of a different binding peptide. Purification of the resulting material by HPLC affords the desired homo- or hetero-dimeric construct bearing a suitable labelling group.

In yet another approach, a modular scheme can be employed to prepare dimeric or higher multimeric constructs bearing suitable labelling groups as defined above. In a simple illustration, fmoc-lysine(iV-Dde) Rink amide resin is treated with piperidine to remove the fmoc moiety. Then a labelling function, such as biotin, 5-carboxyfluorescein or N,N-Dimethyl-Gly-Ser(O-t-Bu)-Cys(Acm)-Gly-OH is coupled to the nitrogen atom. The resin is next treated with hydrazine to remove the iV-Dde group. After thorough washing, the resin is treated with cyanuric chloride and a hindered base such as diisopropylethylamine in a suitable solvent such as DMF, NMP or dichloromethane to provide a monofunctionalized dichlorotriazine bound to the resin. Subsequent successive displacement of the remaining chlorine atoms either by two equivalents of a binding peptide or one equivalent of a binding peptide, followed by a second binding peptide provides a resin-bound, hetero- or homo-dimeric, labelling group-functionalized construct. See, e.g., Falorni, M., et al., *Tetrahedron Lett.* (1998), 39(41), 7607–7610; Johnson, C. R., et al., Tetrahedron (1998), 54(16), 4097–4106; Stankova, M. and Lebl, M., *Mol. Diversity* (1996), 2(1/2), 75–80.

As appropriate, the incoming peptides may be protected or unprotected as the situation warrants. Cleavage of protecting groups is accomplished employing trifluoroacetic acid-based deprotection reagents as described above and the desired materials are purified by high performance liquid chromatography.

It is understood that in each of these methods, lysine derivatives, ornithine, or 2,3-diamino propionic acid may be serially employed to increase the multiplicity of the multimers. The use of related, more rigid molecules bearing the requisite number of masked, or orthogonally protected nitrogen atoms to act as scaffolds, to vary the distance between the binding peptides, and to increase the rigidity of the construct (by constraining the motion and relative positions of the binding peptides relative to each other and the reporter) is entirely within the scope of the synthetic methods described herein.

Direct synthesis of the binding polypeptides may be accomplished using conventional techniques, including solid-phase peptide synthesis, solution-phase synthesis, etc. Solid-phase synthesis is preferred. See Stewart et al., *Solid-Phase Peptide Synthesis* (1989), W.H. Freeman Co., San Francisco; Merrifield, *J. Am. Chem. Soc.*, 85:2149–2154 (1963); Bodanszky and Bodanszky, *The Practice of Peptide Synthesis* (Springer-Verlag, New York 1984), incorporated herein by reference. Polypeptides of the invention may also be prepared commercially by companies providing peptide synthesis as a service (e.g., BACHEM Bioscience, Inc., King of Prussia, Pa.; Quality Controlled Biochemicals, Inc., Hopkinton, Mass.). Automated peptide synthesis machines, such as manufactured by Perkin-Elmer Applied Biosystems, also are available.

The polypeptide compound is preferably purified once it has been isolated or synthesized by either chemical or recombinant techniques. For purification purposes, there are many standard methods that may be employed, including reverse-phase high-pressure liquid chromatography (RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide may be determined by various methods, including identification of a major large peak on HPLC. A polypeptide that produces a single peak that is at least 95% of the input material on an HPLC column is preferred. Even more preferable is a polypeptide that produces a single peak that is at least 97%, at least 98%, at least 99% or even 99.5% or more of the input material on an HPLC column.

To ensure that the peptide obtained using any of the techniques described above is the desired peptide for use in compositions of the present invention, analysis of the peptide composition may be carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine the sequence of the peptide.

For example, binding polypeptides also may be produced using recombinant DNA techniques, utilizing nucleic acids (polynucleotides) encoding the polypeptides of the invention, and then expressing them recombinantly, i.e., by manipulating host cells by introduction of exogenous nucleic acid molecules in known ways to cause such host cells to produce the desired binding polypeptides. Such procedures are within the capability of those skilled in the art (see Davis et al., *Basic Methods in Molecular Biology*, (1986)), which is hereby incorporated by reference in its entirety. Recombinant production of short peptides such as those described herein may not be practical in comparison to direct synthesis, however recombinant means of production may be very advantageous where a binding moiety of this invention is incorporated in a hybrid polypeptide or fusion protein.

In the practice of one embodiment of the present invention, a determination of the affinity of the heteromultimer or a constituent binding moiety for the target relative to another protein or target is a useful measure, and is referred to as affinity for the target. Standard assays for quantitating binding and determining affinity include equilibrium dialysis, equilibrium binding, gel filtration, or the monitoring of numerous spectroscopic changes (such as a change in fluorescence polarization) that may result from the interaction of the binding moiety and its target. These techniques or modifications thereof measure the concentration of bound and free ligand as a function of ligand (or protein) concentration. The concentration of bound heteromultimer or polypeptide ([Bound]) is related to the concentration of free heteromultimer or polypeptide ([Free]) and the concentration of binding sites for the polypeptide, i.e., on KDR, VEGF/KDR complex, cMet, or the cMet/HGF complex (N), as described in the following equation:

$$[Bound] = N \times [Free]/((1/K_a) + [Free]).$$

A solution of the data to this equation yields the association constant, $K_a$, a quantitative measure of the binding affinity. The association constant, $K_a$ is the reciprocal of the dissociation constant, $K_D$. The $K_D$ is more frequently reported in measurements of affinity. In a preferred embodiment heteromultimers of the invention and constituent binding polypeptides bind to the target, e.g. KDR, VEGF/KDR complex, cMet or cMet/HGF and have a $K_D$ for the target in the range of 1 nanomolar (nM) to 100 micromolar (μM) and preferably have $K_D$ values less than 50 μM, preferably less than 1 μM, more preferably less than 50 nM, and most preferably less than 10 nM.

Where heteromultimers are employed as imaging agents, other aspects of binding affinity may become more important. For example, such imaging agents operate in a dynamic system in that binding of the imaging agent to the target (such as KDR or VEGF/KDR complex, e.g., on activated endothelium) is not in a stable equilibrium state throughout the imaging procedure. For example, when the imaging agent is initially injected, the concentration of imaging agent and of agent-target complex rapidly increases. Shortly after injection, however, the circulating (free) imaging agent starts to clear through the kidneys or liver, and the plasma concentration of imaging agent begins to drop. This drop in the concentration of free imaging agent in the plasma eventually causes the agent-target complex to dissociate. The usefulness of an imaging agent depends on the difference in rate of agent-target dissociation relative to the clearing rate of the agent. Ideally, the dissociation rate will be slow compared to the clearing rate, resulting in a long imaging time during which there is a high concentration of agent-target complex and a low concentration of free imaging agent (background signal) in the plasma.

An advantage of heteromultimeric binding compounds, such as those of the present invention, is that they generally possess very slow dissociation rates relative to their constituent monomers (see Tissot et al., J. Immunol. Methods 236(1–2):147–165 (2000)). In addition, heteromultimeric compounds capable of binding to two distinct epitopes on a target molecule simultaneously can achieve multimeric binding regardless of the distance between target molecules on the cell surface. Homomultimeric binding compounds, on the other hand, depend on the presence of two or more target molecules being in close enough proximity such that the homomultimer can span the distance between them. Thus, the heteromultimeric binding compounds of the present invention are particularly well suited for binding to receptors and other cell surface molecules that are less abundant and therefore more distant from each other on the cell surface.

Quantitative measurement of dissociation rates may be easily performed using several methods known in the art, such as fiber optic fluorimetry (see, e.g., Anderson and Miller, Clin. Chem., 34(7):1417–21 (1988)), surface plasmon resonance (see, Malmborg et al., J. Immunol. Methods, 198(1):51–7 (1996) and Schuck, Current Opinion in Biotechnology, 8:498–502 (1997)), resonant mirror, and grating coupled planar waveguiding (see, e.g., Hutchinson, Molec. Biotechnology, 3:47–54 (1995)). Automated biosensors are commercially available for measuring binding kinetics: BIAcore surface plasmon resonance sensor (Biacore AB, Uppsala SE), IAsys resonant mirror sensor (Fisons Applied Sensor Technology, Cambridge GB), BIOS-1 grated coupled planar waveguiding sensor (Artificial Sensor Instruments, Zurich CH).

(ii) Modification or Optimization of Binding Polypeptides

Modification or optimization of heteromultimers is within the scope of the present invention. In particular, modified or optimized heteromultimers are included within the definition of "heteromultimers". Similarly, modified or optimized binding polypeptides are included within the definition of "binding polypeptides" and the phrase "KDR and VEGF/KDR complex binding polypeptides" includes modified or optimized KDR and VEGF/KDR binding polypeptides, and the phrase "cMet and cMet/HGF complex binding polypeptides" includes modified or optimized cMet and cMet/HGF binding polypeptides. Specifically, a polypeptide sequence for use in the heteromultimers of the invention can be modified to optimize its potency, pharmacokinetic behavior, stability and/or other biological, physical and chemical properties.

Substitution of Amino Acid Residues

Susbtitutions of amino acids within the same class (e.g., substituting one basic amino acid for another) are well known in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: Including alanine, leucine, isoleucine, valine, norleucine, S-2-aminobutyric acid, S-cyclohexylalanine or other simple alpha-amino acids substituted by an aliphatic side chain from 1–10 carbons including branched, cyclic and straight chain alkyl, alkenyl or alkynyl substitutions.

Substitution of aromatic-substituted hydrophobic amino acids: Including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy (from $C_1$–$C_4$)-substituted forms of the previous listed aromatic amino acids, illustrative examples of which are: 2-, 3-, or 4-aminophenylalanine, 2-, 3-, or 4-chlorophenylalanine, 2-, 3-, or 4-methylphenylalanine, 2-, 3-, or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-2-, 3- or 4-biphenylalanine, and 2- or 3-pyridylalanine.

Substitution of amino acids containing basic functions: Including arginine, lysine, histidine, ornithine, 2,3-diaminopropionic acid, homoarginine, alkyl, alkenyl, or aryl-substituted (from $C_1$–$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: Including aspartic acid, glutamic acid, homoglutamic acid, tyrosine, alkyl, aryl, aralkyl, and heteroaryl sulfonamides of 2,3-diaminopropionic acid, ornithine or lysine and tetrazole-substituted alkyl amino acids.

Substitution of side chain amide residues: Including asparagine, glutamine, and alkyl or aromatic substituted derivatives of asparagine or glutamine.

Substitution of hydroxyl containing amino acids: Including serine, threonine, homoserine, 2,3-diaminopropionic acid, and alkyl or aromatic substituted derivatives of serine or threonine.

It is also understood that the amino acids within each of the categories listed above may be substituted for another of the same group.

Substitution of Amide Bonds

Another type of modification within the scope of the invention is the substitution of amide bonds within the backbone of a binding polypeptide. For example, to reduce or eliminate undesired proteolysis, or other degradation pathways which diminish serum stability, resulting in reduced or abolished bioactivity, or to restrict or increase conformational flexibility, it is common to substitute amide bonds within the backbone of the peptides with functionality that mimics the existing conformation or alters the conformation in the manner desired. Such modifications may produce increased binding affinity or improved pharmacokinetic behavior. It is understood that those knowledgeable in the art of peptide synthesis can make the following amide bond changes for any amide bond connecting two amino acids with the expectation that the resulting peptides could have the same or improved activity: insertion of alpha-N-methylamides or peptide amide backbone thioamides, removal of the carbonyl to produce the cognate secondary amines, replacement of one amino acid with an aza-aminoacid to produce semicarbazone derivatives, and use of E-olefins and substituted E-olefins as amide bond surrogates.

Introduction of D-Amino Acids

Another approach within the scope of the invention is the introduction of D-alanine, or another D-amino acid, distal or proximal to a labile peptide bond. In this case it is also understood to those skilled in the art that such D-amino acid substitutions can, and at times, must be made, with D-amino acids whose side chains are not conservative replacements for those of the L-amino acid being replaced. This is because of the difference in chirality and hence side-chain orientation, which may result in the accessing of a previously unexplored region of the binding site of the target which has moieties of different charge, hydrophobicity, steric requirements, etc., than that serviced by the side chain of the replaced L-amino acid.

Modifications to Improve Pharmacokinetic or Pharmacodynamic Properties

It is also understood that use of the heteromultimeric constructs of the invention in a particular application may necessitate modifications of the peptide or formulations of the peptide to improve pharmacokinetic and pharmacodynamic behavior. It is expected that the properties of the peptide may be changed by attachment of moieties anticipated to bring about the desired physical or chemical properties. Where the heteromultimer includes binding polypeptides, such moieties affecting the pharmacokinetic and pharmacodynamic behavior may be appended to the peptide using acids or amines, via amide bonds or urea bonds, respectively, to the N- or C-terminus of the peptide, or to the pendant amino group of a suitably located lysine or lysine derivative, diaminopropionic acid, ornithine, or other amino acid in the peptide that possesses a pendant amine group or a pendant alkoxyamino or hydrazine group. The moieties introduced may be groups that are hydrophilic, basic, or nonpolar alkyl or aromatic groups depending on the peptide of interest and the extant requirements for modification of its properties.

Glycosylation of Amino Acid Residues

Yet another modification within the scope of the invention is to employ glycosylated amino acid residues (e.g. serine, threonine or asparagine residues), singly or in combination in the either the binding or the linker moiety or both. Glycosylation, which may be carried out using standard conditions, may be used to enhance solubility, alter pharmacokinetics and pharmacodynamics or to enhance binding via a specific or non-specific interaction involving the glycosidic moiety. In another approach glycosylated amino acids such as O-(2-acetamido-2-deoxy-3,4,6-tri-O-acetyl-β-D-glucopyranosyl) serine or the analogous threonine derivative (either the D- or L-amino acids) may be incorporated into the peptide during manual or automated solid phase peptide synthesis, or in manual or automated solution phase peptide synthesis. Similarly D- or L-$N^\gamma$-(2-acetamido-2-deoxy-3,4,6-tri-O-acetyl-β-D-glucopyranosyl)-asparagine can be employed. The use of amino acids glycosylated on a pendant oxygen, nitrogen or sulfur function by the agency of suitably functionalized and activated carbohydrate moieties that can be employed in glycosylation is anticipated. Such carbohydrate functions could be monosaccharides, disaccharides or even larger assemblies of oligosaccharides (Kihlberg, January (2000) Glycopeptide synthesis. In: Fmoc Solid Phase Peptide Synthesis—A Practical Approach (Chan, W. C. and White, P. D. Eds) Oxford University Press, New York, N.Y. Chap. 8, pp 195–213).

Also anticipated is the appendage of carbohydrate functions to amino acids by means other than glycosylation via activation of a leaving group at the anomeric carbon. Linkage of the amino acid to the glycoside is not limited to the formation of a bond to the anomeric carbon of the carbohydrate function. Instead, linkage of the carbohydrate moiety to the amino acid could be through any suitable, sufficiently reactive oxygen atom, nitrogen atom, carbon atom or other pendant atom of the carbohydrate function via methods employed for formation of C-heteroatom, C—C or heteroatom-heteroatom (examples are S—S, O—N, N—N, P—O, P—N) bonds known in the art.

Formation of Salts

It is also within the scope of the invention to form different salts that may increase the water solubility or the ease of formulation of these peptides. These may include, but are not restricted to, N-methylglucamine (meglumine), acetate, oxalates, ascorbates etc.

Structural Modifications which Retain Structural Features

Yet another modification within the scope of the invention is truncation of cyclic polypeptides. The cyclic nature of many polypeptides of the invention limits the conformational space available to the peptide sequence, particularly within the cycle. Therefore truncation of the peptide by one or more residues distal or even proximal to the cycle, at either the N-terminal or C-terminal region may provide truncated peptides with similar or improved biological activity. A unique sequence of amino acids, even as small as three amino acids, which is responsible for the binding activity, may be identified, as noted for RGD peptides. See e.g., E. F. Plow et al., Blood (1987), 70(1), 110–5; A. Oldberg et al., Journal of Biological Chemistry (1988), 263(36), 19433–19436; R. Taub et al., Journal of Biological Chemistry (1989 Jan. 5), 264(1), 259–65; A. Andrieux et al., Journal of Biological Chemistry (1989 Jun. 5), 264(16), 9258–65; and U.S. Pat. Nos. 5,773,412 and 5,759,996, each of which is incorporated herein by reference in its entirety.

It has also been shown in the literature that large peptide cycles can be substantially shortened, eliminating extraneous amino acids, but substantially including the critical binding residues. See U.S. Pat. No. 5,556,939, which is incorporated herein by reference in its entirety. Shortened cyclic peptides can be formed using disulfide bonds or amide bonds of suitably located carboxylic acid groups and amino groups.

Furthermore, D-amino acids can be added to the peptide sequence to stabilize turn features (especially in the case of glycine). In another approach alpha, beta, gamma or delta dipeptide or turn mimics (such as α, β, γ, or δ turn mimics) some of which are shown in structures 1, 2 and 3, below, can be employed to mimic structural motifs and turn features in a peptide and simultaneously provide stability from proteolysis and enhance other properties such as, for example, conformational stability and solubility (structure 1: Hart et al., *J. Org. Chem.*, 64, 2998–2999(1999); structure 2: Hanessian et al., "Synthesis of a Versatile Peptidomimetic Scaffold" in *Methods in Molecular Medicine*, Vol. 23: Peptidomimetics Protocols, W. M. Kazmierski Ed. (Humana Press Inc. Totowa N.J. 1999), Chapter 10, pp. 161–174; structure 3: WO 01/16135.

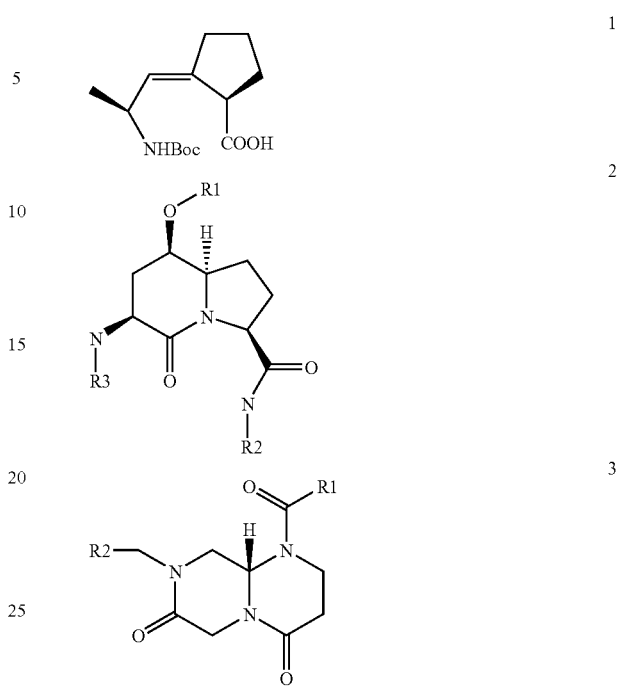

Substitution of Disulfide Mimetics

Also included within the scope of the invention is the substitution of disulfide mimetics for disulfide bonds within the binding polypeptides of the invention. When disulfide-containing peptides are employed in generating heteromultimeric constructs, the disulfide bonds might need to be replaced to avoid certain difficulties that are sometimes posed by the presence of a disulfide bond. For example, when generating heteromultimeric $^{99m}$Tc (or other radionuclide)-based radiopharmaceuticals or certain other hetermultimeric constructs the presence of the disulfide bond can be a significant problem. The integrity of the disulfide bond is difficult to maintain during procedures designed to incorporate $^{99m}$Tc via routes that are reliant upon the reduction of pertechnetate ion and subsequent incorporation of the reduced Tc species into substances bearing Tc-compatible chelating groups. This is because the disulfide bond is rather easily reduced by the reducing agents commonly used in kits devised for one-step preparation of radiopharmaceuticals. Therefore, the ease with which the disulfide bond can be reduced during Tc chelation may require substitution with mimetics of the disulfide bonds. Accordingly, another modification within the scope of the invention is to substitute the disulfide moiety with mimetics, utilizing the methods disclosed herein or known to those skilled in the art, while retaining the activity and other desired properties of the binding polypeptides used in the invention:

1.) Oxime Linker

The oxime moiety has been employed as a linker by investigators in a number of contexts. Of the most interest is the work by Wahl, F and Mutter, M, *Tetrahedron Lett.* (1996) 37, 6861–6864). The amino acids containing an aminoalcohol function (4), and containing an alkoxyamino function (5), are incorporated into the peptide chain, not necessarily at the end of the peptide chain. After formation of the peptide, the sidechain protecting groups are removed. The aldehyde group is unmasked and an oxime linkage is formed.

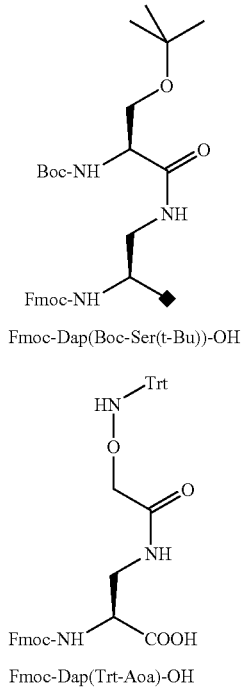

Fmoc-Dap(Boc-Ser(t-Bu))-OH

Fmoc-Dap(Trt-Aoa)-OH

2.) Lanthionine Linker

Lanthionines are cyclic sulfides, wherein the disulfide linkage (S—S) is replaced by a (C—S) linkage. Thus the lability to reduction is far lower and this linkage should be stable to stannous chloride. Lanthionines may be prepared by a number of methods.

Preparation of Lanthionines Using Bromoacetylated Peptides

Lanthionines are readily prepared using known methods. See, for example, Robey et al. (Robey, F. A. and Fields, R. L. Anal. Biochem. (1989) 177, 373–377) and Inman, et al. (Inman, J. K.; Highet, P. F.; Kolodny, N.; and Robey, F. A. Bioconjugate Chem. (1991) 2, 458–463; Ploinsky, A. Cooney, M. C. Toy-Palmer, A. Osapay, G. and Goodman, M. J. Med. Chem. (1992) 35, 4185–4194; Mayer, J. P.; Zhang, J.; and Liu, C. F. in: Tam, J. P. and Kaumaya, P. T. P. (eds), "Peptides, Frontiers of Peptide Science," Proceedings of the 15$^{th}$ American Peptide Symposium, June 14–19 Nashville, Tenn. Klumer Academic Pub. Boston. pp 291–292;. Wakao, Norihiro; Hino, Yoichi; Ishikawa, Ryuichi. Jpn. Kokai Tokkyo Koho (1995), 7 pp. JP 07300452 A2 19951114 Heisei; JP 95-49692 19950309; JP 94-41458 19940311 have published in this area. Preparation of peptides using Boc automated peptide synthesis followed by coupling the peptide terminus with bromoacetic acid gives bromoacetylated peptides in good yield. Cleavage and deprotection of the peptides is accomplished using HF/anisole. If the peptide contains a cysteine group its reactivity can be controlled with low pH. If the pH of the medium is raised to 6–7, then either polymerization or cyclization of the peptide takes place. Polymerization is favored at high (100 mg/mL) concentration, whereas cyclization is favored at lower concentrations (1 mg/mL), e.g., in Scheme 1 below, 6 cyclizes to 7.

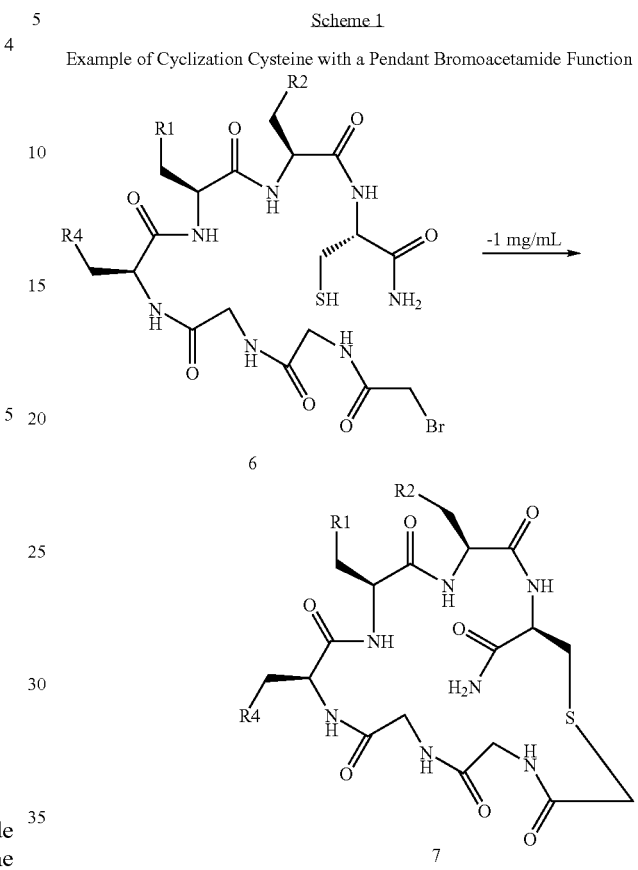

Scheme 1

Example of Cyclization Cysteine with a Pendant Bromoacetamide Function

Inman et al. demonstrated the use of $N^{\alpha}$-(Boc)-$N^{\epsilon}$-[N-(bromoacetyl)-β-alanyl]-L-lysine as a carrier of the bromoacetyl group that could be employed in Boc peptide synthesis thus allowing placement of a bromoacetyl bearing moiety anywhere in a sequence. In preliminary experiments they found that peptides with 4–6 amino acids separating the bromoacetyl-lysine derivative from a cysteine tend to cyclize, indicating the potential utility of this strategy.

Preparation of Lanthionines Via Cysteine Thiol Addition to Acrylamides

Several variants of this strategy may be implemented. Resin-bound serine can be employed to prepare the lanthionine ring on resin either using a bromination-dehydrobromination-thiol addition sequence or by dehydration with disuccinimidyl carbonate followed by thiol addition. Ploinsky et al., *M. J. Med. Chem.*, 35:4185–4194 (1992); Mayer et al., "Peptides, Frontiers of Peptide Science", in *Proceedings of the 15$^{th}$ American Peptide Symposium*, Tam & Kaumaya (eds), Jun. 14–19, 1995, Nashville, Tenn. (Klumer Academic Pub. Boston) pp. 291–292. Conjugate addition of thiols to acrylamides has also been amply demonstrated and a reference to the addition of 2-mercaptoethanol to acrylamide is provided. Wakao et al., Jpn. Kokai Tokkyo Koho, JP 07300452 A2 (1995).

3.) Diaryl Ether or Diarylamine Linkage

Diaryl Ether Linkage From Intramolecular Cyclization of Aryl Boronic Acids and Tyrosine The reaction of arylboronic acids with phenols, amines and heterocyclic amines in the presence of cupric acetate, in air, at ambient temperature, in dichloromethane using either pyridine or triethylamine as a base to provide unsymmetrical diaryl ethers and the related amines in good yields (as high as 98%) has been reported. See, Evans et al., *Tetrahedron Lett.*, 39:2937–2940 (1998); Chan et al., *Tetrahedron Lett.*, 39:2933–2936 (1998); Lam et al., *Tetrahedron Lett.*, 39:2941–2944 (1998). In the case of N-protected tyrosine derivatives as the phenol component the yields were also as high as 98%. This demonstrates that amino acid amides (peptides) are expected to be stable to the transformation and that yields are high. Precedent for an intramolecular reaction exists in view of the facile intramolecular cyclizations of peptides to lactams, intramolecular biaryl ether formation based on the $S_NAR$ reaction and the generality of intramolecular cyclization reactions under high dilution conditions or on resin, wherein the pseudo-dilution effect mimics high dilution conditions.

4.) Formation of Cyclic Peptides with a Lactam Linkage Via Intramolecular Native Chemical Ligation Scheme 2

Formation of Cyclic Peptides with a Thiazolidine Linkage via Intramolecular Reaction of Peptide Aldehydes with Cysteine Moieties

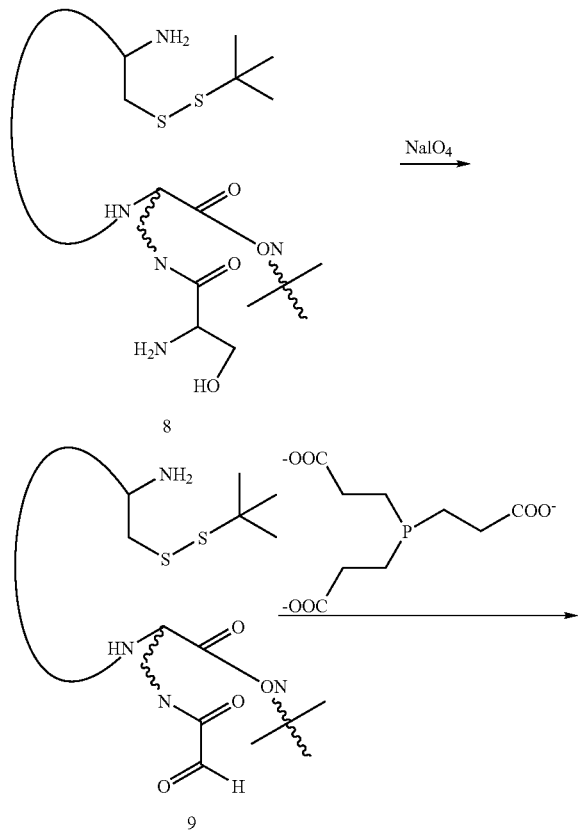

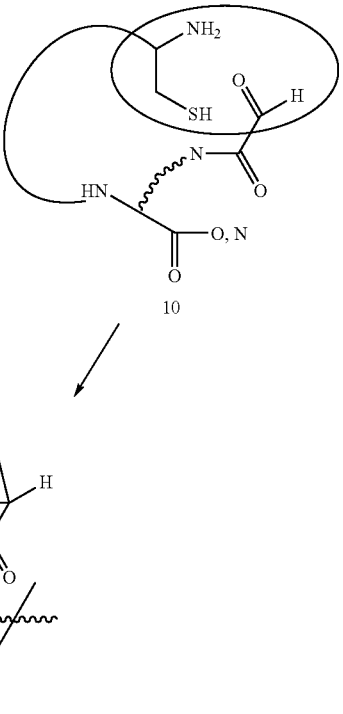

Another approach that may be employed involves intramolecular cyclization of suitably located vicinal amino mercaptan functions (usually derived from placement of a cysteine at a terminus of the linear sequence or tethered to the sequence via a side-chain nitrogen of a lysine, for example) and aldehyde functions to provide thiazolidines which result in the formation of a bicyclic peptide, one ring of which is that formed by the residues in the main chain, and the second ring being the thiazolidine ring. Scheme 2, above, provides an example. The required aldehyde function can be generated by sodium metaperiodate cleavage of a suitably located vicinal aminoalcohol function, which can be present as an unprotected serine tethered to the chain by appendage to a side chain amino group of a lysine moiety. In some cases, the required aldehyde function is generated by unmasking of a protected aldehyde derivative at the C-terminus or the N-terminus of the chain. An example of this strategy is found in: Botti, P.; Pallin, T. D. and Tam, J. P. *J. Am. Chem. Soc.* 1996, 118, 10018–10034.

5.) Lactams Based on Intramolecular Cyclization of Pendant Amino Groups with Carboxyl Groups on Resin Macrocyclic peptides can be prepared by lactam formation by either head to tail or by pendant group cyclization. The basic strategy is to prepare a fully protected peptide wherein it is possible to remove selectively an amine protecting group and a carboxy protecting group. Orthogonal protecting schemes have been developed. Of those that have been developed, the allyl, trityl and Dde methods have been employed most. See, Mellor et al., "Synthesis of Modified Peptides," in *Fmoc Solid Phase Synthesis: A Practical Approach*, White and Chan (eds) ([Oxfoerd University Press, N.Y., 2000]), Chapt. 6, pp. 169–178. The Dde approach is of interest because it utilizes similar protecting groups for both the carboxylic acid function (Dmab ester) and the amino group (Dde group). Both are removed with 2–10% hydrazine in DMF at ambient temperature. Alternatively, the Dde can be used for the amino group and the allyl group can be used for the carboxyl.

A lactam function, available by intramolecular coupling via standard peptide coupling reagents (such as HATU, PyBOP etc), could act as a surrogate for the disulfide bond. The Dde/Dmab approach is shown in Scheme 3a, below.

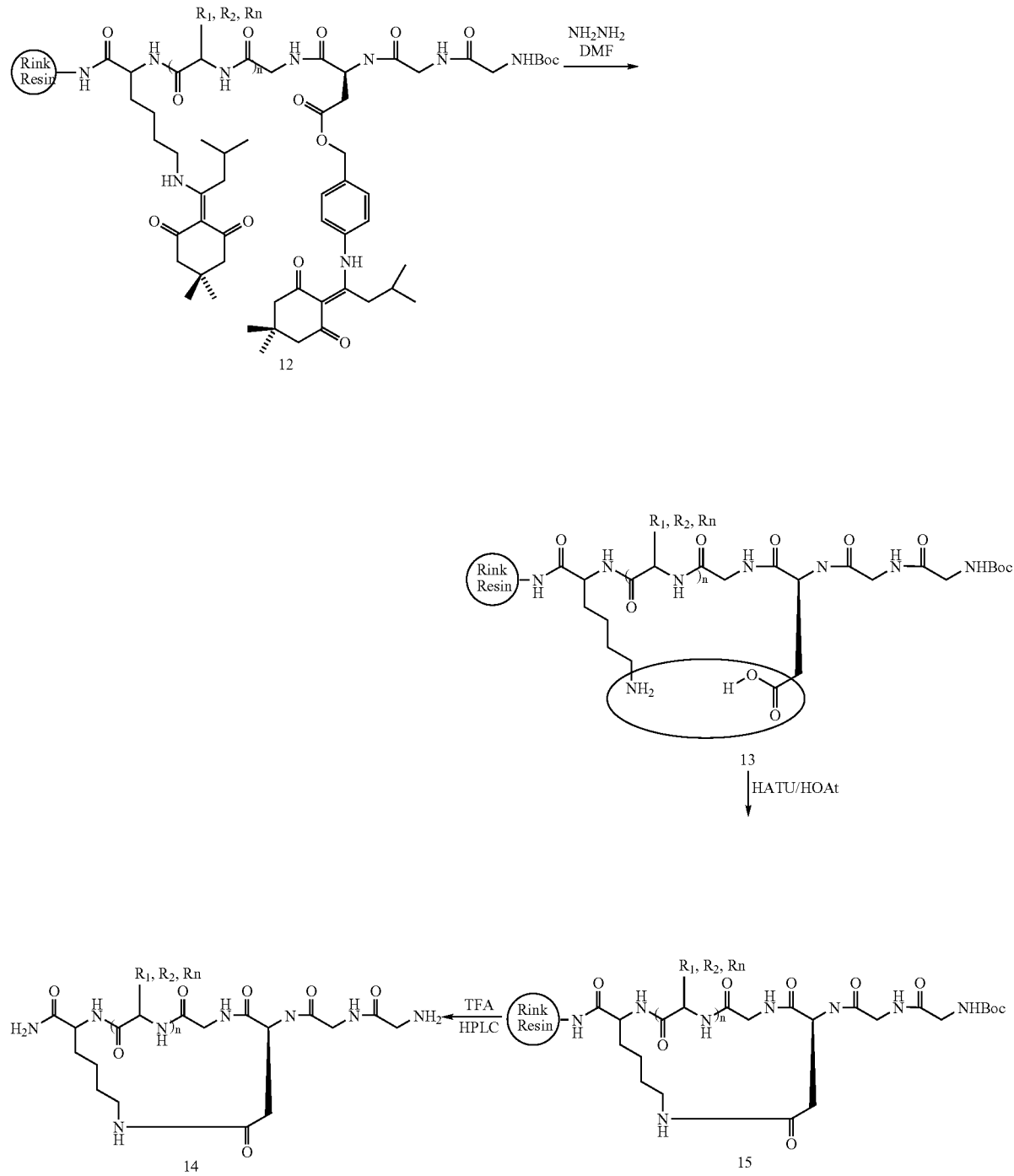

Scheme 3a

Lactam Surrogate for the Disulfide Bond via Quasiorthogonal Deprotection of Lys and Asp Followed by On-Resin Cyclization and Cleacage from Resin Thus, a linear sequence containing, for example, the Dde-protected lysine and Dmab ester may be prepared on a Tentagel-based Rink amide resin at low load (~0.1–0.2 mmol/g). Deprotection of both functions with hydrazine is then followed by on-resin cyclization to give the desired products.

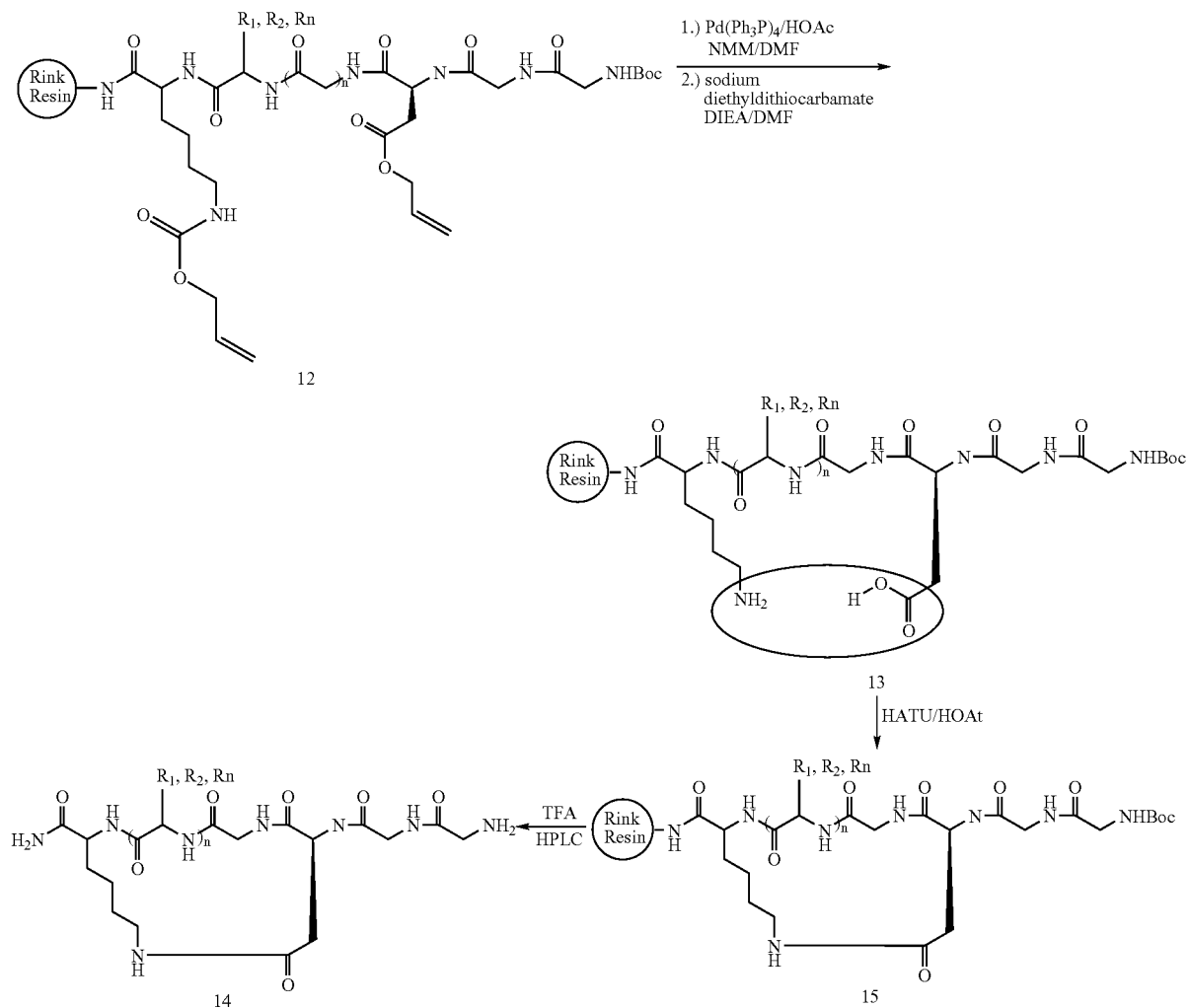

Scheme 3b

Lactam Surrogate for the Disulfide Bond via Quasiorthogonal Deprotection of Lys and Asp Using Allyl-based Protecting Groups Followed by On-Resin Cyclization and Cleavage from Resin In the allyl approach, shown in Scheme 3b, the pendant carboxyl which is to undergo cyclization is protected as an allyl ester and the pendant amino group is protected as an alloc group. On resin, both are selectively unmasked by treatment with palladium tris-triphenylphosphine in the presence of N-methylmorpholine and acetic acid in DMF. Residual palladium salts are removed using sodium diethyldithiocarbamate in the presence of DIEA in DMF, followed by subsequent washings with DMF. The lactam ring is then formed employing HATU/HOAt in the presence of N-methylmorpholine. Other coupling agents can be employed as described above. The processing of the peptide is then carried out as described above to provide the desired peptide lactam.

Subsequently cleavage from resin and purification may also be carried out. For functionalization of the N-terminus of the peptide, it is understood that amino acids, such as trans-4-(iV-Dde)methylaminocyclohexane carboxylic acid, trans-4-(iV-Dde)methylaminobenzoic acid, or their alloc congeners could be employed. Yet another approach is to employ the safety catch method to intramolecular lactam formation during cleavage from the resin.

6.) Cyclic Peptides Based on Olefin Metathesis

The Grubbs reaction (Scheme 4, below) involves the metathesis/cyclization of olefin bonds and is illustrated as shown below. See, Schuster et al., *Angewandte. Chem. Int. Edn Engl.*, 36:2036–2056 (1997); Miller et al., *J. Am. Chem. Soc.*, 118:9606–9614 (1996).

Scheme 4

Grubbs Olefin Methathesis Cyclization

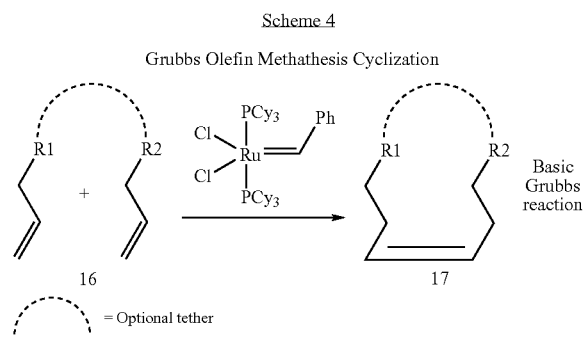

It is readily seen that, if the starting material is a diolefin (16), the resulting product will be cyclic compound 17. The reaction has in fact been applied to creation of cycles from olefin-functionalized peptides. See, e.g., Pemerstorfer et al., *Chem. Commun.*, 20:1949–50 (1997); Covalent capture and stabilization of cylindrical β-sheet peptide assemblies, Clark et al., *Chem. Eur. J*, 5(2):782–792 (1999); Highly efficient synthesis of covalently cross-linked peptide helices by ring-closing metathesis, Blackwell et al., *Angew. Chem., Int. Ed.*, 37(23):3281–3284 (1998); Synthesis of novel cyclic protease inhibitors using Grubbs olefin metathesis, Ripka et al., *Med. Chem. Lett.*, 8(4):357–360 (1998); Application of Ring-Closing Metathesis to the Synthesis of Rigidified Amino Acids and Peptides, Miller et al., *J. Am. Chem. Soc.*, 118(40):9606–9614 (1996); Supramolecular Design by Covalent Capture, Design of a Peptide Cylinder via Hydrogen-Bond-Promoted Intermolecular Olefin Metathesis, Clark et al., *J. Am. Chem. Soc.*, 117(49):12364–12365 (1995); Synthesis of Conformationally Restricted Amino Acids and Peptides Employing Olefin Metathesis, Miller et al., *J. Am. Chem. Soc.*, 117(21):5855–5856 (1995). One can prepare either C-allylated amino acids or possibly N-allylated amino acids and employ them in this reaction in order to prepare carba-bridged cyclic peptides as surrogates for disulfide bond containing peptides.

One may also prepare novel compounds with olefinic groups. Functionalization of the tyrosine hydroxyl with an olefin-containing tether is one option. The lysine ε-amino group may be another option with appendage of the olefin-containing unit as part of an acylating moiety, for example. If instead the lysine side chain amino group is alkylated with an olefin containing tether, it can still function as a point of attachment for a reporter as well. The use of 5-pentenoic acid as an acylating agent for the lysine, ornithine, or diaminopropionic side chain amino groups is another possibility. The length of the olefin-containing tether can also be varied in order to explore structure activity relationships.

Manipulation of Peptide Sequences

Other modifications within the scope of the invention include manipulations of peptide sequences which can be expected to yield peptides with similar or improved biological properties. These include amino acid translocations (swapping amino acids in the sequence), use of retroinverso peptides in place of the original sequence or a modified original sequence, peptoids, retro-inverso peptoid sequences, and synthetic peptides. Structures wherein specific residues are peptoid instead of peptidic, which result in hybrid molecules, neither completely peptidic nor completely peptoid, are contemplated as well.

Linkers

Additionally, modifications within the invention include introduction of linkers or spacers between the targeting sequence of the binding moiety or binding polypeptide and the detectable label or therapeutic agent. For example, use of such linkers/spacers may improve the relevant properties of the binding peptides (e.g. increase serum stability, etc.). These linkers may include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio)propionate (Carlsson et al., 1978, Biochem J. 173:723–737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate. Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-5N-hydroxy-succinimide ester.

Furthermore, linkers which are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g. a chemical "warhead" for therapy), or a combination of these.

Uses of Heteromultimeric Constructs

Heteromultimeric constructs of the present invention can be used in a multitude of applications, including immunoassays (e.g., ELISA), as pharmaceuticals useful for treatments of various diseases, as well as in in vivo diagnostic and therapeutic uses. For example, the heteromultimeric constructs described herein will be extremely useful for detection and/or imaging of target containing tissue in vitro or in vivo. For example, KDR or VEGF/KDR complex binding heteromultimeric constructs will be extremely useful for detection and/or imaging of KDR or VEGF/KDR complex containing tissue, and particularly for detection and/or imaging of sites of angiogenesis, in which VEGF and KDR are intimately involved, as explained above. Any suitable method of assaying or imaging KDR or VEGF/KDR complex may be employed. Similarly, cMet or HGF/cMet complex binding heteromultimeric constructs will be extremely useful for detection and/or imaging of cMet or HGF/cMet complex containing tissue, and particularly for detection and/or imaging tumors or other sites of hyperproliferation, in which HGF and cMet are intimately involved, as explained above. Any suitable method of assaying or imaging cMet or HGF/cMet complex may be employed.

The compounds of the invention also have utility in the treatment of a variety of disease states, whether used alone or in combination with another therapeutic agent. For example, as discussed, a compound of the invention that inhibits a biological process that contributes to a disease state may itself be used as a therapeutic or pharmaceutical composition. Alternatively (or in combination), a compound of the invention may include one or more additional therapeutic agents. In one embodiment, the invention includes heteromultimers including KDR or VEGF/KDR complex binding moieties which may themselves be used as therapeutics or may be used to localize one or more therapeutic agents (e.g. a chemotherapeutic, a radiotherapeutic, genetic material, etc.) to KDR expressing cells, including sites of angiogenesis, or those associated with a number of pathogens. In another embodiment, the invention includes heteromultimers including cMet or HGF/cMet complex binding moieties which may themselves be used as therapeutics or may be used to localize one or more therapeutic agents (e.g. a chemotherapeutic, a radiotherapeutic, genetic material, etc.) to cMet expressing cells, including tumors, sites of hyperproliferation or sites of angiogenesis.

The heteromultimeric constructs of the present invention are particularly useful as therapeutic agents for treating conditions that involve endothelial cells. Because an important function of endothelial cells is angiogenesis, or the formation of blood vessels, the heteromultimers of the invention are particularly useful for treating conditions that involve angiogenesis include, for example, solid tumors, tumor metastases and benign tumors. Such tumors and related disorders are well known in the art and include, for example, melanoma, central nervous system tumors, neuroendocrine tumors, sarcoma, multiple myeloma as well as cancer of the breast, lung, prostate, colon, head & neck, and ovaries. Additional tumors and related disorders are listed in Table 1 of U.S. Pat. No. 6,025,331, issued Feb. 15, 2000 to Moses, et al., the teachings of which are incorporated herein by reference. Benign tumors include, for example, hemangiomas, acoustic neuromas, neurofibromas, trachomas, and pyogenic granulomas. Other relevant diseases that involve angiogenesis include for example, rheumatoid arthritis, psoriasis, and ocular disease, such as diabetic retinopathy, retinopathy of prematurity, macular degeneration, corneal graft rejection, neovascular glaucoma, retrolental fibroplasias, rebeosis, Osler-Webber syndrome, myocardial angiogenesis, plaque neovascularization, telangiectasia, hemophiliac joints, angiofibroma and wound granulation. Other relevant diseases or conditions that involve blood vessel growth include intestinal adhesions, atherosclerosis, scleroderma, and hypertropic scars, and ulcers. Furthermore, the heteromultimers of the present invention can be used to reduce or prevent uterine neovascularization required for embryo implantation, for example, as a birth control agent.

For detection of the target in solution, a heteromultimer according to the invention can be detectably labeled, e.g., fluorescently labeled, enzymatically labeled, or labeled with a radionuclide or paramagnetic metal or attached to bubbles, then contacted with the solution, and thereafter formation of a complex between the heteromultimer and the target can be detected. As an example, a fluorescently labeled KDR or VEGF/KDR complex binding heteromultimeric construct may be used for in vitro KDR or VEGF/KDR complex detection assays, wherein the heteromultimeric construct is added to a solution to be tested for KDR or VEGF/KDR complex under conditions allowing binding to occur. The complex between the fluorescently labeled KDR or VEGF/KDR complex binding heteromultimer and KDR or VEGF/KDR complex target can be detected and quantified by measuring the increased fluorescence polarization arising from the KDR or VEGF/KDR complex-bound heteromultimer relative to that of the free heteromultimer. Heteromultimers comprising cMet binding moieties may be used similarly.

Alternatively, a sandwich-type "ELISA" assay may be used, wherein a heteromultimeric construct is immobilized on a solid support such as a plastic tube or well, then the solution suspected of containing the target is contacted with the immobilized heteromultimeric construct, non-binding materials are washed away, and complexed target is detected using a suitable detection reagent, such as a monoclonal antibody recognizing the target. The monoclonal antibody is detectable by conventional means known in the art, including being detectably labeled, e.g., radiolabeled, conjugated with an enzyme such as horseradish peroxidase and the like, or fluorescently labeled.

For example, for detection or purification of soluble target in or from a solution, heteromultimers of the invention can be immobilized on a solid substrate such as a chromatographic support or other matrix material, then the immobilized heteromultimer can be loaded or contacted with the solution under conditions suitable for formation of a heteromultimer:target complex. The non-binding portion of the solution can be removed and the complex may be detected, e.g., using an antibody against the target, such as an anti-binding polypeptide antibody (e.g., anti-KDR, anti-VEGF/KDR complex, anti-cMet, or anti-cMet/HGF complex antibody), or the heteromultimer:target complex may be released from the binding moiety at appropriate elution conditions.

The biology of angiogenesis and the roles of VEGF and KDR in initiating and maintaining it have been investigated by many researchers and continues to be an active field for research and development. In furtherance of such research and development, a method of purifying bulk amounts of KDR or VEGF/KDR complex in pure form is desirable, and the KDR and VEGF/KDR complex heteromultimers described herein are especially useful for that purpose, using the general purification methodology described above. Similarly, the biology of tumors and other hyperproliferative tissue and the roles of cMet and HGF in initiating and maintaining these have been investigated by many researchers and continues to be an active field for research and development. In furtherance of such research and development, a method of purifying bulk amounts of cMet or HGF/cMet complex in pure form is desirable, and the cMet or HGF/cMet complex heteromultimers described herein are especially useful for that purpose, using the general purification methodology described above.

Diagnostic Imaging

Appropriately labeled heteromultimeric constructs of the present invention may be used in in vivo diagnostic applications to image specific tissues or cellular disorders. A particularly preferred use for the heteromultimeric constructs according to the present invention is for creating visually readable images of target expressing or containing tissue. For this embodiment, the heteromultimers of the invention are conjugated with a label appropriate for diagnostic detection, optionally via a linker Suitable linkers can be substituted or unsubstituted alkyl chains, amino acid chains (e.g., polyglycine), polyethylene glycols, polyamides, and other simple polymeric linkers known in the art. Preferably, a heteromultimer exhibiting much greater specificity for the target than for other serum proteins is conjugated or linked to a label appropriate for the detection methodology to be employed. For example, heteromultimers of the invention may be conjugated with or without a linker to a paramagnetic chelate suitable for magnetic resonance imaging (MRI), with a radiolabel suitable for x-ray, PET or scintigrapic imaging (including if necessary a chelator, such as those described herein, for a radioactive metal) with an ultrasound contrast agent (e.g. a stabilized microbubble, a microballoon, a microsphere or what has been referred to as a gas filled "liposome") suitable for ultrasound detection, or with an optical imaging dye.

For example, KDR or VEGF/KDR complex binding heteromultimeric constructs of the invention or cMet or HGF complex binding heteromultimeric constructs of the invention may be used to image neoplastic tumors, which require angiogenesis for survival and metastasis, or other sites of angiogenic activity. In this embodiment, heteromultimeric constructs including KDR and VEGF/KDR complex binding polypeptides or cMet or HGF/cMet complex binding polypeptides are converted to imaging reagents by conjugation with a label appropriate for diagnostic detection, optionally via a linker, as described herein.

In general, the technique of using a detectably labeled heteromultimeric construct is based on the premise that the label generates a signal that is detectable outside the patient's body. For example, in one embodiment, when a detectably labeled heteromultimer of the invention is administered to the patient in which angiogenesis, e.g., due to a tumor, is occurring, the high affinity of the KDR or VEGF/KDR complex binding moieties included in the heteromultimeric constructs for KDR or VEGF/KDR complex causes the heteromultimeric construct to bind to the site of angiogenesis and accumulate label at the site of angiogenesis. Sufficient time is allowed for the labeled heteromultimeric construct to localize at the site of angiogenesis. The signal generated by the labeled peptide is detected by a scanning device which will vary according to the type of label used, and the signal is then converted to an image of the site of angiogenesis.

In another embodiment, rather than directly labelling a heteromultimer of the invention with a detectable label or radiotherapeutic construct, heteromultimers of the invention can be conjugated with for example, avidin, biotin, or an antibody or antibody fragment that will bind the detectable label or radiotherapeutic. For example, in one embodiment, heteromultimers can be conjugated to streptavidin or avidin for in vivo binding to target-containing or expressing cells. After the unbound heteromultimer has cleared from the body, a biotinylated detectable label or radiotherapeutic construct (e.g. a chelate molecule complexed with a radioactive metal) can be infused which will rapidly concentrate at the site where the targeting construct is bound. This approach in some situations can reduce the time required after administering the detectable label until imaging can take place. It can also increase signal to noise ratio in the target site, and decrease the dose of the detectable label or radiotherapeutic construct required. This is particularly useful when a radioactive label or radiotherapeutic is used as the dose of radiation that is delivered to normal but radiation-sensitive sites in the body, such as bone-marrow, kidneys, and liver is decreased. This approach, sometimes referred to as pre-targeting or two-step, or three-step approaches was reviewed by S. F. Rosebrough (Q. J. Nucl. Med. 40:234–251; 1996, incorporated by reference herein). In a preferred embodiment, heteromultimeric constructs including KDR or VEGF/KDR binding moieties are used. In another preferred embodiment, heteromultimeric constructs including cMet or HGF/cMet binding moieties are used.

A. Magnetic Resonance Imaging

The heteromultimers of the present invention may advantageously be conjugated with one or more paramagnetic metal chelates in order to form a contrast agent for use in MRI. Preferred paramagnetic metal ions have atomic numbers 21–29, 42, 44, or 57–83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III). Additionally, heteromultimers of the present invention may also be conjugated with one or more superparamagnetic particles.

Gd(III) is particularly preferred for MRI due to its high relaxivity and low toxicity, and the availability of only one biologically accessible oxidation state. Gd(III) chelates have been used for clinical and radiologic MR applications since 1988, and approximately 30% of MR exams currently employ a gadolinium-based contrast agent.

One skilled in the art will select a metal according to dose required to detect target containing tisssue and considering other factors such as toxicity of the metal to the subject. See, Tweedle et al., *Magnetic Resonance Imaging* (2nd ed.), vol. 1, Partain et al., eds. (W.B. Saunders Co. 1988), pp. 796–7. Generally, the desired dose for an individual metal will be proportional to its relaxivity, modified by the biodistribution, pharmacokinetics and metabolism of the metal. The trivalent cation, $Gd^{3+}$ is particularly preferred for MRI contrast agents, due to its high relaxivity and low toxicity, with the further advantage that it exists in only one biologically accessible oxidation state, which minimizes undesired metabolization of the metal by a patient. Another useful metal is $Cr^{3+}$, which is relatively inexpensive.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriamine pentaacetic acid (DTPA), 1,4,7,10-tetraazacyclotetradecane-1,4,7,10-tetraacetic acid (DOTA), 1-substituted 1,4,7, -tricarboxymethyl 1,4,7,10 teraazacyclododecane triacetic acid (DO3A), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA;

bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra (methyl tetraacetic acid), and benzo-TETMA, where TETMA is 1,4,8,11-tetraazacyclotetradecane-1,4,8,11-(methyl tetraacetic acid); derivatives of 1,3-propylenediamine-tetraacetic acid (PDTA) and triethylenetetraaminehexaacetic acid (TTHA); derivatives of 1,5,10-N,N',N''-tris(2,3-dihydroxybenzoyl)-tricatecholate (LICAM) and 1,3,5-N,N',N''-tris(2,3-dihydroxybenzoyl) aminomethylbenzene (MECAM). A preferred chelator for use in the present invention is DTPA. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, U.S. Pat. No. 5,474,756, U.S. Pat. No. 5,846,519 and U.S. Pat. No. 6,143,274, each of which is hereby incorporated by reference in its entirety. Use of the chelate DO3A is particularly preferred.

In one embodiment of the present invention, the chelator(s) of the MRI contrast agent is coupled to a heteromultimer, such as, for example one comprised of KDR or VEGF/KDR complex binding polypeptides or cMet or HGF/cMet complex binding polypeptides. The positioning of the chelate(s) should be selected so as not to interfere with the binding affinity or specificity of the heteromultimeric construct. Preferably, the chelate(s) will be appended either to the N-terminus or the C-terminus, however the chelate(s) may also be attached anywhere within the sequence. In preferred embodiments, a chelator having a free central carboxylic acid group (e.g., DTPA-Asp(β-COOH)-OtBu) makes it easy to attach at the N-terminus of a binding peptide by formation of an amide bond. The chelate(s) could also be attached at the C-terminus with the aid of a linker. Alternatively, isothiocyanate conjugation chemistry could be employed as a way of linking the appropriate isothiocyante group bearing DTPA to a free amino group anywhere within the peptide sequence.

For example, the heteromultimer can be bound directly or covalently to the metal chelator(s) (or other detectable label), or it may be coupled or conjugated to the metal chelator(s) using a linker, which may be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the binding moieties); derivatized or underivatized polyethylene glycol, polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, e.g., WO 98/18497, WO 98/18496). Preferably the molecular weight of the linker can be tightly controlled. The molecular weights can range in size from less than 100 to greater than 1000. Preferably the molecular weight of the linker is less than 100. In addition, it may be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and a heteromultimer of the invention using such linkers. See, e.g., WO 95/28967, WO 98/18496, WO 98/18497 and discussion therein. For example, a heteromultimer can be linked through the N- or C-terminus of a component binding moiety via an amide bond, for example, to a metal coordinating backbone nitrogen of a metal chelate or to an acetate arm of the metal chelate itself. The present invention contemplates linking of the chelate(s) on any position, provided the metal chelate retains the ability to bind the metal tightly in order to minimize toxicity. Similarly, a component binding moiety of a heteromultimer may be modified or elongated in order to generate a locus for attachment to a metal chelate, provided such modification or elongation does not eliminate its ability to bind the target.

MRI contrast reagents prepared according to the disclosures herein may be used in the same manner as conventional MRI contrast reagents. When imaging target containing tissue such as, for example, a site of angiogenesis, certain MR techniques and pulse sequences may be preferred to enhance the contrast of the site to the background blood and tissues. These techniques include (but are not limited to), for example, black blood angiography sequences that seek to make blood dark, such as fast spin echo sequences (see, e.g., Alexander et al., *Magnetic Resonance in Medicine*, 40(2): 298–310 (1998)) and flow-spoiled gradient echo sequences (see, e.g., Edelman et al., *Radiology*, 177(1): 45–50 (1990)). These methods also include flow independent techniques that enhance the difference in contrast, such as inversion-recovery prepared or saturation-recovery prepared sequences that will increase the contrast between target containing tissue, such as an angiogenic tumor, and background tissues. Finally, magnetization transfer preparations may also improve contrast with these agents (see, e.g., Goodrich et al., *Investigative Radiology*, 31(6): 323–32 (1996)).

The labeled reagent is administered to the patient in the form of an injectable composition. The method of administering the MRI contrast agent is preferably parenterally, meaning intravenously, intraarterially, intrathecally, interstitially, or intracavitarilly. For imaging active angiogenesis, intravenous or intraarterial administration is preferred.

For MRI, it is contemplated that the subject will receive a dosage of contrast agent sufficient to enhance the MR signal at the target (e.g. a site of angiogenesis) at least 10%. After injection of the heteromultimeric construct including the MRI reagent, the patient is scanned in the MRI machine to determine the location of any sites containing the target. In therapeutic settings, upon target localization, a cytotoxic or therapeutic agent can be immediately administered, if necessary, and the patient can be subsequently scanned to visualize the therapeutic effect.

In a preferred embodiment, heteromultimers including KDR or VEGF/KDR complex binding moieties are conjugated to one or more paramagnetic metal chelates or one or more superparamagnetic particles, optionally via a linker. In another preferred embodiment, heteromultimeric constructs including cMet or HGF/cMet complex binding moieties are used. Such heteromultimeric constructs are complexed with one or more paramagnetic metal and administered in a dose sufficient to enhance the MR signal at the site of angiogenesis at least 10%. After injection, the patient is scanned to determine the location of any sites of angiogenesis (e.g. angiogenic tumors, etc.) or hyperproliferative tissue. If necessary, upon location of an angiogenic or hyperproliferative site, an anti-angiogenic or tumoricidal agent, such as, for example, an inhibitor of VEGF (or VEGF activation of KDR) may be administered. If necessary, the patient may be scanned again to visualize/track the tumor regression, arrest of angiogenesis, etc.

B. Ultrasound Imaging

When ultrasound is transmitted through a substance, the acoustic properties of the substance will depend upon the velocity of the transmissions and the density of the substance. Changes in the acoustic properties will be most prominent at the interface of different substances (solids, liquids, gases). Ultrasound contrast agents are intense sound wave reflectors because of the acoustic differences between the agent and the surrounding tissue. Gas containing or gas generating ultrasound contrast agents are particularly useful because of the acoustic difference between liquid (e.g. blood) and the gas-containing or gas generating ultrasound contrast agent. Because of their size, ultrasound contrast agents comprising microbubbles, microballoons, and the like may remain for a longer time in the blood stream after injection than other detectable moieties; thus a targeted ultrasound agent may demonsrate superior imaging of tissue expressing or containing the target.

In this aspect of the invention, the heteromultimeric constructs may include a material that is useful for ultrasound imaging. For example, heteromultimers of the invention may be linked to materials employed to form vesicles (e.g., microbubbles, microballoons, microspheres, etc.), or emulsions containing a liquid or gas which functions as the detectable label (e.g., an echogenic gas or material capable of generating an echogenic gas). Materials for the preparation of such vesicles include surfactants, lipids, sphingolipids, oligolipids, phospholipids, proteins, polypeptides, carbohydrates, and synthetic or natural polymeric materials. See e.g. WO 98/53857, WO 98/18498, WO 98/18495, WO 98/18497, WO 98/18496, and WO 98/18501 incorporated herein by reference in their entirety.

For contrast agents comprising suspensions of stabilized microbubbles (a preferred embodiment), phospholipids, and particularly saturated phospholipids are preferred. The preferred gas-filled microbubbles can be prepared by means known in the art, such as, for example, by a method described in any one of the following patents: EP 554213, U.S. Pat. No. 5,413,774, U.S. Pat. No. 5,578,292, EP 744962, EP 682530, U.S. Pat. No. 5,556,610, U.S. Pat. No. 5,846,518, U.S. Pat. No. 6,183,725, EP 474833, U.S. Pat. No. 5,271,928, U.S. Pat. No. 5,380,519, U.S. Pat. No. 5,531,980, U.S. Pat. No. 5,567,414, U.S. Pat. No. 5,658,551, U.S. Pat. No. 5,643,553, U.S. Pat. No. 5,911,972, U.S. Pat. No. 6,110,443, U.S. Pat. No. 6,136,293, EP 619743, U.S. Pat. No. 5,445,813, U.S. Pat. No. 5,597,549, U.S. Pat. No. 5,686,060, U.S. Pat. No. 6,187,288, and U.S. Pat. No. 5,908,610, each of which is incorporated by reference herein in its entirety. In a preferred embodiment, at least one of the phospholipid moieties has the structure of formula 18 or formula 19 shown below and described in U.S. Pat. No. 5,686,060, which is herein incorporated by reference in its entirety.

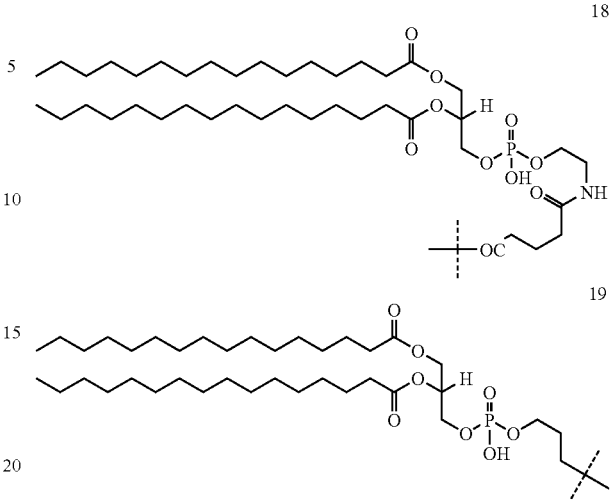

Examples of suitable phospholipids include esters of glycerol with one or two molecules of fatty acids (the same or different) and phosphoric acid, wherein the phosphoric acid residue is in turn bonded to a hydrophilic group, such as choline, serine, inositol, glycerol, ethanolamine, and the like groups. Fatty acids present in the phospholipids are in general long chain aliphatic acids, typically containing from 12 to 24 carbon atoms, preferably from 14 to 22, that may be saturated or may contain one or more unsaturations. Examples of suitable fatty acids are lauric acid, myristic acid, palmitic acid, stearic acid, arachidic acid, behenic acid, oleic acid, linoleic acid, and linolenic acid. Mono esters of phospholipid are also known in the art as the "lyso" forms of the phospholipids.

Further examples of phospholipids are phosphatidic acids, i.e. the diesters of glycerol-phosphoric acid with fatty acids, sphingomyelins, i.e. those phosphatidylcholine analogs where the residue of glycerol diester with fatty acids is replaced by a ceramide chain, cardiolipins, i.e. the esters of 1,3-diphosphatidylglycerol with a fatty acid, gangliosides, cerebrosides, etc.

As used herein, the term phospholipids includes either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins.

Examples of synthetic phospholipids are e.g., dilauryloyl-phosphatidylcholine ("DLPC"), dimyristoylphosphatidyl-choline ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidylcholine ("MPPC"), 1-palmitoyl-2-myristoylphosphatidylcholine ("PMPC"), 1-palmitoyl-2-stearoylphosphatid-ylcholine ("PSPC"), 1-stearoyl-2-palmitoyl-phosphatidylcholine ("SPPC"), dioleoylphosphatidylycholine ("DOPC"), 1,2 Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylglycerol ("DSPG") and its alkali metal salts, dioleoylphosphatidylglycerol ("DOPG") and its alkali metal salts, dimyristoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alkali metal salts, dimyristoyl phosphatidyl-ethanolamine ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), dioleoylphosphatidylserine ("DOPS"), dipalmitoyl sphingomyelin ("DPSP"), and distearoyl sphingomyelin ("DSSP").

Other preferred phospholipids include dipalmitoylphosphatidylcholine, dipalmitoylphosphatidic acid and dipalmitoylphosphatidylserine. The compositions may also contain PEG-4000 and/or palmitic acid. Any of the gases disclosed herein or known to the skilled artisan may be employed; however, inert gases, such as $SF_6$, or fluorocarbons, such as $CF_4$, $C_3F_8$ and $C_4F_{10}$, are preferred.

The preferred microbubble suspensions may be prepared from phospholipids using known processes such as a freeze-drying or spray-drying solutions of the crude phospholipids in a suitable solvent or using the processes set forth in EP 554213, U.S. Pat. No. 5,413,774, U.S. Pat. No. 5,578,292, EP 744962, EP 682530, U.S. Pat. No. 5,556,610, U.S. Pat. No. 5,846,518, U.S. Pat. No. 6,183,725, EP 474833, U.S. Pat. No. 5,271,928, U.S. Pat. No. 5,380,519, U.S. Pat. No. 5,531,980, U.S. Pat. No. 5,567,414, U.S. Pat. No. 5,658,551, U.S. Pat. No. 5,643,553, U.S. Pat. No. 5,911,972, U.S. Pat. No. 6,110,443, U.S. Pat. No. 6,136,293, EP 619743, U.S. Pat. No. 5,445,813, U.S. Pat. No. 5,597,549, U.S. Pat. No. 5,686,060, U.S. Pat. No. 6,187,288, and U.S. Pat. No. 5,908,610, each of which is incorporated by reference herein in its entirety. Most preferably, the phospholipids are dissolved in an organic solvent and the solution is dried without going through a liposome formation stage. This can be done by dissolving the phospholipids in a suitable organic solvent together with a hydrophilic stabilizer substance or a compound soluble both in the organic solvent and water and freeze-drying or spray-drying the solution. In this embodiment the criteria used for selection of the hydrophilic stabilizer is its solubility in the organic solvent of choice. Examples of hydrophilic stabilizer compounds soluble in water and the organic solvent are e.g. a polymer, like polyvinyl pyrrolidone (PVP), polyvinyl alcohol (PVA), polyethylene glycol (PEG), etc., malic acid, glycolic acid, maltol and the like. Such hydrophilic compounds also aid in homogenizing the microbubbles size distribution and enhance stability under storage. Any suitable organic solvent may be used as long as its boiling point is sufficiently low and its melting point is sufficiently high to facilitate subsequent drying. Typical organic solvents include, for example, dioxane, cyclohexanol, tertiary butanol, tetrachlorodifluoro ethylene ($C_2Cl_4F_2$) or 2-methyl-2-butanol however, 2-methyl-2-butanol and $C_2Cl4F_2$ are preferred.

Prior to formation of the suspension of microbubbles by dispersion in an aqueous carrier, the freeze-dried or spray-dried phospholipid powders are contacted with air or another gas. When contacted with the aqueous carrier the powdered phospholipids whose structure has been disrupted will form lamellarized or laminarized segments that will stabilize the microbubbles of the gas dispersed therein. This method permits production of suspensions of microbubbles that are stable even when stored for prolonged periods and are obtained by simple dissolution of the dried laminarized phospholipids (which have been stored under a desired gas) without shaking or any violent agitation.

Alternatively, microbubbles can be prepared by suspending a gas into an aqueous solution at high agitation speed, as disclosed e.g. in WO 97/29783. A further process for preparing microbubbles is disclosed in co-pending European patent application no. 03002373, herein incorporated by reference, which comprises preparing an emulsion of an organic solvent in an aqueous medium in the presence of a phospholipid and subsequently lyophilizing said emulsion, after optional washing and/or filtration steps.

Additives known to those of ordinary skill in the art can be included in the suspensions of stabilized microbubbles. For instance, non-film forming surfactants, including polyoxypropylene glycol and polyoxyethylene glycol and similar compounds, as well as various copolymers thereof; fatty acids such as myristic acid, palmitic acid, stearic acid, arachidic acid or their derivatives, ergosterol, phytosterol, sitosterol, lanosterol, tocopherol, propyl gallate, ascorbyl palmitate and butylated hydroxytoluene may be added. The amount of these non-film forming surfactants is usually up to 50% by weight of the total amount of surfactants but preferably between 0 and 30% by weight.

Other gas containing suspensions include those disclosed in, for example, U.S. Pat. No. 5,798,091 and WO 97/29783, incorporated herein by reference in their entirety. These agents may be prepared as described in U.S. Pat. No. 5,798,091 or WO97/29783, each of which is incorporated by reference in its entirety.

Another preferred ultrasound contrast agent comprises microballoons. The term "microballoon" refers to gas filled bodies with a material boundary or envelope. More on microballoon formulations and methods of preparation may be found in EP-A-0 324 938 U.S. Pat. No. 4,844,882; U.S. Pat. No. 5,711,933; U.S. Pat. No. 5,840,275; U.S. Pat. No. 5,863,520; U.S. Pat. No. 6,123,922; U.S. Pat. No. 6,200,548; U.S. Pat. No. 4,900,540; U.S. Pat. No. 5,123,414; U.S. Pat. Nos. 5,230,882; 5,469,854; 5,585,112; U.S. Pat. No. 4,718, 433; U.S. Pat. No. 4,774,958; WO 9501187; U.S. Pat. No. 5,529,766; U.S. Pat. No. 5,536,490 and U.S. Pat. No. 5,990,263, each of which is incorporated herein by reference in its entirety.

The preferred microballoons have an envelope including a biodegradable physiologically compatible polymer or, a biodegradable solid lipid. The polymers useful for the preparation of the microballoons of the present invention can be selected from the biodegradable physiologically compatible polymers, such as any of those described in any of the following patents: EP 458745, U.S. Pat. No. 5,711,933, U.S. Pat. No. 5,840,275, EP 554213, U.S. Pat. No. 5,413,774 and U.S. Pat. No. 5,578,292, the entire contents of which are incorporated herein by reference. In particular, the polymer can be selected from biodegradable physiologically compatible polymers, such as polysaccharides of low water solubility, polylactides and polyglycolides and their copolymers, copolymers of lactides and lactones such as ε-caprolactone, γ-valerolactone and polypeptides. Other suitable polymers include poly(ortho)esters (see e.g., U.S. Pat. No. 4,093,709; U.S. Pat. No. 4,131,648; U.S. Pat. No. 4,138,344; U.S. Pat. No. 4,180,646); polylactic and polyglycolic acid and their copolymers, for instance DEXON (see J. Heller, Biomaterials 1 (1980), 51; poly(DL-lactide-co-ε-caprolactone), poly (DL-lactide-co-γ-valerolactone), poly(DL-lactide-co-γ-butyrolactone), polyalkylcyanoacrylates; polyamides, polyhydroxybutyrate; polydioxanone; poly-β-aminoketones (A. S. Angeloni, P. Ferruti, M. Tramontini and M. Casolaro, The Mannich bases in polymer synthesis: 3. Reduction of poly(beta-aminoketone)s to poly(gamma-aminoalcohol)s and their N-alkylation to poly(gamma-hydroxyquaternary ammonium salt)s, Polymer 23, pp 1693–1697, 1982.); polyphosphazenes (Allcock, Harry R. Polyphosphazenes: new polymers with inorganic backbone atoms (Science 193 (4259), 1214–19 (1976)) and polyanhydrides. The microballoons of the present invention can also be prepared according to the methods of WO-A-96/15815, incorporated herein by reference, where the microballoons are made from a biodegradable membrane comprising biodegradable lipids, preferably selected from mono- di-, tri-glycerides, fatty acids, sterols, waxes and mixtures thereof. Preferred lipids are di- or tri-glycerides, e.g. di- or tri-myristin, -palmityn or -stearin, in particular tripalmitin or tristearin.

The microballoons may employ any of the gases disclosed herein or known to the skilled artisan; however, inert gases such as fluorinated gases are preferred. The microballoons may be suspended in a pharmaceutically acceptable liquid carrier with optional additives known to those of ordinary skill in the art and stabilizers.

Other gas-containing contrast agent formulations include microparticles (especially aggregates of microparticles) having gas contained therein or otherwise associated therewith (for example being adsorbed on the surface thereof and/or contained within voids, cavities or pores therein). Methods for the preparation of these agents are as described in EP 0122624, EP 0123235, EP 0365467, U.S. Pat. No. 5,558, 857, U.S. Pat. No. 5,607,661, U.S. Pat. No. 5,637,289, U.S. Pat. No. 5,558,856, U.S. Pat. No. 5,137,928, WO 9521631 and WO 9313809, each of which is incorporated herein by reference in its entirety.

Any of these ultrasound compositions should also be, as far as possible, isotonic with blood. Hence, before injection, small amounts of isotonic agents may be added to any of above ultrasound contrast agent suspensions. The isotonic agents are physiological solutions commonly used in medicine and they comprise aqueous saline solution (0.9% NaCl), 2.6% glycerol solution, 5% dextrose solution, etc. Additionally, the ultrasound compositions may include standard pharmaceutically acceptable additives, including, for example, emulsifying agents, viscosity modifiers, cryoprotectants, lyoprotectants, bulking agents etc.

Any biocompatible gas may be used in the ultrasound contrast agents useful in the invention. The term "gas" as used herein includes any substances (including mixtures) substantially in gaseous form at the normal human body temperature. The gas may thus include, for example, air; nitrogen; oxygen; $CO_2$; argon; xenon or krypton, fluorinated gases (including for example, perfluorocarbons, $SF_6$, $SeF_6$) a low molecular weight hydrocarbon (e.g. containing from 1 to 7 carbon atoms), for example, an alkane such as methane, ethane, a propane, a butane or a pentane, a cycloalkane such as cyclopropane, cyclobutane or cyclopentene, an alkene such as ethylene, propene, propadiene or a butene, or an alkyne such as acetylene or propyne and/or mixtures thereof. However, fluorinated gases are preferred. Fluorinated gases include materials which contain at least one fluorine atom such as $SF_6$, freons (organic compounds containing one or more carbon atoms and fluorine, i.e. $CF_4$, $C_2F_6$, $C_3F_8$, $C_4F_8$, $C_4F_{10}$, $CBrF_3$, $CCl_2F_2$, $C_2ClF_5$, and $CBrClF_2$) and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$ $C_5F_{12}$, $C_6F_{12}$, $C_7F_{14}$, $C_8F_{18}$, and $C_9F_{20}$. Most preferably the gas or gas mixture comprises $SF_6$ or a perfluorocarbon selected from the group consisting of $C_3F_8$ $C_4F_8$, $C_4F_{10}$, $C_5F_{12}$, $C_6F_{12}$, $C_7F_{14}$, $C_8F_{18}$, with $C_4F_{10}$ being particularly preferred. See also WO 97/29783, WO 98/53857, WO 98/18498, WO 98/18495, WO 98/18496, WO 98/18497, WO 98/18501, WO 98/05364, and WO 98/17324.

In certain circumstances it may be desirable to include a precursor to a gaseous substance (e.g. a material that is capable of being converted to a gas in vivo, often referred to as a "gas precursor"). Preferably the gas precursor and the gas it produces are physiologically acceptable. The gas precursor may be pH-activated, photo-activated, temperature activated, etc. For example, certain perfluorocarbons may be used as temperature activated gas precursors. These perfluorocarbons, such as perfluoropentane, have a liquid/ gas phase transition temperature above room temperature (or the temperature at which the agents are produced and/or stored) but below body temperature; thus, they undergo a phase shift and are converted to a gas within the human body.

As discussed, the gas can include a mixture of gases. The following combinations are particularly preferred gas mixtures: a mixture of gases (A) and (B) in which, at least one of the gases (B), present in an amount of between 0.5–41% by vol., has a molecular weight greater than 80 daltons and is a fluorinated gas and (A) is selected from the group consisting of air, oxygen, nitrogen, carbon dioxide and mixtures thereof, the balance of the mixture being gas A.

Since ultrasound vesicles may be larger than the other detectable labels described herein, they may be linked or conjugated to a plurality of heteromultimeric constructs in order to increase the targeting efficiency of the agent. Attachment to the ultrasound contrast agents described above (or known to those skilled in the art) may be via direct covalent bond between a binding polypeptide and the material used to make the vesicle or via a linker, as described previously. For example, see WO 98/53857 generally for a description of the attachment of a peptide to a bifunctional PEG linker, which is then reacted with a liposome composition. See also, Lanza et al., *Ultrasound in Med. & Bio.*, 23(6): 863–870 (1997).

A number of methods may be used to prepare suspensions of microbubbles conjugated to heteromultimers. For example, one may prepare maleimide-derivatized microbubbles by incorporating 5% (w/w) of N-MPB-PE (1,2-dipalmitoyl-sn-glycero-3-phosphoethanolamine-4-(p-maleimido-phenyl butyramide), (Avanti Polar-Lipids, Inc) in the phospholipid formulation. Then, solutions of mercaptoacetylated heteromultimers (10 mg/mL in DMF), which have been incubated in deacetylation solution (50 mM sodium phosphate, 25 mM EDTA, 0.5 M hydroxylamine HCl, pH 7.5) are added to the maleimide-activated microbubble suspension. After incubation in the dark, under gentle agitation, the heteromultimer conjugated microbubbles may be purified by centrifugation.

Compounds that can be used for derivatization of microbubbles typically include the following components: (a) a hydrophobic portion, compatible with the material forming the envelope of the microbubble or of the microballoon, in order to allow an effective incorporation of the compound in the envelope of the vesicel; said portion is represented typically by a lipid moiety (dipalmitin, distearoyl); and (b) a spacer (typically PEGs of different molecular weights), which may be optional in some cases (microbubbles may for instance present difficulties to be freeze dried if the spacer is too long e.g) or preferred in some others (e.g. peptides may be less active when conjugated to a microballoon with short spacers); and (c) a reactive group capable of reacting with a corresponding reacting moiety on the peptide to be conjugated (e.g. maleimido with the—SH group of cysteine).

Alternatively, heteromultimers conjugated to microbubbles may be prepared using biotin/avidin. For example, avidin-conjugated microbubbles may be prepared using a maleimide-activated phospholipid microbubble suspension, prepared as described above, which is added to mercaptoacetylated-avidin (which has been incubated with deacetylation solution). Biotinylated heteromultimers (prepared as described herein), are then added to the suspension of avidin-conjugated microbubbles, yielding a suspension of microbubbles conjugated to the heteromultimers.

Unless it contains a hyperpolarized gas, known to require special storage conditions, the lyophilized residue may be stored and transported without need of temperature control of its environment and in particular it may be supplied to hospitals and physicians for on site formulation into a ready-to-use administrable suspension without requiring such users to have special storage facilities. Preferably in such a case it can be supplied in the form of a two-component kit, which can include two separate containers or a dual-chamber container. In the former case preferably the container is a conventional septum-sealed vial, wherein the vial containing the lyophilized residue of step b) is sealed with a septum through which the carrier liquid may be injected using an optionally prefilled syringe. In such a case the syringe used as the container of the second component is also used then for injecting the contrast agent. In the latter case, preferably the dual-chamber container is a dual-chamber syringe and once the lyophilizate has been reconstituted and then suitably mixed or gently shaken, the container can be used directly for injecting the contrast agent. In both cases means for directing or permitting application of sufficient bubble forming energy into the contents of the container are provided. However, as noted above, in the stabilised contrast agents according to the invention the size of the gas microbubbles is substantially independent of the amount of agitation energy applied to the reconstituted dried product. Accordingly, no more than gentle hand shaking is generally required to give reproducible products with consistent microbubble size.

It can be appreciated by one ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g. a targeting ligand to be linked to the phospholipid during reconstitution), it can be packaged with the other components of the kit, preferably in a form or container adapted to facilitate ready combination with the other components of the kit.

No specific containers, vial or connection systems are required; the present invention may use conventional containers, vials and adapters. The only requirement is a good seal between the stopper and the container. The quality of the seal, therefore, becomes a matter of primary concern; any degradation of seal integrity could allow undesirable substances to enter the vial. In addition to assuring sterility, vacuum retention is essential for products stoppered at ambient or reduced pressures to assure safe and proper reconstitution. As to the stopper, it may be a compound or multicomponent formulation based on an elastomer, such as poly(isobutylene) or butyl rubber.

Ultrasound imaging techniques which may be used in accordance with the present invention include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

In ultrasound applications the contrast agents formed by phospholipid stabilized microbubbles may, for example, be administered in doses such that the amount of phospholipid injected is in the range 0.1 to 200 µg/kg body weight, preferably from about 0.1 to 30 µg/kg. Microballoons-containing contrast agents are typically administered in doses such that the amount of wall-forming polymer or lipid is from about 10 µg/kg to about 20 mg/kg of body weight.

In a preferred embodiment, the ultrasound contrast agents described herein are conjugated to one or more heteromultimers comprised of KDR or VEGF/KDR complex binding moieties, and target tissue expressing KDR. As shown in the Examples, these targeted ultrasound contrast agents will localize at sites of angiogenesis and other tissue expressing KDR and may be used to image angiogenic tissue. In another preferred embodiment illustrated in the Examples, the ultrasound contrast agents described herein are conjugated to one or more heteromultimers comprised of cMet or HGF/cMet complex binding moieties, and, target tissue expressing cMet. These targeted ultrasound contrast agents will localize at sites of hyperproliferation or angiogenesis (including tumors) and other tissue expressing cMet and may demonstrate superior imaging of such tissue.

C. Optical Imaging, Sonoluminescence or Photoacoustic Imaging

In accordance with the present invention, a number of optical parameters may be employed to determine the location of a target, such as a KDR, VEGF/KDR complex, cMet or HGF/cMet complex, with in vivo light imaging after injection of the subject with an optically-labeled heteromultimeric construct. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650–1000 nm. NIR radiation can penetrate tissue up to several centimeters, permitting the use of heteromultimeric contructs of the invention to image target-containing tissue in vivo. For example, heteromultimeric constructs comprised of KDR, VEGF/KDR complex, cMet, or HGF/cMet binding polypeptides may be used for optical imaging of KDR, VEGF/KDR complex, cMet, or HGF/cMet complex in vivo.

In another embodiment, the heteromultimeric constructs of the invention may be conjugated with photolabels, such as optical dyes, including organic chromophores or fluorophores, having extensive delocalized ring systems and having absorption or emission maxima in the range of 400–1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. >$10^5$ cm$^{-1}$M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. For example, the photolabels may be covalently linked directly to heteromultimers of the invention, such as, for example, heteromultimers comprised of KDR or VEGF/KDR complex binding peptides or linked to such a heteromultimers via a linker, as described previously.

After injection of the optically-labeled heteromultimeric construct, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of target-containing tissue(, e.g., tissue containing KDR, VEGF/KDR complex, cMet, or HGF/cMet complex) in the subject. Changes in the optical parameter may be monitored over time to detect accumulation of the optically-labeled reagent at the target site (e.g. the site of angiogenesis). Standard image processing and detecting devices may be used in conjunction with the optical imaging reagents of the present invention.

The optical imaging reagents described above may also be used for acousto-optical or sonoluminescent imaging performed with optically-labeled imaging agents (see, U.S. Pat. No. 5,171,298, WO 98/57666, and references therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

D. Nuclear Imaging (Radionuclide Imaging) and Radiotherapy.

Heteromultimers of the invention may be conjugated with a radionuclide reporter appropriate for scintigraphy, SPECT or PET imaging or with a radionuclide appropriate for radiotherapy. Constructs in which the heteromultimers of the invention are conjugated with both a chelator for a radionuclide useful for diagnostic imaging and a chelator for a radionuclide useful for radiotherapy are within the scope of the invention.

For use as a PET agent, a heteromultimer may be complexed with one of the various positron emitting metal ions, such as $^{51}$Mn, $^{52}$Fe, $^{60}$Cu, $^{68}$Ga, $^{72}$As, $^{94m}$Tc, or $^{110}$In. The heteromultimeric constructs can also be labeled by halogenation using radionuclides, such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal or halogen will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$yb, $^{177}$LU, $^{186/188}$Re, and $^{199}$Au. $^{99m}$Tc is particularly preferred for diagnostic applications because of its low cost, availability, imaging properties, and high specific activity. The nuclear and radioactive properties of Tc-99m make this isotope an ideal scintigraphic imaging agent. This isotope has a single photon energy of 140 keV and a radioactive half-life of about 6 hours, and is readily available from a $^{99}$Mo-$^{99m}$Tc generator.

The metal radionuclides may be chelated by, for example, linear, macrocyclic, terpyridine, and $N_3S$, $N_2S_2$, or $N_4$ chelants (see also, U.S. Pat. No. 5,367,080, U.S. Pat. No. 5,364,613, U.S. Pat. No. 5,021,556, U.S. Pat. No. 5,075,099, U.S. Pat. No. 5,886,142), and other chelators known in the art including, but not limited to, HYNIC, DTPA, EDTA, DOTA, TETA, and bisamino bisthiol (BAT) chelators (see also U.S. Pat. No. 5,720,934). For example, $N_4$ chelators are described in U.S. Pat. Nos. 6,143,274; 6,093,382; 5,608,110; 5,665,329; 5,656,254; and 5,688,487. Certain $N_3S$ chelators are described in PCT/CA94/00395, PCT/CA94/00479, PCT/CA95/00249 and in U.S. Pat. Nos. 5,662,885; 5,976,495; and 5,780,006. The chelator may also include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, *Chem Rev.* 1999, 99, 2235–2268 and references therein.

The chelator may also include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

In another embodiment, disulfide bonds of a binding polypeptide of the invention are used as two ligands for chelation of a radionuclide such as $^{99m}$Tc. In this way the peptide loop is expanded by the introduction of Tc (peptide-S—S-peptide changed to peptide-S—Tc—S-peptide). This has also been used in other disulfide containing peptides in the literature (J. Q. Chen, A. Cheng, N. K. Owen, T. H. Hoffman, Y. Miao, S. S. Jurisson, T. P. Quinn. J. Nucl. Med. 2001, 42, 1847–1855) while maintaining biological activity. The other chelating groups for Tc can be supplied by amide nitrogens of the backbone, another cystine amino acid or other modifications of amino acids.

Particularly preferred metal chelators include those of Formula 20, 21, and 22 (for $^{111}$In and lanthanides such as paramagnetic Gd$^{3+}$ and radioactive lanthanides, such as, for example $^{177}$Lu, $^{90}$Y, $^{153}$Sm, and $^{166}$Ho) and those of Formula 23, 24, and 25 (for radioactive $^{99m}$Tc, $^{186}$Re, and $^{188}$Re) set forth below. These and other metal chelating groups are described in U.S. Pat. Nos. 6,093,382 and 5,608,110, which are incorporated by reference herein in their entirety. Additionally, the chelating group of formula 22 is described in, for example, U.S. Pat. No. 6,143,274; the chelating group of formula 24 is described in, for example, U.S. Pat. Nos. 5,627,286 and 6,093,382, and the chelating group of formula 25 is described in, for example, U.S. Pat. Nos. 5,662,885; 5,780,006; and 5,976,495.

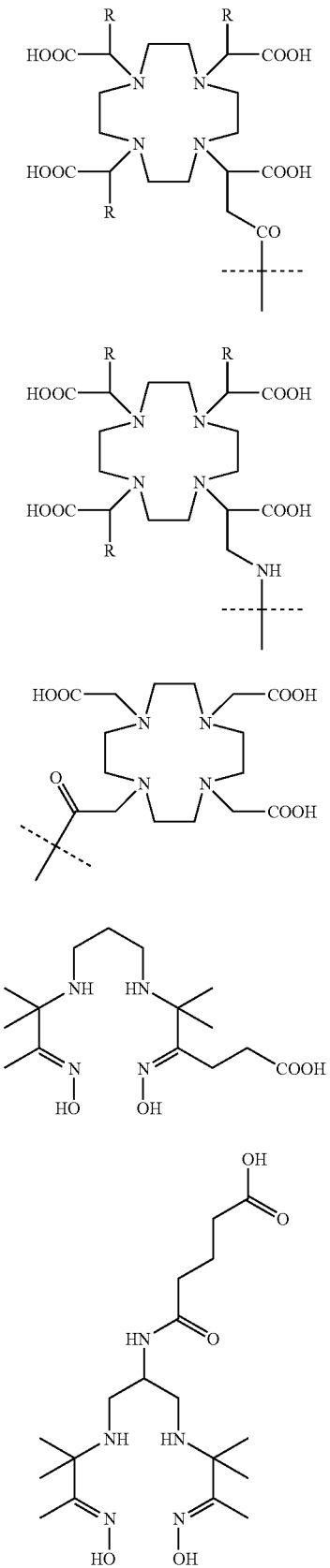

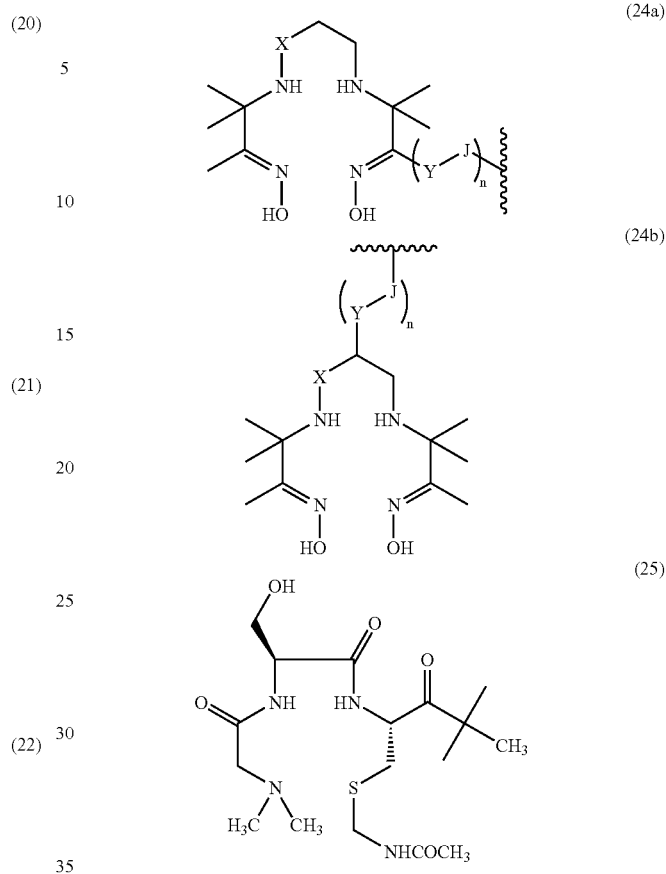

In the above Formulas 20 and 21, R is alkyl, preferably methyl. In the above Formula 24, X is either $CH_2$ or O, Y is either $C_1$–$C_{10}$ branched or unbranched alkyl; Y is aryl, aryloxy, arylamino, arylaminoacyl; Y is arylkyl—where the alkyl group or groups attached to the aryl group are $C_1$–$C_{10}$ branched or unbranched alkyl groups, $C_1$–$C_{10}$ branched or unbranched hydroxy or polyhydroxyalkyl groups or poly-alkoxyalkyl or polyhydroxy-polyalkoxyalkyl groups, J is $C(=O)$—, $OC(=O)$—, $SO_2$—, $NC(=O)$—, $NC(=S)$—, $N(Y)$, $NC(=NCH_3)$—, $NC(=NH)$—, $N=N$—, homopolyamides or heteropolyamines derived from synthetic or naturally occurring amino acids; all where n is 1–100. Other variants of these structures are described, for example, in U.S. Pat. No. 6,093,382. The disclosures of each of the foregoing patents, applications and references are incorporated by reference herein, in their entirety.

The chelators may be covalently linked directly to the heteromultimers or linked to heteromultimers via a linker, as described previously, and then directly labeled with the radioactive metal of choice (see, WO 98/52618, U.S. Pat. No. 5,879,658, and U.S. Pat. No. 5,849,261).

Complexes of radioactive technetium are particularly useful for diagnostic imaging and complexes of radioactive rhenium are particularly useful for radiotherapy. In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a heteromultimer of this invention conjugated with an appropriate chelator with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. Preparation of the complexes of the present invention where the metal is radioactive rhenium may be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4]$ $(NBu_4)$, $[ReOCl_4](AsPh_4)$, $ReOCl_3(PPh_3)_2$ and as $ReO_2$ $(pyridine)_4^+$. (Ph is phenyl; Bu is n-butyl). Other rhenium reagents capable of forming a rhenium complex may also be used.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

Generally, the unit dose to be administered has a radioactivity of about 0.01 mCi to about 100 mCi, preferably 1 mCi to 20 mCi. The solution to be injected at unit dosage is from about 0.01 mL to about 10 mL.

Typical doses of a radionuclide-labeled heteromultimeric construct imaging agent of the invention provide 10–50 mCi. After injection of the heteromultimeric radionuclide imaging agent into the patient, a PET camera or a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods which include, but are not limited to, a single or multiple IV or IP injections, using a quantity of radioactivity that is sufficient to cause damage or ablation of the targeted tissue, but not so much that substantive damage is caused to non-target (normal tissue). The quantity and dose required is different for different constructs, depending on the energy and half-life of the isotope used, the degree of uptake and clearance of the agent from the body and the mass of the tumor. In general, doses can range from a single dose of about 30–50 mCi to a cumulative dose of up to about 3 Curies.

The radiotherapeutic compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentistic acid and the like.

A single, or multi-vial kit that contains all of the components needed to prepare the radiopharmaceuticals of this invention, other than the radionuclide, is an integral part of this invention.

A single-vial kit preferably contains a chelating ligand (if a metal radionuclide is used), a source of stannous salt (if reduction is required, e.g., when using technetium), or other pharmaceutically acceptable reducing agent, and is appropriately buffered with pharmaceutically acceptable acid or base to adjust the pH to a value of about 3 to about 9. The quantity and type of reducing agent used would depend highly on the nature of the exchange complex to be formed. The proper conditions are well known to those that are skilled in the art. It is preferred that the kit contents be in lyophilized form. Such a single vial kit may optionally contain labile or exchange ligands such as glucoheptonate, gluconate, mannitol, malate, citric or tartaric acid and can also contain reaction modifiers such as diethylenetriaminepentaacetic acid (DPTA), ethylenediamine tetraacetic acid (EDTA), or α, β, or γ cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g. the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

In a preferred embodiment, the radiotherapeutic and radiodiagnostic agents described herein are conjugated to one or more heteromultimers comprised of KDR or VEGF/KDR complex binding moieties, and target tissue expressing KDR. As shown in the Examples these targeted radiopharmaceuticals will localize at sites of angiogenesis and other tissue expressing KDR and may be used to treat or image angiogenic tissue. In another preferred embodiment illustrated in the Examples, the radiotherapeutic and radiodiagnostic agents described herein are conjugated to one or more heteromultimers comprised of or cMet or HGF/cMet complex binding moieties, and, target tissue expressing cMet. These targeted radiopharmaceuticals will localize at sites of hyperproliferation or angiogenesis (including tumors) and other tissue expressing cMet and will enable imaging and treatment of such tissue.

Other Therapeutic Applications

The heteromultimeric constructs of the present invention can be used to improve the activity and/or efficacy of therapeutic agents by, for example, improving their affinity for or residence time at the target. In this embodiment heteromultimers are conjugated with the therapeutic agent. Alternatively, as discussed above, a liposome or bubble containing a therapeutic agent may be conjugated to heteromultimers of the invention. The therapeutic agent may be a radiotherapeutic, discussed above, a drug, chemotherapeutic or tumorcidal agent, genetic material, or a gene delivery vehicle, etc. The heteromultimer portion of the conjugate causes the therapeutic to "home" to the sites of target expression/localization and to improve the affinity of the conjugate for these sites, so that the therapeutic activity of the conjugate is more localized and concentrated at the target sites. For example, in one embodiment heteromultimers including KDR or VEGF/KDR complex binding polypeptides, can be used to improve the activity of therapeutic agents (such as anti-angiogenic or tumorcidal agents) against undesired angiogenesis such as occurs in neoplastic tumors, by providing or improving their affinity for KDR or the VEGF/KDR complex and their residence time at a KDR or VEGF/KDR complex on endothelium undergoing angiogenesis. In this aspect of the invention, hybrid agents are provided by conjugating KDR or VEGF/KDR complex binding heteromultimers with a therapeutic agent. Such heteromultimeric constructs will be useful in treating angiogenesis associated diseases, especially neoplastic tumor growth and metastasis, in mammals, including humans. The method of treatment comprises administering to a mammal in need thereof an effective amount of a heteromultimeric construct comprising KDR or VEGF/KDR complex binding polypeptides conjugated with a therapeutic agent. The invention also provides the use of such conjugates in the manufacture of a medicament for the treatment of angiogenesis associated diseases in mammals, including humans. Heteromultimeric constructs of the invention comprising cMet or HGF/cMet complex binding moieties may be used similarly to treat disease associated with hyperproliferation or angiogenesis.

Suitable therapeutic agents for use in this aspect of the invention include, but are not limited to: antineoplastic agents, such as platinum compounds (e.g., spiroplatin, cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, a, L-PAM or phenylalanine mustard), mercaptopurine, mitotane, procarbazine hydrochloride, dactinomycin (actinomycin D), daunorubcin, hydrochloride, doxorubicin hydrochloride, taxol, mitomycin, plicamycin (mithramycin), aminoglutethimide, estramustine phosphate sodium, flutamide, acetate, megestrol acetate, tamoxifen citrate, testolactone, trilostane, amsacrine (m-AMSA), ASPARAGINASE (L-*ASPARAGINASE*) *Erwina aparaginase*, etoposide (VP-16), interferon cx-2a, Interferon cx-2b, teniposide (VM-26, vinblastine sulfate (VLB), vincristine sulfate, bleomycin sulfate, adriamycin, and arabinosyl; anti-angiogenic agents such as; tyrosine kinase inhibitors with activity toward signaling molecules important in angiogenesis and/or tumor growth such as SU5416 and SU6668 (Sugen/Pharmacia & Upjohn), endostatin (EntreMed), angiostatin (EntreMed), Combretastatin (oxigene), cyclosporine, 5-fuorouracil, vinblastine, doxorubicin, paclitaxel, daunorubicin, immunotoxins; coagulation factors; antivirals such as acyclovir, amantadine azidothymidine (AZT or Zidovudine), ribavirin and vidarabine monohydrate (adenine arahinoside, ara-A); antibiotics, antimalarials, antiprotozoans such as chloroquine, hydroxychloroquine, metronidazole, quinine and meglumine antimonate; anti-inflammatories such as diflunisal, ibuprofen, indomethacin, meclofenamate, mefenamic acid, naproxen, oxyphenbutazone, phenylbutazone, piroxicam, sulindac, tolmetin, aspirin and salicylates.

Where heteromultimeric constructs target other tissue and are useful in treating other disease states the skilled artisan may substitute an appropriate therapeutic agent.

The heteromultimeric constructs of the present invention may also be used to target genetic material to specific cells. For example, the heteromultimeric constructs of the present invention may be used to localize genetic material to cells or tissue containing the desired target. Thus such constructs may be useful in gene therapy. The genetic material may include nucleic acids, such as RNA or DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with lipids, proteins or other polymers. Delivery vehicles for genetic material may include, for example, a virus particle, a retroviral or other gene therapy vector, a liposome, a complex of lipids (especially cationic lipids) and genetic material, a complex of dextran derivatives and genetic material, etc.

In a preferred embodiment the heteromultimeric constructs of the invention are utilized in gene therapy for treatment of diseases associated with angiogenesis. In this embodiment, genetic material, or one or more delivery vehicles containing genetic material, e.g., useful in treating an angiogenesis-related disease, may be conjugated to one or more KDR or VEGF/KDR complex binding heteromultimers or cMet or HGF/cMET complex binding heteromultimers of the invention and administered to a patient.

Constructs including genetic material and the KDR binding heteromultimers of the invention may be used, in particular, to selectively introduce genes into angiogenic endothelial cells, which may be useful not only to treat cancer, but also after angioplasty, where inhibition of angiogenesis may inhibit restenosis.

Therapeutic agents and heteromultimers of the invention can be linked or fused in known ways, using the same type of linkers discussed herein. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and a binding polypeptide of the invention may be coexpressed from the same synthetic gene, created using recombinant DNA techniques, as described above. For example, the coding sequence for a binding polypeptide may be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the binding polypeptide. A particular advantage of this general approach is that concatamerization of multiple, tandemly arranged binding polypeptides is possible, thereby increasing the number and concentration of binding sites associated with each therapeutic protein. In this manner binding peptide avidity is increased which would be expected to improve the efficacy of the recombinant therapeutic fusion protein.

Similar recombinant proteins containing one or more coding sequences for a binding polypeptide may be useful in imaging or therapeutic applications. For example, in a variation of the pre-targeting applications discussed infra, the coding sequence for a KDR, VEGF/KDR complex, cMet, or HGF/cMet binding peptide may be fused in frame to a sequence encoding an antibody (or an antibody fragment or recombinant DNA construct including an antibody, etc.) which, for example, binds to a chelator for a radionuclide (or another detectable label). The antibody expressing the KDR, VEGF/KDR complex, cMet, or HGF/cMet binding polypeptide is then administered to a patient and allowed to localize and bind to KDR- or cMet-expressing tissue. After the non-binding antibodies have been allowed to clear, the chelator-radionuclide complex (or other detectable label), which the antibody recognizes is administered, permitting imaging of or radiotherapy to the KDR- or cMet-expressing tissues. Additionally, the coding sequence for a binding peptide may be fused in frame to a sequence encoding, for example, serum proteins or other proteins that produce biological effects (such as apoptosis, coagulation, internalization, differentiation, cellular stasis, immune system stimulation or suppression, or combinations thereof). The resulting recombinant proteins are useful in imaging, radiotherapy, and therapies directed against cancer and other diseases that involve angiogenesis or diseases associated with the pathogens discussed herein.

Additionally, heteromultimers of the present invention may themselves be used as therapeutics to treat a number of diseases. For example, where binding of a protein or other molecule (e.g. a growth factor, hormone etc.) is necessary for or contributes to a disease process and a binding moiety inhibits such binding, heteromultimers including such binding moieties may be useful as therapeutics. Similarly, where binding of a binding moiety itself inhibits a disease process, heteromultimers containing such binding moieties may also be useful as therapeutics.

As binding of VEGF and activation of KDR is necessary for angiogenic activity, in one embodiment heteromultimers including KDR or VEGF/KDR complex binding polypeptides that inhibit the binding or inhibit VEGF to KDR (or otherwise inhibit activation of KDR) may be used as anti-angiogenic agents. Certain heteromultimers of the invention that inhibit activation of KDR are discussed in the Examples. A particularly preferred heteromultimer is the heterodimer-containing construct D1 (structure shown below in Example 9). Other preferred heterodimer constructs include D4, D5, D6, D7, D10, D13, D17, D23, D24, D25, and D26 (structures provided in the Examples below). These and other heteromultimers may be useful in the treatment of cancer or other diseases associated with inappropriate or excessive angiogenesis, such as, for example arthritis and atherosclerotic plaques, trachoma, corneal graft neovascularization, psoriasis, scleroderma, hemangioma and hypertrophic scarring, vascular adhesions, angiofibroma, and ocular diseases, such as diabetic retinopathy, retinopathy of prematurity, macular degeneration, corneal graft rejection, neovascular glaucoma, retrolental fibroplasia, rebeosis, Osler-Webber Syndrome, myocardial angiogenesis, plaque neovascularization, telangiectasia, hemophiliac joints, angiofibroma and wound granulation. Other conditions that involve angiogenesis include, for example, solid tumors, tumor metastases and benign tumors. Such tumors and related disorders are well known in the art and include, for example, melanoma, central nervous system tumors, neuroendocrine tumors, sarcoma, multiple myeloma as wells as cancer of the breast, lung, prostate, colon, head & neck, and ovaries. Additional tumors and related disorders are listed in Table I of U.S. Pat. No. 6,025,331, issued Feb. 15, 2000 to Moses, et al., the teachings of which are incorporated herein by reference. Benign tumors include, for example, hemangiomas, acoustic neuromas, neurofibromas, trachomas, and pyogenic granulomas. Other relevant diseases or conditions that involve blood vessel growth include intestinal adhesions, atherosclerosis, scleroderma, and hypertropic scars, and ulcers. Furthermore, the heteromultimers of the present invention can be used to reduce or prevent uterine neovascularization required for embryo implantation, for example, as a birth control agent.

Heteromultimers of this invention can also be useful for treating vascular permeability events that can result when VEGF binds KDR. See e.g. Example 30. In renal failure it has been shown that anti-VEGF antibodies can reverse damage and in a similar way the compounds of the invention can reverse renal permeability pathogenesis in, for example, diabetes.

As the interruption of the HGF interaction with the cMet receptor slows tumor progression, in another embodiment, the heteromultimers include cMet or HGF/cMet complex binding polypeptides that inbhit the binding of cMet to HGF (or otherwise inhibit the activation of cMet) may be used to treat tumors and other hyperproliferative disorders. Particular heteromultimers that inhibit cMet are discussed in the Examples. A preferred heteromultimer is D28 (structure shown below in Example 9).

Furthermore, heteromultimers of the present invention may be useful in treating diseases associated with certain pathogens, including, for example, malaria, HIV, SIV, Simian hemorrhagic fever virus, etc. Sequence homology searches of KDR-binding peptides identified by phage display using the BLAST program at NCBI has identified a number of homologous proteins known or expected to be present on the surface of pathogenic organisms. Homologies were noted between KDR and VEGF/KDR complex binding polypeptides and proteins from various malaria strains, HIV, SIV, simian hemorrhagic fever virus, and an enterohemorrhagic E. coli strain. Some of the homologous proteins, such as PfEMP 1 and EBL-1, are hypermutable adhesion proteins known to play roles in virulence. These proteins possess multiple binding sites that are capable of binding to more than one target molecule on the host's surface. Their high mutation and recombination rates allow them to quickly develop new binding sites to promote survival and/or invasion. Similarly, proteins such as gp120 of HIV (which also has homology to some of the KDR-binding peptides disclosed herein) play critical roles in the adhesion of pathogens to their hosts. Although not reported previously, it is possible that many of the pathogen proteins with homology to the KDR-binding peptides disclosed herein also bind to KDR. Comparison of the pathogen protein sequences with the corresponding peptide sequences may suggest changes in the peptide sequence or other modifications that will enhance its binding properties. Additionally, heteromultimeric constructs including the KDR-binding peptide sequences disclosed herein may have usefulness in blocking infection with the pathogen species that possesses the homology. Indeed, a strategy is being employed to block HIV infection by trying to prevent virus envelope proteins from binding to their known cellular surface targets such as CD4. Howie SE, et al., FASEB J 1998 August; 12(11): 991–8, "Synthetic peptides representing discontinuous CD4 binding epitopes of HIV-1 gp120 that induce T cell apoptosis and block cell death induced by gp120." Thus, KDR may represent a previously unknown target for a number of pathogens and the heteromultimeric constructs including KDR or VEGF/KDR complex binding peptides may be useful in treating the diseases associated with these pathogens.

In the above treatment methods, the compounds may be administered by any convenient route customary for therapeutic agents, for example parenterally, enterally or intranasaly, and preferably by infusion or bolus injection, or by depot or slow release formulation. In a preferred embodiment, the composition may be formulated in accordance with routine procedures as a pharmaceutical composition adapted for intravenous administration to human beings. Typically, compositions for intravenous administration are solutions in sterile isotonic aqueous buffer. Other pharmaceutically acceptable carriers include, but are not limited to, sterile water, saline solution, buffered saline (including buffers like phosphate or acetate), alcohol, vegetable oils, polyethylene glycols, gelatin, lactose, amylose, magnesium stearate, talc, silicic acid, paraffin, etc. Where necessary, the composition may also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition may comprise conventional excipients, i.e. pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to administration. The quantity of material administered will depend on the seriousness of the condition. For example, for treatment of anangiogenic condition, e.g., in the case of neoplastic tumor growth, the position and size of the tumor will affect the quantity of material to be administered. The precise dose to be employed and mode of administration must per force in view of the nature of the complaint be decided according to the circumstances by the physician supervising treatment. In general, dosages of the heteromultimer/therapeutic agent conjugate will follow the dosages that are routine for the therapeutic agent alone, although the improved affinity of a heteromultimer of the invention for its target may allow a decrease in the standard dosage.

Such conjugate pharmaceutical compositions are preferably formulated for parenteral administration, and most preferably for intravenous or intra-arterial administration. Generally, and particularly when administration is intravenous or intra-arterial, pharmaceutical compositions may be given as a bolus, as two or more doses separated in time, or as a constant or non-linear flow infusion.

The heteromultimers can be administered to an individual over a suitable time course depending on the nature of the condition and the desired outcome. The heteromultimeric constructs can be administered prophylactically, e.g. before the condition is diagnosed or to an individual predisposed to a condition. Alternatively, the heteromultimers of the invention can be administered while the individual exhibits symptoms of the condition or after the symptoms have passed or otherwise been relieved (such as after removal of a tumor).

In addition, the heteromultimers of the present invention can be administered a part of a maintenance regimen, for example to prevent or lessen the recurrence or the symptoms or condition. As described herein, the heteromultimers of the present invention can be administered systemically or locally.

As used herein the term "therapeutic" includes at least partial alleviation of symptoms of a given condition. The heteromultimeric constructs of the present invention do not have to produce a complete alleviation of symptoms to be useful. For example, treatment of an individual can result in a decrease in the size of a tumor or diseased area, or prevention of an increase in size of the tumor or diseased area or partial alleviation of other symptoms. Treatment can result in reduction in the number of blood vessels in an area of interest or can prevent an increase in the number of blood vessels in an area of interest. Treatment can also prevent or lessen the number or size of metastic outgrowths of the main tumor(s).

In one embodiment, symptoms that can be alleviated include physiological characteristics such as VEGF receptor activity and migration ability of endothelial cells. The heteromultimers of the present invention can inhibit activity of VEGF receptors, including VEGF-2/KDR, VEGF-1/Flt-1 and VEGF-3/Flt-4. Such inhibition can also be detected, for example, by measuring the phosphorylation state of the receptor in the presence of or after treatment with the binding polypeptides or constructs thereof. Based on the teachings provided herein, one of ordinary skill in the art would know how and be able to administer a suitable dose of binding polypeptide or construct thereof as provided herein and measured before and after treatment. In another embodiment, the phosphorylation state of the relevant receptor, or the migration ability of endothelial in an area of interest can be measured in samples taken from the individual. The VEGF receptors or endothelial cells can be isolated from the sample and used in assays described herein.

The dosage of the heteromultimers may depend on the age, sex, health, and weight of the individual, a well as the nature of the condition and overall treatment regimen. The biological effects of the multimers are described herein. Therefore, based on the biological effects of the heteromultimers provided herein, and the desired outcome of treatment, the referred dosage is determinable by one of ordinary skill in the art through route optimization procedures. Typically, the daily regiment is in the range of about 0.1 µg/kg to about 1 mg/kg.

The heteromultimers provided herein can be administered as the sole active ingredient together with a pharmaceutically acceptable excipient, or can be administered together with other binding polypeptides and constructs thereof, other therapeutic agents, or combination thereof. In addition, the heteromultimers can be conjugated to therapeutic agents, for example, to improve specificity, residence time in the body, or therapeutic effect. Such other therapeutic agents include, for example, other antiangiogenic compounds, and tumoricidal compounds. The therapeutic agent can also include antibodies.

Furthermore, the heteromultimers of the present invention can be used as an endothelial cell homing device. Therefore, the heteromultimeric constructs can be conjugated to nucleic acids encoding, for example, a therapeutic polypeptide, in order to target the nucleic acid to endothelial cells. Once exposed to the nucleic acid, thereby delivering the therapeutic peptide to the target cells.

In another embodiment of the invention, the therapeutic agent can be associated with an ultrasound contrast agent composition, said ultrasound contrast agent including the KDR, VEGF/KDR complex, cMet, or HGF/cMet binding peptides of the invention linked to the material employed to form the vesicles (particularly microbubbles or microballoons) comprised in the contrast agent, as previously described. For instance, said contrast agent/therapeutic agent association can be carried out as described in U.S. Pat. No. 6,258,378, herein incorporated by reference. Thus, after administration of the ultrasound contrast agent and the optional imaging of the contrast agent bound to the pathogenic site expressing the KDR, VEGF/KDR complex, cMet, or HGF/cMet complex, the pathogenic site can be irradiated with an energy beam (preferably ultrasonic, e.g. with a frequency of from 0.3 to 3 MHz), to cause the bursting of microvesicles, as disclosed for instance in the above cited U.S. Pat. No. 6,258,378. The therapeutic effect of the therapeutic agent can thus be advantageously enhanced by the energy released by the burst of the microvesicles, in particular causing an effective delivery of the therapeutic agent to the targeted pathogenic site.

As discussed above, the heteromultimers can be administered by any suitable route. Suitable routes of administration include, but are not limited to, topical application, transdermal, parenteral, gastrointestinal, intravaginal, and transalvcolar. Compositions for the desired route of administration can be prepared by any of the methods well known in the pharmaceutical arts. Details concerning dosages, dosage forms, modes of administration, composition and the like are further discussed in a standard pharmaceutical text, such as *Remington's Pharmaceutical Sciences,* 18th ed., Alfonso R. Gennaro, ed. (Mack Publishing Co., Easton, Pa. 1990), which is hereby incorporated by reference.

For topical applications, the heteromultimers can be suspended, for example, in a cream, gel or rinse which allows the polypeptides or constructs to penetrate the skin and enter the blood stream, for systemic delivery, or contact the are of interest, for localized delivery. Compositions suitable for topical application include any pharmaceutically acceptable base in which the polypeptides are at least minimally soluble.

For transdermal administration, the heteromultimers can be applied in pharmaceutically acceptable suspension together with a suitable transdermal device or "patch." Examples of suitable transdermal devices for administration of the heteromultimers of the present invention are described, for example, in U.S. Pat. No. 6,165,458, issued Dec. 26, 2000 to Foldvari, et al., and U.S. Pat. No. 6,274, 166B 1, issued Aug. 4, 2001 to Sintov, et al., the teachings of which are incorporated herein by reference.

For parenteral administration, the heteromultimers can be suspended, for example, in a pharmaceutically acceptable sterile isotonic solution, such as saline and phosphate buffered saline. The constructs of the invention can then be injected intravenously, intramuscularly, intraperitoneally, or subcutaneously.

For gastrointestinal and intravaginal administration, the heteromultimers can be incorporated into pharmaceutically acceptable powders, pills or liquids for ingestion, and suppositories for rectal or vaginal administration.

For transalveolar, buccal or pulmonary administration, the heteromultimers can be suspended in a pharmaceutically acceptable excipient suitable for aerosolization and inhalation or as a mouthwash. Devices suitable for transalveolar administration such as atomizers and vaporizes are also included within the scope of the invention. Suitable formulations for aerosol delivery of polypeptides using buccal or pulmonary routes can be found, for example in U.S. Pat. No. 6,312,665B1, issued Nov. 6, 2001 to Pankaj Modi, the teachings of which are incorporated herein by reference.

In addition, the heteromultimers of the present invention can be administered nasally or ocularly, where the heteromultimers are suspended in a liquid pharmaceutically acceptable agent suitable for dropwise dosing.

The heteromultimers of the present invention can be administered such that the polypeptide is released in the individual over an extended period of time (sustained or controlled release). For example, the heteromultimers can be formulated into a composition such that a single administration provides delivery of the constructs of the invention for at least one week, or over the period of a year or more. Controlled release systems include monolithic or reservoir-type microcapsules, depot implants, osmotic pumps, vesicles, micelles, liposomes, transdermal patches and iontophoretic devices. In one embodiment, the heteromultimers of the present invention are encapsulated or admixed in a slow degrading, non-toxic polymer. Additional formulations suitable for controlled release of constructs of the invention are described in U.S. Pat. No. 4,391,797, issued Jul. 5, 1983, to Folkman, et al., the teachings of which are incorporated herein by reference.

Another suitable method for delivering the heteromultimers of the present invention to an individual is via in vivo production of the polypeptides. Genes encoding the polypeptides can be administered to the individual such that the encoded polypeptides are expressed. The genes can be transiently expressed. In a particular embodiment, the genes encoding the polypeptide are transfected into cells that have been obtained from the patient, a method referred to as ex vivo gene therapy. Cells expressing the polypeptides are then returned to the patient's body. Methods of ex vivo gene therapy are well known in the art, and are described, for example, in U.S. Pat. No. 4,391,797, issued Mar. 21, 1998 to Anderson, et al., the teachings of which are incorporated herein by reference.

Preparation and tests of heteromultimeric constructs in accordance with this invention will be further illustrated in the following examples. The specific parameters included in the following examples are intended to illustrate the practice of the invention, and they are not presented to in any way limit the scope of the invention.

EXAMPLE 1

Peptide Synthesis and Fluorescein Labelling

Selected KDR or VEGF/KDR binding peptides corresponding to positive phage isolates were synthesized on solid phase using 9-fluorenylmethoxycarbonyl protocols and purified by reverse phase chromatography. Peptide masses were confirmed by electrospray mass spectrometry, and peptides were quantified by absorbance at 280 nm. For synthesis, two N-terminal and two C-terminal amino acids from the phage vector sequence from which the peptide was excised were retained and a -Gly-Gly-Gly-Lys-NH$_2$ linker was added to the C-terminus of each peptide. Peptides with selected lysine residues were protected with 1-(4,4-dimethyl-2,6-dioxocyclohex-1-ylidene)-3-methybutyl (ivDde), which allows selective coupling to the C-terminal lysine, is not removed during peptide cleavage, and can be removed after coupling with 2% hydrazine in DMF or 0.5 M hydroxylamine, pH 8, in water.

Each peptide was labeled with fluorescein on the C-terminal lysine using Fluorescein (N-hydroxysuccinimide ester derivative) or Fluorescein Isothiocyanate (FITC) in DMF, 2% diisopropylethylamine (DIPEA). If the peptide contained an ivDde protected lysine, the reaction was quenched by the addition of 2% hydrazine, which reacts with all free NHS-fluorescein and removes the internal protecting group. For all other peptides, the reaction was quenched by the addition of an equal volume of 0.5 M hydroxylamine, pH 8. The quenched reactions were then diluted with water to less than 10% DMF and then purified using C18 reverse phase chromatography. The peptides were characterized for purity and correct mass on an LC-MS system (HP1100 HPLC with in-line SCIEX AP150 single quadrapole mass spectrometer).

Fluorescence Anisotropy Measurements and BiaCore Assays

Fluorescence anisotropy measurements were performed in 384-well microplates in a volume of 10 μL in binding buffer (PBS, 0.01% Tween-20, pH 7.5) using a Tecan Polarion fluorescence polarization plate reader. In some cases, heparin (0.5 μg/mL) or 10% human serum was added to the binding buffer. The concentration of fluorescein labeled peptide was held constant (20 nM) and the concentration of KDR-Fc (or similar target) was varied. Binding mixtures were equilibrated for 10 minutes in the microplate at 30° C. before measurement. The observed change in anisotropy was fit to Equation (1) below via nonlinear regression to obtain the apparent $K_D$. Equation (1) assumes that the synthetic peptide and HSA form a reversible complex in solution with 1:1 stoichiometry:

$$\frac{(K_D + KDR + P) - \sqrt{(K_D + KDR + P)^2 - 4 \cdot KDR \cdot P}}{2 \cdot P}, \quad (1)$$

where $r_{obs}$ is the observed anisotropy, $r_{free}$ is the anisotropy of the free peptide, $r_{bound}$ is the anisotropy of the bound peptide, $K_D$ is the apparent dissociation constant, KDR is the total KDR concentration, and P is the total fluorescein-labeled peptide concentration.

KDR-Fc (or another protein target) was cross-linked to the dextran surface of a CM5 sensor chip by the standard amine coupling procedure (0.5 mg/mL solutions diluted 1:20 with 50 mM acetate, pH 6.0, $R_L$ KDR-Fc=12859). Experiments were performed in HBS-P buffer (0.01 M HEPES, pH 7.4, 0.15 M NaCl, 0.005% polysorbate 20 (v/v)). Peptide solutions quantitated by extinction coefficient were diluted to 400 nM in HBS-P. Serial dilutions were performed to produce 200, 100, 50, and 25 nM solutions. For association, peptides were injected at 20 μL/min for 1 minute using the kinject program. Following a 1-minute dissociation, any remaining peptide was stripped from the target surface with a quick injection of 1M NaCl for 25 sec. at 50 μL/min. All samples were injected in duplicate. Between each peptide series a buffer injection and a non-target binding peptide injection served as additional controls. Sensorgrams were analyzed using the simultaneous ka/kd fitting program in the BIAevaluation software 3.1.

The following common abbreviations are used throughout this specification: 9-fluorenylmethyloxycarbonyl (fmoc or Fmoc), 1-hydroxybenozotriazole (HOBt), N,N'-diisopropylcarbodiimide (DIC), N-methylpyrrolidinone (NMP), acetic anhydride (Ac$_2$O), (4,4-dimethyl-2,6-dioxocyclohex-1-ylidene)-3-methylbutyl (ivdde), trifluoroacetic acid (TFA), Reagent B (TFA:H$_2$O:phenol:triisopropylsilane, 88:5:5:2), diisopropylethylanine (DIEA), O-(1H-benzotriazole-1-yl)-N,N,N',N'-tetramethyluronium hexafluorophosphate (HBTU), O-(7-azabenzotriazol-1-yl)-1,1,3,3-tetramethyluronium hexafluorphosphate (HATU), N-hydroxysuccinimide (NHS), solid phase peptide synthesis (SPPS), dimethyl sulfoxide (DMSO), dichloromethane (DCM), dimethylformamide (DMF), human serum albumin (HSA), and radiochemical purity (RCP).

Experimental Methods

The following methods were employed in the Examples.

(a) Method 1 for ACT 357 MPS and ACT 496 MOS Synthesizers

The peptides were synthesized on NovaSyn TGR (Rink amide) resin (0.2 mmol/g) using the Advanced ChemTech ACT 357 or ACT 496 Synthesizers employing Fmoc peptide synthesis protocols, specifically using HOBt/DIC as the coupling reagents and NMP as the solvent. The Fmoc was removed by treating the Nova-Syn TGR (Rink amide-available from NovaBiochem, San Diego, Calif.) resin-bound peptide with 25% piperidine in DMF twice (4 min and 10 min). All amino acids were dissolved in NMP (DMF was added when the amino acid was not soluble in pure NMP). The concentration of the amino acid was 0.25 M, and the concentration for both HOBt and DIC was 0.5 M.

For a 0.04 mmol scale synthesis:

A typical amino acid coupling cycle (not including wash steps) was to dispense piperidine solution (2.4 mL) to each well and mix for 4 min, then empty all wells. NMP (320 μL), HOBt solution (320 μL, 4 eq), amino acid (640 μL, 4 eq) and DIC (320 μL, 4 eq) solutions were dispensed to each well. The coupling time was 3 h; then the resin was washed. The cycle was repeated for each amino acid. After the last amino acid coupling, the resin-bound peptide was treated with 25% piperidine to remove the Fmoc protecting group. After washing, the resin bound peptide was capped with 1.0 M Ac$_2$O (1.2 mL per well) and diisopropylethylamine in DMF, optionally including varying amounts of HOBt in the mixture for 30 min. The resin was washed first with methanol and then with dichloromethane and dried. Cleavage of the peptides from the resin and side-chain deprotection was accomplished using Reagent B for 4.5 h. The cleavage solutions were collected and the resins were washing with an additional aliquot of Reagant B. The combined solutions were concentrated to dryness. Ether was added to the residue with swirling or stirring to precipitate the peptides. The ether was decanted, and solid was collected. This procedure was repeated 2–3 times to remove impurities. The crude peptides were dissolved in DMSO and water mixture, and purified by HPLC (column: Water's Associates Xterra C18, 19×50 mm; solvents: H$_2$O with 0.1% TFA and CH$_3$CN with 0.1% TFA; UV 220 nm; Flow rate: 50–60 mL/min). The solutions containing the peptide were lyophilized to give the desired peptides as white fluffy lyophilizates (>90% purity).

The purified linear di-cysteine containing peptides were dissolved in water, mixtures of water-acetonitrile, or mixtures of water-DMSO at concentrations between 0.1 mg/mL and 2.0 mg/mL. The choice of solvent was a function of the solubility of the crude peptide in the solvent. The pH of the solution was adjusted to 7.5–8.5 with aqueous ammonia, aqueous ammonium carbonate or aqueous ammonium bicarbonate. The mixture was stirred vigorously in air for 24–48 h. In the case of non-DMSO containing solvent systems, the pH of the solution was adjusted to 2 with aqueous trifluoroacetic acid. The mixture was lyophilized to provide the crude cyclic disulfide containing peptide. The cyclic disulfide peptide was then dissolved to a volume of 1–2 mL in aqueous (0.1% TFA) containing a minimum of acetonitrile (0.1% TFA). The resulting solution was loaded onto a reverse phase column and the desired compound obtained by a gradient elution of acetonitrile into water, employing a C18, or C8 reverse phase semipreparative or preparative HPLC column. In the case of the DMSO-containing solutions, the solution was diluted until the DMSO concentration was minimal without precipitation of the peptide. The resulting mixture was quickly acidified to pH 2 with dilute trifluoroacetic acid and loaded onto the reverse phase HPLC system and purified as described. Fractions containing the desired materials were pooled and the peptides isolated by lyophilization.

(b) Method 2 for ACT 357 MPS and ACT 496 MOS Synthesizers

The peptides were synthesized as in Method 1, with the following changes. HBTU/HOBt/DIEA were used as the coupling reagent and NMP as the solvent. A low load (~0.2 mmol/g) Fmoc-GGGK(Boc)-NovSyn-TGR-resin prepared from the above-described Nova-Syn TGR resin was employed for peptides synthesis on 0.01 mmol scale synthesis.

For a 0.01 mmol scale synthesis:

After the Fmoc group was removed, a standard coupling procedure used a solution of HOBt (720 μL, 6 eq), amino acid (804 μL, 6.6 eq), HBTU (720 μL, 6 eq) and DIEA (798 μL, 13.3 eq). The mixture was agitated for 15 min, emptied and the resin washed. After all couplings and after cleavage and purification as above, the solutions containing desired linear peptides were lyophilized to give the peptides as white fluffy solids (>90% purity).

The crude ether-precipitated linear di-cysteine containing peptides were cyclized by dissolution in water, mixtures of aqueous acetonitrile (0.1% TFA), or aqueous DMSO and adjustment of the pH of the solution to 7.5–8.5 by addition of aqueous ammonia, aqueous ammonium carbonate, or aqueous ammonium bicarbonate solution. The peptide concentration was between 0.1 and 2.0 mg/mL. The mixture was stirred in air for 24–48 h, acidified to a pH of 2 with aqueous trifluoroacetic acid and then purified by preparative reverse phase HPLC employing a gradient of acetonitrile into water. Fractions containing the desired material were pooled and the peptides were isolated by lyophilization.

Method 3 for the ACT 496 MOS Synthesizer

The peptides were synthesized using an Advanced ChemTech ACT 496 MOS Synthesizer as in Method 1. The low load (~0.2 mmol/g) GGGK(Boc)-NovaSyn-TGR resin was employed for peptide synthesis. The coupling solvent was NMP/DMSO 8:2. The synthesis was performed at a 0.02 mmol scale using a coupling time of 3 h. The crude linear peptides were further processed as described above for Method 1.

(a)

(b) Method 4 for the ACT 496 MOS Synthesizer

The peptides were synthesized using method 3 on the ACT 496 with HBTU/DIEA as the coupling reagents, and NMP as the solvent. 2,4,6-collidine as a 1 M solution was used as the base. The low load Fmoc-GGGK(ivDde)-Novsyn-TGR resin (~0.2 mmol/g) was used for peptide synthesis. The coupling time was 30 minutes. The crude linear peptides were further processed as described above for Method 1.

Method 5 for the ABI 433A Synthesizer

Synthesis of peptides was carried out on a 0.25 mmol scale using the FastMoc protocol (Applied Biosystems Inc.) In each cycle of this protocol, 1.0 mmol of a dry protected amino acid in a cartridge was dissolved in a solution of 0.9 mmol of HBTU, 2 mmol of DIEA, and 0.9 mmol of HOBt in DMF with additional NMP added. The peptides were made using 0.1 mmol of NovaSyn TGR (Rink amide) resin (resin substitution 0.2 mmol/g). The coupling time in this protocol was 21 min. Fmoc deprotection was carried out with 20% piperidine in NMP. At the end of the last cycle, the synthesized peptide was acetylated using acetic anhydride/DIEA/HOBt/NMP. The peptide resin was washed and dried for further manipulations or cleaved from the resin (using reagent B). Generally, the cleaved peptides were cyclized, as in Method 1, above.

Method 6

Biotinylation of Resin Bound Peptides

The peptides were prepared by Method 5. The ivDde protecting group on the C-terminal lysine was selectively removed by treatment with 10% hydrazine in DMF. The resin was then treated with a solution of Biotin-N-hydroxysuccinimidyl ester in DMF in the presence of DIEA. After washing, the resin was dried and cleavage was performed using Reagent B. The resin was filtered off and the filtrate concentrated to dryness. The biotinylated peptide was dissolved in neat DMSO and treated with DIEA and stirred for 4–6 h to effect disulfide cyclization. The crude mixture was purified by preparative HPLC.

In a typical experiment, 200 mg of the resin-bound peptide was treated with 10% hydrazine in DMF (2×20 mL) and washed with DMF (2×20 mL) and then with dichloromethane (1×20 mL). The resin was resuspended in DMF (10 mL) and treated with a solution of Biotin-NIHS ester (0.2 mmol, 5 equivalent) and DIEA (0.2 mmol) and the resin was mixed with the reagents for 4 h. The completion of the reaction was checked by the ninhydrin test. The peptide was then released from the resin by treatment with Reagent B (10 mL) for 4 h. The resin was filtered off, Reagent B was removed in vacuo and the peptide was precipitated by addition of anhydrous ether. The solid formed was collected, washed with ether and dried. The solid was dissolved in anhydrous DMSO and the mixture was adjusted to pH 7.5 with DIEA and stirred for 4–6 h to effect disulfide cyclization. The disulfide cyclization reaction was monitored by analytical HPLC. After completion of the cyclization, the mixture solution was diluted with 25% acetonitrile in water and directly purified by HPLC on reverse phase C-18 column using a gradient of acetonitrile into water (both containing 0.1% TFA). Fractions were analyzed by analytical HPLC and those containing the pure product were collected and lyophilized to obtain the required biotinylated peptide.

Method 7

Biotinylation of Purified Peptides

The purified peptide (10 mg, prepared by methods 1–5) containing a free amino group was dissolved in anhydrous DMF or DMSO (1 mL) and Biotin-NHS ester of (5 equivalents) and DIEA (5 equivalents) were added. The reaction was monitored by HPLC and after the completion of the reaction (1–2 h), the crude reaction mixture was directly purified by preparative HPLC. Fractions were analyzed by analytical HPLC and those containing the pure product were collected and lyophilized to obtain the required biotinylated peptide.

(a) Method 8

Biotinylation of Resin Bound Peptides Containing Linkers

In a typical experiment, 400 mg of the resin-containing peptide (made using the ABI-433 A Synthesizer and bearing an ivDde-protected lysine) was treated with 10% hydrazine in DMF (2×20 mL). The resin was washed with DMF (2×20 mL) and DCM (1×20 mL). The resin was resuspended in DMF (10 mL) and treated with Fmoc-aminodioxaoctanoic acid (0.4 mmol), HOBt (0.4 mmol), DIC (0.4 mmol), DIEA (0.8 mmol) with mixing for 4 h. After the reaction, the resin was washed with DMF (2×10 ml) and with DCM (1×10 mL). The resin was then treated with 20% piperidine in DMF (2×15 mL) for 10 min each time. The resin was washed and the coupling with Fmoc-diaminodioxaoctanoic acid and removal of the Fmoc protecting group were repeated once more. The resulting resin, containing a peptide with a free amino group, was treated with a solution of Biotin-NHS ester (0.4 mmol, 5 equivalent) and DIEA (0.4 mmol, 5 equivalents) in DMF for 2 h. The peptide-resin was washed and dried as described previously and then treated with reagent B (20 mL) for 4 h. The mixture was filtered and the filtrate concentrated to dryness. The residue was stirred with ether to produce a solid that was collected, washed with ether, and dried. The solid was dissolved in anhydrous DMSO and the pH adjusted to pH 7.5 with DIEA. The mixture was stirred for 4–6 hr. to effect the disulfide cyclization reaction which was monitored by analytical HPLC. After the completion of the cyclization, the DMSO solution was diluted with 25% acetonitrile in water and applied directly to a reverse phase C-18 column. Purification was effected using a gradient of acetonitrile into water (both containing 0.1% TFA). Fractions were analyzed by analytical HPLC and those containing the pure product were collected and lyophilized to provide the required biotinylated peptide.

Method 9

Formation of 5-Carboxyfluorescein Labeled Peptides

Peptide-resin obtained via from Method 5, containing an ivDde protecting group on the epsilon nitrogen of lysine, was mixed with a solution of hydrazine in DMF (10% hydrazine/DMF, 2×10 mL, 10 min) to remove the ivDde group. The epsilon nitrogen of the lysine was labeled with fluorescein-5-isothiocyanate (0.12 mmol) and diisopropylethylamine (0.12 mmol) in DMF. The mixture was agitated for 12 h (fluorescein-containing compounds were protected from light). The resin was then washed with DMF (3×10 mL) and twice with $CH_2Cl_2$ (10 mL) and dried under nitrogen for 1 h. The peptide was cleaved from the resin using Reagent B for 4 h and the solution collected by filtration. The volatiles were removed under reduced pressure and the residue was dried under vacuum. The peptide was precipitated with ether, collected and the precipitate was dried under a stream of nitrogen. The precipitate was added to water (1 mg/mL) and the pH of the mixture was adjusted to 8 with 10% aqueous meglumine. Cyclization of the peptide was carried out for 48 h and the solution was freeze-dried. The crude cyclic peptide was dissolved in water and purified by RP-HPLC on a $C_{18}$ column with linear gradient of acetonitrile into water (both phases contained 0.1% TFA). Fractions containing the pure product were collected and freeze dried. The peptides were characterized by ES-MS and the purity was determined by RP-HPLC (linear gradient of acetonitrile into water/0.1% TFA).

Method 10A

Preparation of Peptidic Chelate for Binding to Tc By Coupling of Single Amino Acids Peptides were synthesized starting with 0.1 mmol of NovaSyn-TGR resin (0.2 mmol/g substitution). Deprotected (ivDde) resin was then treated according to the protocol A for the incorporation of Fmoc (Gly)-OH, Fmoc-Cys(Acm)-OH and, Fmoc-Ser(tBu)-OH.

Protocol A for Manual Coupling of Single Amino Acid:
1. Treat with 4 equivalents of corresponding Fmoc-amino acid and 4.1 equivalents of hydroxy benzotriazole and 4.1 equivalents of HOB and 4.1 equivalents of DIC for 5 h.
2. Wash with DMF (3×10 mL)
3. Treat with 20% piperidine in DMF (2×10 mL, 10 min)
4. Wash with DMF (3×10 mL)

The Fmoc-protected peptide loaded resin was then treated with 20% piperidine in DMF (2×10 mL, 10 min) and washed with DMF (3×10 mL). A solution of N,N-dimethylglycine (0.11 mmol), HATU (1 mmol), and DIEA (0.11 mmol) in DMF (10 mL) was then added to the peptide loaded resin and the manual coupling was continued for 5 h. After the reaction the resin was washed with DMF (3×10 mL) and $CH_2Cl_2$ (3×10 mL) and dried under vacuum.

Method 10B

Preparation of Peptidic Chelate for Binding to Tc by Appendage of the Glutaryl-PnAO6 Chelator to the Peptide Preparation of 4-{2-(2-Hydroxyimino-1,1-dimethylpropylamino)-1-[(2-hydroxyimino-1,1-dimethyl-propylamino)-methyl]-ethylcarbamoyl}-butyric acid, N-hydroxysuccinimide ester—Compound B 4-{2-(2-Hydroxyimino-1,1-dimethyl-propylamino)-1-[(2-hydroxyimino-1,1-dimethyl-propylamino)-methyl]-ethylcarbamoyl}-butyric acid (Compound A) (40 mg) was dissolved in DMF (700 μL). N-Hydroxysuccinimide (1.5 equiv, 17.2 mg) and 1,3-diisopropylcarbodiimide (1.5 equiv, 24 μL) were added. The progress of the reaction was monitored by mass spectroscopy. After 17 h, the reaction was complete. The volatiles were removed in vacuo and the residue was washed with ether (5×) to remove the unreacted NHS. The residue was dried to provide compound B, which was used directly without further treatment or purification.

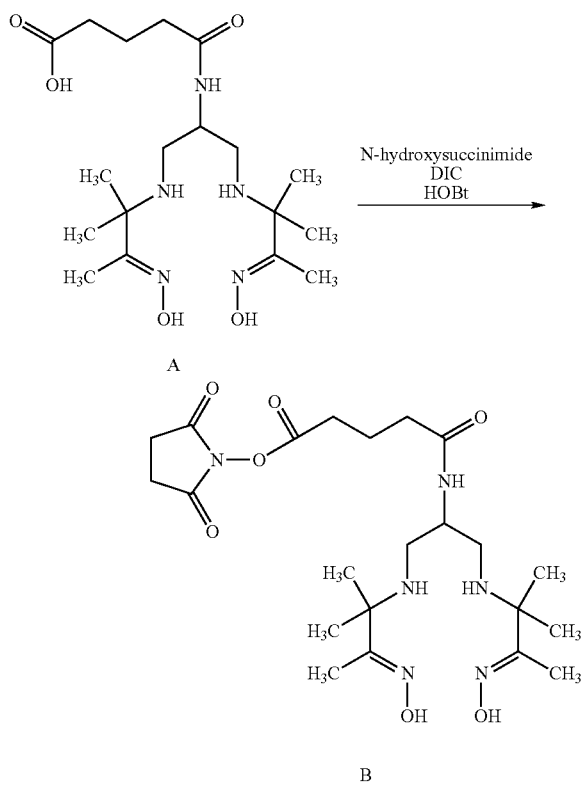

A

B

Functionalization of Peptides with 4-{2-(2-Hydroxyimino-1,1-dimethylpropylamino)-1-[(2-hydroxyimino-1,1-dimethyl-propylamino)-methyl]-ethylcarbamoyl}-butyric acid, N-hydroxysuccinimide ester—(Compound B)

The peptide (prepared, for example, by Methods 1–13) is dissolved in DMF and treated with compound B and DIEA sufficient to maintain the basicity of the mixture. The progress of the reaction is monitored by HPLC and mass spectroscopy. At completion of the reaction the volatiles are removed in vacuo and the residue is either purified by reverse phase HPLC or processed further by selective removal of side chain protecting groups or subjected to cleavage of all remaining protecting groups as required by the next steps in the synthesis scheme.

Method 11

Formation of Mercapto-Acetylated Peptides Using S-Acetylthioglycolic Acid N-Hydroxysuccinimide Ester To a solution of a peptide (0.005 mmol, obtained from Methods 1–5 with a free amine) in DMF (0.25 mL) was added S-acetylthioglycolic acid N-hydroxysuccinimide ester (SATA) (0.0055 mmol) and the reaction mixture was stirred at ambient temperature for 6 h. The volatile were removed under vacuum and the residue was purified by preparative HPLC using acetonitrile-water containing 0.1% TFA. Fractions containing the pure product were collected and freeze-dried to yield the mercaptoacetylated peptide. The mercaptoacetylated peptide was characterized by ESI-MS and the purity was determined by reverse phase PHLC analysis employing a linear gradient of acetonitrile into water (both containing 0.1% TFA).

Method 12

Formation of Mercaptoacetylated Peptide Using S-Acetylthioglycolic Acid

Purified peptides from Method 5, after disulfide cyclization, were coupled with S-acetylthioglycolic acid (1.5–10 eq.)/HOBt (1.5–10 eq.)/DIC (1.5–10 eq.) in NMP for 2–16 h at room temperature. The mixture was then purified by preparative HPLC and the fractions containing pure peptide combined and lyophilized. In the case of compounds with another lysine protected by an ivDde group, the deprotection reaction employed 2% hydrazine in DMSO for 3 h at room temperature. Purification of the reaction mixture afforded pure peptide.

In the case of preparing a compound with S-acetylthioglycolic acid coupled to two aminodioxaoctanoic acid groups and the peptide, the purified peptide from Method 5 (having a free amino group, was coupled to AcSCH$_2$—CO—(NH—CH$_2$—CH$_2$—O—CH$_2$—CH$_2$—O—CH$_2$—CO)$_2$—OH (30 eq.)/HOBt (30 eq.)/DIC (30 eq.) in NMP for 40 h at room temperature. The mixture was purified and the ivDde group was removed. A second purification gave the final product as a white lyophilizate.

Alternatively Fmoc aminodioxaoctanoic acid was coupled twice successively to the peptide (produced by method 5) followed by Fmoc removal and coupling to S-acetylthioglycolic acid.

Method 13

Preparation of Homodimers and Heterodimers

The required purified peptides were prepared by SPPS using Method 5. To prepare homodimers, half of the peptide needed to prepare the dimer was dissolved in DMF and treated with 10 equivalents of glutaric acid bis N-hydoxysuccinimidyl ester The progress of the reaction was monitored by HPLC analysis and mass spectroscopy. At completion of the reaction, the volatiles were removed in vacuo and the residue was washed with ethyl acetate to remove the unreacted bis-NHS ester. The residue was dried, re-dissolved in anhydrous DMF and treated with another half portion of the peptide in the presence of 2 equivalents of DIEA. The reaction was allowed to proceed for 24 hr. This mixture was applied directly to a Waters Associates C-18 XTerra RP-HPLC column and purified by elution with a linear gradient of acetonitrile into water (both containing 0.1% TFA).

In the case of heterodimers, one of the monomers was reacted with the bis NHS ester of glutaric acid and after washing off the excess of bis NHS ester, the second amine was added in the presence of DIEA. After the reaction, the mixture was purified by preparative HPLC.

Preparation of KDR and VEGF/KDR Complex Binding Polypeptides

Utilizing the methods described above, the KDR and VEGF/KDR complex binding polypeptides in Table 1 were prepared. As used in Table 1, the letter "J" in the peptide sequences refers to the spacer or linker group, 8-amino-3,6-dioxaoctanoyl. Also as used in Table 1, the designation "C*" refers to a cysteine residue that contributes to a disulfide bond. The ability of the biotinylated polypeptides to bind to KDR was assessed using the assay set described below.

The following biotinylated peptides bound well to the KDR-expressing cells: P13-XB (Kd 1.81 nM+/−0.27), P5-XB (Kd 14.87+/−5.07 nM, four experiment average), P6-XB (Kd 10.00+/−2.36 nM, four experiment average), P12-XB (Kd 4.031+/−0.86 nM, three experiment average), P6-F-XB (Kd 6.94+/−1.94 nM, one experiment), and P12-F-XB (Kd 3.02+/−0.75 nM, one experiment).

TABLE 1

Sequence or Structure of Peptides and Peptide Derivatives

| Ref. Number | Structure or Sequence | SEQ. ID NO |
|---|---|---|
| P1 | Control Peptide | |
| P1-B | Biotinylated Control Peptide | |
| P1-XB | Biotinylated Control Peptide with Spacer | |
| P2 | AGWIECYHPDGICYHFGT | 1 |
| P2-D | Ac-AGWIEC*YHPDGIC*YHFGTGGGK-NH$_2$ | |
| P3 | AGWLECYAEFGHCYNFGT | 2 |
| P3-D | Ac-AGWLEC*YAEFGHC*YNFGTGGGK-NH$_2$ | |
| P4 | AGDSWCSTEYTYCEMIGT | 3 |
| P4-D | Ac-AGDSWC*STEYTYC*EMIGT-GGGK-NH$_2$ | |
| P5 | AGPKWCEEDWYYCMITGT | 4 |
| P5-D | Ac-AGPKWC*EEDWYYC*MITGT-GGGK-NH$_2$ | |
| P5-E | Ac-AGPK(ivDde)WC*EEDWYYC*MITGTGGGK-NH$_2$ | |
| P5-B | Ac-AGPKWC*EEDWYYC*MITGT-GGGK-(Biotin)-NH$_2$ | |
| P5-XB | Ac-AGPKWC*EEDWYYC*MITGTGGGK-(Biotin-JJ-)-NH$_2$ | |
| P6 | GDSRVCWEDSWGGEVCFRYDP | 5 |
| P6-D | Ac-GDSRVC*WEDSWGGEVC*FRYDPGGGK-NH$_2$ | |
| P6-B | Ac-GDSRVC*WEDSWGGEVC*FRYDP-GGGK-(Biotin)-NH$_2$ | |
| P6-XB | Ac-GDSRVC*WEDSWGGEVC*FRYDPGGGK-(Biotin-JJ-)-NH$_2$ | |
| P6-F-XB | Ac-VC*WEDSWGGEVC*FRYDPGGGK-(Biotin-JJ-)-NH$_2$ | |
| P7 | GDWWECKREEYRNTTWCAWADP | 6 |
| P7-D | Ac-GDWWEC*KREEYRNTTWC*AWADPGGGK-NH$_2$ | |
| P7-E | Ac-GDWWEC*K(ivDde)REEYRNTTWC*AWADPGGGK-NH$_2$ | |
| P8 | GDPDTCTMWGDSGRWYCFPADP | 7 |
| P8-D | Ac-GDPDTC*TMWGDSGRWYC*FPADPGGGK-NH$_2$ | |
| P9 | AQEPEGYAYWEVITLYHEEDGDGG | 8 |
| P9-D | Ac-AQEPEGYAYWEVITLYHEEDGDGGK-NH$_2$ | |
| P10 | AQAFPRFGGDDYWIQQYLRYTDGG | 9 |
| P10-D | Ac-AQAFPRFGGDDYWIQQYLRYTDGGK-NH$_2$ | |
| P11 | AQGDYVYWEIIELTGATDHTPPGG | 10 |
| P11-D | Ac-AQGDYVYWEIIELTGATDHTPPGGGK-NH$_2$ | |
| P12 | AGPTWCEDDWYYCWLFGT | 11 |
| P12-D | Ac-AGPTWC*EDDWYYC*WLFGT-NH$_2$ | |
| P12-XB | Ac-AGPTWC*EDDWYYC*WLFGT-GGGK-(Biotin-JJ-)-NH$_2$ | |
| P12-F-XB | Ac-AGPTWCEDDWYYCWLFGTJK-(Biotin-JJ-)-NH$_2$ | |
| P12-C | Ac-AGPTWC*EDDWYYC*WLFGTGGGKJJGC(Acm)-(N,N-dimethyl-GSC(Acm)-NH$_2$ | |
| P13 | AQDWYYDEILSMADQLRHAFLSGG | 12 |
| P13-D | Ac-AQDWYYDEILSMADQLRHAFLSGG-NH$_2$ | |
| P13-XB | Ac-AQDWYYDEILSMADQLRHAFLSGG-GGGK-(Biotin-JJ-)-NH$_2$ | |
| P14 | GSDHHCYLHNGQWICYPFAPGGGK | 13 |
| P14-D | Ac-GSDHHC*YLHNGQWIC*YPFAPGGGK-NH$_2$ | |
| P15 | GDYPWCHELSDSVTRFCVPWDPGGGK | 14 |
| P15-D | Ac-GDYPWC*HELSDSVTRFC*VPWDPGGGK-NH$_2$ | |
| P16 | GDDHMCRSPDYQDHVFCMYWDPGGGK | 15 |
| P16-D | Ac-GDDHMC*RSPDYQDHVFC*MYWDPGGGK-NH$_2$ | |
| P17 | GDPPLCYFVGTQEWHHCNPFDPGGGK | 16 |
| P17-D | Ac-GDPPLC*YFVGTQEWHHC*NPFDPGGGK-NH$_2$ | |
| P18 | GDGSWCEMRQDVGKWNCFSDDPGGGK | 17 |
| P18-E | Ac-GDGSWC*EMRQDVGK(-ivDde-)WNC*FSDDPGGGK-NH$_2$ | |
| P19 | AQRGDYQEQYWHQQLVEQLKLLGGGK | 18 |
| P19-E | Ac-AQRGDYQEQYWHQQLVEQLK(-ivDde-)LLGGGK-NH$_2$ | |
| P20 | GDNWECGWSNMFQKEFCARPDPGGGK | 19 |
| P20-E | Ac-GDNWEC*GWSNMFQK(-ivDde-)EFC*ARPDPGGGK-NH$_2$ | |
| P21 | AGPGPCK(-ivDde-)GYMPHQCWYMGTGGGK | 20 |
| P21-E | Ac-AGPGPC*K(-ivDde-)GYMPHQC*WYMGTGGGK-NH$_2$ | |
| P22 | AGYGPCAEMSPWLCWYPGTGGGK | 21 |
| P22-D | Ac-AGYGPC*AEMSPWLC*WYPGTGGGK-NH$_2$ | |

Library Screening Against KDR and KDR/VEGF Complex Targets

Chimeric fusions of Ig Fc region with human KDR (#357-KD-050), murine KDR (#443-KD-050), human VEGFR-1 (#321-FL-050), human VEGFR-3 (#349-F4-050), and human Trail R4 (#633-TR-100) were purchased in carrier-free form (no BSA) from R & D Systems (Minneapolis, Minn.). Trail R4 Fc is an irrelevant Fc fusion protein with the same Fc fusion region as the target Fc fusion (KDR Fc) and is used to deplete the libraries of Fc binders. VEGF$_{165}$ (#100-20) was purchased in carrier-free form from Peprotech (Rocky Hill, N.J.). Protein A Magnetic Beads (#100.02) were purchased from Dynal (Oslo, Norway). Heparin (#H-3393) was purchased from Sigma Chemical Company (St. Louis, Mo.). A 2-component tetramethyl benzidine (TMB) system was purchased from KPL (Gaithersburg, Md.).

In the following procedures, microtiter plates were washed with a Bio-Tek 404 plate washer (Winooski, Vt.). ELISA signals were read with a Bio-Tek plate reader (Winooski, Vt.). Agitation of 96-well plates was on a LabQuake shaker (Labindustries, Berkeley, Calif.).

Eight M13 phage display libraries were prepared for screening against immobilized KDR and VEGF/KDR targets: Cyclic peptide display libraries TN6/VI, TN7/IV, TN8/IX, TN9/IV, TN10/IX, TN12/I, and MTN13/I, and a linear display library, Lin20. The design of these libraries has been described, supra.

The DNA encoding the library was synthesized with constant DNA on either side so that the DNA can be PCR amplified using Taq DNA polymerase (Perkin-Elmer, Wellesley, Mass.), cleaved with NcoI and PstI, and ligated to similarly cleaved phage display vector. XL1-Blue MFR' E. coli cells were transformed with the ligated DNA. All of the libraries were constructed in same manner.

KDR Selection Protocol in the Presence of Heparin

Protein A Magnetic Beads were blocked once with 1×PBS (pH 7.5), 0.01% Tween-20, 0.1% HSA (Blocking Buffer) for 30 minutes at room temperature and then washed five times with 1×PBS (pH 7.5), 0.01% Tween-20, 5 µg/mL heparin (PBSTH Buffer).

The cyclic peptide, or "constrained loop", libraries were pooled for the initial screening into two pools: TN6/VI, TN7/IV and TN8/IX were in one pool; TN9/IV, TN10/IX and TN12/I were in the second pool. The two pooled libraries and the linear library (Lin20) were depleted against Trail R4 Fc fusion (an irrelevant Fc fusion) and then selected against KDR Fc fusion. $10^{11}$ plaque forming units (pfu) from each library per 100 µL PBSTH were pooled together, e.g., 3 pooled libraries would result in a total volume of 350 µl in PBSTH.

To prepare the irrelevant Fc fusion beads, 500 µl of Trail R4-Fc fusion (0.1 µg/µl stock in PBST (no heparin)) were added to 1000 µl of washed, blocked protein A magnetic beads. The fusion was allowed to bind to the beads overnight with agitation at 4° C. The next day, the magnetic beads were washed 5 times with PBSTH. Each phage pool was incubated with 50 µl of Trail R4 Fc fusion beads on a Labquake shaker for 1 hour at room temperature (RT). After incubation, the phage supernatant was removed and incubated with another 50 µL of Trail R4 beads. This was repeated for a total of 5 rounds of depletion, to remove non-specific Fc fusion and bead binding phage from the libraries.

To prepare the KDR target beads, 500 µl of KDR-Fc fusion (0.1 µg/µl stock in PBST (no heparin)) were added to 500 µL of washed, blocked beads. The KDR-Fc fusion was allowed to bind overnight with agitation at 4° C. The next day, the beads were washed 5 times with PBSTH. Each depleted library pool was added to 100 µL of KDR-Fc beads and allowed to incubate on a LabQuake shaker for 1 hour at RT. Beads were then washed as rapidly as possible with 5×1 mL PBSTH using a magnetic stand (Promega) to separate the beads from the wash buffer. Phage still bound to beads after the washing were eluted once with 250 µl of VEGF (50 µg/mL, ~1 µM) in PBSTH for 1 hour at RT on a LabQuake shaker. The 1-hour elution was removed and saved. After the first elution, the beads were incubated again with 250 µl of VEGF (50 µg/mL, ~1 µM) overnight at RT on a LabQuake shaker. The two VEGF elutions were kept separate and a small aliquot taken from each for titering. Each elution was mixed with an aliquot of XL1-Blue MRF' (or other F' cell line) E. coli cells that had been chilled on ice after having been grown to mid-logarithmic phase. The remaining beads after VEGF elution were also mixed with cells to amplify the phage still bound to the beads, i.e., KDR-binding phage that had not been competed off by the two VEGF incubations (1-hour and overnight (O/N) elutions). After approximately 15 minutes at room temperature, the phage/cell mixtures were spread onto Bio-Assay Dishes (243×243×18 mm, Nalge Nunc) containing 250 mL of NZCYM agar with 50 µg/mL of ampicillin. The plate was incubated overnight at 37° C. The next day, each amplified phage culture was harvested from its respective plate. Over the next day, the input, output and amplified phage cultures were titered for FOI (i.e., Fraction of Input=phage output divided by phage input).

In the first round, each pool yielded three amplified eluates. These eluates were panned for 2-3 more additional rounds of selection using ~$10^{10}$ input phage/round according to the same protocol as described above. For each additional round, the KDR-Fc beads were prepared the night before the round was initiated. For the elution step in subsequent rounds, the amplified elution re-screen on KDR-Fc beads was always eluted in the same manner, and all other elutions were treated as washes. For example, for the amplified elution recovered by using th4e still-bound beads to infect E. coli, the 1-hour and overnight VEGF elutions were performed and then discarded as washes. Then the beads were used to again infect E. coli and produce the next round amplified elution. Using this procedure, each library pool only yielded three final elutions at the end of the selection. Two pools and one linear library, therefore, yielded a total of 9 final elutions at the end of the selection.

This selection procedure was repeated for all libraries in the absence of heparin in all binding buffers, i.e., substituting PBST (PBS (pH 7.5), 0.01% Tween-20) for PBSTH in all steps.

KDR Selection Protocol in the Absence of Heparin

A true TN11/1 library was used to screen for KDR binders. The same selection protocol as above (KDR Selection Protocol in the Presence of Heparin) was used, except heparin was omitted. The three elution conditions were VEGF elution (1 uM; 1 hr; same as original protocol), Dimer D6 elution (0.1 uM; 1 hr), and then bead elution (same as above). TN11/1 alone was used in the selection and screening. For selected peptides, see FIG. 40A-R.

EXAMPLE 2

Bead-Binding Assay to Confirm Ability of Peptides Identified by Phase Display to Bind KDR-Expressing Cells The following experiments were performed to assess the ability of KDR-binding peptides to bind to KDR-expressing cells. In this experiment, KDR-binding peptides P5-B and P5-XB and P6-B and P6-XB were conjugated to fluorescent beads and their ability to bind to KDR-expressing 293H cells was assessed. The experiments show that both peptide sequences can be used to bind particles such as beads to KDR-expressing sites. In general, the P6 peptides exhibited better binding to the KDR expressing cells than P5. However, the binding of both peptides improved with the addition of a spacer.

Biotinylation of an Anti-KDR Antibody

Anti-KDR from Sigma (V-9134), as ascites fluid, was biotinylated using a kit from Molecular Probes (F-6347) according to the manufacturer's instructions.

Preparation of Peptide-Conjugated Fluorescent Beads 0.1 mL of a 0.2 mM stock solution of each biotinylated peptide (prepared as set forth above, in 50% DMSO) was incubated with 0.1 mL of Neutravidin-coated red fluorescent microspheres (2 micron diameter, custom-ordered from Molecular Probes) and 0.2 mL of 50 mM MES (Sigma M-8250) buffer, pH 6.0 for 1 hour at room temperature on a rotator. As a positive control, biotinylated anti-KDR antibody was incubated with the Neutravidin-coated beads as above, except that 0.03 mg of the biotinylated antibody preparation in PBS (Gibco 14190-136) was used instead of peptide solution. Beads can be stored at 4° C. until needed for up to 1 week.

Transfection of 293H Cells 293H cells were transfected using the protocol described in Example 6. Transfection was done in black/clear 96-well plates (Becton Dickinson, cat. # 354640). The cells in one half of the plate (48 wells) were mock-transfected (with no DNA) and those in the other half of the plate were transfected with KDR cDNA. The cells were 80–90% confluent at the time of transfection and completely confluent the next day, at the time of the assay; otherwise the assay was aborted.

Binding Assay

From the above bead preparations, 0.12 mL was spun for 10 minutes at 2000 rpm in a microcentrifuge at room temperature. The supernatant was removed and 0.06 mL of MES pH 6.0 was added. Each bead solution was then vortexed and sonicated in a water bath 15 min. To 1.47 mL of DMEM, high glucose (GIBCO 11965-084) with 1×MEM Non-Essential Amino Acids Solution (NEAA) (GIBCO 11140-050) and 40% FBS (Hyclone SH30070.02) 0.03 mL of the sonicated bead preparations was added. 96-well plates seeded with 293H cells which have been mock-transfected in columns 1 to 6, and KDR-transfected in columns 7 to 12 (as described above), were drained and washed once with DMEM, high glucose with 1×NEAA and 40% FBS. To each well was added 0.1 mL of bead solution, six wells per bead preparation. After incubating at room temperature for 30 minutes, the wells were drained by inverting the plates and washed four times with 0.1 mL PBS with $Ca^{++}Mg^{++}$ (GIBCO 14040-117) with shaking at room temperature for 5 minutes each wash. After draining, 0.1 mL of PBS was added per well. The plates were then read on a Packard FluoroCount fluorometer at excitation 550 nm/emission 620 nm. Unconjugated Neutravidin beads were used as a negative control while beads conjugated with a biotinylated anti-KDR antibody were used as the positive control for the assay.

To calculate the number of beads bound per well, a standard curve with increasing numbers of the same fluorescent beads was included in each assay plate. The standard curve was used to calculate the number of beads bound per well based on the fluorescence intensity of each well.

As shown in FIG. 1, the positive control beads with anti-KDR attached clearly bound preferentially to the KDR-expressing cells while avidin beads with nothing attached did not bind to either cell type. Biotinylated P5 beads did not bind to the KDR-transfected cells significantly more than to mock-transfected cells, but adding a hydrophilic spacer between the peptide moiety and the biotin group enhanced binding to KDR cells without increasing the binding to mock-transfected cells. Biotinylated P6 beads showed greater binding to KDR-transfected cells. As was the case for P5, adding a hydrophilic spacer between the peptide portion and the biotin of the molecule significantly improved the specific binding to KDR in the transfected cells. Thus the peptide sequences of both P5 and P6 can be used to bind particles such as beads to KDR expressing sites.

EXAMPLE 3

Competition of KDR Binding Peptides and $^{125}$I-Labeled VEGF for Binding to KDR-Transfected 293H Cells The following experiment assesses the ability of KDR-binding peptides to compete with $^{125}$I-labeled VEGF for binding to KDR expressed by transfected 293H cells. While KDR-binding polypeptide P4 did not compete significantly with $^{125}$I-labeled VEGF, P5-XB, P6 and P12-XB competed very well with $^{125}$I-labeled VEGF, inhibiting 96.29±2.97% and 104.48±2.07% of $^{125}$I-labeled VEGF binding.

Transfection of 293H Cells 293H cells were transfected using the protocol described in Example 6. Transfection was done in black/clear 96-well plates (Becton Dickinson, cat. # 354640). The cells in one half of the plate (48 wells) were mock-transfected (with no DNA) and those in the other half of the plate were transfected with KDR cDNA. The cells were 80–90% confluent at the time of transfection and completely confluent the next day, at the time of the assay; otherwise the assay was aborted.

Preparation of M199 Media

To prepare M199 medium for the assay, one M199 medium packet (GIBCO, cat. # 31100-035), 20 mL of 1 mM HEPES (GIBCO, cat. #15630-080), and 2 g of DIFCO Gelatin (DIFCO, cat. # 0143-15-1) were added to 950 mL of double distilled (dd) $H_2O$ and the pH of the solution was adjusted to 7.4 by adding approximately 4 mL of 1N NaOH. After pH adjustment, the M199 medium was warmed to 37° C. in a water bath for 2 h to dissolve the gelatin, then filter sterilized using 0.2 μm filters (Corning, cat. # 43109), and stored at 4° C. to be used later in the assay.

Preparation of Peptide Solutions 3 mM stock solutions of peptides P6, P4, P5-XB, and P12-XB, (prepared as described above) in 50% DMSO were prepared.

Preparation of $^{125}$I-Labeled VEGF Solution for the Assay

25 μCi of lyophilized $^{125}$I-labeled VEGF (Amersham, cat. # IM274) were reconstituted with 250 μL of dd$H_2O$ to create a stock solution, which was stored at −80° C. for later use. For each assay, a 300 pM solution of $^{125}$I-labeled VEGF was made fresh by diluting the above stock solution in M199 medium. The concentration of $^{125}$I-labeled VEGF was calculated daily based on the specific activity of the material on that day.

Preparation of 30 μM and 0.3 μM Peptide Solution in 300 pM $^{125}$I-Labeled VEGF For each 96 well plate, 10 mL of 300 pM $^{125}$I-labeled VEGF in M199 medium was prepared at 4° C. Each peptide solution (3 mM, prepared as described above) was diluted 1:100 and 1:10000 in 300 μL of M199 media with 300 pM $^{125}$I-labeled VEGF to prepare 30 μM and 0.3 μM peptide solutions containing 300 pM of $^{125}$I-labeled VEGF. Once prepared, the solutions were kept on ice until ready to use. The dilution of peptides in M199 media containing 300 pM $^{125}$I-labeled VEGF was done freshly for each experiment.

Assay to Detect Competition with $^{125}$I-Labeled VEGF in 293H Cells

Cells were used 24 h after transfection, and to prepare the cells for the assay, they were washed 3 times with room temperature M199 medium and placed in the refrigerator. After 15 minutes, the M199 medium was removed from the plate and replaced with 75 μL of 300 pM $^{125}$I-labeled VEGF in M199 medium (prepared as above). Each dilution was added to three separate wells of mock and KDR transfected cells. After incubating at 4° C. for 2 h, the plates were washed 5 times with cold binding buffer, gently blotted dry and checked under a microscope for cell loss. 100 μL of solubilizing solution (2% Triton X-100, 10% Glycerol, 0.1% BSA) was added to each well and the plates were incubated at room temperature for 30 minutes. The solubilizing solution in each well was mixed by pipeting up and down, and transferred to 1.2 mL tubes. Each well was washed twice with 100 μL of solubilizing solution and the washes were added to the corresponding 1.2 mL tube. Each 1.2 mL tube was then transferred to a 15.7 mm×10 cm tube to be counted in an LKB Gamma Counter ($^{125}$I window for 1 minute).

Competition of Peptides with $^{125}$I-Labeled VEGF in 293H Cells

The ability of KDR-binding peptides P6, P4, P5-XB, and P12-XB, to specifically block $^{125}$I-labeled VEGF binding to KDR was assessed in mock-transfected and KDR-transfected cells. P4 was used in the assay as a negative control. It was selected because it exhibits only poor binding to KDR in FP assays, and thus would not be expected to displace or compete with VEGF. To calculate the specific binding to KDR, the binding of $^{125}$I-labeled VEGF to mock-transfected cells was subtracted from KDR-transfected cells. Therefore, the binding of $^{125}$I-labeled VEGF to sites other than KDR (which may or may not be present in 293H cells) is not included when calculating the inhibition of $^{125}$I-labeled VEGF binding to 293H cells by KDR-binding peptides.

Figure 2:
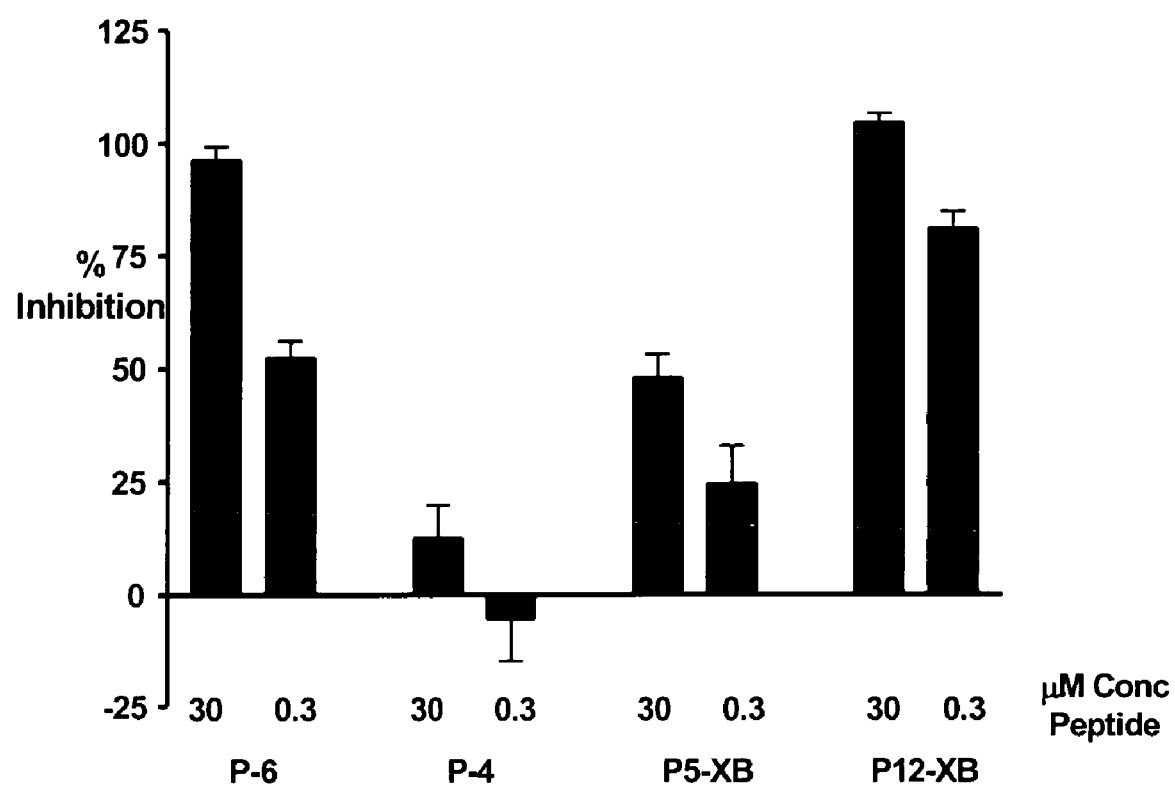
FIG. 2 shows the percentage inhibition of $^{125}$I-labeled VEGF binding by peptides [P6, P4, P5-X-B and P12-X-B] at two different concentrations (30 μM and 0.3 μM) to KDR-transfected 293H cells, as described in Example 3. The results for P6, P4 and P5-X-B are the average of three experiments±SD, whereas the result for P12-X-B is based on one experiment.

FIG. 2 shows the percentage inhibition of $^{125}$I-labeled VEGF binding by peptides (P6, P4, P5-XB, and P12-XB) at two different concentrations (30 μM and 0.3 μM) to KDR-transfected 293H cells. Percentage inhibition was calculated using formula [(Y1−Y2)×100/Y1], where Y1 is specific binding to KDR-transfected 293H cells in the absence of peptides, and Y2 is specific binding to KDR-transfected 293H cells in the presence of peptides or DMSO (vehicle). Specific binding to KDR-transfected 293H cells was calculated by subtracting binding to mock-transfected 293H cells from binding to KDR-transfected 293H cells. Results for P6, P4 and P5-XB are the average of three experiments±SD, whereas the result for P12-XB is from one experiment.

As shown in FIG. 2, P4, which, due to its relatively high Kd (>2 μM, measured by FP against KDR-Fc), was used as a negative control, did not compete significantly with $^{125}$I-labeled VEGF, 12.69±7.18% at 30 μM and −5.45±9.37% at 0.3 μM (FIG. 2). At the same time, P6, and P12-XB competed very well with $^{125}$I-labeled VEGF, inhibiting 96.29±2.97% and 104.48±2.07% of $^{125}$I-labeled VEGF binding at 30 μM and 52.27±3.78% and 80.96±3.8% at 0.3 μM, respectively. The percentage inhibition with P5-X-B was 47.95±5.09% of $^{125}$I-labeled VEGF binding at 30 μM and 24.41±8.43% at 0.3 μM (FIG. 2). Thus, as one would expect, a peptide that only binds KDR poorly did not block VEGF binding, while three other KDR-binding peptides did compete with VEGF, and their potency increased with their binding affinity. This assay should also be useful for identifying peptides that bind tightly to KDR but do not compete with VEGF, a feature that may be useful for imaging KDR in tumors, where there is frequently a high local concentration of VEGF that would otherwise block the binding of KDR-targeting molecules.

EXAMPLE 4

Inhibition of VEGF-Induced KDR Receptor Activation by Peptides Identified by Phage Display The ability of KDR-binding peptides identified by phage display to inhibit VEGF induced activation (phosphorylation) of KDR was assessed using the following assay. A number of peptides of the invention were shown to inhibit activation of KDR in monomeric and/or tetrameric constructs, including P5-D, P6-D, P10-D and P11-D. As discussed above, peptides that inhibit activation of KDR may be useful as anti-angiogenic agents.

Human umbilical vein endothelial cells (HUVECs) (Biowhittaker Cat No. CC-2519) were obtained frozen on dry ice and stored in liquid nitrogen until thawing. These cells were thawed, passaged, and maintained as described by the manufacturer in EGM-MV medium (Biowhittaker Cat No. CC-3125). Cells seeded into 100 mm dishes were allowed to become confluent, then cultured overnight in basal EBM medium lacking serum (Biowhittaker Cat No. CC-3121). The next morning, the medium in the dishes was replaced with 10 mL fresh EBM medium at 37° C. containing either no additive (negative control), 5 ng/mL VEGF (Calbiochem Cat No. 676472 or Peprotech Cat No. 100-20) (positive control), or 5 ng/mL VEGF plus the indicated concentration of the KDR-binding peptide (prepared as described above). In some cases, a neutralizing anti-KDR antibody (Cat No. AF357, R&D Systems) was used as a positive control inhibitor of activation. In such cases, the antibody was pre-incubated with the test cells for 30 min at 37° C. prior to the addition of fresh medium containing both VEGF and the antibody. After incubating the dishes 5 min in a 37° C. tissue culture incubator they were washed three times with ice-cold Dulbecco's phosphate buffered saline (D-PBS) containing calcium and magnesium and placed on ice without removing the last 10 mL of D-PBS. The first dish of a set was drained and 0.5 mL of Triton lysis buffer was added (20 mM Tris base pH 8.0, 137 mM NaCl, 10% glycerol, 1% Triton X-100, 2 mM EDTA (ethylenediaminetetraacetic acid), 1 mM PMSF (phenylmethylsulfonylfluoride), 1 mM sodium orthovanadate, 100 mM NaF, 50 mM sodium pyrophosphate, 10 μg/mL leupeptin, 10 μg/mL aprotinin). The cells were quickly scraped into the lysis buffer using a cell scraper (Falcon, Cat No. 353087), dispersed by pipeting up and down briefly, and the resulting lysate was transferred to the second drained dish of the pair. Another 0.5 mL of lysis buffer was used to rinse out the first dish then transferred to the second dish, which was then also scraped and dispersed. The pooled lysate from the two dishes was transferred to a 1.5 mL Eppindorf tube. The above procedure was repeated for each of the controls and test samples (KDR-binding peptides), one at a time. The lysates were stored on ice until all the samples had been processed. At this point samples were either stored at −70° C. or processed to the end of the assay without interruption.

The lysates, either freshly prepared or frozen and thawed, were precleared by adding 20 μL of protein A-sepharose beads (Sigma 3391, preswollen in D-PBS), washed three times with a large excess of D-PBS, reconstituted with 6 mL D-PBS to generate a 50% slurry) and rocked at 4° C. for 30 min. The beads were pelleted by centrifugation for 2 min in a Picofuge (Stratgene, Cat No. 400550) at 2000×g and the supernatants transferred to new 1.5 mL tubes. 20 µg of anti-Flk-1 antibody (Santa Cruz Biotechnology, Cat No. sc-504) was added to each tube, and the tubes were incubated overnight (16–18 h) at 4° C. on a rotator to immunoprecipitate KDR. The next day 40 µL of protein A-sepharose beads were added to the tubes, which were then incubated at 4° C. for 1 h on a rotator. The beads in each tube were subsequently washed three times by centrifuging for 2 min in a Picofuge, discarding the supernatant, and dispersing the beads in 1 mL freshly added TBST buffer (20 mM Tris base pH 7.5, 137 mM NaCl, and 0.1% Tween 20). After centrifuging and removing the liquid from the last wash, 40 µL of Laemmli SDS-PAGE sample buffer (Bio-Rad, Cat No. 161-0737) was added to each tube and the tubes were capped and boiled for 5 min. After cooling, the beads in each tube were pelleted by centrifuging and the supernatants containing the immunoprecipitated KDR were transferred to new tubes and used immediately or frozen and stored at −70° C. for later analysis.

Detection of phosphorylated KDR as well as total KDR in the immunoprecipitates was carried out by immunoblot analysis. Half (20 µL) of each immunoprecipitate was resolved on a 7.5% precast Ready Gel (Bio-Rad, Cat No. 161-1154) by SDS-PAGE according to the method of Laemmli (U. K. Laemmli "Cleavage of structural proteins during assembly of the head of bacteriophage T4." Nature (1970); 227, 680–685).

Using a Bio-Rad mini-Protean 3 apparatus (Cat No. 165-3302). The resolved proteins in each gel were electroblotted to a PVDF membrane (Bio-Rad, Cat. No. 162-0174) in a Bio-Rad mini Trans-Blot cell (Cat No. 170-3930) in CAPS buffer (10 mM CAPS, Sigma Cat No. C-6070, 1% ACS grade methanol, pH 11.0) for 2 h at 140 mA according to the method of Matsudaira (P. Matsudaira. "Sequence from picomole quantities of proteins electroblotted onto polyvinylidine diflouride membranes." J. Biol. Chem. (1987); 262, 10035–10038). Blots were blocked at room temperature in 5% Blotto-TBS (Pierce Cat No. 37530) pre-warmed to 37° C. for 2 h. The blots were first probed with an anti-phosphotyrosine antibody (Transduction Labs, Cat No. P11120), diluted 1:200 in 5% Blotto-TBS with 0.1% Tween 20 added for 2 h at room temp. The unbound antibody was removed by washing the blots four times with D-PBS containing 0.1% Tween 20 (D-PBST), 5 min per wash. Subsequently, blots were probed with an HRP-conjugated sheep anti-mouse antibody (Amersham Biosciences Cat No. NA931) diluted 1:25,000 in 5% Blotto-TBS with 0.1% Tween 20 added for 1 h at room temperature, and washed four times with D-PBST. Finally, the blots were incubated with 2 mL of a chemiluminescent substrate (ECL Plus, Amersham Cat No. RPN2132) spread on top for 2 min, drip-drained well, placed in plastic sheet protector (C-Line Products, Cat No. 62038), and exposed to X-ray film (Kodak BioMax ML, Cat No. 1139435) for varying lengths of time to achieve optimal contrast.

To confirm that similar amounts of KDR were compared in the assay, the blots were stripped by incubating for 30 min at 37° C. in TBST with its pH adjusted to 2.4 with HCl, blocked for 1 h at room temp with 5% Blotto-TBS with 0.1% Tween 20 (Blotto-TBST), and reprobed with an anti-Flk-1 polyclonal antibody (Cat No. sc-315 from Santa Cruz Biotech), 1:200 in 5% Blotto-TBST with 1% normal goat serum (Life Tech Cat No. 16210064) for 2 h at room temp. The unbound antibody was removed by washing the blots four times with D-PBST, 5 min per wash. Subsequently, the blots were probed with an HRP-conjugated donkey anti-rabbit secondary antibody (Amersham Biosciences Cat No. NA934) diluted 1:10,000 in 5% Blotto-TBST for 1 h at room temperature, and washed four times with D-PBST. Finally, the blots were incubated with 2 mL of chemiluminescent substrate and exposed to X-ray film as described above.

Figure 3:
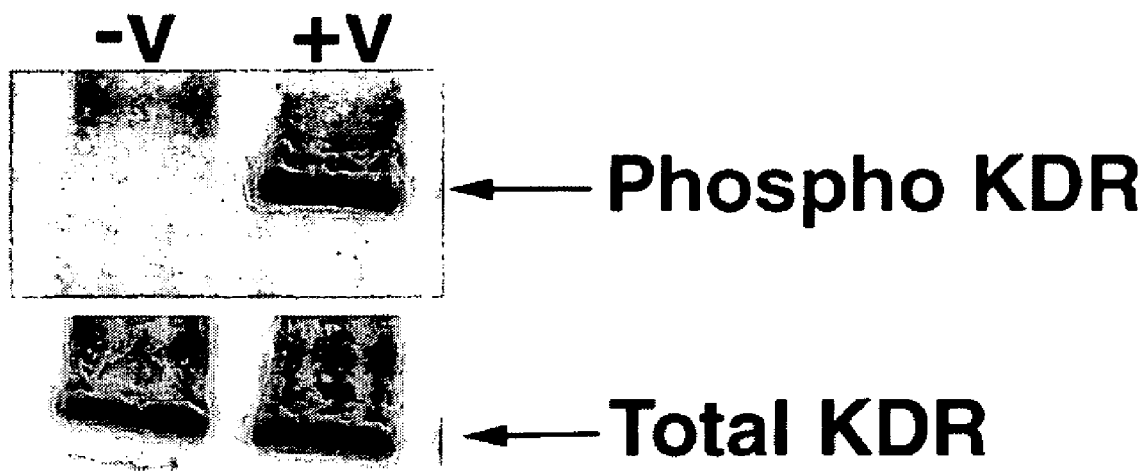
FIG. 3 depicts immunoblots of KDR immunoprecipitates from unstimulated (–V) and VEGF-stimulated (+V) HUVECs which were resolved by SDS-PAGE, blotted, and sequentially probed with anti-phosphotyrosine ("Phospho KDR") and anti-KDR ("Total KDR") antibodies. Activated (phosphorylated) KDR was not detected in unstimulated (–V) HUVECs, but was abundant in immunoprecipitates from VEGF-stimulated (+V) HUVECs. Reprobing the blot with anti-KDR demonstrated that comparable amounts of total KDR were present in both immunoprecipitates. This figure is representative of twelve experiments that followed the same protocol.

Immunoblots of KDR immunoprecipitates prepared from HUVECs with and without prior VEGF stimulation, shown in FIG. 3, demonstrated that activated (phosphorylated) KDR could be detected when the HUVECs were stimulated with VEGF. An anti-phosphotyrosine antibody (PY-20) detected no phosphorylated proteins close to the migration position of KDR from unstimulated HUVECs on the blots, but after five minutes of VEGF stimulation, an intense band was consistently observed at the expected location (FIG. 3, upper panel). When the blots were stripped of bound antibodies by incubation in acidic solution then reprobed with an anti-KDR antibody (sc-315), the identity of the phosphorylated protein band was confirmed to be KDR. Moreover, it was observed that immunopreciptates from unstimulated HUVECs contained about as much total KDR as immunoprecipitates from VEGF-stimulation HUVECs (FIG. 3, lower panel).

It is reasonable to conclude that the phosphorylated KDR detected was formed from pre-existing KDR through autophosphorylation of KDR dimers resulting from VEGF binding as five minutes is not enough time to synthesize and process a large glycosylated cell-surface receptor such as KDR.

Figure 4:
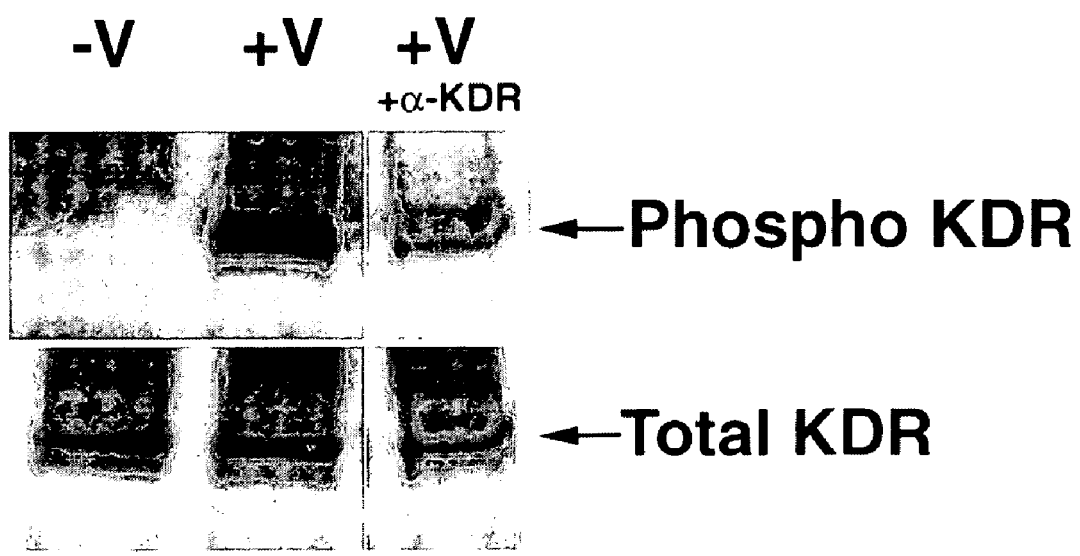
FIG. 4 depicts immunoblots demonstrating inhibition of KDR phosphorylation (activation) with a neutralizing anti-KDR antibody, as described in Example 4. Immunoprecipitates from unstimulated (–V), VEGF-stimulated (+V), and simultaneously VEGF/anti-KDR (1 μg/mL) (+V+α-KDR)-treated HUVECs were resolved by SDS-PAGE, blotted, and sequentially probed with anti-phosphotyrosine ("Phospho KDR") and anti-KDR ("Total KDR") antibodies. As described in Example 4, the neutralizing antibody was able to partially block the VEGF-induced activation of KDR.

The ability of the assay to detect agents capable of blocking the VEGF activation of KDR was assessed by adding a series of compounds to HUVECs in combination with VEGF and measuring KDR phosphorylation with the immunoblot assay described above. As negative and positive controls, immunoprecipitates from unstimulated HUVECs and from HUVECs stimulated with VEGF in the absence of any test compounds were also tested in every assay. When a neutralizing anti-KDR antibody (Cat No. AF-357 from R&D Systems) was combined with the VEGF, the extent of KDR phosphorylation was greatly reduced (FIG. 4, upper panel), indicating that the antibody was able to interfere with the ability of VEGF to bind to and activate KDR. This result was expected because the ability of the antibody to block VEGF-induced DNA synthesis is part of the manufacturer's quality control testing of the antibody. Re-probing the blot with an anti-KDR antibody (FIG. 4, lower panel) indicated that slightly less total KDR was present in the VEGF+ antibody-treated lane (+V+α-KDR) relative to the VEGF-only-treated lane (+V), but the difference was not great enough to account for the much lower abundance of phosphorylated KDR in the antibody-treated lane.

Figure 5:
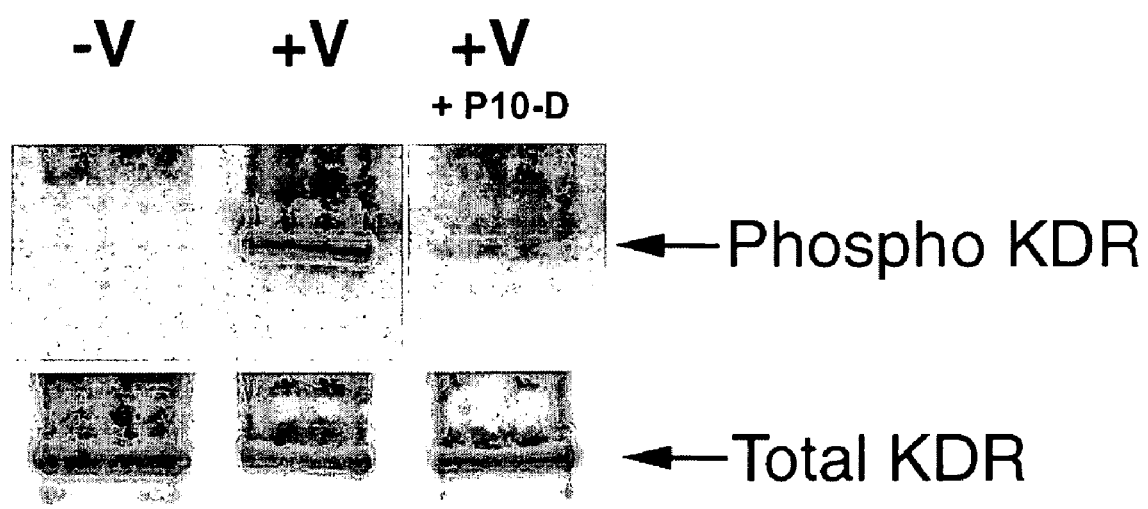
FIG. 5 depicts immunoblots demonstrating inhibition of KDR phosphorylation (activation) with a KDR-binding peptide (repeat experiment). Immunoprecipitates from unstimulated (–V), VEGF-stimulated (+V), and a KDR-binding peptide (10 μM) (+V+P10)-treated HUVECs were resolved by SDS-PAGE, blotted, and sequentially probed with anti-phosphotyrosine ("Phospho KDR") and anti-KDR ("Total KDR"). As described in Example 4, the KDR-binding peptide P10 was clearly able to partially block the VEGF-induced activation of KDR at 10 μM.

To assess the potency of a KDR-binding peptide (P10-D) identified by phage display, the experiment was repeated with P10-D in the presence of VEGF. P10-D was able to largely inhibit the VEGF-induced phosphorylation of KDR. Re-probing the blot for total KDR showed that there is even more total KDR in the VEGF+P10-D-treated cells (+V+ P10-D) than in the VEGF only-treated cells (+V) (FIG. 5, lower panel). Thus, it is clear that the decreased phosphorylation of KDR in the presence of P10-D is not due to differential sample loading, but rather the ability of the compound to inhibit VEGF-activation of KDR.

Using the methods of this Example, the following peptides demonstrated at least a 50% inhibition of VEGF-induced KDR phosphorylation at 10 µM:

P2-D, P3-D, P6-D, P7-E, P8-D, P9-D, P10-D, P11-D.

P2 and P6 were the most potent compounds in the assay, producing at least a 50% inhibition of VEGF-induced KDR phosphorylation at 1 µM.

The following peptides were tested in the assay and did not produce significant inhibition of KDR activation at 10 µM:
P5-E, P14-D, P15-D, P16-D, P17-D, P18-E, P19-E, P20-E, P21-E, P23-D In addition, tetrameric complexes of biotinylated derivatives P6-XB or P12-XB (prepared as described above and discussed in Example 6, infra) produced at least a 50% inhibition of VEGF-induced KDR phosphorylation at 10 nM.

EXAMPLE 5

Binding of Tc-Labeled Polypeptide to KDR-Transfected 293H Cells

In this Example, the ability of Tc-labeled P12-C to bind KDR was assessed using KDR-transfected 293H cells. The results show that Tc-labeled P12-C bound significantly better to KDR transfected 293H cells than to mock transfected 293H cells, and binding increased with concentration of the Tc-labeled polypeptide in a linear manner.

Preparation of Peptidic Chelate (P12-C) for Binding to Tc by SPPS

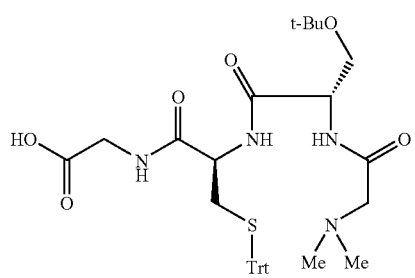

To a 250 ml of SPPS reaction vessel was added 6.64 mmol of H-Gly-2-Cl-trityl resin (0.84 mmol/g, Novabiochem). It was swelled in 80 mL of DMF for 1 h. For each coupling cycle the resin was added 26.6 mmol of DIEA, 26.6 mmol of a Fmoc-amino acid in DMF (EM Science), 26.6 mmol of HOBT (Novabiochem) in DMF, and 26.6 mmol of DIC. The total volume of DMF was 80 mL. The reaction mixture was shaken for 4 h. The resin then was filtered and washed with DMF (3×80 mL). A solution of 20% piperidine in DMF (80 mL) was added to the resin and it was shaken for 10 min. The resin was filtered and this piperidine treatment was repeated. The resin finally was washed with DMF (3×80 mL) and ready for next coupling cycle. At the last coupling cycle, N,N-dimethyl glycine (Aldrich) was coupled using HATU/DIEA activation. Thus, to a suspension of N,N-dimethyl glycine (26.6 mmol) in DMF was added a solution of 26.6 mmol of HATU (Perseptive Biosystems) in DMF and 53.1 mmol of DIEA. The clear solution was added to the resin and shaken for 16 h. Following the synthesis, the resin was filtered and washed with DMF (3×80 mL), $CH_2Cl_2$ (3×80 ml) and dried. The resin was mixed with 80 mL of $AcOH/CF_3CH_2OH/DCM$ (1/1/8, v/v/v) and shaken for 45 min. The resin was filtered and the filtrate was evaporated to a paste. Purification of the crude material by silica gel chromatography using 25% MeOH/DCM afforded 2.0 g of the final product.

Coupling of the Peptidic Chelate (P12-C) to the Peptide (Fragment Coupling)

To a mixture of purified $Me_2$N-Gly-Cys-(Trt)-Ser(tBu)-Gly-OH-and hydroxybenzotriazole (0.0055 mmol) in DMF (0.25 mL), diisopropylcarbodiimide (0.0055 mmol) was added and the mixture was stirred at RT for 6 h. The peptide (0.005 mmol) in DMF (0.25 mL) was then added to the reaction mixture and stirring was continued for an additional 6 h. DMF was removed under vacuum and the residue was treated with reagent B and stirred for 3 h. TFA was removed under reduced pressure and the residue was purified by preparative HPLC using acetonitrile-water containing 0.1% TFA. Fractions containing the pure product were collected and freeze dried to yield the peptide. The peptide was characterized by ES-MS and the purity was determined by RP-HPLC (acetonitrile-water/0.1% TFA) gradient.

Synthesis of $^{99m}$Tc-Labeled Peptide

A stannous gluconate solution was prepared by adding 2 mL of a 20 µg/mL $SnCl_2 \cdot 2H_2O$ solution in nitrogen-purged 1N HCl to 1.0 mL of nitrogen-purged water containing 13 mg of sodium glucoheptonate. To a 4 mL autosampler vial was added 20–40 µL (20–40 µg) of P12-C ligand dissolved in 50/50 ethanol/$H_2O$, 6–12 mCi of $^{99m}TcO_4^-$ in saline and 100 µL of stannous glucoheptonate solution. The mixture was heated at 100° C. for 22 min. The resulting radiochemical purity (RCP) was 10–47% when analyzed using a Vydac C18 Peptide and Protein column that was eluted at a flow rate of 1 mL/min with 66% $H_2O$ (0.1% TFA)/34% ACN (0.085% TFA). The reaction mixture was purified by HPLC on a Vydac C18 column (4.6 mm×250 mm) at a flow rate of 1 mL/min, using 0.1% TFA in water as aqueous phase and 0.085% TFA in acetonitrile as the organic phase. The following gradient was used; 29.5% org. for 35 min., ramp to 85% org. over 5 min, hold for 10 min. The fraction containing $^{99m}$Tc-P12-C (which no longer contained the ACM protecting group) was collected into 500 µL of a stabilizing buffer containing 5 mg/mL ascorbic acid and 16 mg/mL hydroxypropyl-γ-cyclodextrin in 50 mM phosphate buffer. The mixture was concentrated using a speed vacuum apparatus to remove acetonitrile, and 200 µL of 0.1% HSA in 50 mM pH 5 citrate buffer was added. The resulting product had an RCP of 100%. Prior to injection into animals, the compound was diluted to the desired radioconcentration with normal saline.

Transfection of 293H Cells 293H cells were transfected using the protocol described in avidin HRP example. Transfection was done in black/clear 96-well plates (Becton Dickinson, cat. # 354640). The cells in one half of the plates (48 wells) were mock-transfected (with no DNA) and the cells in the other half of the plate were transfected with KDR cDNA. The cells were 80–90% confluent at the time of transfection and completely confluent the next day, at the time of the assay; otherwise the assay was aborted.

Preparation of Opti-MEMI Media with 0.1% HSA

Opti-MEMI was obtained from Invitrogen (cat. # 11058-021) and human serum albumin (HSA) was obtained from Sigma (cat. # A-3782). To prepare opti-MEMI media with 0.1% HSA, 0.1% w/v HSA was added to opti-MEMI, stirred at room temperature for 20 minutes, and then filter sterilized using 0.2 µM filter.

Preparation of Tc-Labeled Peptide Dilutions for the Assay

Stock solution of Tc-labeled P12-C (117 µCi/ml) was diluted 1:100, 1:50, 1:25 and 1:10 in opti-MEMI with 0.1%

HSA to provide solutions with final concentration of 1.17, 2.34, 4.68 and 11.7 μCi/mL of Tc-labeled P12-C Assay to Detect the Binding of Tc-Labeled Peptide Cells were used 24 h after transfection, and to prepare the cells for the assay, they were washed 1× with 100 μL of room temperature opti-MEMI with 0.1% HSA. After washing, the opti-MEMI with 0.1% HSA was removed from the plate and replaced with 70 μL of 1.17, 2.34, 4.68 and 11.7 μCi/mL of Tc-labeled P12-C (prepared as above). Each dilution was added to three separate wells of mock and KDR transfected cells. After incubating at room temperature for 1 h, the plates were transferred to 4° C. for 15 minutes and washed 5 times with 100 μL of cold binding buffer (opti-MEMI with 0.1% HSA), gently blotted dry and checked under a microscope for cell loss. 100 μL of solubilizing solution (2% Triton X-100, 10% Glycerol, 0.1% BSA) was added to each well and the plates were incubated at 37° C. for 10 minutes. The solubilizing solution in each well was mixed by pipeting up and down, and transferred to 1.2 mL tubes. Each well was washed once with 100 μL of solubilizing solution and the washes were added to the corresponding 1.2 mL tube. Each 1.2 mL tube was then transferred to a 15.7 mm×100 cm tube to be counted in an LKB Gamma Counter (Tc-window for 20 sec).

Binding of Tc-Labeled Peptide to KDR Transfected Cells

Figure 6:
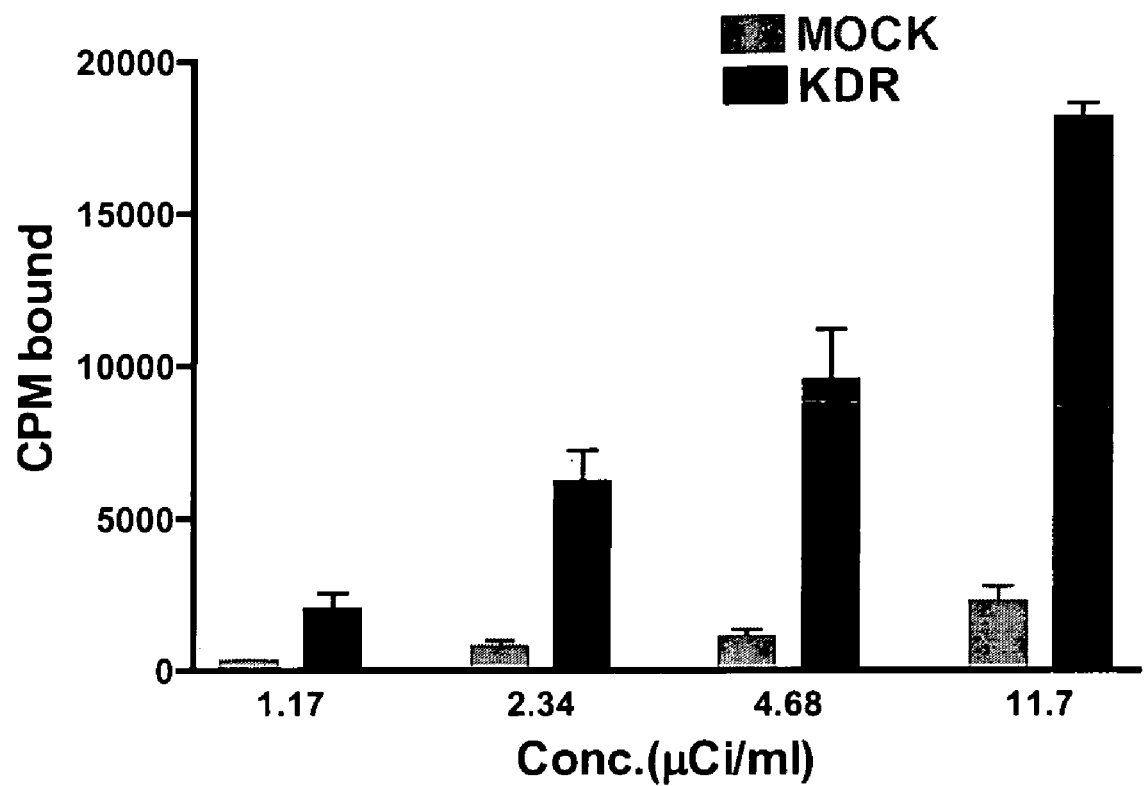
FIG. 6 depicts binding of Tc-labeled P12-C to mock and KDR transfected 293H cells, as described in Example 5.
Figure 7:
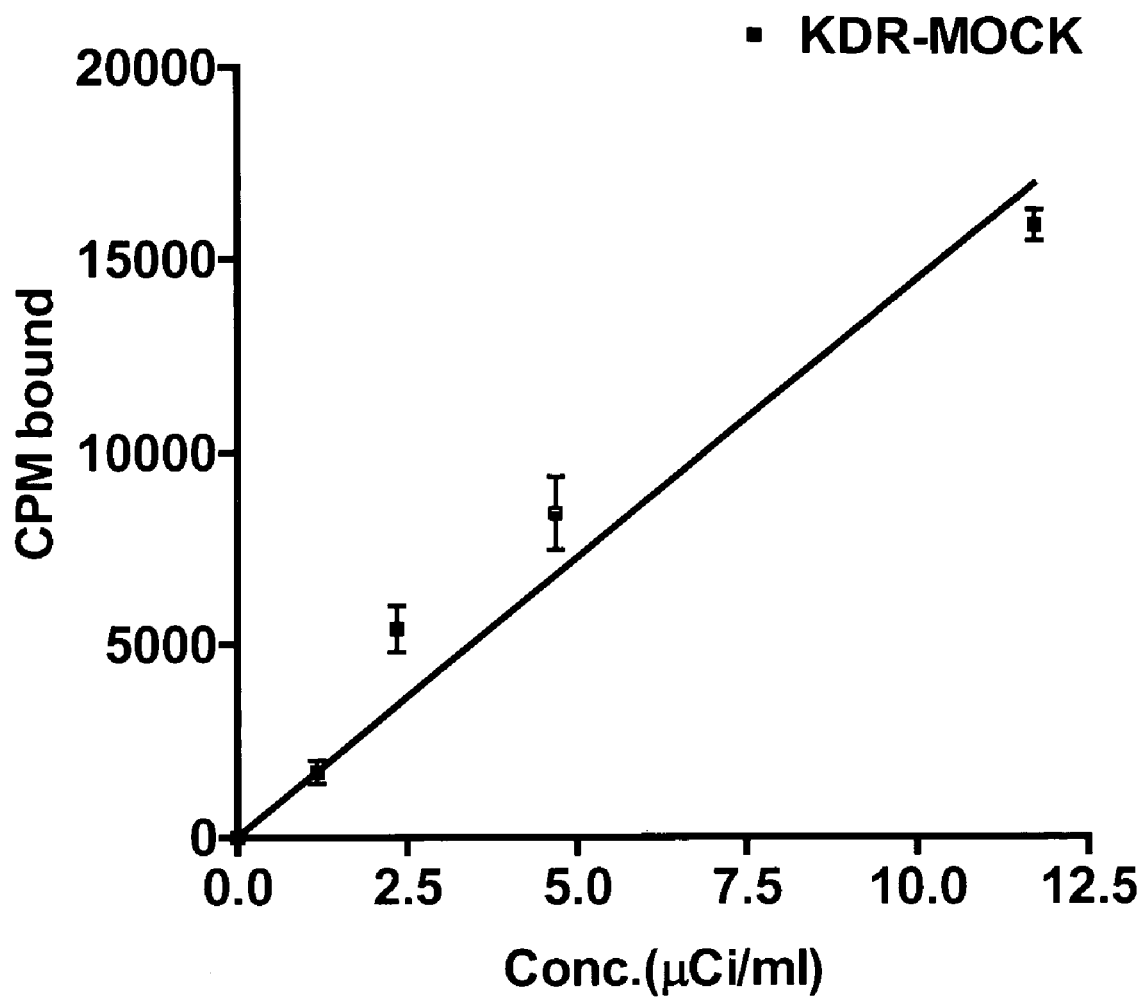
FIG. 7 depicts specific binding of Tc-labeled P12-C to KDR transfected 293H cells, as described in Example 5.

The ability of Tc-labeled P12-C to bind specifically to KDR was demonstrated using transiently transfected 293H cells. As shown in FIG. 6, Tc-labeled P12-C bound significantly better to KDR transfected 293H cells, as compared to mock transfected 293H cells. To calculate specific binding to KDR, the binding of Tc-labeled P12-C to mock transfected cells was subtracted from the binding to KDR transfected cells. As shown in FIG. 7, a linear increase in the specific binding of Tc-labeled P12-C to KDR was observed with increasing concentration of Tc-labeled P12-C. Linear binding was expected because the concentration of Tc-labeled P12-C was only ~100 pM (even at the highest concentration, 11.7 μCi/mL, tested in the assay), which is far below the $K_D$ value of ~3–4 nM of P12 (as calculated using the avidin HRP assay), so no saturation of binding would be expected.

EXAMPLE 6

Binding of KDR Binding Peptide/Avidin HRP Complex to KDR Transfected 293H Cells

To determine the binding of peptides identified by phage display to KDR expressed in transiently-transfected 293H cells, a novel assay that measures the binding of biotinylated peptides complexed with neutravidin HRP to KDR on the surface of the transfected cells was developed. This assay was used to screen the biotinylated peptides described above. Neutravidin HRP was used instead of streptavidin or avidin because it has lower non-specific binding to molecules other than biotin, due to the absence of lectin binding carbohydrate moieties and also due to the absence of the cell adhesion receptor-binding RYD domain in neutravidin.

In the experiments described herein, tetrameric complexes of KDR-binding peptides P6-XB, P5-XB, P12-XB, and P13-XB and a control peptide, P1-XB, were prepared and tested for their ability to bind 293H cells that were transiently-transfected with KDR. All four tetrameric complexes of KDR-binding peptides bound to the KDR-expressing cells; however, P13-XB exhibited the best Kd (1.81 nM). The tetrameric complexes of KDR-binding peptides P6-XB and P5-XB exhibited improved binding over monomers of the same peptides. Moreover, inclusion of a spacer (between the KDR-binding peptide and the biotin) in these constructs was shown to improve binding in Experiment B.

Experiment C, demonstrates the use of this assay to assess the effect of serum on binding of peptides of the invention to KDR and VEGF/KDR complex. The binding of P5-XB, P6-XB and P13-XB was not significantly affected by the presence of serum, while the binding of P12-XB was reduced more than 50% in the presence of serum.

Experiment D demonstrates that this assay is useful in evaluating distinct combinations of KDR and VEGF/KDR complex binding polypeptides for use in multimeric targeting constructs which contain more than one KDR and VEGF/KDR complex binding polypeptide. Moreover, Experiments D and E establish that heteromeric constructs, which have two or more KDR binding peptides that bind to different binding sites, exhibited superior binding to "homotetrameric" constructs of the targeting peptides alone.

Experiment A

Preparation of m-RNA and 5' RACE ready cDNA Library

HUVEC cells were grown to almost 80% confluence in 175 cm² tissue culture flasks (Becton Dickinson, Biocoat, cat # 6478) and then 10 ng/mL of bFGF (Oncogene, cat # PF003) was added for 24 h to induce expression of KDR. mRNA was isolated using the micro-fast track 2.0 kit from Invitrogen (cat. # K1520-02). 12 μg of mRNA (measured by absorbance at 260 nM) was obtained from two flasks (about 30 million cells) following the kit instructions. Reverse transcription to generate cDNA was performed with 2 μg of mRNA, oligo dT primer (5'-(T)$_{25}$GC-3') and/or smart II oligo (5'AAGCAGTGGTAACAACGCAGAGTA CGCGGG-3') using Moloney Murine Leukemia Virus (MMLV) reverse transcriptase. The reaction was performed in a total volume of 20 μL and the reaction mix contained 2 μL of RNA, 1 μL smart II oligo, 1 μL of oligo dT primer, 4 μL of 5× first-strand buffer (250 mM Tris HCl pH 8.3, 375 mM KCl, 30 mM MgCl$_2$) 1 μL DTT (20 mM, also supplied with reverse transcriptase), 1 μL dNTP mix (10 mM each of dATP, dCTP, dGTP, and dTTP in ddH$_2$O, Stratagene, cat. # 200415), 9 μL ddH$_2$O and 1 μL MMLV reverse transcriptase (Clonetech, cat #8460-1). The reverse transcription reaction was performed for 90 minutes at 42° C., and the reaction was stopped by adding 250 μL of tricine-EDTA buffer (10 mM tricine, 1.0 mM EDTA). The reverse transcription product, a 5' RACE ready cDNA library, can be stored for 3 months at −20° C. All water used for DNA and RNA applications was DNAse and RNAse free from USB (cat. # 70783).

Cloning of s-KDR into TOPOII Vector

To clone s-KDR, a 5' oligo (G ATG GAG AGC AAG GTG CTG CTG G) and a 3' oligo (C CAA GTT CGT CTT TTC CTG GGC A) were used. These were designed to amplify the complete extracellular domain of KDR (~2.2 kbps) from the 5' RACE ready cDNA library (prepared above) using polymerase chain reaction (PCR) with pfu polymerase (Stratagene, cat. # 600135). The PCR reaction was done in total volume of 50 μL and the reaction mix contained 2 μL 5' RACE ready cDNA library, 1 μL 5' oligo (10 μM), 1 μL 3' oligo (10 μM), 5 μL 10×PCR buffer [PCR buffer (200 mM Tris-HCl pH 8.8, 20 mM MgSO$_4$, 100 mM KCl, 100 mM (NH$_4$)$_2$SO$_4$) supplied with pfu enzyme plus 1% DMSO and 8% glycerol], 1 μL dNTP mix (10 mM) and 40 μL ddH$_2$O. The PCR reaction was performed by using a program set for 40 cycles of 1 minute at 94° C., 1 minute at 68° C. and 4 minutes at 72° C. The PCR product was purified by extraction with 1 volume of phenol, followed by extraction with 1 volume of chloroform and precipitated using 3 volume of ethanol and 1/10 volume of 3M sodium acetate. The PCR product was resuspended in 17 µL of ddH$_2$O, the 2 µL of 10×Taq polymerase buffer (100 mM Tris-HCl pH 8.8, 500 mM KCl, 15 mM MgCl$_2$, 0.01% gelatin) and 1 µL of Taq polymerase (Stratagene, cat. # 600131) was added to generate an A overhang to each end of the product. After incubating for 1 hour at 72° C. the modified product was cloned directly into a TOPOII vector from invitrogen (cat. # K4600-01) following the manufacturer's protocol to give TOPO-sKDR. The TOPO vector allows easy cloning of PCR products because of the A-overhang in Taq (PCR enzyme)-treated PCR products.

Cloning the Transmembrane and Cytoplasmic Domains of KDR into TOPO II Vector

To clone the transmembrane and cytoplasmic domains of KDR, a 5' oligo (TCC CCC GGG ATC ATT ATT CTA GTA GGC ACG GCG GTG) and a 3' oligo (C AGG AGG AGA GCT CAG TGT GGT C) were used. These were designed to amplify the complete transmembrane and cytoplasmic domains of KDR (~1.8 kbps) from the 5' RACE ready cDNA library (described above) using polymerase chain reaction (PCR) with pfu polymerase. PCR reaction conditions and the program were exactly the same as described above for s-KDR. Just as with the s-KDR sequence, the PCR product was purified using phenol chloroform extraction, treated with Taq polymerase and cloned into TOPOII vector from invitrogen to give TOPO-CYTO.

Cloning of Full-Length KDR into pcDNA6 Vector

To create the full-length receptor, the extra-cellular domain and the cytoplasmic domain (with trans-membrane domain) were amplified by PCR separately from TOPO-sKDR and TOPO-CYTO respectively and ligated later to create the full-length receptor. An oligo with a Not1 site at the 5' end of the extracellular domain (A TAA GAA TGC GGC CGC AGG ATG GAG AGC AAG GTG CTG CTG G) and an oligo complimentary to the 3' end of the extracellular domain (TTC CAA GTT CGT CTT TTC CTG GGC ACC) were used to amplify by PCR the extracellular domain from TOPO-sKDR. Similarly, the 5' oligo (ATC ATT ATT CTA GTA GGC ACG GCG GTG) and the 3' oligo, with a Not1 site (A TAA GAA TGC GGC CGC AAC AGG AGG AGA GCT CAG TGT GGT C), were used to amplify by PCR the cytoplasmic domain of KDR (with transmembrane domain) from TOPO-CYTO. Both PCR products were digested with Not1 and ligated together to create the full-length receptor. The cDNA encoding the full-length receptor was purified on an agarose gel and ligated into the Not1 site of the pcDNA6/V5-His C vector. Purification of DNA and ligation was done as described earlier for psKDR. The ligation reaction was used to transform a culture of DH5α bacteria and a number of individual clones were analyzed for the presence and orientation of insert by restriction analysis of purified plasmid from each clone with EcoRI enzyme.

Cell Culture 293H cells were obtained from Invitrogen (cat. # 11631) and grown as monolayer cultures in their recommended media plus 1 mL/L pen/strep (Invitrogen, cat. # 15140-148). All the cells were grown in presence of antibiotic for everyday culture but were split into antibiotic free media for 16–20 hour prior to transfection.

Preparation of DNA for Transfection

*E. coli.* bacteria DH5α containing pf-KDR was streaked onto LB with 50 µg/mL ampicillin (LB agar from US biologicals, cat. # 75851 and ampicillin from Sigma, cat. #A2804) plates from a glycerol stock and plates were left in a 37° C. incubator to grow overnight. Next morning, a single colony was picked from the plate and grown in 3 mL of LB/ampicillin media (LB from US biologicals, cat. # US75852) at 37° C. After 8 hours, 100 µL of bacterial culture from the 3 mL tube was transferred to 250 mL of LB/ampicillin media for overnight incubation at 37° C. Bacteria were grown up with circular agitation in a 500 mL bottle (Beckman, cat. # 355605) at 220 rpm in a Lab-Line incubator shaker. The next day, the bacterial culture was processed using maxi-prep kit (QIAGEN, cat. # 12163). Generally, about 1 mg of plasmid DNA (as quantitated by absorbance at 260 nm) was obtained from 250 mL of bacterial culture.

Transfection of 293H Cells In 96 Well Plate

Transfection was done as recommended in the lipofectamine 2000 protocol (Invitrogen, cat# 11668-019) using a poly-D-lysine-coated 96 well plate. 320 ng of KDR DNA (pc-DNA6-fKDR)/per well in 0.1 mL was used for 96 well plate transfections. Transfection was done in serum-containing media, the transfection reagent mix was removed from cells after 6–8 hours and replaced with regular serum-containing medium. Transfection was done in black/clear 96-well plates (Becton Dickinson, cat. # 354640). The cell in one half of the plate (48 wells) were mock-transfected (with no DNA) and the cells in the other half of the plate were transfected with KDR cDNA. The cells were 80–90% confluent at the time of transfection and completely confluent next day, at the time of the assay, otherwise the assay was aborted.

Preparation of M199 Media

M199 media was prepared as described above

Preparation of SoftLink Soft Release Avidin-Sepharose

SoftLink soft release avidin-sepharose was prepared by centrifuging the sepharose obtained from Promega (cat. # V2011) at 12,000 rpm for 2 minutes, washing twice with ice cold water (centrifuging in-between the washes) and resuspending the pellet in ice cold water to make a 50% slurry in ddH$_2$O. A fresh 50% slurry of avidin-sepharose was prepared for each experiment.

Preparation of Peptide/Neutravidin HRP Solution

Biotinylated peptides P6-XB, P5-XB, P12-XB, P13-XB and the biotinylated control peptide, P1-XB, (prepared as described above) were used to prepare 250 µM stock solutions in 50% DMSO and a 33 µM stock solution of Neutravidin HRP was prepared by dissolving 2 mg of Neutravidin HRP (Pierce, cat. # 31001) in 1 mL of ddH$_2$O. Peptide stock solutions were stored at −20° C., whereas the Neutravidin HRP stock solution was stored at −80° C. The structures of the biotinylated peptides are shown in Table 1. To prepare peptide/neutravidin HRP complexes, 10 µL of 250 µM biotinylated peptide stock solution and 10 µL of 33 µM Neutravidin HRP were added to 1 ml of M199 medium. This mixture was incubated on a rotator at 4° C. for 60 minutes, followed by addition of 50 µL of soft release avidin-sepharose (50% slurry in ddH$_2$O) to remove excess peptides and another incubation for 30 minutes on a rotator at 4° C. Finally, the soft release avidin-sepharose was pelleted by centrifuging at 12,000 rpm for 5 minutes at room temperature, and the resulting supernatant was used for the assays. Fresh peptide/neutravidin HRP complexes were prepared for each experiment.

Preparation of Peptide/Neutravidin HRP Dilutions for the Assay

For saturation binding experiments, 120 µL, 60 µL, 20 µL, 10 µL, 8 µL, 6 µL, 4 µL and 1 µL of peptide/neutravidin HRP complex were added to 1.2 ml aliquots of M199 medium to create dilutions with final concentrations of 33.33 nM, 16.65 nM, 5.55 nM, 2.78 nM, 1.67 nM, 1.11 nM and 0.28 nM complex, respectively.

Preparation of Blocking Solution for Transfected 293H Cells

Blocking solution was prepared by adding 20 mL of M199 medium to 10 mg of lyophilized unlabeled neutravidin (Pierce, cat. # 31000). Fresh blocking solution was used for each experiment.

Assay to Detect the Binding of Peptide/Neutravidin HRP 24 h after transfection, each well of the 293H cells was washed 1× with 100 µL of M199 medium and incubated with 80 µL of blocking solution at 37° C. After one hour, cells were washed 2× with 100 µL of M199 media and incubated with 70 µL of peptide/neutravidin HRP dilutions of P1-XB, P6-XB, P5-XB, P12-XB and P13-XB for two and half hours at room temperature. Each dilution was added to three separate wells of mock as well as KDR-transfected 293H cells (two plates were used for each saturation binding experiment). After incubation at room temperature, plates were transferred to 4° C. for another half-hour incubation. Subsequently, cells were washed five times with ice-cold M199 media and 1× with ice-cold PBS (in that order). After the final wash, 100 µL of ice cold TMB solution (KPL, cat. # 50-76-00) was added to each well and each plate was incubated for 30 minutes at 37° C. in an air incubator. Finally, the HRP enzyme reaction was stopped by adding 50 µL of 1N phosphoric acid to each well, and binding was quantitated by measuring absorbance at 450 nm using a microplate reader (BioRad Model 3550).

Binding of Peptide/Neutravidin HRP to KDR-Transfected Cells

In this assay, complexes of P6-XB, P5-XB, P12-XB, P13-XB peptides, and the control peptide, P1-XB, with neutravidin HRP were prepared as described above and tested for their ability to bind 293H cells that were transiently-transfected with KDR. During the peptide/neutravidin complex preparation, a 7.5 fold excess of biotinylated peptides over neutravidin HRP was used to ensure that all four biotin binding sites on neutravidin were occupied. After complex formation, the excess of free biotinylated peptides was removed using soft release avidin-sepharose to avoid any competition between free biotinylated peptides and neutravidin HRP-complexed biotinylated peptides.

Figure 8:
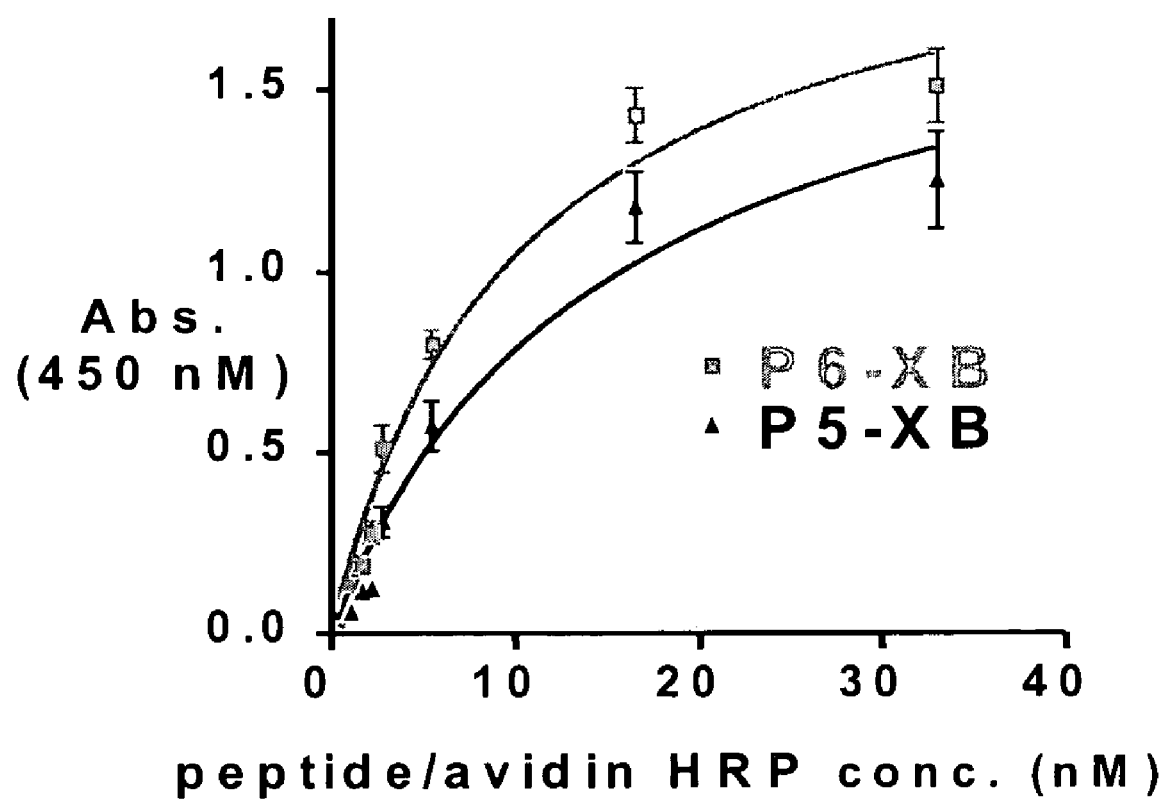
FIG. 8 depicts saturation binding of peptide/Neutravidin HRP complexes, as described in Example 6.
Figure 9:
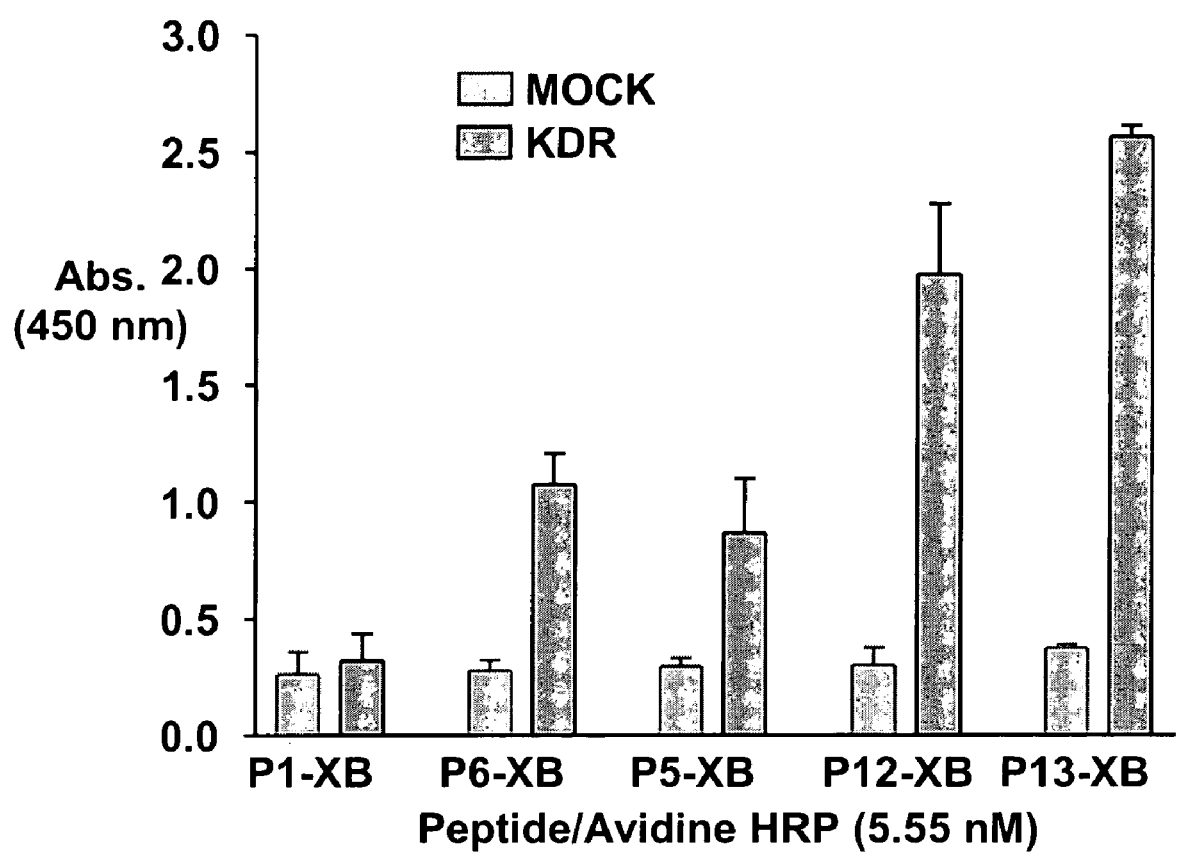
FIG. 9 depicts binding of peptide/neutravidin HRP complexes (P1-X-B, P5-X-B, P6-XB, P12-XB and P13-XB) to KDR-transfected and mock-transfected 293H cells at a single concentration (5.5 nM), as described in Example 6.

The experiment was performed at several different concentrations of peptide/neutravidin HRP, from 0.28 nM to 33.33 nM, to generate saturation binding curves for P5-XB and P6-XB (FIG. 8A) and 0.28 to 5.55 nM to generate saturation binding curve for P12-XB and P13-XB (FIG. 8B). To draw the saturation binding curve, the background binding to mock-transfected cells was subtracted from the binding to KDR-transfected cells for each distinct peptide/neutravidin HRP complex at each concentration tested. Therefore, absorbance on the Y-axis of FIG. 8 is differential absorbance (KDR minus mock) and not the absolute absorbance. Analysis of the saturation binding data in FIG. 8 using Graph Pad Prism software (version 3.0) yielded a Kd of 10.00 nM (+/−2.36) for the tetrameric P6-XB, 14.87 nM (+/−5.07) for the tetrameric P5-XB, 4.03 nM (+/−0.86) for the tetrameric P12-XB and 1.81 nM (+/−0.27) for the tetrameric P13-XB peptide complexes. These binding constants are, as expected, lower than those measured by FP against the KDRFc construct for the related monodentate peptides P6 (69 nM) and P5 (280 nM) (fluoresceinated) but similar for the monodentate peptide P12 (3 nM). As expected, no saturation of binding for the control P1-X-B peptide/neutravidin HRP-complex was observed. As shown in FIG. 9, the binding of peptide/neutravidin HRP complexes at a single concentration (5.55 nM) was plotted to demonstrate that a single concentration experiment can be used to differentiate between a KDR binding peptide (P6-XB, P5-XB and P12-XB) from a non-binding peptide (P1-XB).

Experiment B

Experiment B was designed to look at the effect of a spacer (X) between the KDR binding sequence (P6 and P5) and biotin. In this experiment, biotinylated P6 and P5 (with and without spacer X, prepared as set forth above) were tested, and P1 (with and without spacer, prepared as set forth above) was used as a negative control.

Figure 10:
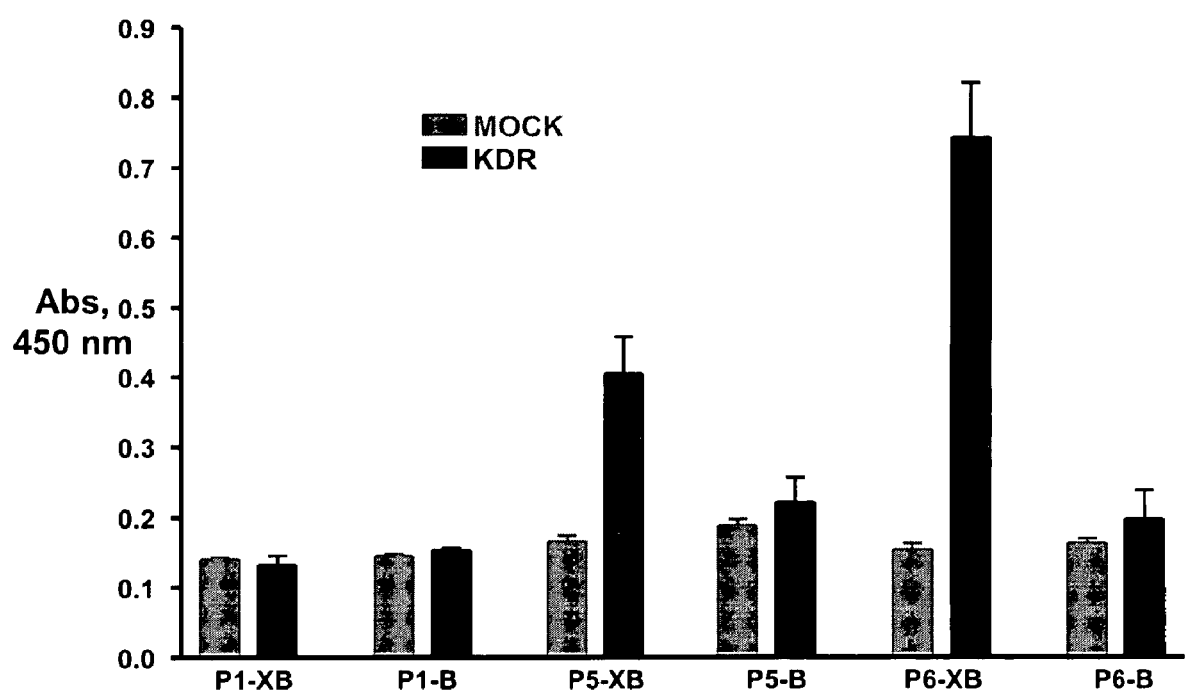
FIG. 10 depicts binding of peptide/neutravidin HRP complexes (P1-XB, P1-B, P5-XB, P5-B, P6-XB and P6-B) to KDR-transfected and mock-transfected 293H cells at a single concentration (2.78 nM), as described in Experiment B of Example 6.

This experiment was performed as set forth in Experiment A described above, except that it was only done at single concentration of 2.78 nM. It is evident from the results, shown in FIG. 10, that a spacer (X) is required for effective binding of P6 and P5. The spacer (X) between the binding sequence and biotin can be helpful in enhancing binding to target molecule by multiple mechanisms. First, it may help reduce the steric hindrance between four biotinylated peptides after their binding to a single avidin molecule. Second, it may provide extra length necessary to reach multiple binding sites available on a single cell.

Experiment C

Experiment C examined the serum effect on the binding of P6-XB, P5-XB, P12-XB, and P13-XB. In this experiment, biotinylated peptide/avidin HRP complexes of P6-XB, P5-XB, P12-XB, and P13-XB were tested in M199 media (as described above in Experiment A) with and without 40% rat serum. This experiment was performed as described for Experiment A, except that it was only done at single concentration of 6.66 nM for P6-XB and P5-XB, 3.33 nM for P12-XB and 2.22 nM for P13XB.

Figure 11:
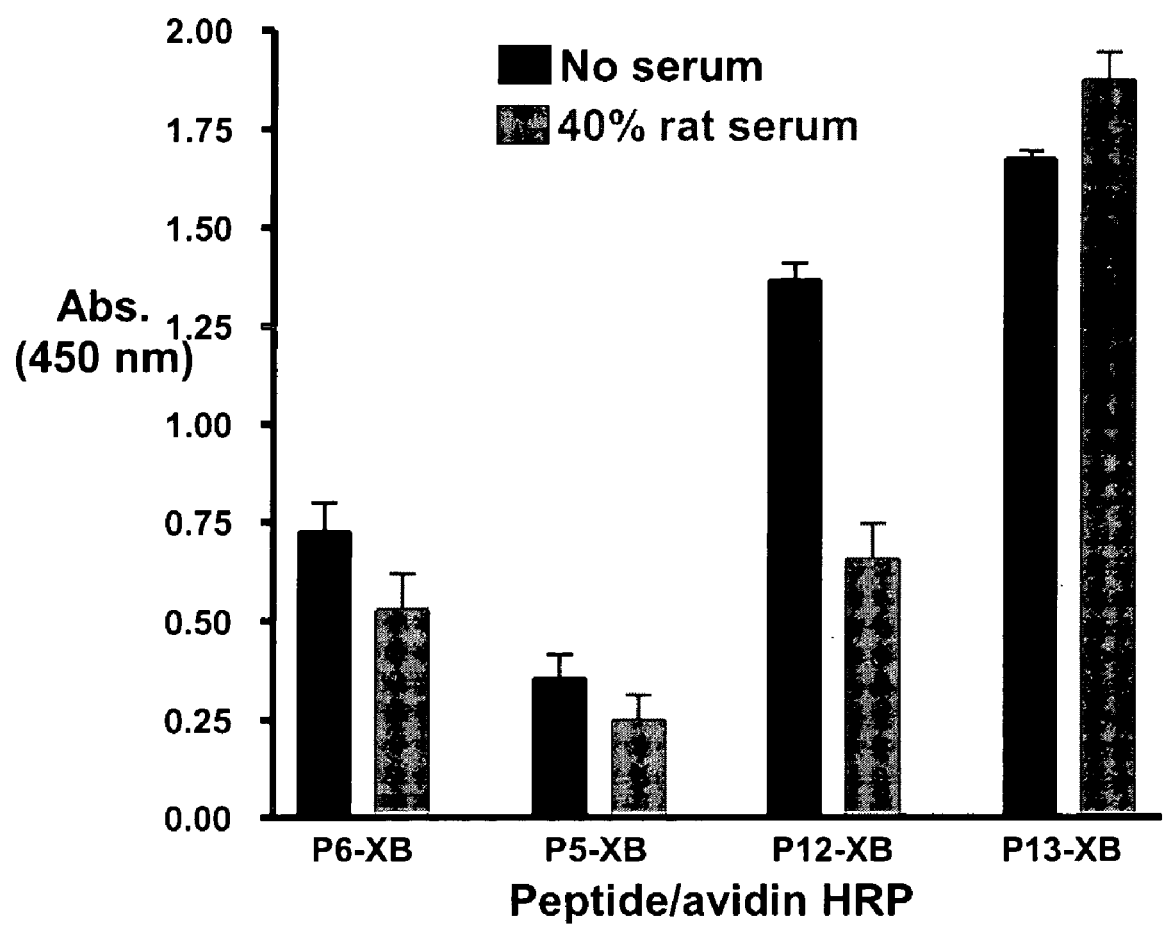
FIG. 11 depicts specific binding (binding to KDR transfected cells minus binding to mock transfected cells) of peptide/neutravidin HRP complexes (P6-XB, P5-XB, P12-XB and P13-XB) with and without 40% rat serum, as described in Experiment C of Example 6. The concentration of peptide/avidin HRP solution was 6.66 nM for P6-XB and P5-XB, 3.33 nM for P12-XB and 2.22 nM for P13-XB.
Figure 25:
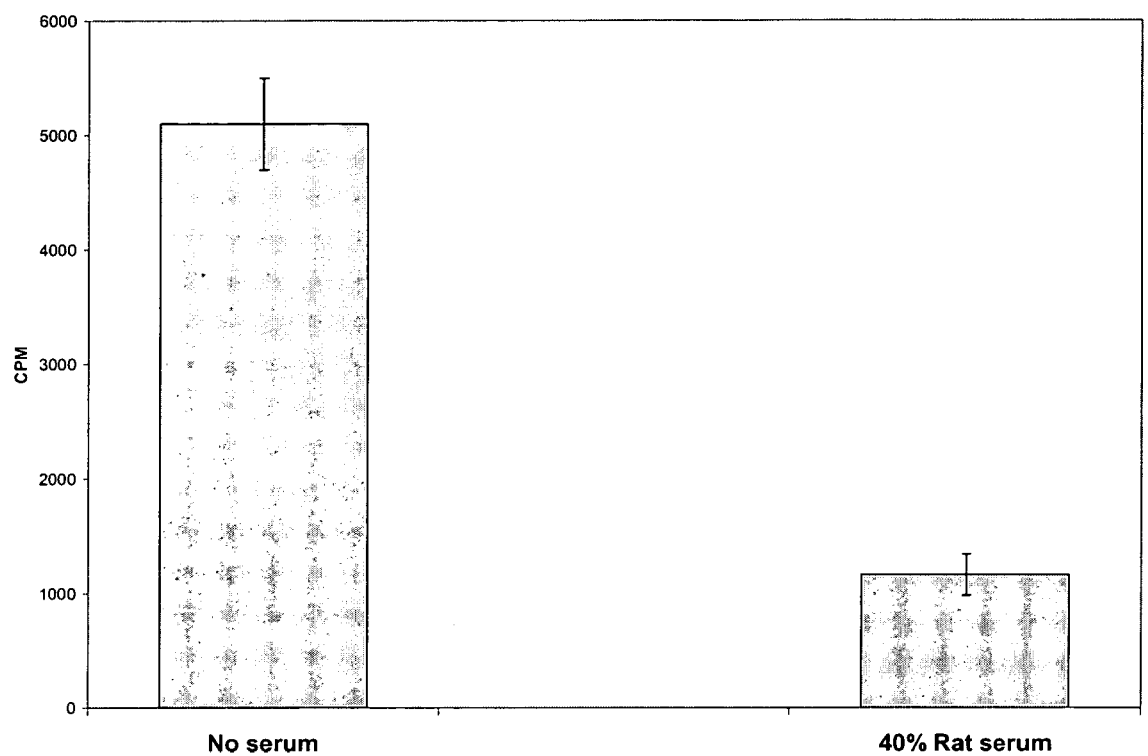
FIG. 25 is a graph showing the specific binding (binding to KDR-transfected cells minus binding to mock-transfected cells) of $^{99m}$Tc-labeled P12C in the presence and absence of 40% rat serum, as described in Experiment C of Example 6. Results are plotted as specific CPM bound +/−s.d.

The results, shown in FIG. 11, indicate that binding of P6-XB, P5-XB and P13-XB was not significantly affected by 40% rat serum whereas binding of P12-XB dropped more than 50% in presence of 40% rat serum. More than an 80% drop in the binding of Tc-labeled P12-C (P12 with Tc-chelate), prepared by the method described in Example 5 above, was observed in the presence of 40% rat serum (data shown in FIG. 25). Because the serum effect on the binding of Tc-labeled P12-C is mimicked in the avidin HP assay disclosed herein, this assay may be used to rapidly evaluate the serum effect on the binding of peptide(s) to KDR.

Experiment D

Experiment D was designed to evaluate the binding of tetrameric complexes of KDR and VEGF/KDR complex-binding polypeptides P6-XB and P5-XB, particularly where the constructs included at least two KDR binding polypeptides. The KDR binding peptides and control binding peptide (P1-XB) were prepared as described above. This experiment was performed using the protocol set forth for Experiment A, except the procedures set forth below were unique to this experiment.

Preparation of Peptide/Neutravidin HRP Solutions

250 µM stock solutions of biotinylated peptides P1-X-B, P6-XB, and P5-XB were prepared in 50% DMSO and a 33 µM stock solution of Neutravidin HRP was prepared by dissolving 2 mg of Neutravidin HRP (Pierce, cat. # 31001) in 1 mL of ddH$_2$O. Peptide stock solutions were stored at −20° C., whereas the Neutravidin HRP stock solution was stored at −80° C. To prepare peptide/neutravidin HRP complexes, a total 5.36 µL of 250 µM biotinylated peptide stock solution (or a mixture of peptide solutions, to give peptide molecules four times the number of avidin HRP molecules) and 10 µL of 33 µM Neutravidin HRP were added to 1 mL of M199 medium. This mixture was incubated on a rotator at 4° C. for 60 minutes, followed by addition of 50 µL of soft release avidin-sepharose (50% slurry in ddH$_2$O) to remove excess peptides and another incubation for 30 minutes on a rotator at 4° C. Finally, the soft release avidin-sepharose was pelleted by centrifuging at 12,000 rpm for 5 minutes at room temperature, and the resulting supernatant was used for the assays. Fresh peptide/neutravidin HRP complexes were prepared for each experiment.

Assay to Detect the Binding of Peptide/Neutravidin HRP

The procedure described above was used to detect binding of the peptide/neutravidin HRP. The results of this experiment establish that P6-XB and P5-XB bind to KDR in multimeric fashion, and cooperate with each other for binding to KDR in 293H transfected cells.

Figure 12:
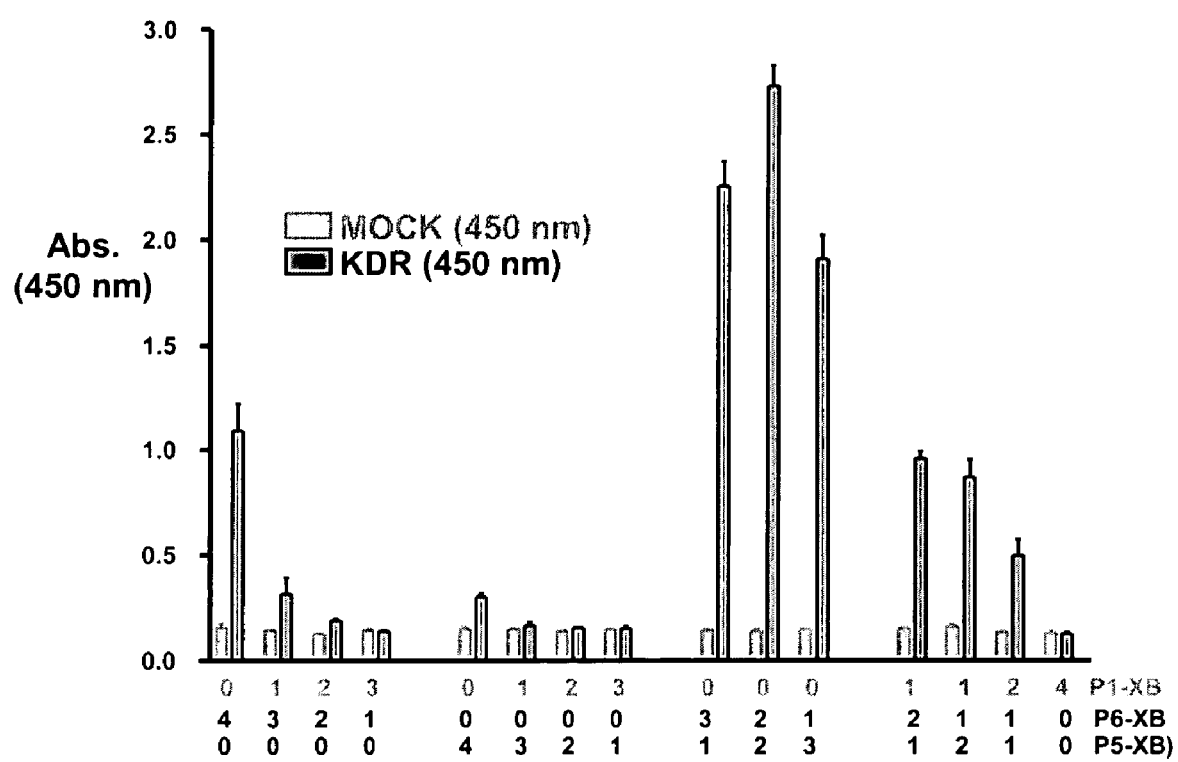
FIG. 12 shows the binding of peptide/avidin HRP with mock and KDR transfected cells, plotted as absorbance at 450 nm. The proportions of control and KDR binding peptides used to form each tetrameric complex are indicated in the legend, for each tested multimer.

P1-XB is a biotinylated derivative of P1, a control peptide that does not bind to KDR. As expected, a tetrameric complex of P1-XB with avidin-HRP did not show enhanced binding to KDR-transfected cells. As shown in FIG. 12, tetrameric complexes of P6-XB or P5-XB bound to KDR-transfected cells significantly better than to mock-transfected cells. P6-XB tetramers however, bound much better than P5-X tetramers. When P1-XB was added to the peptide mixture used to form the tetrameric complexes, the binding to the KDR-transfected cells was decreased. The ratios of specific binding of tetramer to monomer, dimer and trimer were calculated by dividing the specific binding (obtained by subtracting the binding to mock transfected cells from KDR transfected cells) of tetramer, trimer & dimer with that of monomer. Results suggest that there is coperative effect of multimerization of P5-XB, P6-XB and P13-XB on the binding to KDR transfected cells.

TABLE 2

Enhanced binding of homomultimeric constructs over monomers

| Ref. Number | Tetramer | Trimer | Dimer |
|---|---|---|---|
| P5-XB | 45.4 | 5 | 4.3 |
| P6-XB* | 38.6 | 7.1 | 2.7 |
| P12-XB | 1 | 1.1 | 1.1 |
| P13-XB | 16 | 5.7 | 2.3 |

*Monomeric Peptide binding at 3.33 nM was zero and therefore the ratios were calculated using binding at 5.55 nM.

A mixture of 25% P1-XB with 75% P5-XB did not bind significantly over background to KDR-transfected cells, indicating that multivalent binding is critical for the P5-XB/avidn-HRP complex to remain bound to KDR throughout the assay. This phenomenon also held true for P6-XB, where substituting 50% of the peptide with P1-XB in the tetrameric complex abolished almost all binding to KDR on the transfected cells.

A peptide mixture composed of 50% P1-XB with 25% P6-XB and 25% P5-XB bound quite well to KDR-transfected cells relative to mock-transfected cells, indicating that there is a great advantage to targeting two binding sites on the same target molecule. Furthermore, it was noted that tetrameric complexes containing different ratios of P6-XB and P5-XB (3:1, 2:2, and 1:3) all bound much better to KDR-transfected cells than pure tetramers of either peptide, in agreement with the idea that targeting two distinct sites on a single target molecule is superior to multimeric binding to a single site. This may be because multimeric binding to a single target requires that the multimeric binding entity span two or more separate target molecules which are close enough together for it to bind them simultaneously, whereas a multimeric binder which can bind two or more distinct sites on a single target molecule does not depend on finding another target molecule within its reach to achieve multimeric binding. The ratios of specific binding of heterotetramer, heterotrimer and heterodimer to monomer were calculated by dividing the specific binding (obtained by subtracting the binding to mock transfected cells from KDR transfected cells) of tetramer, trimer and dimer with that of monomer. Monomer, which was used to calculate the ratios, for each set of heteromers is recorded at the end of each heteromer listing in the table and given the ratio of 1.

TABLE 3

Enhanced binding of heteromultimeric constructs over monomers

| Peptide Mix Where (1X, 2X, 3X) is the occupancy of the four avidin sites | Heteromer/Monomer Ratio | Conc. (nM) |
|---|---|---|
| P6-XB(1X) + P5-XB(3X) | 529 | 3.33 |
| P6-XB(2X) + P5-XB(2X) | 777 | 3.33 |
| P6-XB(3X) + P5-XB(1X) | 633 | 3.33 |
| P1-XB(1X) + P6-XB(1X) + P5-XB(2X) | 213 | 3.33 |
| P1-XB(1X) + P6-XB(2X) + P5-XB(1X) | 242 | 3.33 |
| P1-XB(2X) + P6-XB(1X) + P5-XB(1X) | 109 | 3.33 |
| P5-XB(1X) + P1-XB(3X) | 1 | 3.33 |
| P6-XB(1X) + P12-XB(3X) | 46 | 2.78 |
| P6-XB(2X) + P12-XB(2X) | 42 | 2.78 |
| P6-XB(3X) + P12-XB(1X) | 43 | 2.78 |
| P1-XB(1X) + P6-XB(1X) + P12-XB(2X) | 47 | 2.78 |
| P1-XB(1X) + P6-XB(2X) + P12-XB(1X) | 52 | 2.78 |
| P1-XB(2X) + P6-XB(1X) + P12-XB(1X) | 40 | 2.78 |
| P1-XB(3X) + P6-XB(1X)* | 1 | 5.55 |
| P1-XB(1X) + P13-XB(1X) + P12-XB(2X) | 5 | 2.78 |
| P1-XB(1X) + P13-XB(2X) + P12-XB(1X) | 7 | 2.78 |
| P1-XB(2X) + P13-XB(1X) + P12-XB(1X) | 2 | 2.78 |
| P13-XB(1X) + P1-XB(3X) | 1 | 2.78 |
| P1-XB(1X) + P6-XB(1X) + P13-XB(2X) | 83 | 2.78 |
| P1-XB(1X) + P6-XB(2X) + P13-XB(1X) | 31 | 2.78 |
| P1-XB(2X) + P6-XB(1X) + P13-XB(1X) | 31 | 2.78 |
| P1-XB(3X) + P6-XB(1X)* | 1 | 5.55 |

The enhanced binding ratios of the homodimers range from about 1–4 fold as seen in table 2 whereas the binding of the heterodimers ranges from 2–110 fold, demonstrating the synergistic effect on binding strength of complementary sequences (Table 3).

Experiment E

Experiment E was designed to confirm that P6-XB and P5-XB bind to distinct binding sites on KDR. If the peptides bind to the same site on KDR, they would likely compete with each other for binding to KDR, whereas if the peptides bind to different sites, there should be no competition between the peptides for binding to KDR. This experiment was performed using a single concentration of P5-XB/avidin HRP (3.33 nM) solution in each well and adding a varying concentration (0–2.5 µM) of P1-XB, P5-XB and P6-XB, none of which were complexed with avidin.

Figure 13:
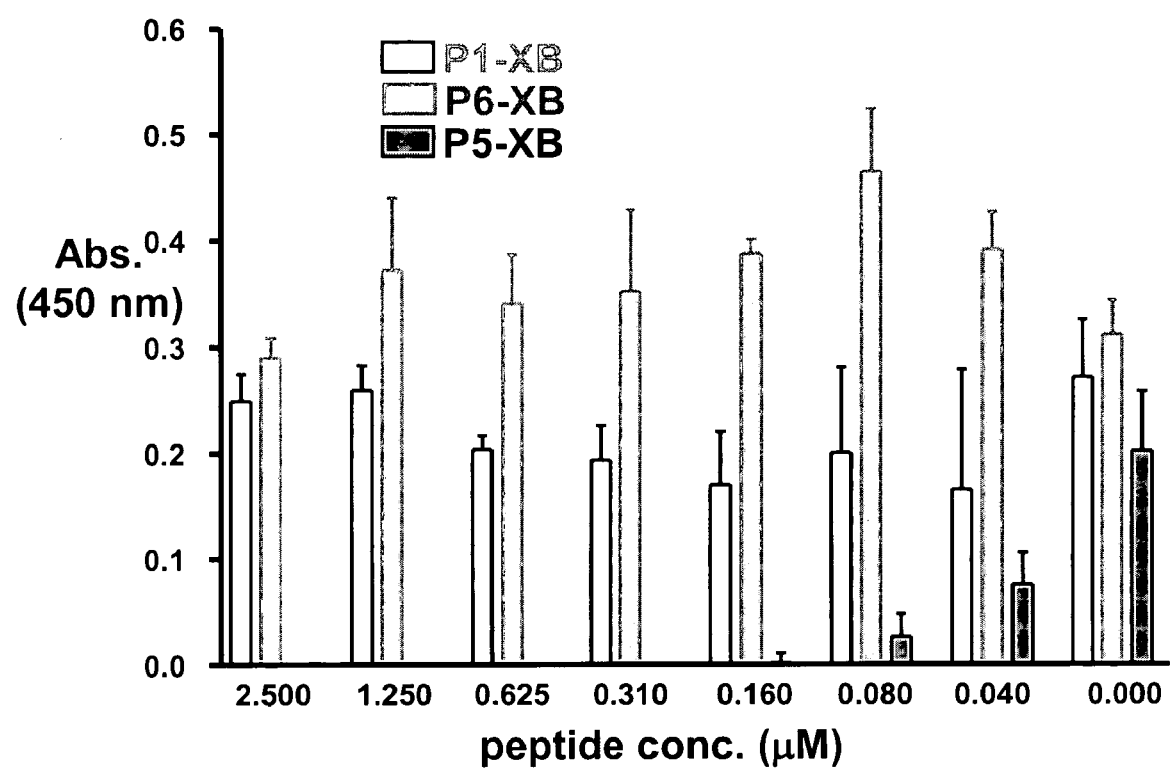
FIG. 13 depicts specific binding of a P5-XB/avidin-HRP complex to KDR transfected cells (background binding to mock-transfected cells subtracted), plotted as absorbance at 450 nm. Increasing concentrations (as indicated by the X axis) of uncomplexed peptides were added to the assay as indicated in the legend. Only free P5-XB was able to decrease the binding of the P5-XB/avidin complex to KDR-transfected cells.

It is evident from the results, shown in FIG. 13, that P5-XB does compete with P5-XB/avidin HRP solution for binding to KDR transfected cells whereas P1-XB and P6-XB do not compete with P5-XB/avidin HRP solution for binding to KDR transfected cells. Thus, P5-XB and P6-XB bind to distinct and complementary sites on KDR.

EXAMPLE 7

Preparation of Heterodimeric Constructs

To obtain a higher affinity peptide binder to the KDR receptor, two linear peptides (P9, P10) were linked together to form a heterodimer. As determined by VEGF competition assays, these two peptides bind different sites on KDR. It is possible, therefore, that both peptides in the heterodimer could bind a single protein molecule at the same time and as result, bind with a higher overall affinity for the receptor. Two forms of the heterodimer were synthesized in an effort to determine the optimal orientation for this bidentate binding event. The peptides were either linked together in a tail-to-tail orientation via their C-terminal lysine residues or in a head-to-head orientation via their N-terminal amino groups.

The peptides were synthesized using standard Fmoc solid-phase peptide synthesis protocols. To add spacing between the two peptides in the dimer, each individual peptide monomer was modified at either the C-terminal lysine (to make the tail-to-tail dimer) or N-terminal amino (to make the head-to-head dimer) with a monodispersed PEG-based amino acid linker (Fmoc-NH-PEG$_4$-CO$_2$H). After deprotection of the Fmoc group of each PEG linker, the P9 peptide was labeled with levulinic acid (CH$_3$(C=O)(CH$_2$)$_2$CO$_2$H) and the P10 peptide was labeled with Boc-amino-oxyacetic acid. After deprotection, cleavage and purification, the two peptides were ligated together in a 1:1 ratio in denaturing buffer (8M Urea, 0.1M sodium acetate, pH 4.6) to form an oxime linkage (—CH=N—O—) between the two different peptides. Using the two different sets of monomers, the tail-to-tail and head-to-head heterodimers were formed in solution and purified to homogeneity by standard reverse phase protocols. A more detailed description of this linkage chemistry is found in K. Rose, et al. *JACS*, 1999, 121: 7034–7038, which is hereby incorporated by reference in its entirety.

Assay for Binding Affinity of Heterodimeric Constructs

To assay for improved binding affinity relative to either monomeric peptide, each heterodimer was assayed for binding using a surface plasmon resonance instrument (Biacore 3000). Soluble KDR receptor was cross-linked to the dextran surface of a CM5 sensor chip by the standard amine coupling procedure. A 0.5 mg/mL solution was diluted 1:40 with 50 mM acetate, pH 6.0 to immobilize a total $R_L$ of 12721. Experiments were performed in PBST buffer (5.5 mM phosphate, pH 7.65, 0.15M NaCl, 0.1% Tween-20 (v/v)). Peptide solutions quantified by extinction coefficient were diluted to produce 1000, 500, 250, 125, 62.5 and 31.3 nM solutions. For association, peptides were injected at 20 µL/min for 2 minutes using the kinject program. Following a 3 minute dissociation, any remaining peptide was stripped from the KDR surface with a quickinject of 50 mM NaOH, 1M NaCl for 15 s at 75 µL/min. Monomeric P9 and P10 were run as standards. Sensorgrams were analyzed by global analysis using BIAevaluation software 3.1.

The peptide dimers investigated in this study by BIAcore analysis bind KDR with significantly higher affinity than either of the constituent monomers. By design, the interaction of a dimeric peptide with KDR is expected to proceed through two kinetic steps. With more detailed analysis it may be possible to accurately dissect the individual rate constants for these steps. However, an apparent $K_D$ was calculated for the dimer interaction using the rate describing the initial encounter ($k_{a,1}$) and the predominant off-rate ($k_{d,2}$). From this analysis, the apparent $K_D$ of the head-to-head dimer was 2.2 nM and that of the tail-to-tail dimer was 11 nM (Table 4). These estimates represent an increase in affinity over the individual monomers of greater than 60-fold for the comparison of the P9 to T—T dimer $K_D$ (732 nM/11.1 nM) and greater than 560-fold for the P10 to H—H dimer $K_D$ (1260 nM/2.24 nM).

TABLE 4

Summary of Kinetic Parameters

| Peptide | $k_{a,1}$ (1/Ms) | $k_{d,1}$ (1/s) | $K_{D,1}$ (nM) | Chi2* |
|---|---|---|---|---|
| P9 | $4.53 \times 10^3$ | $3.32 \times 10^{-3}$ | 732 | 0.67 |
| P10 | $3.60 \times 10^5$ | $4.5 \times 10^{-1}$ | 1260 | 1.2 |
| Head-to-head dimer | $1.11 \times 10^5$ | $2.49 \times 10^{-4}$ | 2.24 | 1.25 |
| Tail-to-tail dimer | $1.15 \times 10^5$ | $1.28 \times 10^{-3}$ | 11.1 | 2.33 |

EXAMPLE 8

The following methods were used for the preparation of individual peptides and dimeric peptide constructs described in Examples (8–12).

Automated Peptide Synthesis

Peptide synthesis was carried out on an ABI-433A Synthesizer (Applied Biosystems Inc., Foster City, Calif.) on a 0.25 mmol scale using the FastMoc protocol. In each cycle of this protocol preactivation was accomplished by dissolution of 1.0 mmol of the requisite dry N$^\alpha$-Fmoc side-chain protected amino acid in a cartridge with a solution of 0.9 mmol of HBTU, 2 mmol of DIEA, and 0.9 mmol of HOBt in a DMF-NMP mixture. The peptides were assembled on NovaSyn TGR (Rink amide) resin (substitution level 0.2 mmol/g). Coupling was conducted for 21 min. Fmoc deprotection was carried out with 20% piperidine in NMP. At the end of the last cycle, the N-terminal Fmoc group was removed and the fully protected resin-bound peptide was acetylated using acetic anhydride/DIEA/HOBt/NMP.

Cleavage, Side-Chain Deprotection and Isolation of Crude Peptides

Cleavage of the peptides from the resin and side-chain deprotection was accomplished using Reagent B for 4.5 h at ambient temperature. The cleavage solutions were collected and the resins were washed with an additional aliquot of Reagant B. The combined solutions were concentrated to dryness. Diethyl ether was added to the residue with swirling or stirring to precipitate the peptides. The liquid phase was decanted, and solid was collected. This procedure was repeated 2–3 times to remove impurities and residual cleavage cocktail components.

Cyclization of Di-Cysteine Peptides

The crude ether-precipitated linear di-cysteine containing peptides were cyclized by dissolution in water, mixtures of aqueous acetonitrile (0.1% TFA), aqueous DMSO or 100% DMSO and adjustment of the pH of the solution to 7.5–8.5 by addition of aqueous ammonia, aqueous ammonium carbonate, aqueous ammonium bicarbonate solution or DIEA. The mixture was stirred in air for 16–48 h, acidified to pH 2 with aqueous trifluoroacetic acid and then purified by preparative reverse phase HPLC employing a gradient of acetonitrile into water. Fractions containing the desired material were pooled and the purified peptides were isolated by lyophilization.

Preparation of Peptides Containing Linkers

In a typical experiment, 400 mg of the resin-bound peptide bearing an ivDde-protected lysine) was treated with 10% hydrazine in DMF (2×20 mL). The resin was washed with DMF (2×20 mL) and DCM (1×20 mL). The resin was resuspended in DMF (10 mL) and treated with Fmoc-8-amino-3,6-dioxaoctanoic acid (0.4 mmol), HOBt (0.4 mmol), DIC (0.4 mmol) and DIEA (0.8 mmol) with mixing for 4 h. After the reaction, the resin was washed with DMF (2×10 mL) and with DCM (1×10 mL). The resin was then treated with 20% piperidine in DMF (2×15 mL) for 10 min each time. The resin was washed and the coupling with Fmoc-8-amino-3,6-dioxaoctanoic acid and Fmoc protecting group removal were repeated once more.

The resulting resin-bound peptide with a free amino group was washed and dried and then treated with reagent B (20 mL) for 4 h. The mixture was filtered and the filtrate concentrated to dryness. The residue was stirred with ether to produce a solid, which was washed with ether and dried. The solid was dissolved in anhydrous DMSO and the pH adjusted to 7.5 with DIEA. The mixture was stirred for 16 h to effect the disulfide cyclization and the reaction was monitored by analytical HPLC. After completion of the cyclization, the reaction mixture was diluted with 25% acetonitrile in water and applied directly to a reverse phase C-18 column. Purification was effected using a gradient of acetonitrile into water (both containing 0.1% TFA). Fractions were analyzed by HPLC and those containing the pure product were combined and lyophilized to provide the required peptide.

Preparation of Biotinylated Peptides Containing Linkers

In a typical experiment, 400 mg of the resin-bound peptide bearing an ivDde-protected lysine, was treated with 10% hydrazine in DMF (2×20 mL). The resin was washed with DMF (2×20 mL) and DCM (1×20 mL). The resin was resuspended in DMF (10 mL) and treated with Fmoc-8-amino-3,6-dioxaoctanoic acid (0.4 mmol), HOBt (0.4 mmol), DIC (0.4 mmol) and DIEA (0.8 mmol) with mixing for 4 h. After the reaction, the resin was washed with DMF (2×10 mL) and with DCM (1×10 mL). The resin was then treated with 20% piperidine in DMF (2×15 mL) for 10 min each time. The resin was washed and the coupling with Fmoc-8-amino-3,6-dioxaoctanoic acid and removal of the Fmoc protecting group were repeated once more.

The resulting resin-bound peptide with a free amino group was treated with a solution of Biotin-NHS ester (0.4 mmol, 5 equiv.) and DIEA (0.4 mmol, 5 equiv.) in DMF for 2 h. The resin was washed and dried as described previously and then treated with Reagent B (20 mL) for 4 h. The mixture was filtered and the filtrate concentrated to dryness. The residue was stirred with ether to produce a solid that was collected, washed with ether, and dried. The solid was dissolved in anhydrous DMSO and the pH adjusted to 7.5 with DIEA. The mixture was stirred for 4–6 h to effect the disulfide cyclization which was monitored by HPLC. Upon completion of the cyclization, the reaction mixture was diluted with 25% acetonitrile in water and applied directly to a reverse phase C-18 column. Purification was effected using a gradient of acetonitrile into water (both containing 0.1% TFA). Fractions were analyzed by HPLC and those containing the pure product were collected and lyophilized to provide the required biotinylated peptide.

Preparation of DOTA-Conjugated Peptides for Labeling with Selected Gadolinium or Indium Isotopes In a typical experiment, 400 mg of the resin-bound peptide bearing an $N^\epsilon$-ivDde-protected lysine moiety was treated with 10% hydrazine in DMF (2×20 mL). The resin was washed with DMF (2×20 mL) and DCM (1×20 mL). The resin was resuspended in DMF (10 mL) and treated with Fmoc-8-amino-3,6-dioxaoctanoic acid (0.4 mmol), HOBt (0.4 mmol), DIC (0.4 mmol), DIEA (0.8 mmol) with mixing for 4 h. After the reaction, the resin was washed with DMF (2×10 mL) and with DCM (1×10 mL). The resin was then treated with 20% piperidine in DMF (2×15 mL) for 10 min each time. The resin was washed and the coupling with Fmoc-8-amino-3,6-dioxaoctanoic acid and removal of the Fmoc protecting group were repeated once. The resulting resin-bound peptide with a free amino group was resuspended in DMF (10 mL) and treated with a solution of 1,4,7,10-tetraazacyclododecane-1,4,7,10-tetraacetic acid, -1,4,7-tris-t-butyl ester (DOTA-tris-t-butyl ester, 0.4 mmol, 5 equiv.), HOBt (0.4 mmol), DIC (0.4 mmol) and DIEA (0.8 mmol) in DMF (10 mL) with mixing for 4 h. Upon completion of the reaction, the resin was washed with DMF (2×10 mL) and with DCM (1×10 mL) and treated with Reagent B (20 mL) for 4 h. The mixture was filtered and the filtrate concentrated to dryness. The residue was stirred in ether to produce a solid that was collected, washed with ether, and dried. The solid was dissolved in anhydrous DMSO and the pH adjusted to 7.5 with DIEA. The mixture was stirred for 16 h to effect the disulfide cyclization, which was monitored by HPLC. Upon completion of the cyclization, the mixture was diluted with 25% acetonitrile in water and applied directly to a reverse phase C-18 HPLC column. Purification was effected using a gradient of acetonitrile into water (both containing 0.1% TFA). Fractions were analyzed by HPLC and those containing the pure product were combined and lyophilized to provide the required biotinylated peptide.

The following monomeric peptides of Table 5 were prepared by the above methods.

TABLE 5

Sequence or Structure of Monomeric Peptides and Peptide Derivatives

| Ref. Number | Structure or Sequence | Seq Id. No: |
|---|---|---|
| P12-XB-K | Ac-AGPTWC*EDDWYYC*WLFGTGGGK(BiotinJJ-K)-NH$_2$ | — |
| P12-XDT-K | Ac-AGPTWC*EDDWYYC*WLFGTJK(DOTAJJ-K)-NH$_2$ | — |
| P12-X | Ac-AGPTWC*EDDWYYC*WLFGTJK(JJ)-NH$_2$ | — |

TABLE 5-continued

Sequence or Structure of Monomeric Peptides and Peptide Derivatives

| Ref. Number | Structure or Sequence | Seq Id. No: |
|---|---|---|
| P12-E | Ac-AGPTWC*EDDWYYC*WLFGTGGGK[K(ivDde)]-NH$_2$ | — |
| P6-F-XB-K | Ac-VC*WEDSWGGEVC*FRYDPGGGK(Biotin-JJK)-NH$_2$ | — |
| P6-F-X | Ac-VC*WEDSWGGEVC*FRYDPGGGK(JJ)-NH$_2$ | — |
| P13-EB-K | Ac-AQDWYYDEILSMADQLRHAFLSGGGGGK(ivDde)K(Biotin-JJ)-NH$_2$ | — |
| P13-X | Ac-AQDWYYDEILSMADQLRHAFLSGGGGGK(J)-NH$_2$ | — |
| P13-K-E | Ac-AQDWYYDEILSMADQLRHAFLSGGGGGKK(ivDde) | — |
| P6-X | Ac-GDSRVC*WEDSWGGEVC*FRYDPGGGK(JJ)-NH$_2$ | — |
| P12-A | Ac-AGPTWC*EDDWYYC*WLFGTGGGK[(PnAO6-C(=O)(CH$_2$)$_3$C(=O)—K]—NH$_2$ | — |
| P12-XDT-K-E | Ac-AGPTWC*EDDWYYC*WLFGTGGGK[(DOTA-JJK(iV-Dde)]-NH$_2$ | — |
| P6-F | Ac-VC*WEDSWGGEVC*FRYDPGGGK-NH$_2$ | — |
| P12-O | Ac-AGPTWC*EDDWYYC*WLFGTGGGK[K(BOA)]-NH$_2$ | — |
| P13-A-E | Ac-AQDWYYDEILSMADQLRHAFLSGGGGGK[PnAO6-C(=O)(CH$_2$)$_3$C(=O)—K(iV-Dde)]-NH$_2$ | — |
| P23 | AQDWYYEILJGRGGRGGRGGK | 22 |
| P23-K-E | Ac-AQDWYYEILJGRGGRGGRGGK[K(ivDde)]-NH$_2$ | — |
| P24 | APGTWCDYDWEYCWLGTFGGGK | 23 |
| P24-A | Ac-APGTWC*DYDWEYC*WLGTFGGGK[(6PnAO-C(=O)(CH$_2$)$_3$C(=O)—K]—NH$_2$ | — |
| P25 | GVDFRCEWSDWGEVGCRSPDYGGGK | 24 |
| P25-X | Ac-GVDFRC*EWSDWGEVGC*RSPDYGGGK(JJ)-NH$_2$ | — |
| P12-BK | Ac-AGPTWC*EDDWYYC*WLFGTGGGK(Biotin-K)-NH$_2$ | — |
| P12-JE | JJAGPTWC*EDDWYYC*WLFGTGGGK(iV-Dde)-NH$_2$ | — |
| P6-J-F | JJVC*WEDSWGGEVC*FRYDPGGG-NH$_2$ | — |
| P12-JA | [-JJAGPTWCEDDWYYCWLFGTGGGGK(PnAO6-Glut)-NH$_2$]- | — |
| P12-S | Ac-AGPTWC*EDDWYYC*WLFGTGGGK[K(SATA)]-NH$_2$ | — |
| P12-SX-K | Ac-AGPTWC*EDDWYYC*WLFGTGGGK[SATA-JJ-K]-NH$_2$ | — |
| P12-NE | H$_2$N-AGPTWC*EDDWYYC*WLFGTGGGK[K(iV-Dde)]-NH$_2$ | — |
| P12-Q | Ac-AGPTWC*EDDWYYC*WLFGTGGGK{Biotin-JJK[NH$_2$-Ser(GalNAc-alpha-D)-Gly-Ser(GalNAc$_3$-alpha-D)]}-NH$_2$ | — |
| P6-F-Q | Ac-VC*WEDSWGGEVC*FRYDPGGGK(NH$_2$-Ser(GalNAc-alpha-D)-Gly-Ser(GalNAc-alpha-D)-NH$_2$ | — |
| P26 | GSPEMCMMFPFLYPCNHHAPGGGK | 25 |
| P26-A | Ac-GSPEMC*MMFPFLYPC*NHHAPGGGK[(PnAO6)-C(=O)(CH$_2$)$_3$C(=O)—K]}—NH$_2$ | — |
| P27 | GSFFPCWRIDRFGYCHANAPGGGK | 26 |
| P27-X | Ac-GSFFPC*WRIDRFGYC*HANAPGGGK(JJ)-NH$_2$ | — |
| P27-A | Ac-GSFFPC*WRIDRFGYC*HANAPGGGK[(PnAO6)-C(=O)(CH$_2$)$_3$C(=O)—K]}—NH$_2$ | — |
| P28 | AQEWEREYFVDGFWGSWFGIPHGGGK | 27 |
| P28-X | Ac-AQEWEREYFVDGFWGSWFGIPHGGGK(JJ)-NH$_2$. | — |
| P29 | GDYSECFFEPDSFEVKCYDRDPGGGK | 28 |
| P29-X | Ac-GDYSEC*FFEPDSFEVKC* YDRDPGGGK(JJ)-NH$_2$ | — |

As used in Table 5 above and elsewhere herein, the designation "C*" refers to a cysteine residue that contributes to a disulfide bond. In general, the monomeric peptides described herein are prepared as cyclic disulfide peptides and then linked together to form dimers. Consequently, even if a cysteine residue lacks the "C*" designation, the presence of a disulfide bond to the nearest cysteine in the monomer can generally be assumed. The monomer components of the dimers will also generally contain such disulfide bonds, regardless of whether the cysteine residues contain the "C*" designation or not. However, one skilled in the art will appreciate that the dimers and other heteromultimers of the present invention could alternatively be prepared by performing the cyclization of Di-cysteine peptides after the monomers are linked to form dimers, and the present inven-

EXAMPLE 9

The purified peptide monomers mentioned above in Example 8 were used in the preparation of various homodimeric and heterodimeric constructs.

Preparation of Homodimer-Containing Constructs

To prepare homodimeric compounds, half of the peptide needed to prepare the dimer was dissolved in DMF and treated with 10 equivalents of glutaric acid bis-N-hydoxysuccinimidyl ester. The progress of the reaction was monitored by HPLC analysis and mass spectroscopy. At completion of the reaction, the volatiles were removed in vacuo and the residue was washed with ethyl acetate to remove the unreacted bis-NHS ester. The residue was dried, re-dissolved in anhydrous DMF and treated with another half portion of the peptide in the presence of 2 equivalents of DIEA. The reaction was allowed to proceed for 24 h. This mixture was applied directly to a YMC reverse phase HPLC column and purified by elution with a linear gradient of acetonitrile into water (both containing 0.1% TFA).

Preparation of Heterodimer-Containing Constructs

In the case of heterodimers, one of the monomers ("A") was reacted with the bis-NHS ester of glutaric acid and after washing off the excess of bis-NHS ester (as described for the homodimeric compounds), the second monomer ("B") was added in the presence of DIEA. After the reaction the mixture was purified by preparative HPLC. Typically, to a solution of glutaric acid bis N-hydoxysuccinimidyl ester (0.02 mmol, 10 eqivalents) in DMF (0.3 mL) was added a solution of peptide A and DIEA (2 equiv) in DMF (0.5 mL) and the mixture was stirred for 2 h. The progress of the reaction was monitored by HPLC analysis and mass spectroscopy. At completion of the reaction, the volatiles were removed in vacuo and the residue was washed with ethyl acetate (3×1.0 mL) to remove the unreacted bis-NHS ester. The residue was dried, re-dissolved in anhydrous DMF (0.5 mL) and treated with a solution of peptide B and DIEA (2 equiv) in DMF (0.5 mL) for 24 h. The mixture was diluted with water (1:1,v/v) and applied directly to a YMC C-18 reverse phase HPLC column and purified by elution with a linear gradient of acetonitrile into water (both containing 0.1% TFA). Fractions were analyzed by analytical HPLC and those containing the pure product were combined and lyophilized to obtain the required dimer. The following dimers were prepared by this method (structure, name, compound reference number):

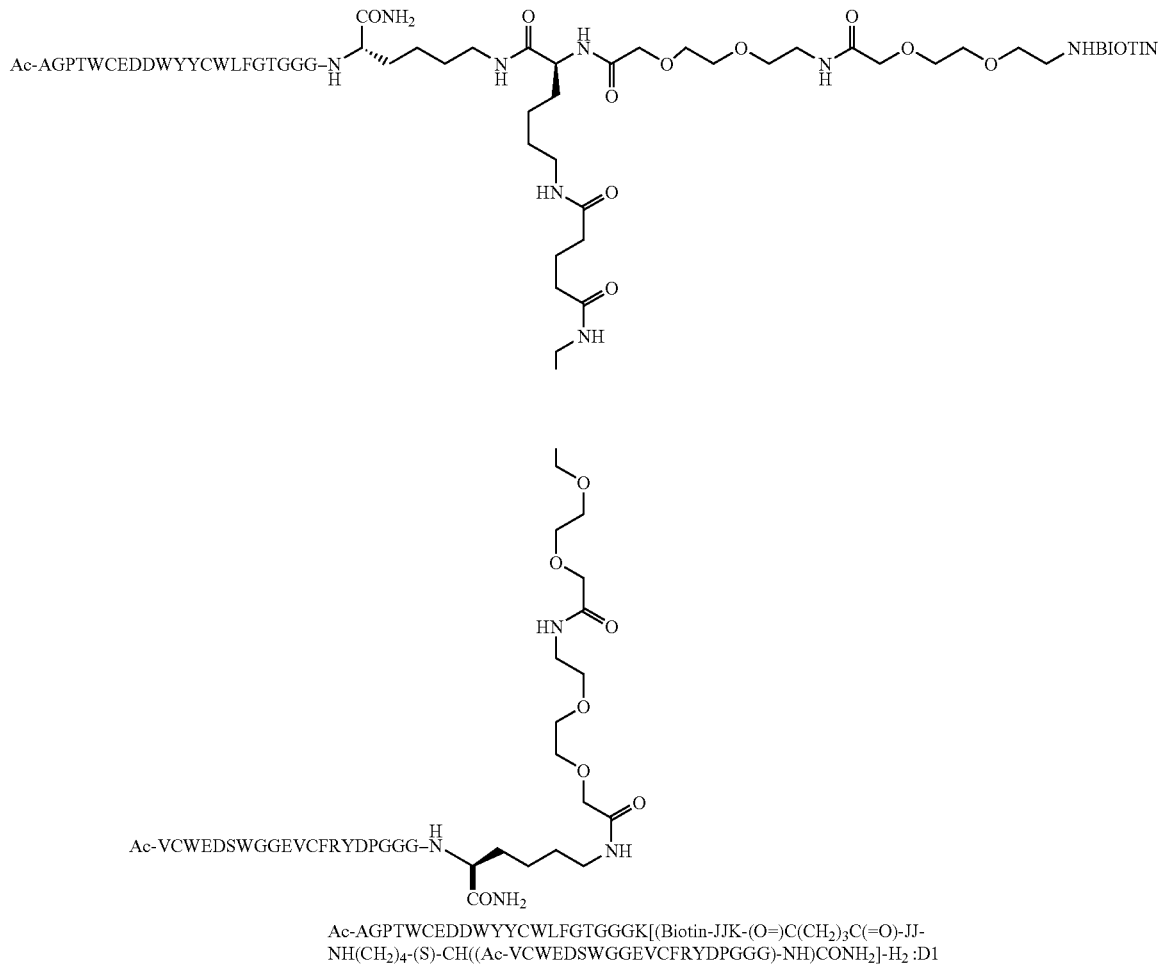

Ac-AGPTWCEDDWYYCWLFGTGGGK[(Biotin-JJK-(O=)C(CH$_2$)$_3$C(=O)-JJ-NH(CH$_2$)$_4$-(S)-CH((Ac-VCWEDSWGGEVCFRYDPGGG)-NH)CONH$_2$]-H$_2$ :D1

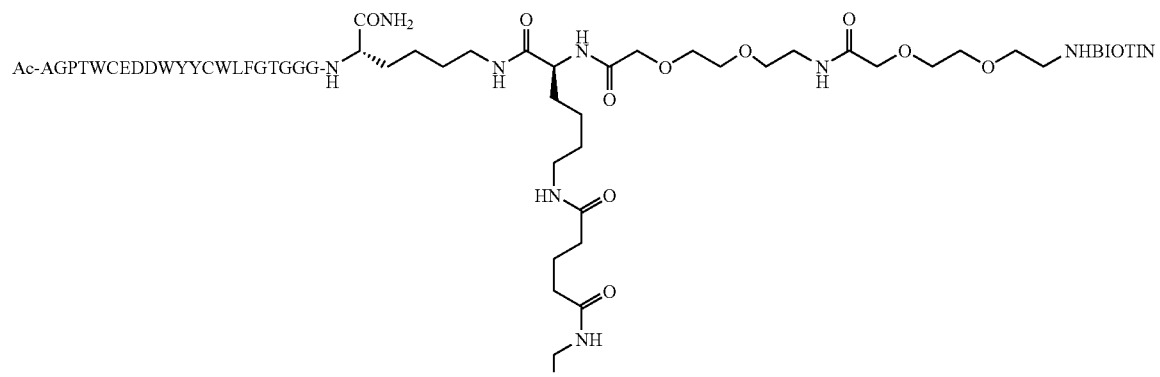
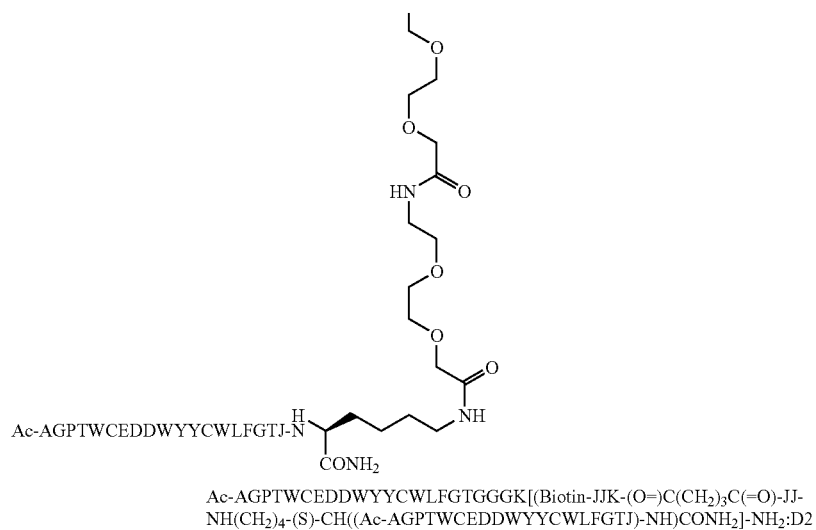
Ac-AGPTWCEDDWYYCWLFGTGGGK[(Biotin-JJK-(O=)C(CH₂)₃C(=O)-JJ-NH(CH₂)₄-(S)-CH((Ac-AGPTWCEDDWYYCWLFGTJ)-NH)CONH₂]-NH₂:D2
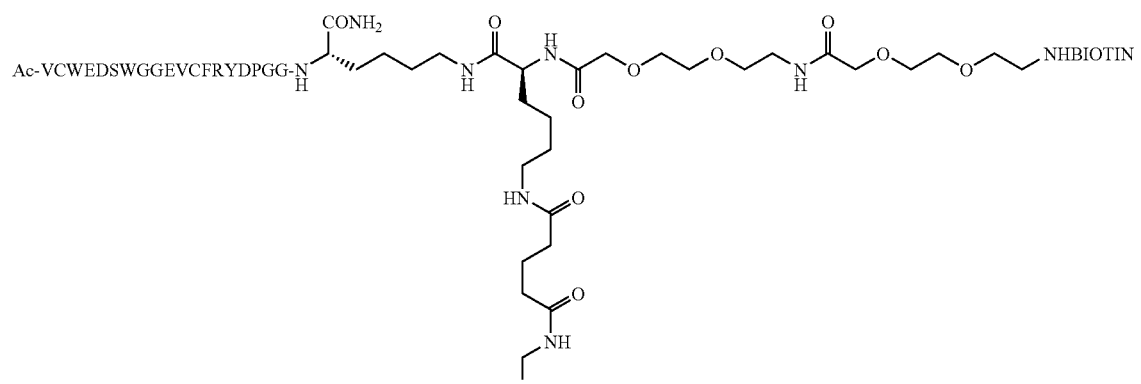

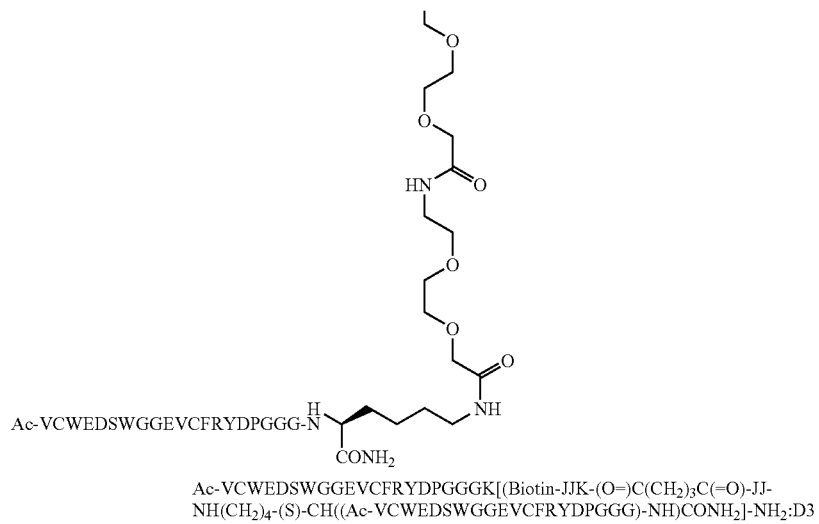
Ac-VCWEDSWGGEVCFRYDPGGGK[(Biotin-JJK-(O=)C(CH₂)₃C(=O)-JJ-NH(CH₂)₄-(S)-CH((Ac-VCWEDSWGGEVCFRYDPGGG)-NH)CONH₂]-NH₂:D3
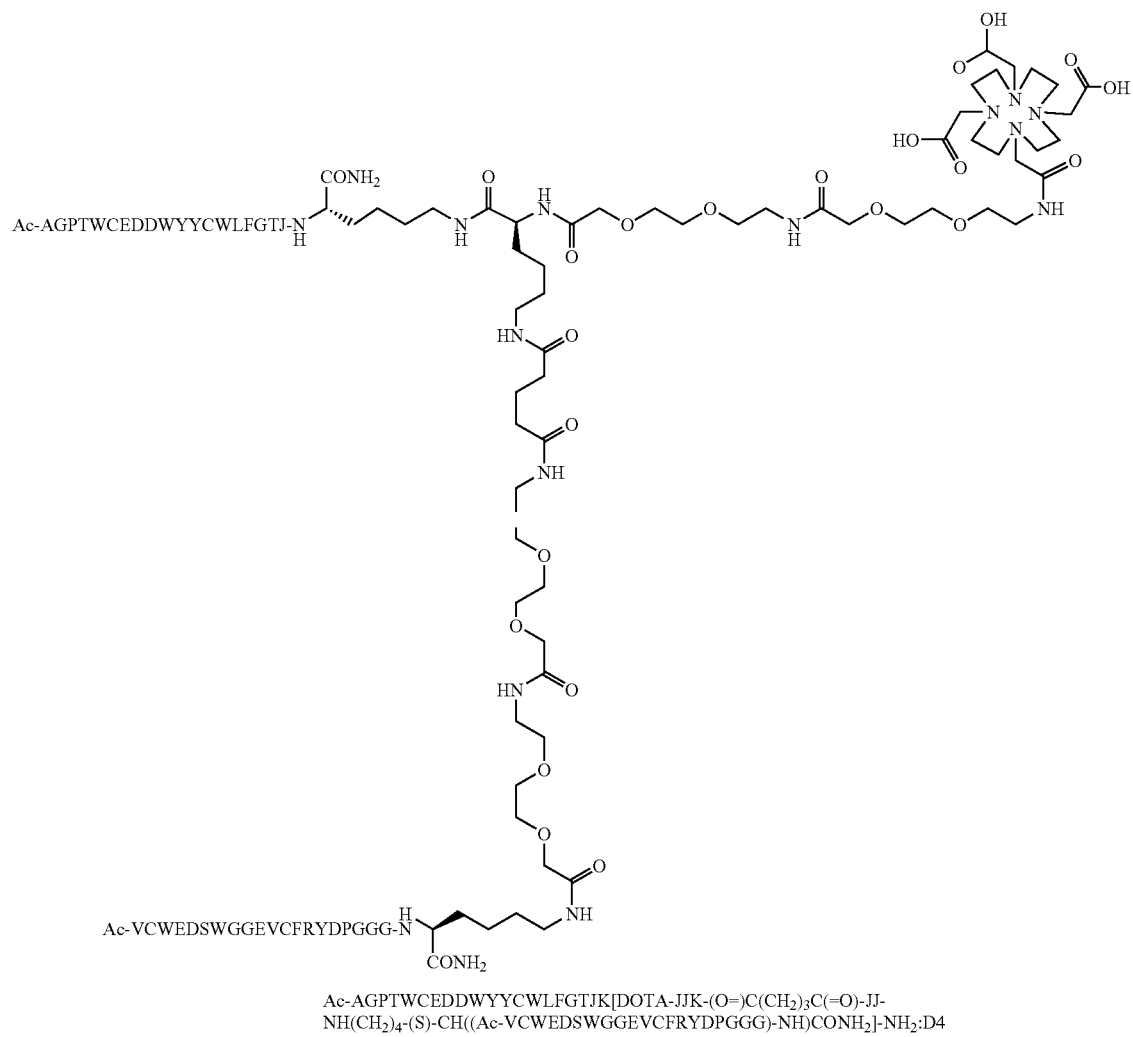
Ac-AGPTWCEDDWYYCWLFGTJK[DOTA-JJK-(O=)C(CH₂)₃C(=O)-JJ-NH(CH₂)₄-(S)-CH((Ac-VCWEDSWGGEVCFRYDPGGG)-NH)CONH₂]-NH₂:D4

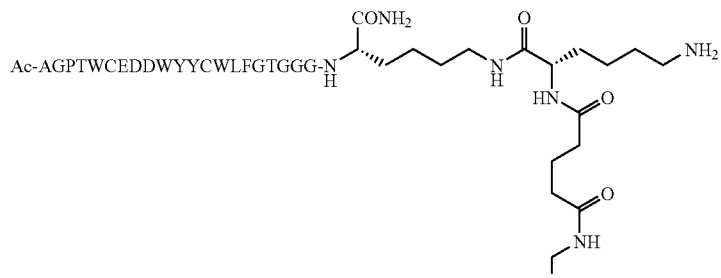
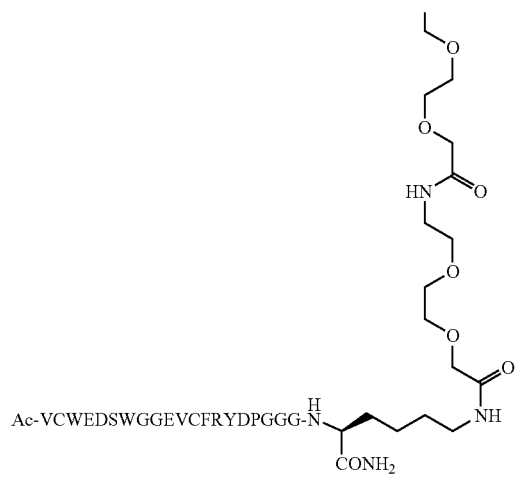
Ac-VCWEDSWGGEVCFRYDPGGGK(JJ-C(=O)(CH$_2$)$_3$C(=O)-K-NH(CH$_2$)$_4$-(S)-CH((Ac-AGPTWCEDDWYYCWLFGTGGG)-NH)CONH$_2$)-NH$_2$ :D5
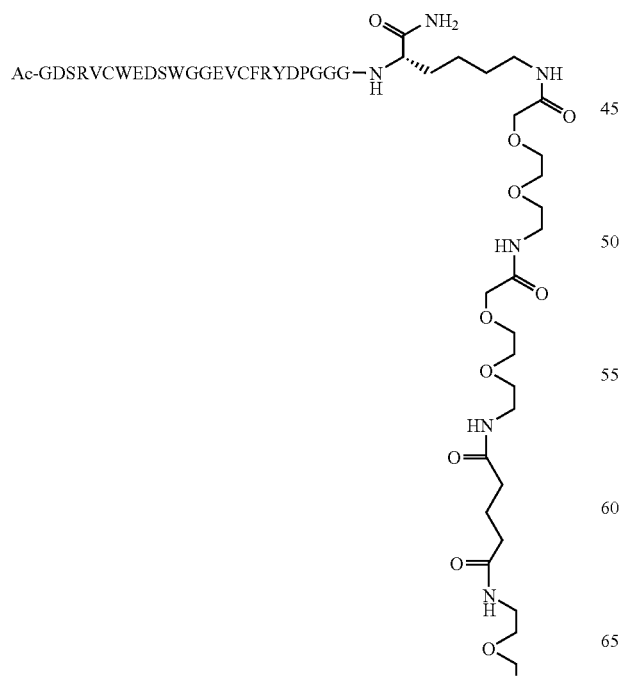
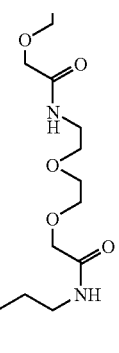
Molecular Weight=6030.58
Exact Mass=6024
Molecular Formula=C$_{269}$H$_{368}$N$_{66}$O$_{86}$S$_4$
Molecular Composition=C, 53.58%; H, 6.15%; N, 15.33%; O, 22.82% S 2.13%
Peptide Heterodimer: D6

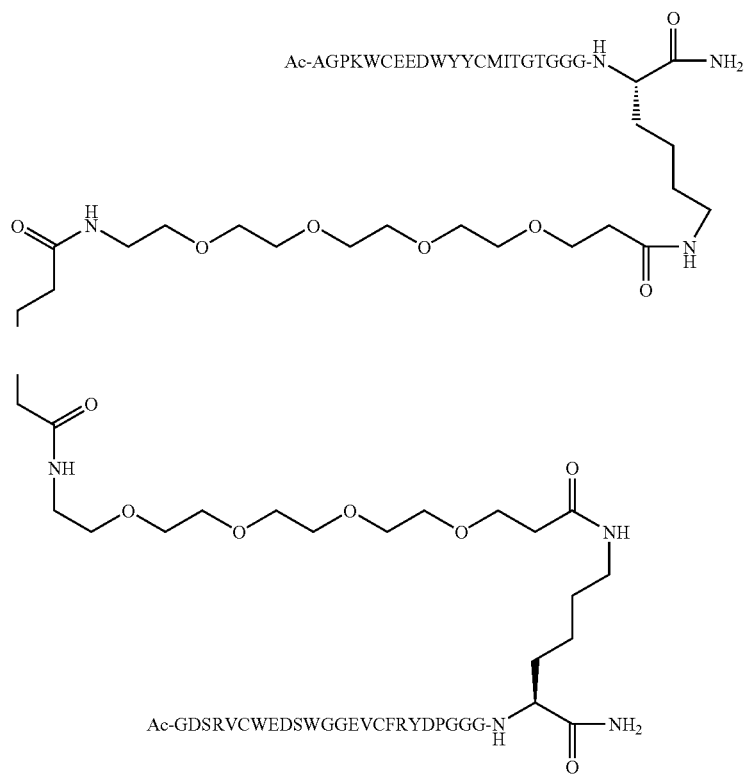
D7: Ac-AGPKWC*EEDWYYC*MITGTGGK(Ac-GDSRVC*WEDSWGGEVC*FRYDPGGGK(-(O=)C(CH₂CH₂O)₄CH₂CH₂NHC(=O)(CH₂)₃C(=O)NHCH₂CH₂(OCH₂CH₂)₄C(=O)-)NH₂)NH₂
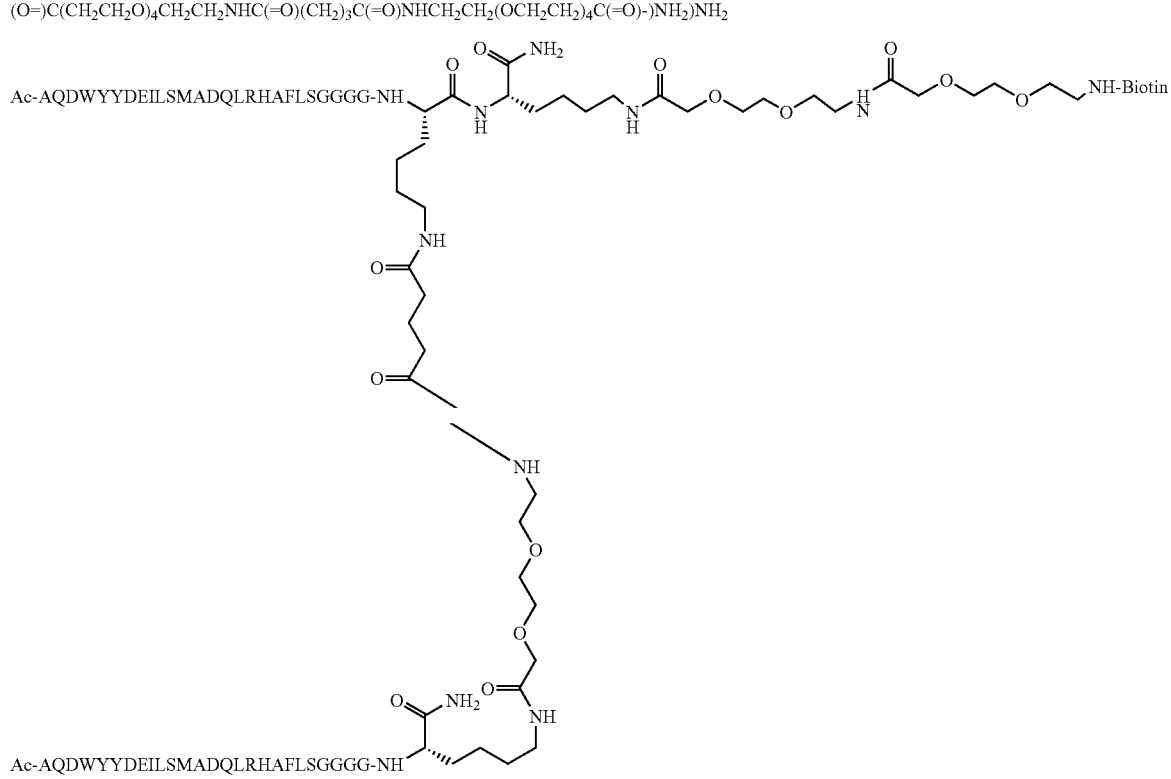
Ac-AQDWYYDEILSMADQLRHAFLSGGGGGK{Ac-AQDWYYDEILSMADQLRHAFLSGGGG
GK(J-Glut-)-NH₂}K(Biotin-JJ)-NH₂ : D8

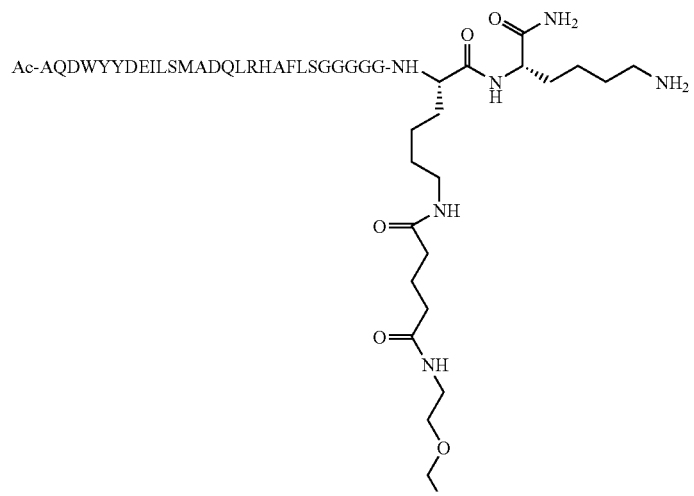
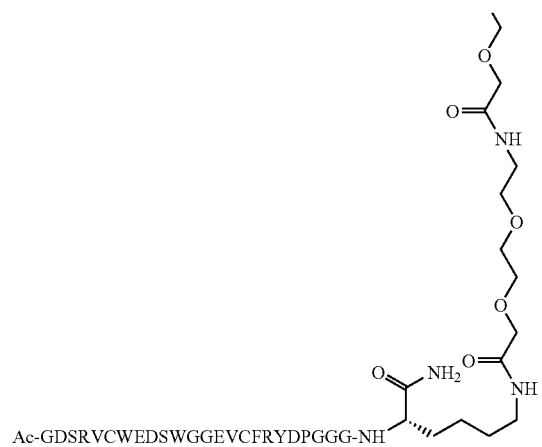
Ac-AQDWYYDEILSMADQLRHAFLSGGGGGK{[Ac-GDSRVCWEDSWGGEVCFRYDPGGGK(JJ-Glut-)]-NH$_2$}K-NH$_2$ : D9
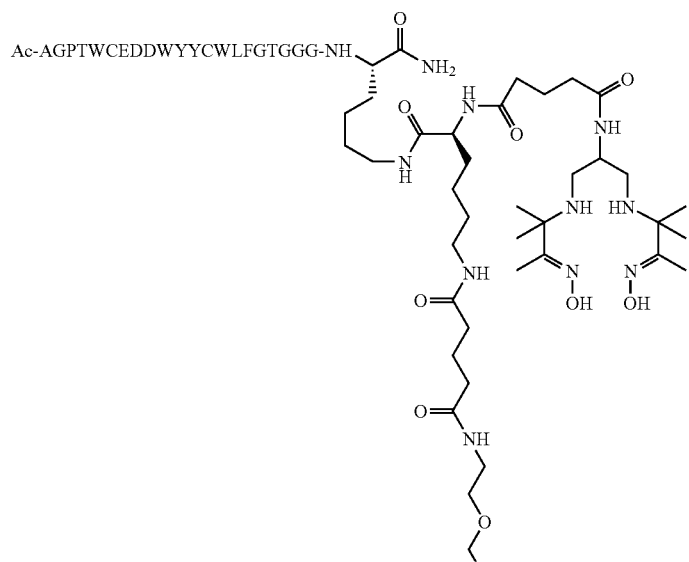

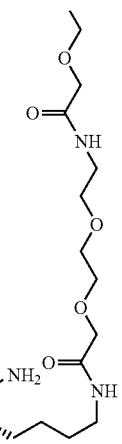
Ac-GDSRVCWEDSWGGEVCFRYDPGGG-NH
Ac-AGPTWCEDDWYYCWLFGTGGGK{[Ac-GDSRVCWEDSWGGEVCFRYDPGGGK(JJ-Glut-NH(CH₂)₄-(S)-CH(PnAO6-Glut-NH)(C=O-)]-NH₂}-NH₂:D10
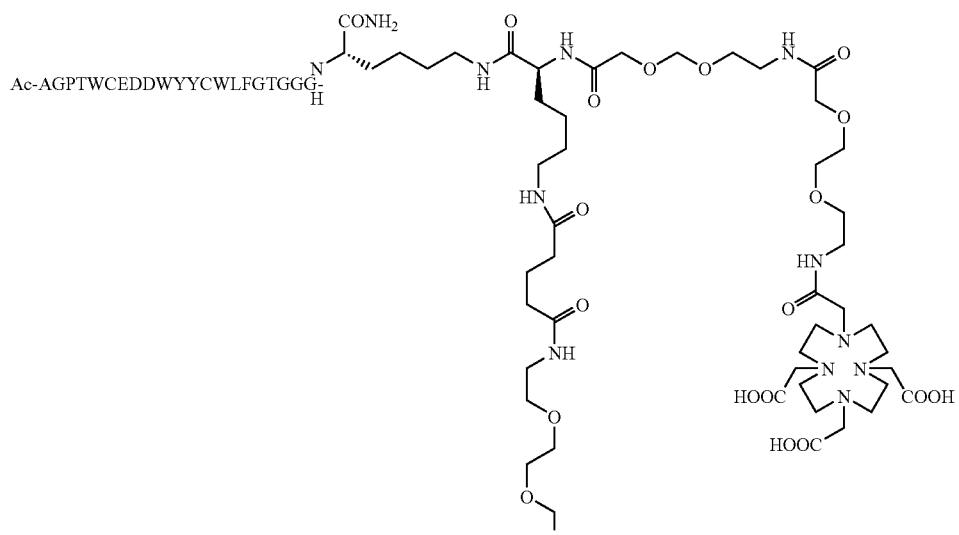
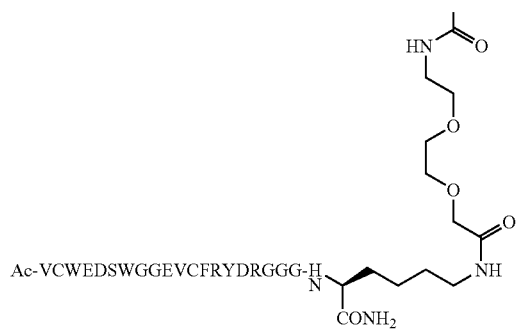
Ac-VCWEDSWGGEVCFRYDRGGG-
Ac-AGPTWCEDDWYYCWLFGTGGGK{Ac-VCWEDSWGGEVCFRYDPGGGK[JJ-Glut-NH(CH₂)₄-(S)-CH(DOTA-JJ-NH-)(C=O)-]-NH₂}-NH₂ : D11

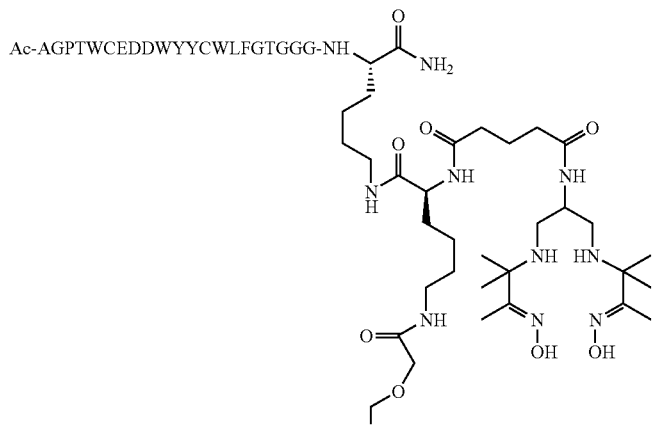
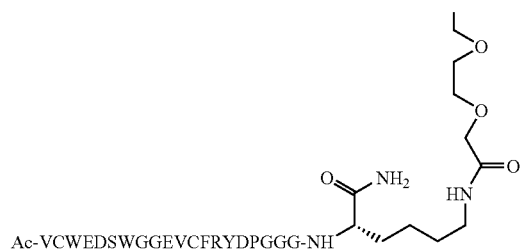
Ac-AGPTWCEDDWYYCWLFGTGGGK{[PnAO6-Glut-K(Ac-VCWEDSWGGEVCFRYDPGGGK(-C(=O)CH$_2$(OCH$_2$CH$_2$)$_2$OCH$_2$C(=O)-)-NH$_2$]}-NH$_2$:D12
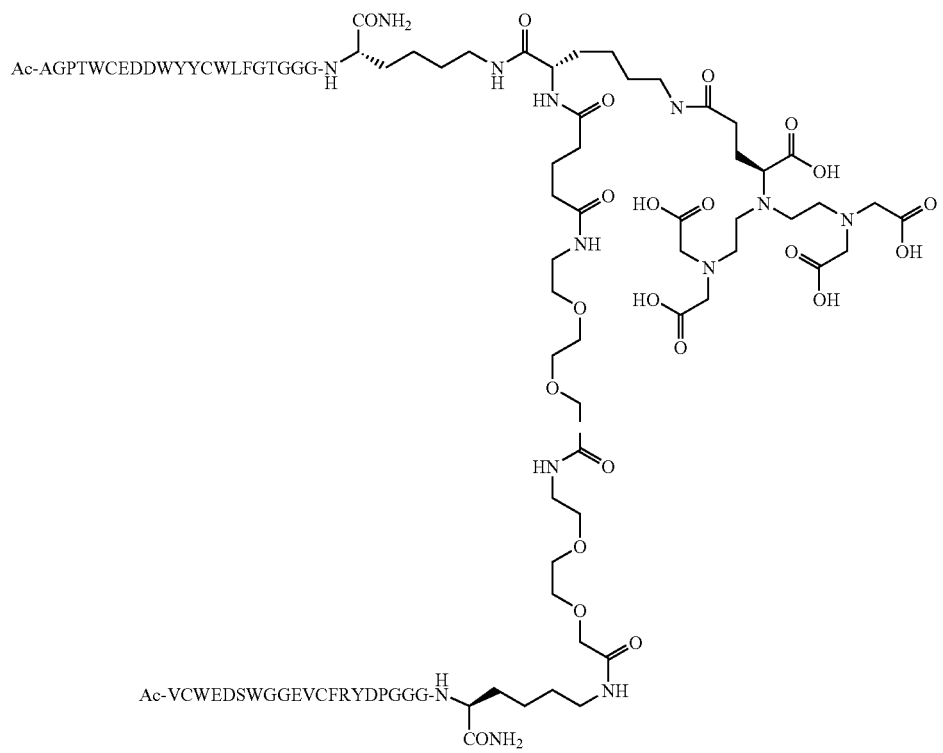
Ac-AGPTWCEDDWYYCWLFGTGGG{Ac-VCWEDSWGGEVCFRYDPGGGK[JJ-Glut-K(BOA)]-NH$_2$}-NH$_2$ : D13

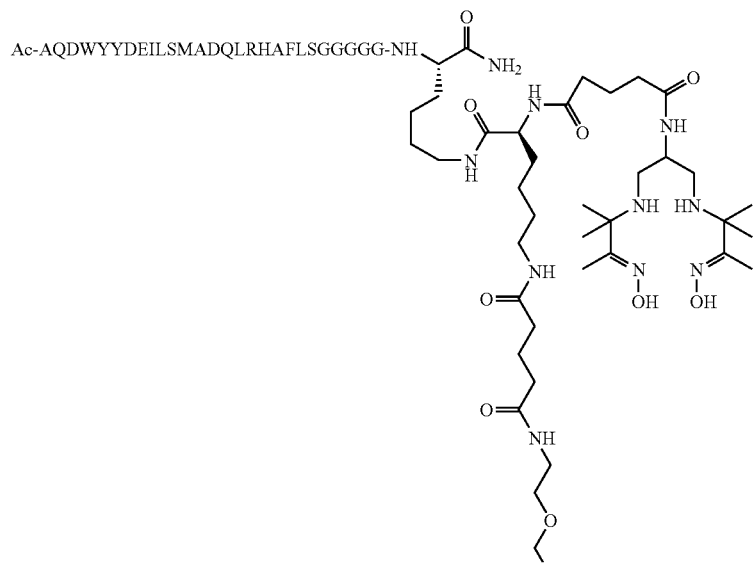
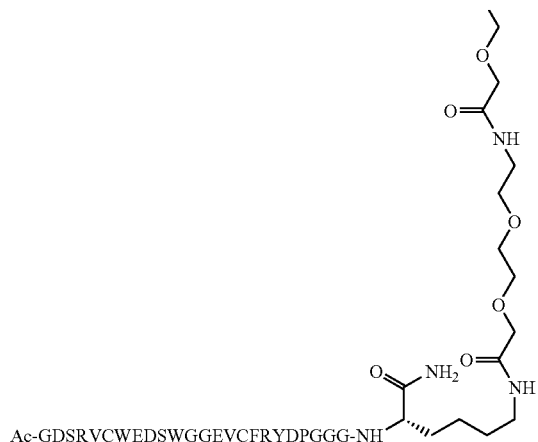
Ac-AQDWYYDEILSMADQLRHAFLSGGGGGK{PnAO6-Glut-K[Ac-GSDRVCWEDSWGGEVCFRYDPGGGK(JJ-Glut)-NH₂]}-NH₂:D14
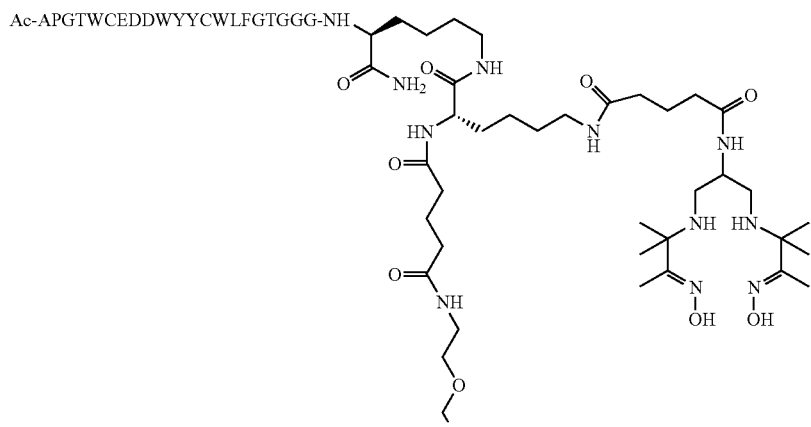

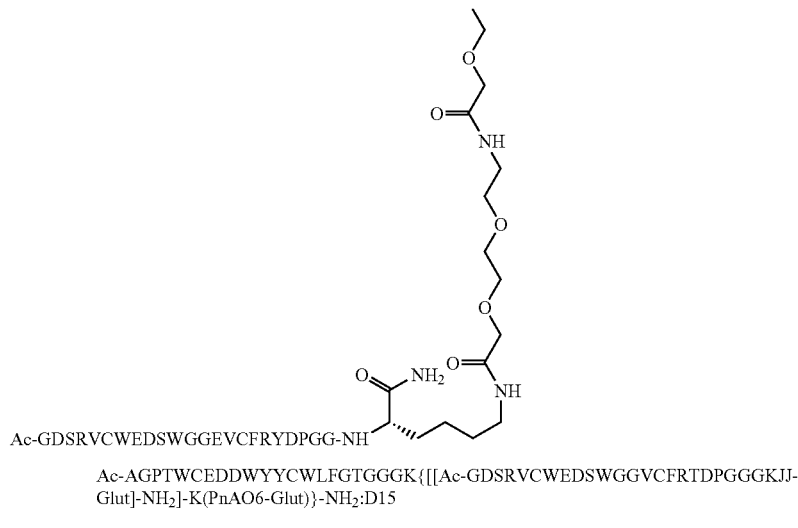
Ac-AGPTWCEDDWYYCWLFGTGGGK{[[Ac-GDSRVCWEDSWGGVCFRTDPGGGKJJ-Glut]-NH$_2$]-K(PnAO6-Glut)}-NH$_2$:D15
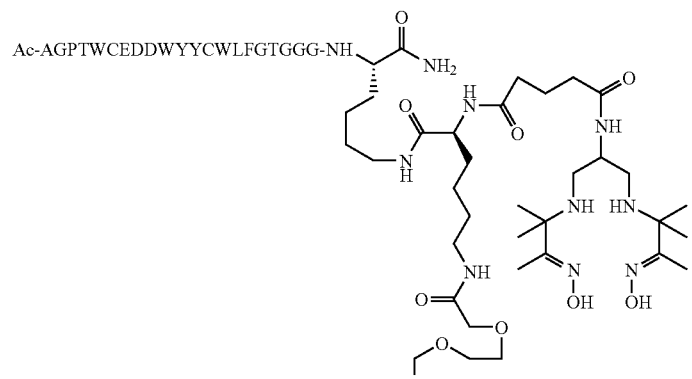
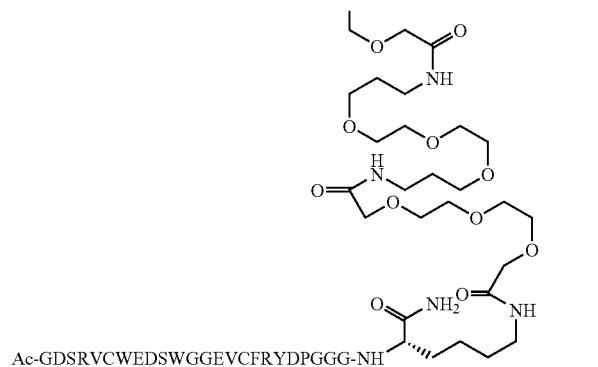
Ac-AGPTWDEDDWYYCWLFGTGGGK{PnA06-Glut-K[Ac-GDSRVCWEDSWGGVCFRYDPGGGK[-C(=O)CH$_2$O(CH$_2$CH$_2$O)$_2$CH$_2$C(=O)NH(CH$_2$)$_3$O(CH$_2$CH$_2$O)$_2$(CH$_2$)$_3$NHC(=O)CH$_2$O(CH$_2$CH$_2$O)$_2$CH$_2$C(=O)-]-NH$_2$]}-NH$_2$:D16

-continued
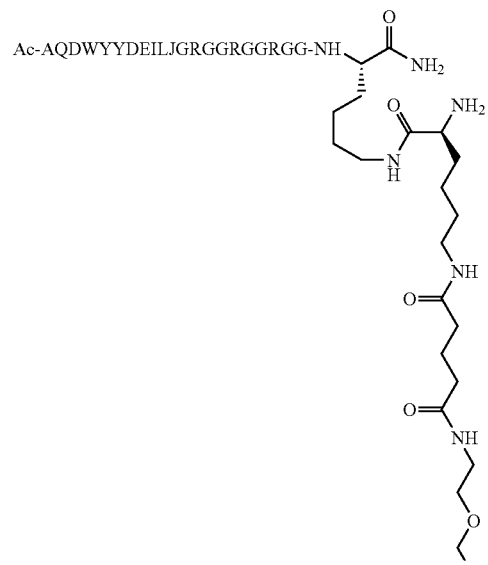
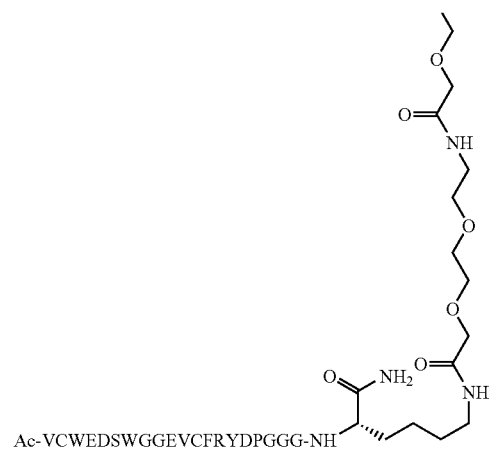
Ac-AQDWYYDEILJGRGGRGGRGGK{K[Ac-
VCWEDSWGGEVCFRYDPGGGK(JJ-Glut)-NH₂]}-NH₂:D17

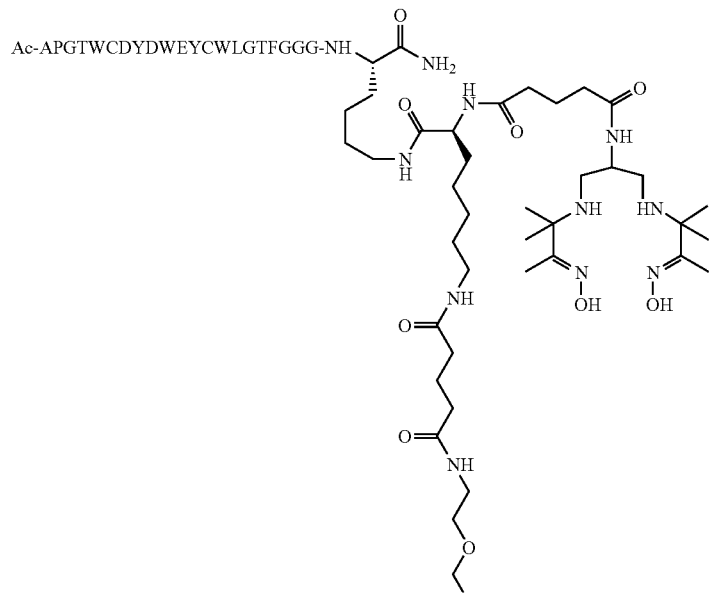
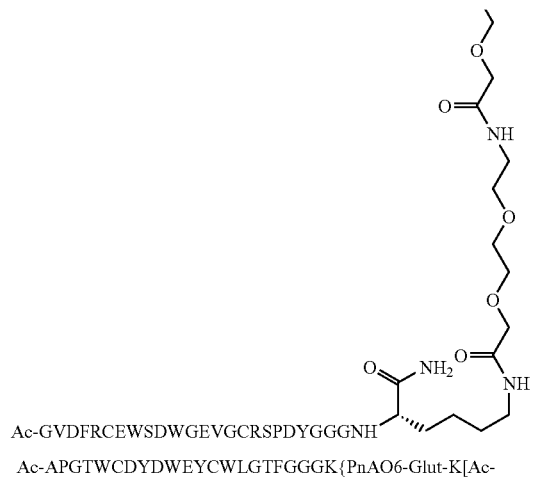
Ac-APGTWCDYDWEYCWLGTFGGGK{PnAO6-Glut-K[Ac-GVDFRCEWSDWGEVGCRSPDYGGGK(JJ-Glut)-NH₂]}-NH₂:D18
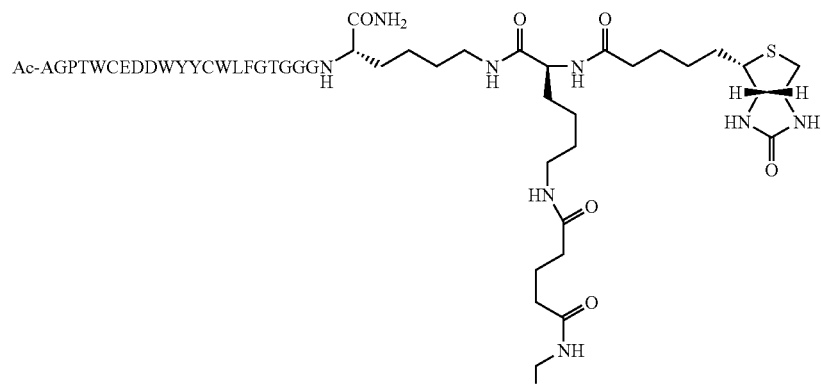

-continued
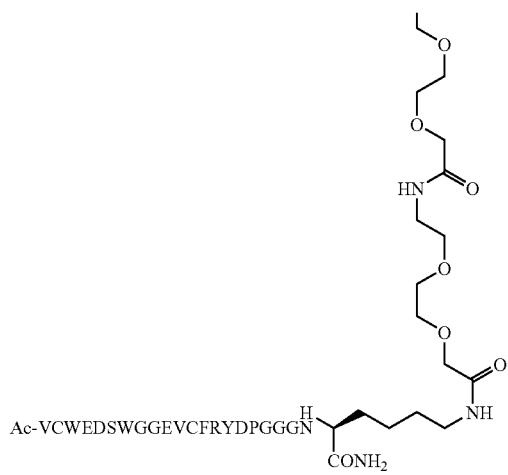
Ac-AGPTWCEDDWYYCWLFGTGGGK{Biotin-K[Ac-VCWEDSWGGEVCFRYDPGGGK(JJ-GluT)-NH₂]}-NH₂ : D19
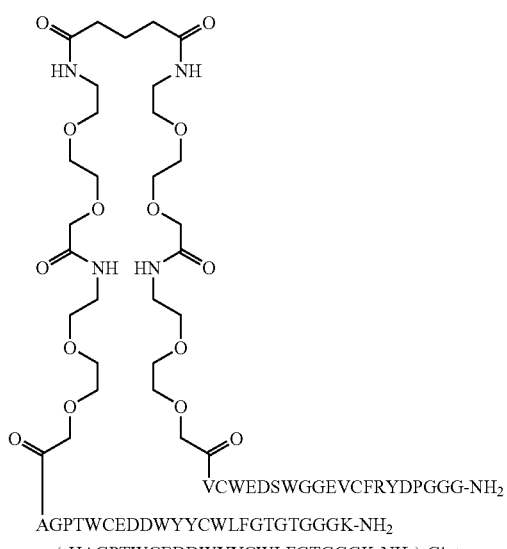
(-JJAGPTWCEDDWYYCWLFGTGGGK-NH₂)-Glut-
JJVCWEDSWGGEVCFRYDPGGG-NH₂ : D20
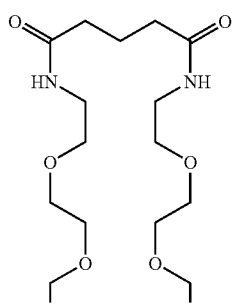

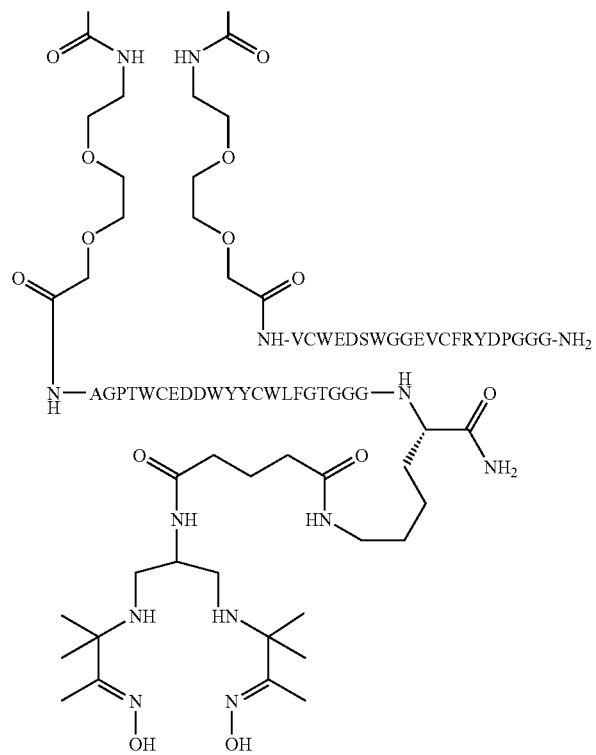
[-JJAGPTWCEDDWYYCWLFGTGGGK(PnAO6-Glut)-NH$_2$]-Glut-JJVCWEDSWGGEVCFRYDPGGG-NH$_2$ ; D21
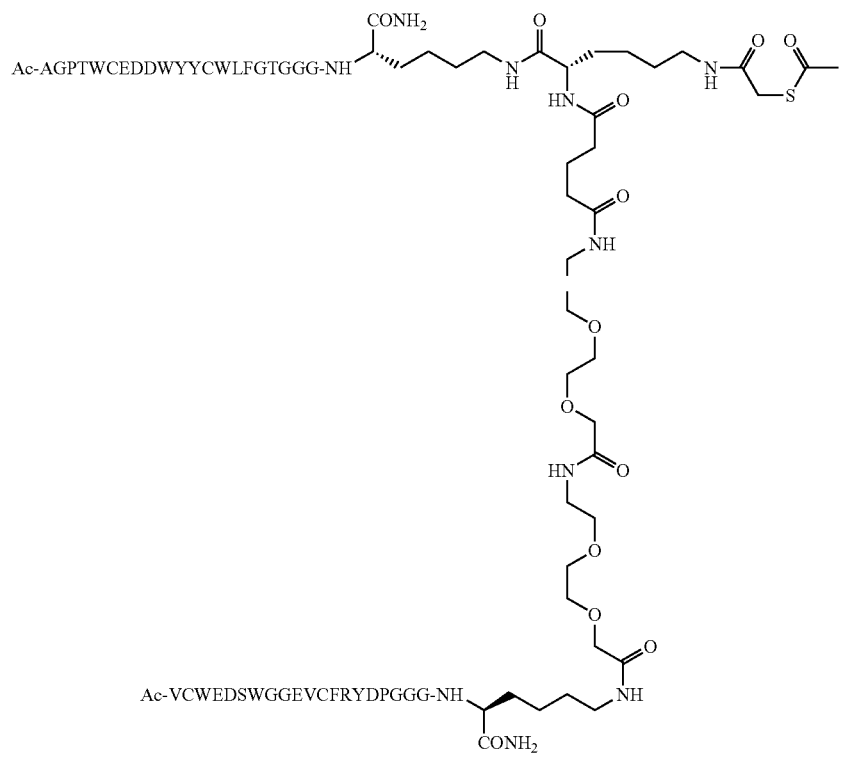
Ac-AGPTWCEDDWYYCWLFGTGGGK{Ac-VCWEDSWGGEVCFRYDPGGGK[JJ-Glut-K(SATA)]-NH$_2$}-NH$_2$:D23 (D5 functionalized with the SATA(S-Acetylthioacetyl) group)

-continued
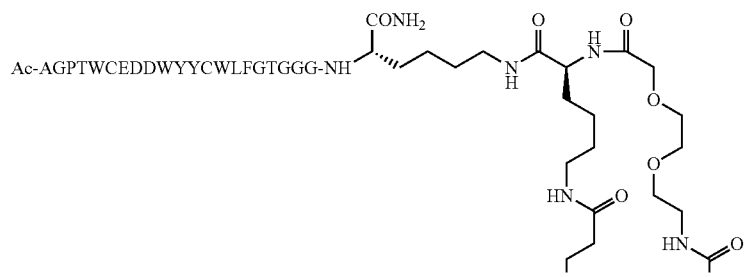
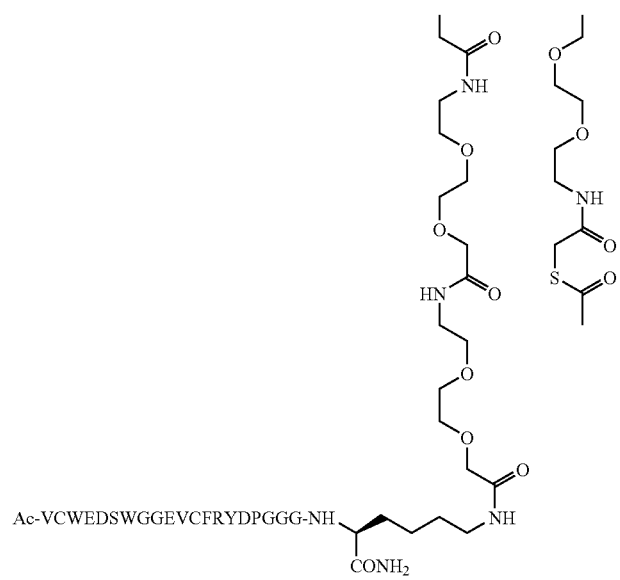
Ac-AGPTWCEDDWYYCWLFGTGGGK{SATA-JJK
[Ac-VCWEDSWGGEVCFRYDPGGGGK(JJ-Glut)-Nh2]}-NH2 : D24
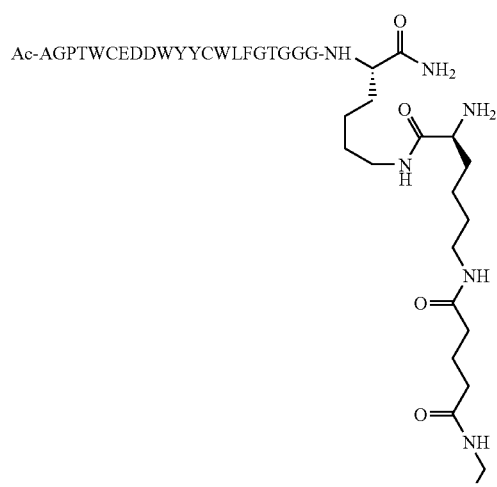

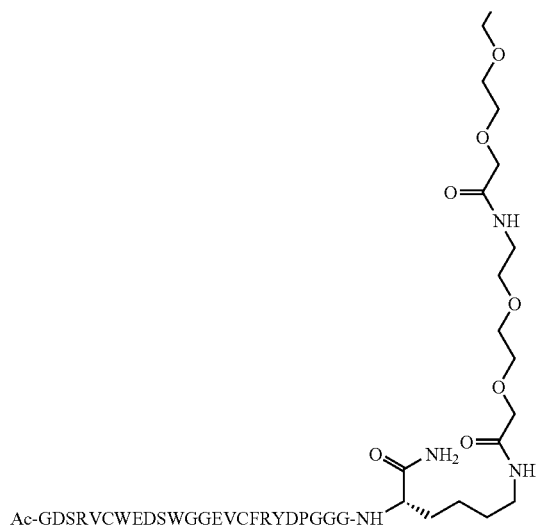
Ac-AGPTWCEDDWYYCWLFGTGGGK{Ac-GDSRVCWEDSWGGEVCFRYDPGGGK[JJ-Glut-NH(CH₂)4-(S)-CH(NH₂)C(=O)-]-NH₂}-NH₂:D25
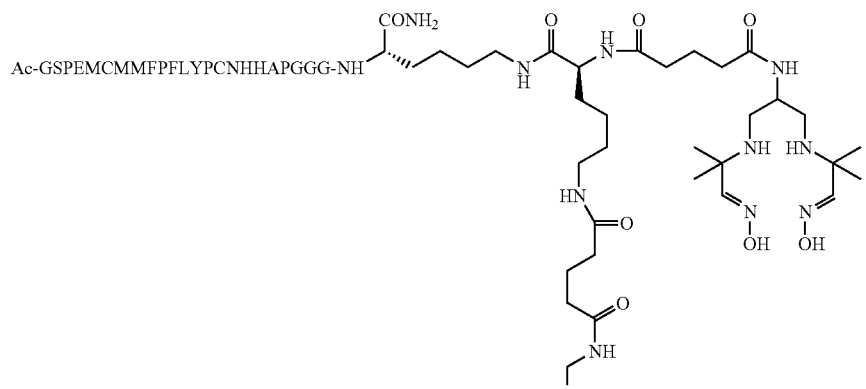
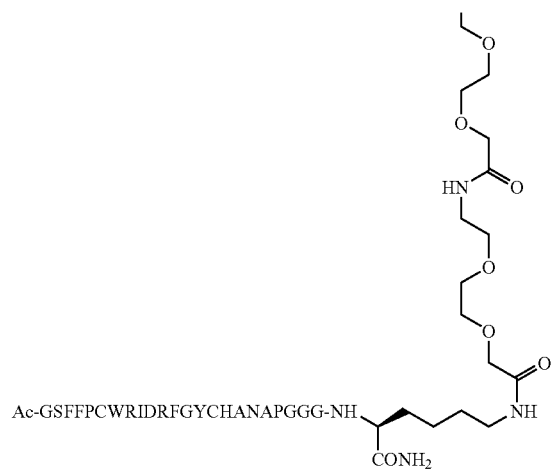
Ac-GSPEMCMMFPFLYPCNHHAPGGG{PnAO₆-Glut-K[Ac-GSFFPCWRIDRFGYCHANAPGGGKJJ-Glut]-NH₂}-NH₂:D28 (A heterodimeric c-Met binder)

-continued
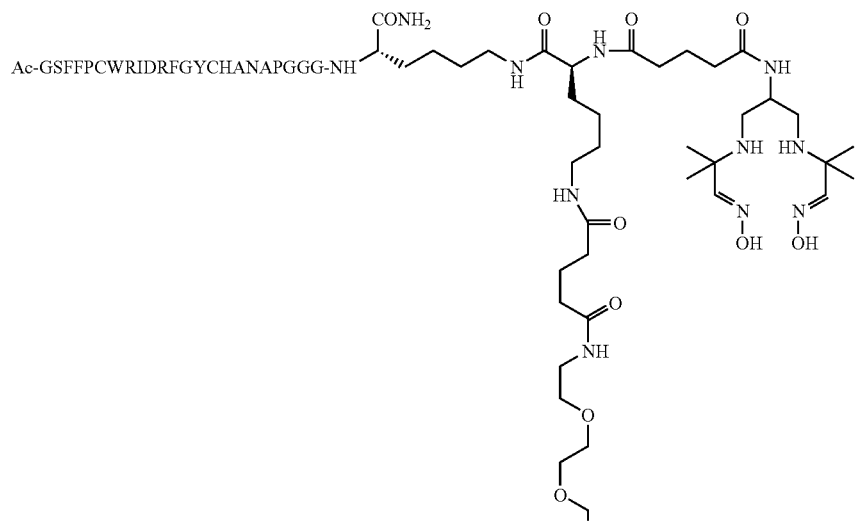
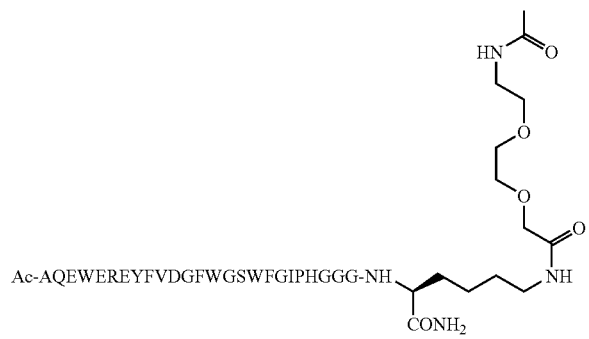
Ac-GSFFPCWRIDRFGYCHANAPGGGK{PnAO6-Glut-K[Ac-
AQEWEREYFVDGFWGSWFGIPHGGGK(JJ-Glut]-NH₂]}-NH₂:D29 (A heterodimeric c-Met binder)
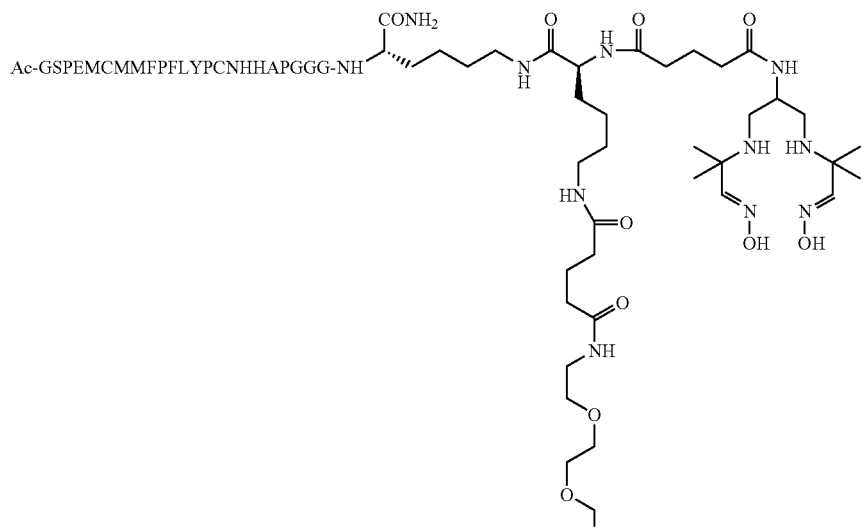

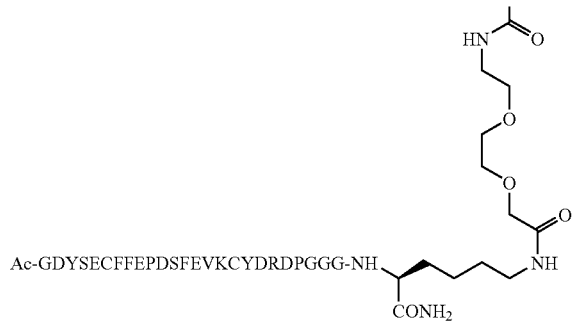
Ac-GSPEMCMMFPFLYPCNHHAPGGG{PnAO6-Glut-K[Ac-GDYSECFFEPDSFEVKCYDRDPGGG-JJ-Glut]-NH$_2$}-NH$_2$:D30 (A heterodimeric c-Met binder)
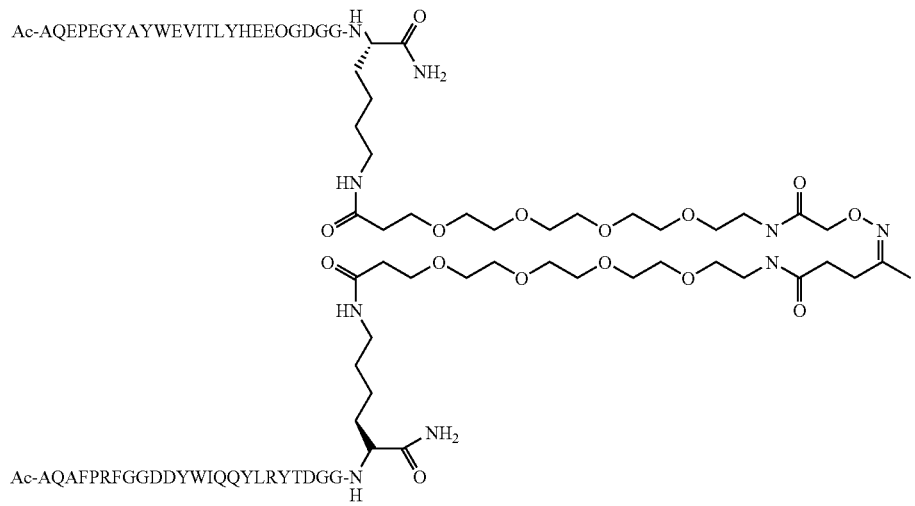
D31:Ac-AQEPEGYAYWEVITLYHEEDGDGGK9Ac-AQAFPRFGGDDYWIQQYLRYTDGGK(-(O=)C(CH$_2$CH$_2$O)$_4$CH$_2$CH$_2$NHC(=O)CH$_2$CH$_2$C(CH$_3$)=NOCH$_2$C(=)NH(CH$_2$CH$_2$O)$_4$CH$_2$CH$_2$C(=O)-)NH$_2$)NH$_2$
D32
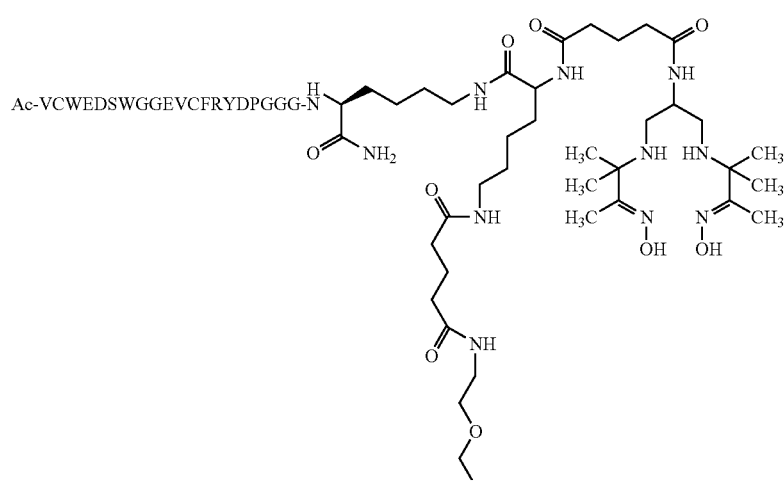

-continued

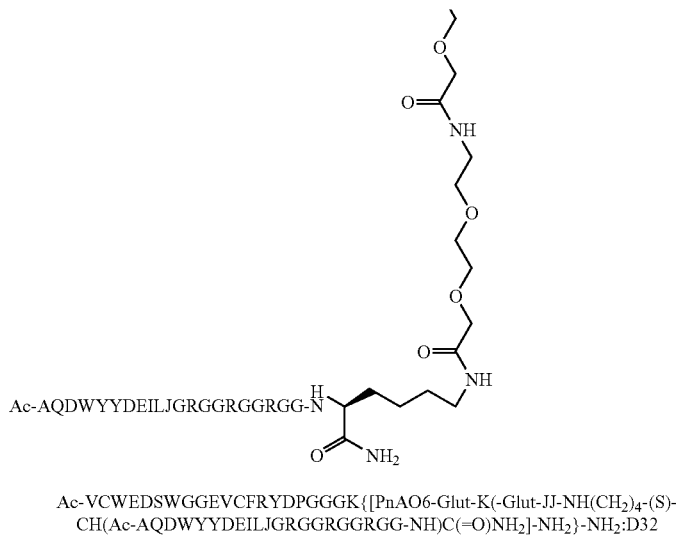

Ac-VCWEDSWGGEVCFRYDPGGGK{[PnAO6-Glut-K(-Glut-JJ-NH(CH$_2$)$_4$-(S)-CH(Ac-AQDWYYDEILJGRGGRGGRGG-NH)C(=O)NH$_2$]-NH$_2$}-NH$_2$:D32

For the preparation of the dimer D5, after the coupling reaction of the individual peptides, 50 μl of hydrazine was added to the reaction mixture (to expose the lysine N$^\epsilon$-amino group) and the solution was stirred for 2 min. The reaction mixture was diluted with water (1.0 mL) and the pH was adjusted to 2 with TFA. This was then purified by the method described above.

Synthesis of D27

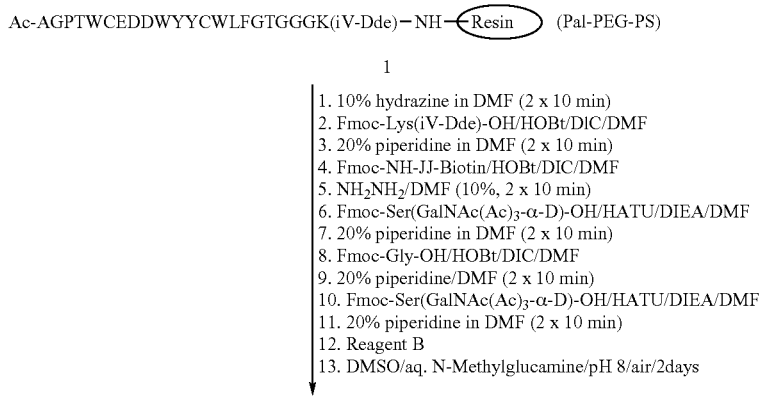

Scheme 1
Synthesis of Compound 2 (P12-Q)

Ac-AGPTWCEDDWYYCWLFGTGGGK(iV-Dde)—NH—Resin (Pal-PEG-PS)

1

1. 10% hydrazine in DMF (2 x 10 min)
2. Fmoc-Lys(iV-Dde)-OH/HOBt/DIC/DMF
3. 20% piperidine in DMF (2 x 10 min)
4. Fmoc-NH-JJ-Biotin/HOBt/DIC/DMF
5. NH$_2$NH$_2$/DMF (10%, 2 x 10 min)
6. Fmoc-Ser(GalNAc(Ac)$_3$-α-D)-OH/HATU/DIEA/DMF
7. 20% piperidine in DMF (2 x 10 min)
8. Fmoc-Gly-OH/HOBt/DIC/DMF
9. 20% piperidine/DMF (2 x 10 min)
10. Fmoc-Ser(GalNAc(Ac)$_3$-α-D)-OH/HATU/DIEA/DMF
11. 20% piperidine in DMF (2 x 10 min)
12. Reagent B
13. DMSO/aq. N-Methylglucamine/pH 8/air/2days -continued
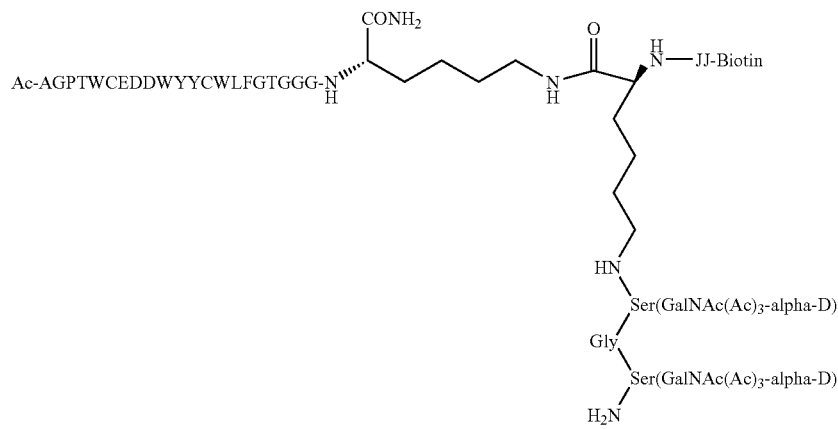
2
Scheme 2
Synthesis of Compound 4 (P6-F-Q)
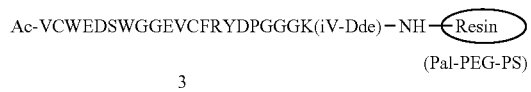
(Pal-PEG-PS)
3
1. 10% hydrazine in DMF (2 x 10 min)
2. Fmoc-Ser(GalNAc(Ac)$_3$-α-D)-OH/HATU/DIEA/DMF
3. 20% piperidine in DMF (2 x 10 min)
4. Fmoc-Gly-OH/HOBt/DIC/DMF
5. 20% piperidine in DMF (2 x 10 min)
6. Fmoc-Ser(GalNAc(Ac)$_3$-α-D)-OH/HATU/DIEA/DMF
7. 20% piperidine in DMF (2 x 10min)
8. reagent B
9. DMSO/N-Methylglucamine/pH 8/air/2days
Ac-VCWEDSWGGEVCFRYDPGGG-N
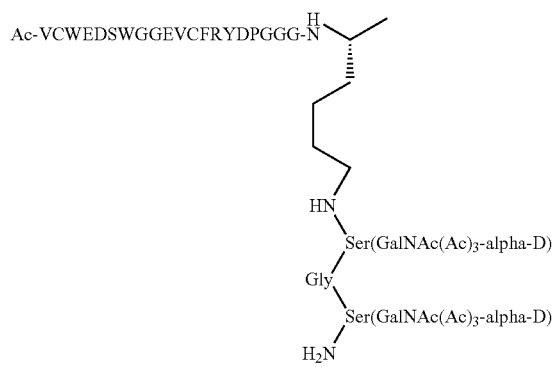
4

Synthesis of 1 and 3

Synthesis of the monomers were carried out as described in Method 5 on a 0.25 mmol scale employing as the starting resin Fmoc-GGGK(iV-Dde)NH-PAL-PEG-PS resin. The peptide resin was washed and dried before cleavage or further derivatization by automated or manual methods.

Procedure for Synthesis of 2 and 4

Appendage of Biotin-JJ, Lysyl, Glycyl and Serinyl(GalNAc(Ac)$_3$-α-D) moieties onto 1 and 3 was done by manual SPPS such as described in Method 6 and Method 8. The coupling of amino acids was carried out in DMF using HOBt/DIC activation (except for Ser(GalNAc(Ac)$_3$-α-D). Fmoc removal was carried out with 20% piperidine in DMF. All couplings were 5–16 hours duration. After each coupling, the completion was confirmed by the Kaiser test. In the case of Ser(GalNAc(Ac)$_3$-α-D), the coupling was performed in DMF employing HATU/DIEA as the coupling agent. In cases where the Kaiser test indicated unreacted amino groups the coupling was repeated. Removal of the N-terminal Fmoc group and cleavage from resin was performed. The crude peptide was precipitated in ether and washed twice by ether and dried under vacuum. The linear crude peptide was directly cyclized by dissolving the peptide in DMSO (40 mg/mL). The pH of the solution was adjusted to 8 by addition of aqueous N-methylglucamine and the solution was was stirred in air for 48 h at room temperature. The peptides were then purified employing gradient HPLC as described in Method 1 employing a Waters-YMC C-18 ODS preparative column (250 mm×4.6 mm i.d.). The pure product-containing fractions were combined and lyophilized to provide the needed peptides.

Scheme 3
Synthesis of D27(6)

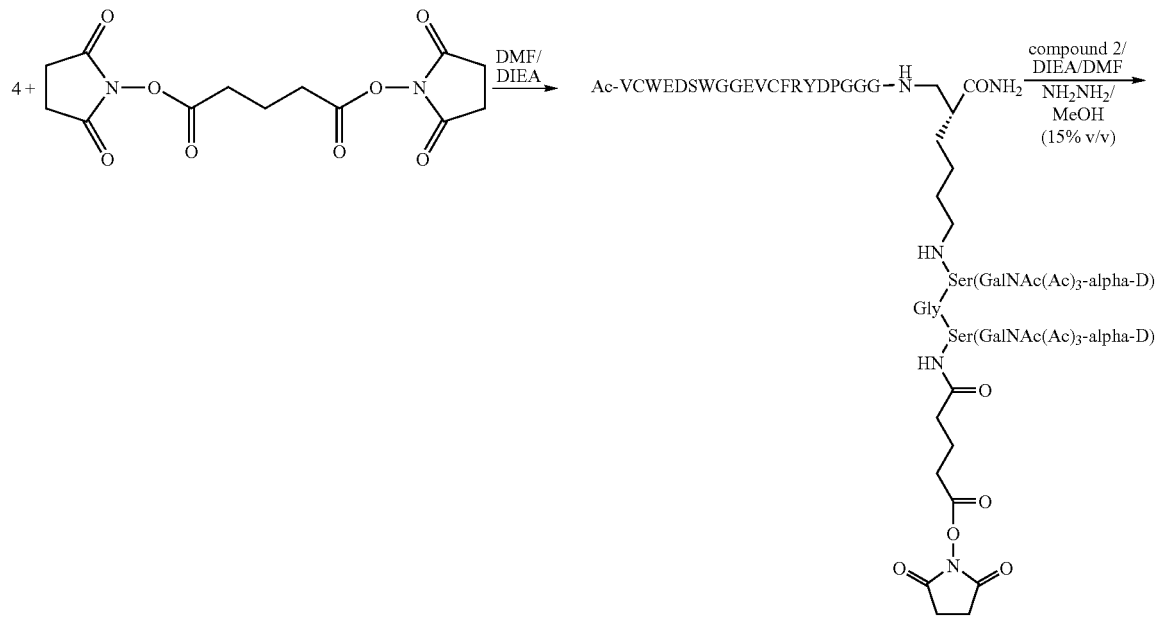

5

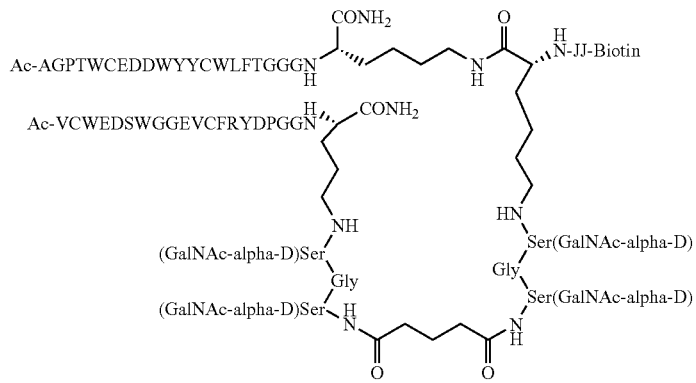

6

Procedure: Synthesis of D27—Compound 6

To a solution of glutaric acid bis-NHS ester (0.122 mmol, Pierce Scientific Co.) in anhydrous DMF was added dropwise a solution of 4 in DMF (40 mg, 0.0122 mmol). DIEA was added to neutralize the trifluoroacetic acid bound to the peptide and N-hydroxysuccinimide formed during the reaction. This 0.7 mL solution was stirred for 4 h. The reaction was monitored by HPLC and mass spectroscopy. DMF was removed under vacuum. The excess diester was removed by addition of ethyl acetate which precipitated the peptide-monoester 5 while dissolving glutaric acid bis-NHS ester. The mixture was centrifuged and the liquid portion decanted. This was repeated twice. The residue was kept under vacuum for 10 min. The residue was dissolved in DMF and mixed with a solution of 2 (37 mg, 0.009 mmol) in DMF (pH 7). It was stirred at ambient temperature for 16 h. The volatiles were removed under high vacuum and the acetate functions were removed by treatment of the residue with 1 mL of hydrazine/MeOH (15/85, v/v) solution with stirring for 2.5 h at ambient temperature. Acetone was added to quench the excess of hydrazine and the volatiles were removed under vacuum. The resulting residue was dissolved in DMSO and purified by preparative HPLC as described above to provide 9 mg of the pure material.

Synthesis of D32

Preparation of Ac-VCWEDSWGGEVCFRYDPGGGK{[PnAO6-Glut-K(-Glut-JJ-NH(CH$_2$)$_4$—(S)—CH(Ac-AQD-WYYDEILJGRGGRGGRGG-NH)C(=O)NH$_2$]—NH$_2$}—NH$_2$: D32

Preparation of Ac-VCWEDSWGGEVCFRYDPGGGK[K(PnAO6)]-NH$_2$(3)

Ac-VCWEDSWGGEVCFRYDPGGGK[K(iV-Dde)]-NH$_2$ [(1), a new P6 sequence derivative, 48 mg) was prepared by the procedures of Method 5. The compound was dissolved in DMF (0.85 ml) and treated with compound B and DIEA (7 μL) was added to maintain the basicity of the reaction mixture. The progress of the reaction was monitored by HPLC and mass spectroscopy. At the completion of the reaction (20 h), the volatiles were removed in vacuo. The residue which consists of compound 2 was treated with 10% hydrazine in DMF (5 μL) for 10 min. HPLC analysis and mass spectroscopy indicated the completion of the reaction. The mixture then was applied directly to a Waters Associates XTerra MSC18 preparative HPLC column (50 mm×19 mm i.d.) and purified by elution with a linear gradient of acetonitrile into water (both containing 0.1% TFA) to provide 11 mg of pure compound 3.

Scheme 4:
Preparation of Monomer Compound 3

Preparation of the Dimer D32 from Compound 3 and Ac-AQDWYYDEIL-Adoa-GRGGRGGRGGGK(Adoa-Adoa)-NH$_2$ Compound 4 (New F3 Derivative)

Disuccinimidyl glutarate (12 mg) was dissolved in DMF (500 μL), and DIEA was added (1 μL). Compound 3 in DMF was added into the DMF solution of disuccinimidyl glutarate/DIEA. The mixture was stirred for 2.5 h. HPLC and mass spectroscopy indicated the completion of the reaction. The volatiles were removed in vacuo and the residue was washed with ether (3×) to remove the unreacted bis-NHS ester. The residue was dried, re-dissolved in anhydrous DMF and treated with the Compound 4, Ac-AQDWYYDEIL-Adoa-GRGGRGGRGGGK(Adoa-Adoa)-NH$_2$, which was prepared by Method 5 and Method 8, in the presence of 2 equiv. of DIEA. The reaction was allowed to proceed for 20 h. The mixture then was applied directly to a Waters Associates MSC18 reverse phase preparative (50 mm×19 mm i.d.) HPLC column and purified by elution with a linear gradient of acetonitrile into water (both containing 0.1% TFA) to provide 2 mg of D32.

Scheme 5:
Preparation of Ac-VCWEDSWGGEVCFRYDPGGGK{[PnAO6-Glut-K(-Glut-JJ-NH(CH$_2$)$_4$-(S)-CH(Ac-AQDWYYDEILJGRGGRGGRGG-NH)C(=O)NH$_2$]-NH$_2$}-NH$_2$:D32 from Compound 3 and Compound 4

Disuccinimidyl Glutarate/DIEA/DMF

1) Ac-VCWEDSWGGEVCFRYDPGGGK[PnAO6-Glut-K]-NH$_2$(Compound 3) in DMF
2) Remove DMF, wash with ether 3X
3) Dry and re-dissolve
4) Ac-AQDWYYDEILJGRGGRGGRGGGK(JJ)-NH$_2$
5) HPLC Purification

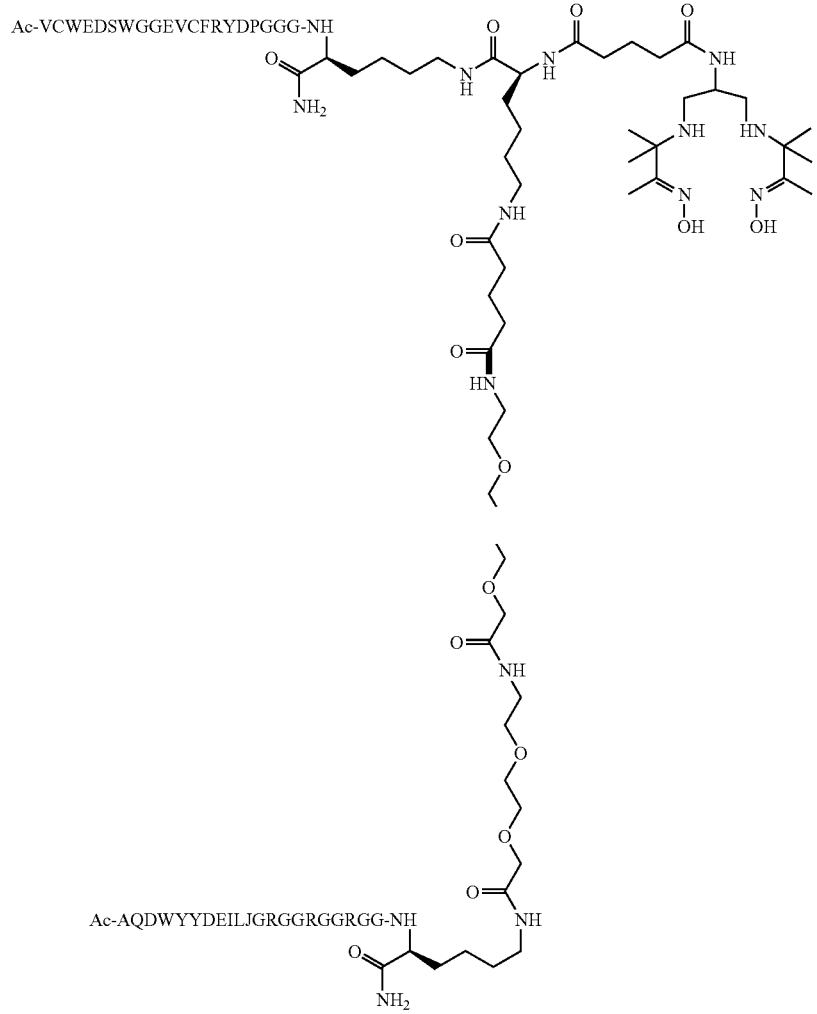

Synthesis of D33

Synthesis of Ac-AGPTWCEDDWYYCWLFGTGGGK[Ac-VCWEDSWGGEVCFRYDPGGGK[SGS-Glut-SGS-(S)—NH(CH$_2$)$_4$—CH(Biotin-JJ-NH)—C(=O)]—NH$_2$]—NH$_2$: D33

Preparation of Monomer Compound 2 and Monomer Compound 4

Scheme 7:
Prepapration of Monomer Compound 4

1. 10% hydrazine in DMF (2 x 10 min)
2. Fmoc-Ser(tBu)-OH/HOBt/DIC/DMF
3. 20% piperidine in DMF (2 x 10 min)
4. Fmoc-Gly-OH/HOBt/DIC/DMF
5. 20% piperidine in DMF (2 x 10 min)
6. repeat step 2.
7. 20% piperidine in DMF (2 x 10 min)
8. Reagent B-(Cleavage)
9. DMSO/aq. N-methylglucamine/pH 8/air/48 h -continued

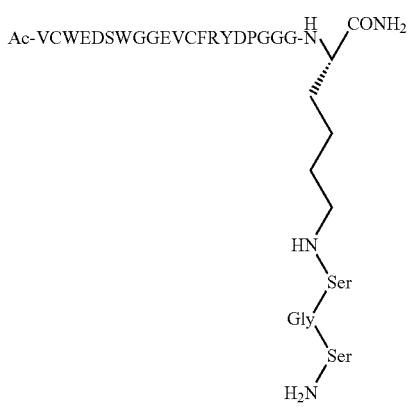

4

Synthesis of Monomer Peptide 1 and Monomer Peptide 3

Synthesis of the monomers 1 and 3 were carried out using the procedures of Method 5 for the ABI 433A synthesizer.

Synthesis of Monomer Peptide 2 and Monomer Peptide 4

Appendage of Biotin-JJ, Lys, Gly and Ser onto 1 and 3 was done by SPPS manually using the appropriate Fmoc amino acids, Biotin-JJ and Fmoc-J (J=8-amino-3,6-dioxaoctanoic acid) according to the procedures of Methods 6, 7 and 8. Cleavage of the peptides from the resin, processing of the crude peptides was carried out as described in Method 1 for the synthesis of peptides. Cyclization of the cysteine moieties to form the cyclic disulfide peptides was performed by the procedures of Method 9.

Purification of the peptides was carried out using a Shimadzu LC-10A HPLC system and a YMC C-18 ODS preparative HPLC column employing a linear gradient elution of acetonitrile (0.1% TFA) into 0.1% aqueous TFA. Pure fractions were combined and lyophilized.

Scheme 8:
Preparation of Ac-AGPTWCEDDWYYCWLFGTGGGK[Ac-VCWEDSWGGEVCFRYDPGGGK[SGS-Glut-SGS-(S)-NH(CH$_2$)$_4$-CH(Biotin-JJ-NH)C(=O)]-NH$_2$]-NH$_2$:D33

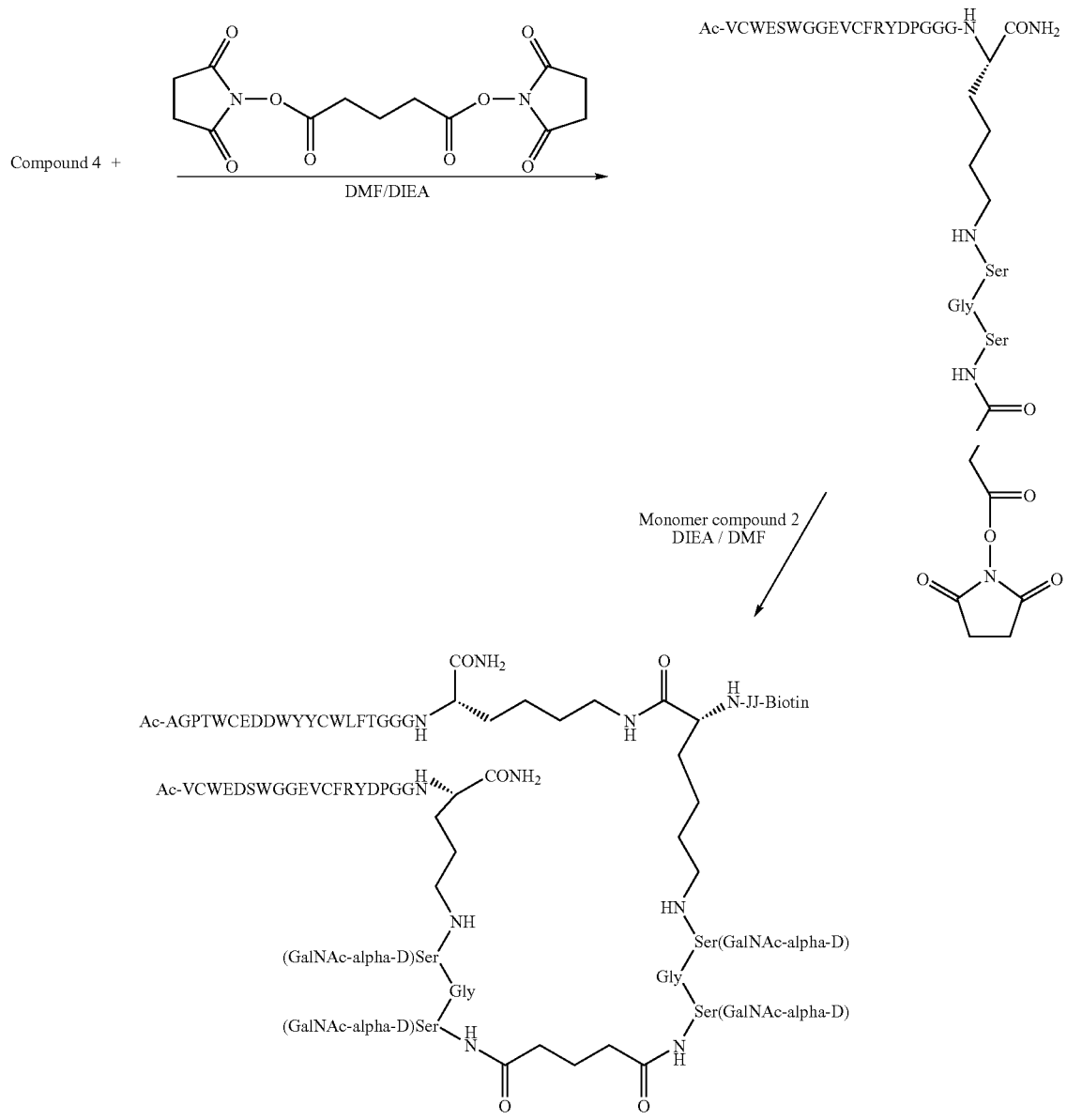

The dimer D33 was prepared using monomer compound 4 to generate in situ the activated monomer compound 5 which was then reacted with monomer compound 2 using the procedures described in Method 13 and Example 9, entitled: 'Preparation of Heterodimer Containing Constructs'. Compound D33 was purified by preparative reverse phase HPLC using a Waters-YMC C-18 ODS column to provide 10 mg of the dimer D33.

Analytical Data

The HPLC analysis data and mass spectral data for the dimeric peptides D1–5 and D8–30 and 32–33 identified above, as well as that for peptide components of dimer D27, are given in Table 6 below.

TABLE 6

Analytical Data for Homodimeric and Heterodimeric Peptide Constructs

| | 1. Retention Time (System) | Mass Spectral data (API-ES, - ion) |
|---|---|---|
| D1 | 8.98 min. (A) | 1987.7 [M − 3H]/3, 1490.6 [M − 4H]/4, 1192.3 [M − 5H]/5 |
| D2 | 16.17 min (B) | 2035.3 [M − 3H]/3, 1526.1 [M − 4H]/4, 1220.7 [M − 5H]/5 |
| D3 | 8.74 min (C) | 1933.6 [M − 3H]/3, 1449.9 [M − 4H]/4, 1159.4 [M − 5H]/5 |
| D4 | 10.96 min (D) | 2032.8 [M − 3H]/3 |
| D5 | 6.57 min (E) | 1816.2 [M − 3H]/3, 1361.8 [M − 4H]/4, 1089.4 [M − 5H]/5, 907.7 [M − 6H]/6 |
| D8 | 4.96 min; (F) | 2379.3 [M − 3H]/3 |
| D9 | 5.49 min; (G) | 2146.4 [M − 3H]/3 |
| D10 | 5.44 min; (H) | 2082.7 [M − 3H]/3, 1561.7 [M − 4H]/4, 1249.1 [M − 5H]/5, 1040.7 [M − 6H]/6 |
| D11 | 7.23 min; (E) | 2041.8 [M − 3H]/3, 1531.1 [M − 4H]/4, 1224.6 [M − 5H]/5 |
| D12 | 5.84 min; (H) | 1877.1 [M − 3H]/3, 1407.6 [M − 4H]/4, 1125.9 [M − 5H]/5, 938.1 [M − 6H]/6. |
| D13 | 5.367 min; (E) | 1965.3 [M − 3H]/3, 1473.8 [M − 4H]/4, 1178.8 [M − 5H]/5, 982.2 [M − 6H]/6 |
| D14 | 4.78 min; (I) | 2275.0 [M − 3H]/3, 1362.8 [M − 5H]/5 |
| D15 | 5.41 min; (H) | 1561.3 [M − 4H]/4, 1249.1 [M − 5H]/5, 1040.8 [M − 6H]/6, 891.8 [M − 7H]/7. |
| D16 | 5.44 min; (J) | 2150.8 [M − 3H]/3, 1613.1 [M − 4H]/4, 1289.9 [M − 5H]/5, 1074.8 [M − 6H]/6, 920.9 [M − 7H]/7. |
| D17 | 4.78 min; (K) | 1789.4 [M − 3H]/3, 1347.7 [M − 4H]/4. |
| D18 | 4.74 min; (L) | 2083.1 [M − 3H]/3, 1562.7 [M − 4H]/4, 1249.5 [M − 5H]/5. |
| D19 | 7.13 min; (O) | 1891.9 [M − 3H]/3, 1418.4 [M − 4H]/4, 1134.8 [M − 5H]/5, 945.5 [M − 6H]/6. |
| D20 | 9.7 min; (P) | 2700.4 [M − 2H]/2, 1799.3 [M − 3H]/3 |
| D21 | 6.1 min; (P) | 2891.3 [M − 2H]/2, 1927.2 [M − 3H]/3, 1445.1 [M − 4H]/4, 1155.8 [M − 5H]/5. |
| D22 | 6.23 min; (Q) | 1994.4 [M − 3H]/3, 1495.7 [M − 4H]/4, 1196.3 [M − 5H]/5 |
| D23 | 7.58 min; (J) | 1854.4 [M − 3H]/3, 1390.8 [M − 4H]/4, 1112.7 [M − 5H]/5, 927 [M − 6H]/6 |
| D24 | 8.913 min; (R) | 1952.1 [M − 3H]/3, 1463.4 [M − 4H]/4, 1171.1 [M − 5H]/5, 975.3 [M − 6H]/6 |
| D25 | 5.95 min; (E) | 1954.9 [M − 3H]/3, 1466.1 [M − 4H]/4, 1172.4 [M − 5H]/5, 976.8 [M − 6H]/6. |
| D26 | 6.957 min; (S) | 1759.1 [M − 3H]/3, 1319.6 [M − 4H]/4, 1055.1 [M − 5H]/5 |
| D27 | 5.50 min; (M) | 2317.6 [M − 3H]/3, 1737.2 [M − 4H]/4, 1389.3 [M − 5H]/5, 1157.7 [M − 6H]/6. |
| D28 | 4.89 min; (N) | 6229 [M + H] |
| D29 | 5.01 min; (N) | 2258.1 [M − 3H + TFA]/3 |
| D30 | 4.35 min; (N) | 2176.0 [M − 3H]/3, 1631.5 [M − 4H]/4, 1302.6 [M − 5H]/5, 1087.7 [M − 6H]/6, 932.1 [M − 7H]/7 |

TABLE 6-continued

Analytical Data for Homodimeric and Heterodimeric Peptide Constructs

| | 1. Retention Time (System) | Mass Spectral data (API-ES, - ion) |
|---|---|---|
| P12-Q | 7.4 min (T) | 2041.3 [M − 2H]/2 |
| P6-F-Q | 8.0 min (T) | 1636.3 [M − 2H]/2 |
| D32 | 4.29 min (L) | 5782.3 [M + H], 1146.6 [M + 4H]/4, 1157.4 [M + 5H]/5, 964.7 [M + 6H]/6 |
| D33 | 6.6 min (T) | 2045.3 [M − 3H]/3 |

HPLC Analysis Systems

System A: Column: YMC C-4 (4.6×250 mm); Eluents: A: Water (0.1% TFA), B: Acetonitrile (0.1% TFA); Elution: Initial condition, 25% B, Linear Gradient 25–60% B in 10 min; Flow rate: 2.0 ml/min; Detection: UV @ 220 nm.

System B: Column: YMC C-4 (4.6×250 mm); Eluents: A: Water (0.1% TFA), B: Acetonitrile (0.1% TFA); Elution: Initial condition, 25% B, Linear Gradient 25–60% B in 20 min; Flow rate: 2.0 mL/min; Detection: UV @ 220 nm.

System C: Column: YMC C-4 (4.6×250 mm); Eluents: A: Water (0.1% TFA), B: Acetonitrile (0.1% TFA); Elution: Initial condition, 30% B, Linear Gradient 30–60% B in 10 min; Flow rate: 2.0 mL/min; Detection: UV @ 220 nm.

System D: Column: YMC C-4 (4.6×250 mm); Eluents: A: Water (0.1% TFA), B: Acetonitrile (0.1% TFA); Elution: Initial condition, 20% B, Linear Gradient 20–60% B in 10 min; Flow rate: 2.0 mL/min; Detection: UV @ 220 nm.

System E: Column: Waters XTerra, 4.6×50 mm; Eluents: A: Water (0.1% TFA), B: Acetonitrile (0.1% TFA): Elution: Initial condition, 10% B, Linear Gradient 10–60% B in 10 min; Flow rate: 3.0 mL/min; Detection: UV @ 220 nm.

System F: Column: Waters XTerra, 4.6×50 mm; Eluents: A: Water (0.1% TFA), B: Acetonitrile (0.1% TFA): Elution: Initial condition, 30% B, Linear Gradient 30–70% B in 10 min; Flow rate: 3.0 mL/min; Detection: UV @ 220 nm.

System G: Column: Waters XTerra, 4.6×50 mm; Eluents: A: Water (0.1% TFA), B: Acetonitrile (0.1% TFA): Elution: Initial condition, 30% B, Linear Gradient 30–75% B in 10 min; Flow rate: 3.0 mL/min; Detection: UV @ 220 nm.

System H: Column: Waters XTerra, 4.6×50 mm; Eluents: A: Water (0.1% TFA), B: Acetonitrile (0.1% TFA): Elution: Initial condition, 20% B, Linear Gradient 20–52% B in 10 min; Flow rate: 3.0 mL/min; Detection: UV @ 220 nm.

System I: Column: Waters XTerra, 4.6×50 mm; Eluents: A: Water (0.1% TFA), B: Acetonitrile (0.1% TFA): Elution: Initial condition, 10% B, Linear Gradient 10–65% B in 10 min; Flow rate: 3.0 mL/min; Detection: UV @ 220 nm.

System J: Column: Waters XTerra, 4.6×50 mm; Eluents: A: Water (0.1% TFA), B: Acetonitrile (0.1% TFA): Elution: Initial condition, 20% B, Linear Gradient 20–60% B in 10 min; Flow rate: 3.0 mL/min; Detection: UV @ 220 nm.

System K: Column: Waters XTerra, 4.6×50 mm; Eluents: A: Water (0.1% TFA), B: Acetonitrile (0.1% TFA): Elution: Initial condition, 5% B, Linear Gradient 5–60% B in 10 min; Flow rate: 3.0 mL/min; Detection: UV @ 220 nm.

System L: Column: Waters XTerra, 4.6×50 mm; Eluents: A: Water (0.1% TFA), B: Acetonitrile (0.1% TFA): Elution:

Initial condition, 5% B, Linear Gradient 5–65% B in 10 min; Flow rate: 3.0 mL/min; Detection: UV @ 220 nm.

System M: Column: Waters XTerra, 4.6×50 mm; Eluents: A: Water (0.1% TFA), B: Acetonitrile (0.1% TFA): Elution: Initial condition, 15% B, Linear Gradient 15–50% B in 10 min; Flow rate: 3.0 mL/min; Detection: UV @ 220 nm.

System N: Column: Waters XTerra, 4.6×50 mm; Eluents: A: Water (0.1% TFA), B: Acetonitrile (0.1% TFA): Elution: Initial condition, 10% B, Linear Gradient 20–80% B in 10 min; Flow rate: 3.0 mL/min; Detection: UV @ 220 nm.

System O: Column: YMC-C18, 4.6×250 mm; Eluents: A: Water (0.1% TFA), B: Acetonitrile (0.1% TFA): Elution: Initial condition, 30% B, Linear Gradient 30–60% B in 10 min; Flow rate: 2.0 mL/min; Detection: UV @ 220 nm.

System P: Column: YMC-C18, 4.6×250 mm; Eluents: A: Water (0.1% TFA), B: Acetonitrile (0.1% TFA): Elution: Initial condition, 20% B, Linear Gradient 20–80% B in 20 min; Flow rate: 2.0 mL/min; Detection: UV @ 220 nm.

System Q: Column: YMC-C18, 4.6×250 mm; Eluents: A: Water (0.1% TFA), B: Acetonitrile (0.1% TFA): Elution: Initial condition, 20% B, Linear Gradient 20–60% B in 6 min; Flow rate: 2.0 mL/min; Detection: UV @ 220 nm.

System R: Column: YMC-C18, 4.6×250 mm; Eluents: A: Water (0.1% TFA), B: Acetonitrile (0.1% TFA): Elution: Initial condition, 25% B, Linear Gradient 25–60% B in 10 min; Flow rate: 2.0 mL/min; Detection: UV @ 220 nm.

System S: Column: YMC-C18, 4.6×100 mm;; Eluents: A: Water (0.1% TFA), B: Acetonitrile (0.1% TFA): Elution: Initial condition, 10% B, Linear Gradient 10–60% B in 10 min; Flow rate: 3.0 mL/min; Detection: UV @ 220 nm.

System T: Column: Waters XTerra, 4.6×50 mm; Eluents: A: Water (0.1% TFA), B: Acetonitrile (0.1% TFA): Elution: Initial condition, 15% B, Linear Gradient 15–50% B in 8 min; Flow rate: 3.0 mL/min; Detection: UV @ 220 nm.

EXAMPLE 10

Competition with $^{125}$I-VEGF for Binding to KDR on HUVECs and KDR-Transfected Cells The following experiment assessed the ability of KDR-binding polypeptides, homodimers and heterodimers of the invention to compete with $^{125}$I-labeled VEGF for binding to KDR expressed by transfected 293H cells.

Protocol:

293H cells were transfected with the KDR cDNA or mock-transfected by standard techniques described herein. The cells were incubated with $^{125}$I-VEGF in the presence or absence of competing compounds (at 10 µM, 0.3 µM, and 0.03 µM). After washing the cells, the bound radioactivity was quantitated on a gamma counter. The percentage inhibition of VEGF binding was calculated using the formula [(Y1−Y2)×100/Y1], where Y1 is specific binding to KDR-transfected 293H cells in the absence peptides, and Y2 is specific binding to KDR-transfected 293H cells in the presence of peptide competitors. Specific binding to KDR-transfected 293H cells was calculated by subtracting the binding to mock-transfected 293H cells from the binding to KDR-transfected 293H cells.

Figure 14:
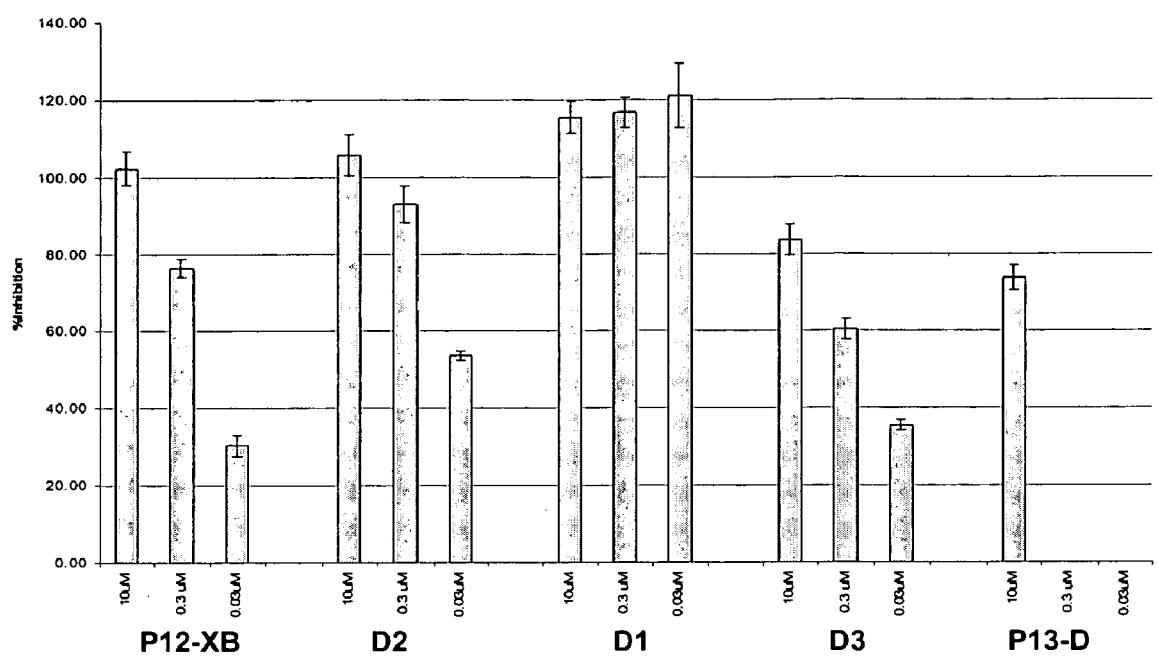
FIG. 14 is a graph showing the percentage inhibition of $^{125}$I-labeled VEGF binding by peptides (P12-XB, D2, D1, D3, and P13-D) at three different concentrations (10 μM, 0.3 μM, and 0.03 μM) to KDR-transfected 293H cells. The results are from one experiment carried out in triplicate +/–S.D.

Results:

As shown in FIG. 14, all of the KDR-binding compounds assayed were able to compete with $^{125}$I-VEGF for binding to KDR-transfected cells. The heterodimer (D1) was clearly the most effective at competing with $^{125}$I-VEGF, even over the two homodimers (D2 and D3), confirming the superior binding of D1.

EXAMPLE 11

Receptor Activation Assay

The ability of KDR-binding multimeric constructs, including heteromultimers of the invention, to inhibit VEGF induced activation (phosphorylation) of KDR was assessed using the following assay (see also Example 4 above).

Protocol:

Dishes of nearly confluent HUVECs were placed in basal medium lacking serum or growth factors overnight. The next day, the dishes in group (c) below were pretreated for 15 min in basal medium with a KDR-binding peptide, then the cells in the dishes in groups (a), (b), and (c) were placed in fresh basal medium containing:

(a) no additives (negative control), (b) 5 ng/mL VEGF (positive control), or (c) 5 ng/mL VEGF plus the putative competing/inhibiting peptide.

After 5 min of treatment, lysates were prepared from the dishes. Immunoprecipitated KDR from the lysates was analyzed sequentially by immunoblotting for phosphorylation with an anti-phosphotyrosine antibody, and for total KDR with an anti-KDR antibody (to control for sample loading).

Figure 15:
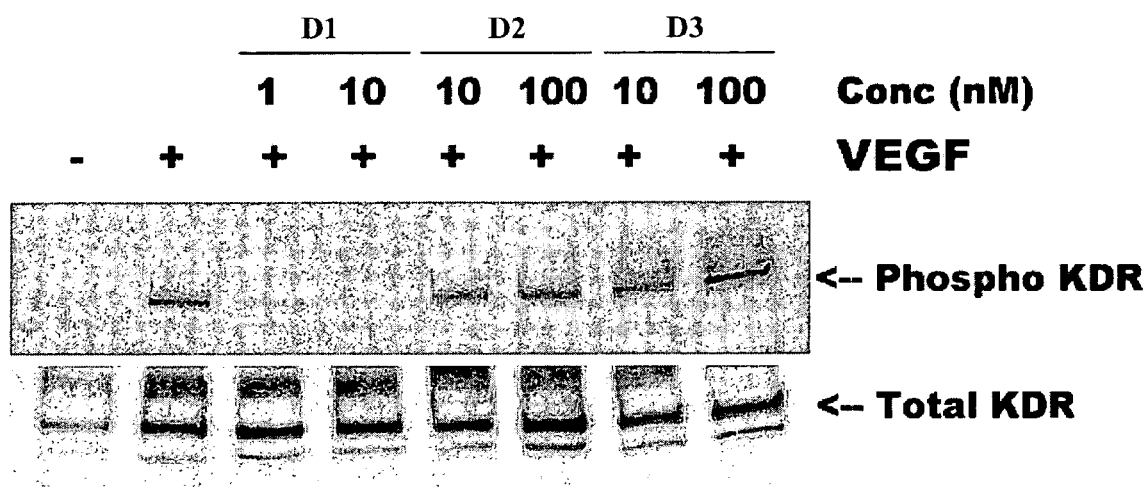
FIG. 15 is a photograph showing the ability of D1 to completely block the VEGF-induced phosphorylation of KDR in HUVECs at 10 nM and the majority of phosphorylation at 1 nM. Reprobing the blot for total KDR (lower panel) demonstrated that the effects of the tested compounds was not due to reduced sample loading. Homodimers composed of the two binding sequences contained in D1 did not interfere with the phosphorylation at up to 100 nM.

Results:

As shown in FIG. 15, D1 was able to completely block the VEGF-induced phosphorylation of KDR in HUVECs at 10 nM. More than half of the phosphorylation was inhibited by the compound at 1 nM. Homodimers D2 and D3, made up of the two individual binding moieties that are contained in D1, had no effect on phosphorylation at up to 100 nM, demonstrating the benefit achievable by using an appropriate heterodimer to block a receptor-ligand interaction. In multiple experiments, the IC$_{50}$ for D1 in this assay varied between 0.5 and 1 nM. A different heterodimer containing unrelated binding sequences, D31 (structure shown below), had no effect on phosphorylation at 100 nM in spite of it's high binding affinity (11 nM for KDR by Biacore), suggesting that the choice of KDR-binding moieties is important when constructing a multimer to compete with VEGF for binding to KDR. Even though the affinity of D1 for KDR is 10-fold higher than that of D2 (by SPR analysis), it's IC$_{50}$ in the activation assay is at least 100-fold lower, suggesting that targeting two distinct epitopes on KDR with a single binding molecule can generate greater steric hindrance than a molecule with similar affinity that only binds to a single epitope on KDR. Similarly, it should be pointed out that the two KDR-binding moieties within D1 when tested as monomeric free peptides (P12-XB and P6-D) in the receptor activation assay had IC$_{50}$S of 0.11 and 1 micromolar respectively, which is 100 to 1000-fold higher than the IC$_{50}$ for D1 in the assay and 14 to 30-fold higher than the K$_D$s for the fluoresceinated derivatives of the monomeric peptides. Thus, creating a dimer containing two peptides with weak VEGF-blocking activity has resulted in a molecule with very

153 potent VEGF-blocking activity that goes well beyond the increased binding affinity of D1.

EXAMPLE 12

Migration Assay

The following experiment assessed the ability of D1, a heteromultimer of the invention, to block the VEGF-induced migration of HUVECs in culture.

Protocol:

Serum-starved HUVECs were placed, 100,000 cells per well, into the upper chambers of BD Matrigel-coated FluoroBlok 24-well insert plates (#354141). Basal medium, containing either nothing or different attractants such as VEGF (10 ng/mL) or serum (5% FBS) in the presence or absence of potential VEGF-blocking/inhibiting compounds, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. The VEGF-induced migration was calculated by subtracting the migration that occurred when only basal medium was placed in the lower chamber of the wells.

Figure 16:
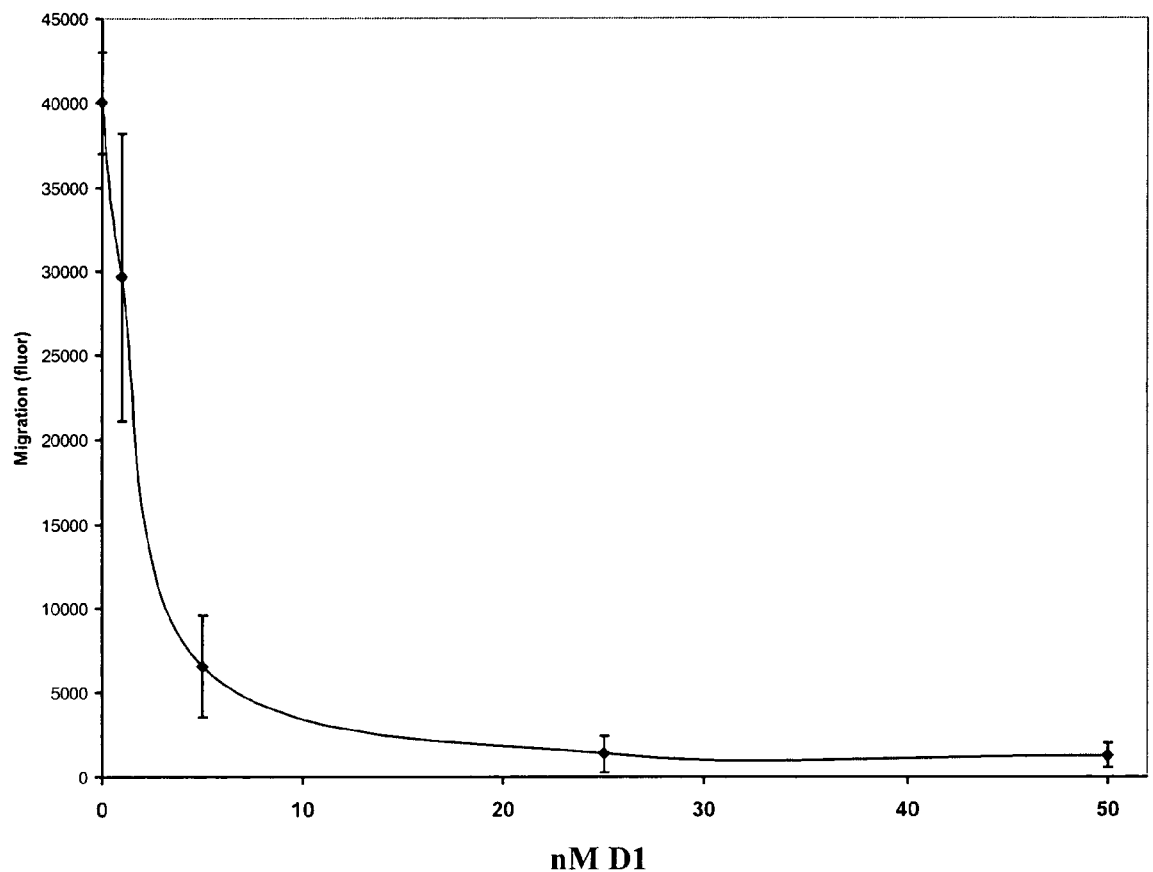
FIG. 16 shows that D1 potently blocks the migration/invasion of endothelial cells induced by VEGF. Migrating cells were quantitated by fluorescence measurement after staining the migrated cells with a fluorescent dye.

Results:

VEGF induced a large increase in endothelial cell migration in the assay, which was potently blocked by D1. At 5 nM D1, the VEGF-stimulated endothelial cell migration was 84% blocked (see FIG. 16). At 25 nM D1, this migration was almost completely blocked. In other experiments, a known KDR inhibitor, SU-1498 ((E)-3-(3,5-Diisopropyl-4-hydroxyphenyl)-2-[(3-phenyl-n-propyl)aminocarbonyl]acrylonitrile]was tested in the assay. SU1498 at 3 micromolar did not block the VEGF-induced migration as well as D1 (47% blocked at 3 micromolar). D7 at 50 nM, also produced essentially complete inhibition of the migration stimulated by VEGF. Serum was a very powerful attractant in the assay when used in place of VEGF, but its effect was not significantly diminished by D1, indicating that D1 specifically inhibits endothelial migration induced by VEGF.

EXAMPLE 13

The Following Experiments Describe Methods Used to Prepare Tc, In, Lu, and I-Labelled Compounds.

Preparation of $^{99m}$Tc-P12-P

SnCl$_2$.2H$_2$O (20 mg) was dissolved in 1 mL of 1 N HCl, and 10 µL of this solution was added to 1 mL of a DTPA solution that was prepared by dissolving 10 mg of Ca Na$_2$ DTPA.2.5 H$_2$O (Fluka) in 1 mL of water. The pH of the stannous DTPA solution was adjusted to pH 6–8 using 1N NaOH. 50 µg of P12-P (Ac-AGPTwC*EDDWYYC*wLFGTGGGK(PnAO6-NH—(O═)C(CH$_2$)$_3$C(═O)-JJ)-NH$_2$) in 50 µL of 10% DMF was mixed with 20 µL of $^{99m}$TcO$_4^-$ (2.4 to 4 mCi, Syncor), followed by 100 µL of the stannous Sn-DTPA solution. After 30 minutes at RT, the radiochemical purity (RCP) was 93%. The product was purified on a Supelco Discovery C16 amide column (4×250 mm, 5 um pore size) eluted at a flow rate of 0.5 mL/min using an aqueous/organic gradient of 1 g/L ammonium acetate in water (A) and acetonitrile (B). The following gradient was used: 30.5% B to 35% B in 30 minutes, ramp up to 70% B in 10 min. The compound, which eluted at a retention time of 21.2 minutes was collected into 500 µL of 50 mM citrate buffer (pH 5.2) containing 1% ascorbic acid and 0.1% HSA, and acetonitrile was removed using a Speed Vacuum (Savant). After purification, the compound had an RCP of >98%.

Preparation of $^{111}$In-P12-XDT

50 µg of P12-XDT (Ac-AGPTWCEDDWYYCWLF-GTJK(JJ-DOTA)-NH$_2$) in 50 µL of 10% DMF was mixed with $^{111}$InCl$_3$ (50 µL, 400 µCi, Mallinckrodt) and 100 µL of 0.2M ammonium acetate or citrate buffer at a pH of 5.3. After being heated at 85° C. for 45 minutes, the radiochemical purity (RCP) ranged from 44% to 52.2% as determined using HPLC. The $^{111}$In-labeled compound was separated from unlabeled ligand using a Vydac C18 column (4.6×25 cm, 5 micron pore size) under the following conditions: aqueous phase, 1 g/L ammonium acetate (pH 6.8); organic phase, acetonitrile. Gradient: 23% org. to 25% org. in 30 minutes, up to 30% org. in 2 minutes, hold for 10 minutes. The compound, which eluted at a retention time of 20.8 min, was collected into 200 µL of 50 mM citrate buffer (pH 5.2) containing 1% ascorbic acid and 0.1% HSA, and the acetonitrile was removed using a Speed Vacuum (Savant). After purification the compound had an RCP of >93%.

Preparation of $^{111}$In-D4

A histidine buffer was prepared by adjusting a 0.1M solution of histidine (Sigma) to pH 6.25 with concentrated ammonium hydroxide. Ammonium acetate buffer was prepared by adjusting a 0.2 M solution of ammonium acetate (99.99%, Aldrich) to pH 5.5 using concentrated HCl (J. T. Baker, Ultra Pure). High purity $^{111}$InCl$_3$ (100 µL, 1.2 mCi, Mallinckrodt) was added to D4 (200 µg in 200 of 50% DMF, 10% DMSO, 20% acetonitrile and 20% water), followed by addition of 300 µL of histidine buffer. The final pH was 5.5. After incubation of the reaction mixture at 85° C. for 45 minutes, the RCP was 20%.

Alternatively, $^{111}$InCl$_3$ provided with a commercially available OctreoScan™ Kit (134 µL, 0.6 mCi, Mallinkrodt) was added to D4 (135 µg) in 162 µL of 0.2M ammonium acetate buffer. The final pH was 5.5. After incubation of the reaction mixture at 85° C. for 45 min. the RCP was 20%.

Preparation of $^{125}$I-D5

D5 (200 µg), in 30 µL of DMF that had been previously adjusted to pH 8.5–9.0 using diisopropyl amine, was added to 1 mCi of mono-iodinated $^{125}$I Bolton-Hunter Reagent (NEX-120, Perkin-Elmer) that had been evaporated to dryness. The vial was shaken and then incubated on ice for 30 minutes with occasional shaking. After this time, the RCP was 23%. $^{125}$I-D5 (shown below) was purified by HPLC at a flow rate of 1 mL/min using a Vydac C18 column (4.6×250 mm, 5 micron pore size) under the following conditions. Aqueous phase: 0.1% TFA in water; organic phase: 0.085% TFA in acetonitrile. Gradient: 30% org. to 36% org. in 30 minutes, up to 60% org. in 5 minutes, hold for 5 minutes. The compound was collected into 200 µL of 50 mM citrate buffer (pH 5.2) containing 1% ascorbic acid and 0.1% HSA. Acetonitrile was removed using a Speed Vacuum (Savant). The resulting compound had an RCP of 97%.

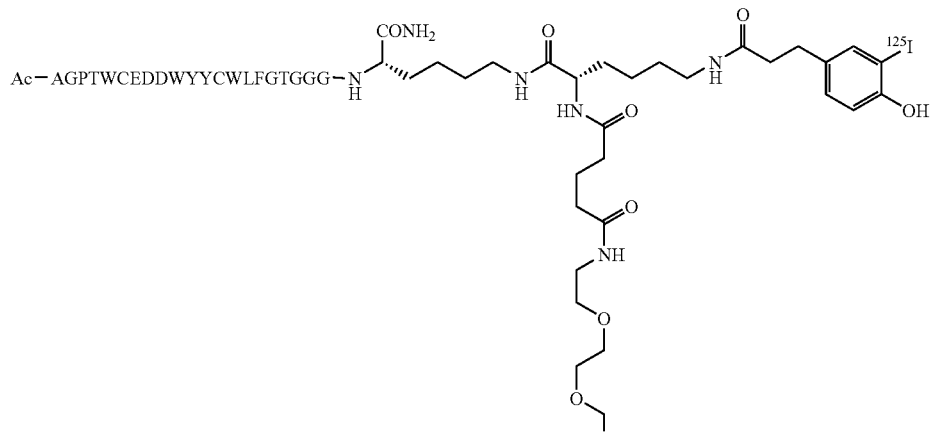

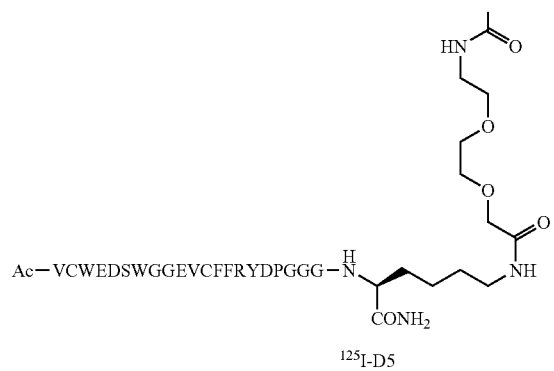

125I-D5

Preparation of 177Lu-D11

D11 (5 μL of a ~1 μg/μL solution in 0.05N NH$_4$OH/10% EtOH) was added to a glass insert microvial containing 80 μL of 0.2M NaOAc buffer, pH 5.6. Enough 177Lu was added to bring the ligand:Lu ratio to ≦2:1 (1–5 mCi). The vial was crimp-sealed and heated at 100° C. for 15–20 minutes, cooled for 5 minutes, and treated with 3 μL of 1% Na$_2$EDTA.2H$_2$O in H$_2$O. The entire reaction mixture was injected onto a Supelco Discovery RP Amide C16 column (4 mm×250 mm×5 μm). The following HPLC conditions were used: Column temperature=50° C., Solvent A=H$_2$O W/0.1% TFA, Solvent B=ACN w/0.085% TFA, gradient 0.6/0.25 mL/min A/B at t=0 minutes to 0.5/0.4 mL/min A/B at t=60 minutes. The retention time for D11 was ~40 minutes; that of 177Lu-D11 1334 was ~42 minutes. The radioactive peak was collected into 0.7 ml of 0.05M citrate buffer, pH 5.3 containing 0.1% Human Serum Albumin Fraction V and 1.0% Ascorbic Acid, and the mixture was spun down in a Savant Speed Vac to remove organic solvents. Radiochemical purities of greater than 80% were obtained.

Preparation of 99mTc-D12

SnCl$_2$.2H$_2$O (20 mg) was dissolved in 1 mL of 1 N HCl, and 10 μL of this solution was added to 1 mL of a DTPA solution that was prepared by dissolving 10 mg of Ca Na$_2$ DTPA.2.5 H$_2$O (Fluka) in 1 mL of water. D12 (100 μg in 100 μL of 50% DMF) was mixed with 75 μL of 0.1 M, pH 9 phosphate buffer and 60 μL of 99mTcO$_4^-$ (2.4 to 4 mCi, Syncor), followed by 100 μL of the stannous Sn-DTPA solution. After 10 min at 40° C., the radiochemical purity (RCP) was 16%. The product was purified on a Supelco Discovery C16 amide column (4×250 mm, 5 um pore size) eluted at a flow rate of 0.7 mL/min using an aqueous/organic gradient of 0.1% TFA in water (A) and 0.085% TFA in acetonitrile (B). The following gradient was used: 30% B to 42% B in 36 min, ramp up to 70% B in 10 min. The compound, which eluted at a retention time of 37.1 min. was collected into 500 μL of 50 mM citrate buffer (pH 5.2) containing 0.2% HSA, and acetonitrile was removed using a Speed Vacuum (Savant). After purification, the compound had an RCP of >90%.

Preparation of 99mTc-D14

SnCl$_2$.2H$_2$O (20 mg) was dissolved in 1 mL of 1 N HCl, and 10 μL of this solution was added to 1 mL of a DTPA solution that was prepared by dissolving 10 mg of CaNa$_2$DTPA.2.5H$_2$O (Fluka) in 1 mL of water. D14 (100 μg in 100 μL of 50% DMF) was mixed with 50 μL of 99mTcO$_4^-$ (6 mCi, Syncor) and 125 μL of 0.1M phosphate buffer, pH 9 followed by 100 μL of the stannous Sn-DTPA solution. After 15 min at 40°, the radiochemical purity (RCP) was 21%. The product was purified on a Vydac peptide C18 column (4.6×250 mm) eluted at a flow rate of 1 mL/min using an aqueous/organic gradient of 0.1% TFA in water (A) and 0.085% TFA in acetonitrile (B). The following gradient was used: 30% B to 45% B in 40 min. The compound, which eluted at a retention time of 34.9 min., was collected into 500 μL of 50 mM citrate buffer (pH 5.3) containing 0.2% HSA, and acetonitrile was removed using a Speed Vacuum (Savant). After purification, the compound had an RCP of 92.5%.

Preparation of $^{99m}$Tc-D32

SnCl$_2$.2H$_2$O (20 mg) was dissolved in 1 mL of 1 N HCl, and 10 μL of this solution was added to 1 mL of a DTPA solution that was prepared by dissolving 10 mg of Ca Na$_2$ DTPA.2.5 H$_2$O (Fluka) in 1 mL of water. D32 (100 μg in 100 μL of DMF) was mixed with 150 μL of 0.1 M pH 8 phosphate buffer and 50 μL of $^{99m}$TcO$_4^-$ (5.2 mCi, Syncor), followed by 100 μL of the stannous Sn-DTPA solution. After 15 min at 100° C., the radiochemical purity (RCP) was 13%. The product was purified on a Vydac C18 peptide column (4.6×250 mm, 5 um pore size) eluted at a flow rate of 1 mL/min using an aqueous/organic gradient of 0.1% TFA in water (A) and 0.085% TFA in acetonitrile (B). The following gradient was used: 10% B to 50% B in 30 min, hold 50% B for 5 min, back to 70% B in 5 min. The compound, which eluted at a retention time of 33.2 min. was collected into 3 mL of 50 mM citrate buffer (pH 5.5) containing 0.2% HSA, and acetonitrile was removed using a Speed Vacuum (Savant). After purification, the compound had an RCP of 92.4%.

EXAMPLE 14

Binding of $^{125}$I-Labeled Heteromultimers of the Invention to KDR-Transfected Cells An experiment was performed to test the ability of $^{125}$I-labeled D5 to bind to KDR-transfected 293H cells. In this experiment, different amounts of $^{125}$I-labeled D5 (1–4 μCi/ml, labeled with $^{125}$I-Bolton-Hunter reagent and HPLC-purified) were incubated with mock & KDR-transfected 293H cells in 96-well plates for 1 hr at room temperature. Binding was performed with and without 40% mouse serum to evaluate the serum effect on binding to KDR-transfected cells. After washing away the unbound compound, the cells in each well were lysed with 0.5 N NaOH and the lysates were counted with a gamma counter.

Figure 17:
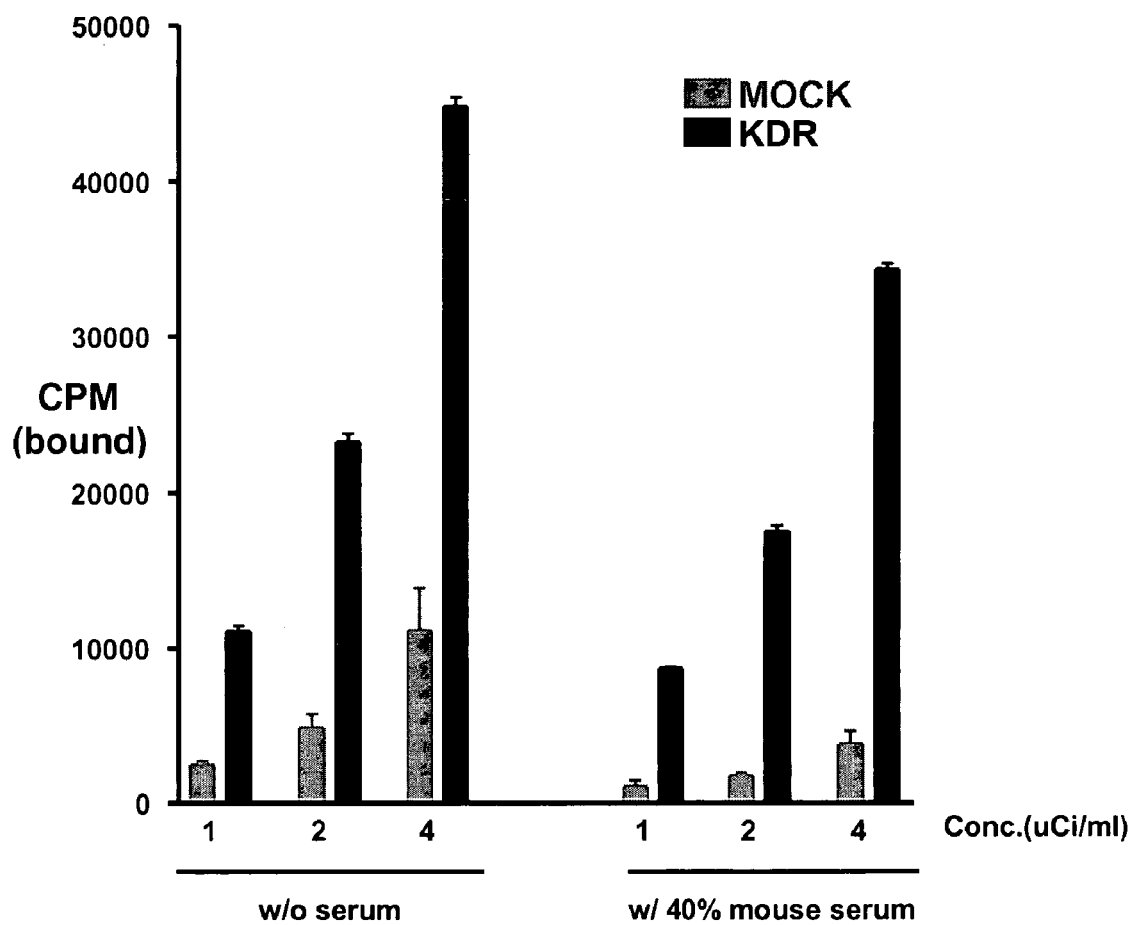
FIG. 17 is a graph showing the binding of 125I-labeled D5 to mock and KDR transfected 293H cells in the absence and presence of 40% mouse serum.
Figure 18:
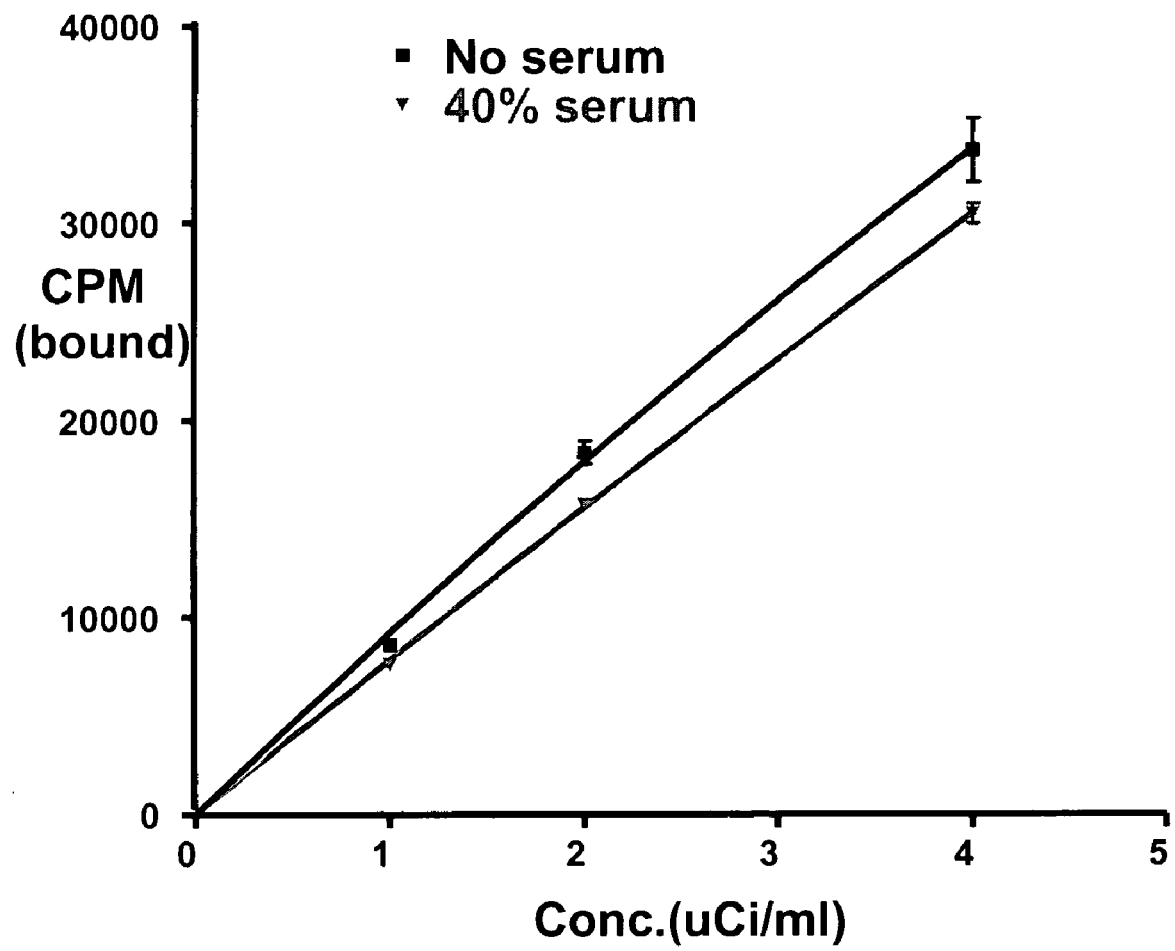
FIG. 18 is a graph showing the specific binding (KDR-MOCK) of $^{125}$I-labeled D5 to KDR-transfected 293H cells in the absence and presence of 40% mouse serum.

The results of this experiment are summarized in FIG. 17 and FIG. 18. It is clearly evident from these results that $^{125}$I-labeled D5 is able to specifically bind to KDR-transfected cells and its binding is not affected by the presence of 40% mouse serum. Somewhat more binding to KDR-transfected cells was observed in the absence of serum as compared to binding in the presence of 40% mouse serum. However, the binding of $^{125}$I-D5 to mock-transfected cells was also increased by about the same extent when serum was omitted during the assay, indicating that the increased binding in the absence of serum was non-specific (FIG. 17). Specific binding to KDR-transfected cells (after subtracting binding to mock-transfected cells) looked almost identical with or without mouse serum (as shown in FIG. 18). In this experiment, 10–14% of the total CPM added were specifically bound to KDR-transfected cells (data not shown).

EXAMPLE 15

A peptide heterodimer (D6, shown below) was prepared as previously described in Example 9 using glutaric acid bis N-hydoxysuccinimidyl ester. The heterodimer was tested for binding to KDR-Fc using Biacore and an affinity constant was determined as follows.

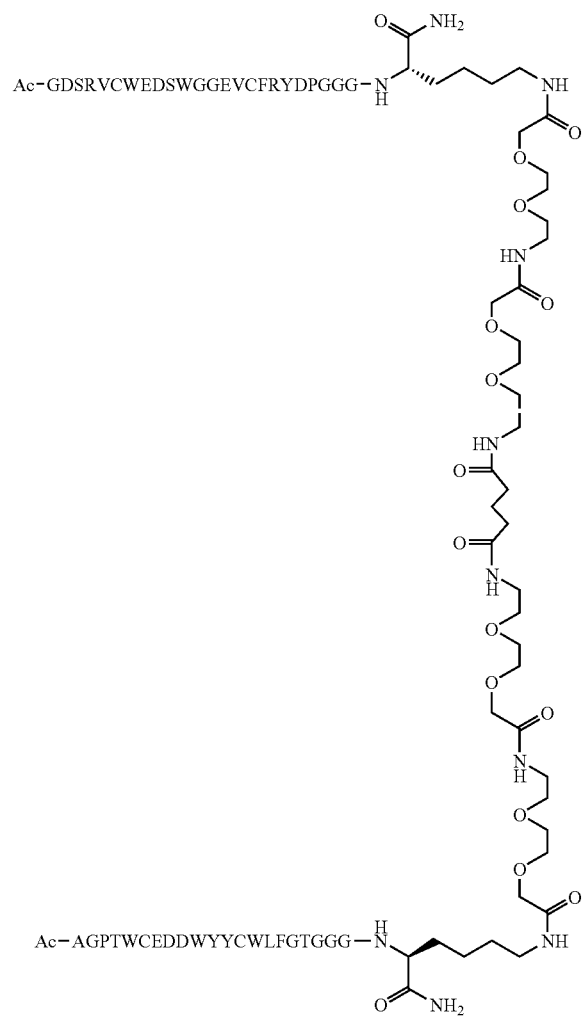

Molecular Weight=6030.58
Exact Mass=6024
Molecular Formula=$C_{269}H_{368}N_{66}O_{86}S_4$
Molecular Composition=C, 53.58%, H, 6.15%, N, 15.33%, O, 22.82%, S, 2.13%
Peptide Heterodimer: D6
Three densities of KDR-Fc were cross-linked to the dextran surface of a CM5 sensor chip by the standard amine coupling procedure (0.5 mg/mL solution diluted 1:100 or 1:50 with 50 mM acetate, pH 6.0). Flow cell 1 was activated and then blocked to serve as a reference subtraction. Final immobilization levels achieved:
$R_L$ Fc 2 KDR-Fc=1607
$R_L$ Fc 3 KDR-Fc=3001
$R_L$ Fc 4 KDR-Fc=6319

Experiments were performed in PBS buffer (5.5 mM phosphate, pH 7.65, 0.15 M NaCl)+0.005% P-20 (v/v)). D6 was diluted to 250 nM in PBS and serial dilutions were performed to produce 125, 62.5, 31.3 15.6, 7.8, and 3.9 nM solutions. All samples were injected in duplicate. For association, peptides were injected at 20 μL/min for 12.5 minutes using the kinject program. Following a 10 minute dissociation, any remaining peptide was stripped from the KDR surface with a quickinject of 50 mM NaOH+1M NaCl for 12 s at 75 μL/min. Sensorgrams were analyzed using BLAevaluation software 3.1 and a hyperbolic double rectangular regression equation in SigmaPlot 6.0. Heterodimer steady state binding affinities ($KD_{AV}$) were determined at all three KDR immobilization densities (Table 7).

TABLE 7

Summary of Parameters

|  | $KD_1$ (nM) | $RMax_1$ | $KD_{AV}$ (nM) | $RMax_{AV}$ | $R^{2*}$ |
|---|---|---|---|---|---|
| D6 vs. 1600RU | 46 | 13.1 | 1.5 | 12.6 | 0.995 |
| vs. 3000RU | 25.5 | 21.2 | 0.665 | 22.7 | 0.991 |
| vs. 6000RU | 17 | 61.3 | 0.662 | 62.2 | 0.993 |

From this data, it appears that at the higher immobilization densities, the heterodimer binds KDR with a sub-nanomolar affinity (~0.6 nM).

To assess the in-vivo clearance of this peptide heterodimer, a small amount of material was iodinated using iodogen and $Na^{125}I$ according to standard protocols (Pierce). Radio iodination was done in the Radiation Safety lab, within the designated hood. One tube coated with the iodogen reagent was pre-wet with 1 mL of 25 mM Tris, 0.4M NaCl, pH 7.5. This was discarded and 100 μl of the same buffer added. Using a Hamilton syringe 11 μL of the $^{125}$I-NaI was transferred to the reaction tube. Based on original estimates of the Na $^{125}$I concentration of 143.555 mCi/ml, the 11 μL should contain about 1.5 mCi. No dose calibrator was in the room. After addition, the sample was swirled and set in a lead pig to incubate for 6 min with a swirl every 30 sec. After 6 min, the entire sample was transferred to the peptide that was in an Eppendorf tube. The sample was swirled and set to incubate for 8 min, with a swirl every 30 sec. After 8 min the reaction was quenched (terminated) with tyrosine (10 mg/mL, a saturated solution), allowed to sit for 5 min, and then 2 μL was removed for a standard.

For purification a 10 mL column of the D-salt polyacrylamide 1800 was used to separate the labeled peptide from labeled tyrosine. The column was first washed with 10 mL saline, then 5 mL of 25 mM Tris, 0.4M NaCl, pH 7.5 containing 2.5% HSA to block non-specific sites. After the HSA buffer wash, the column was eluted with 60 mL of the 25 mM Tris, 0.4 M NaCl buffer, and the column was stored overnight at 4° C. The labeled sample contained 1.355 mCi, as determined by the dose calibrator. The 2 μl sample that was removed as a standard contained 8.8 μCi. The peptide sample was applied to the D-salt 1800 column and eluted with the Tris/NaCl buffer, pH 7.5. The flow was controlled by applying single 0.5 ml aliquots for each fraction, #1–14, and then 1.0 mL for fractions 25–43. The peak of activity in fractions # 9, 10, and 11, was assumed to be the peptide. The radioactivity in 24 through 40 is likely the labeled tyrosine. From this purification, fractions #9–12 were pooled together and used for the subsequent clearance study (concentration of $^{125}$I-D6 in pool is 7.023 μg/mL; 100 μL=0.702 μg with 8.6 μCi).

Figure 19:
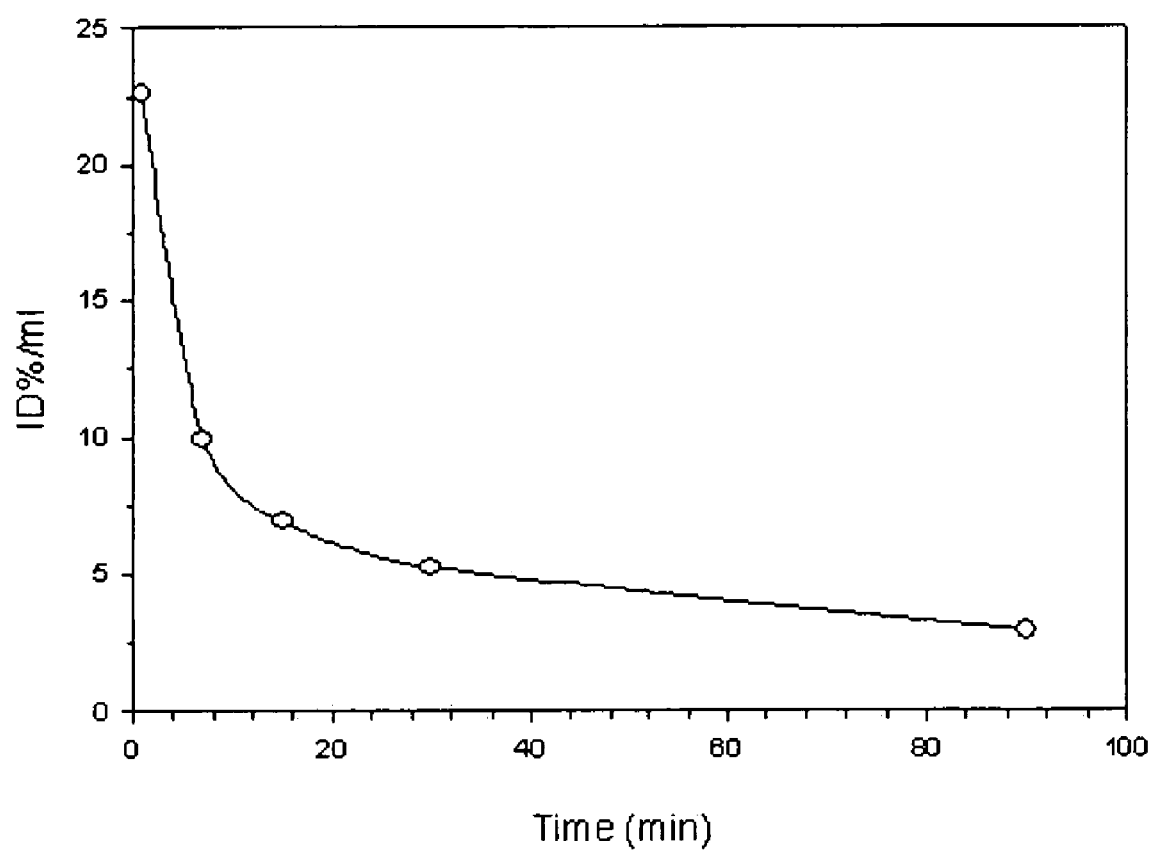
FIG. 19 is a graph of plasma clearance as percent injected dose per mL versus time.

A total of 15 mice were injected with 100 μL $^{125}$I-D6 and mice (in sets of 3) were sacrificed at the following time points: 0, 7, 15, 30, 90 minutes. Actual activity injected was about 6 μCi. With 6 μCi injected the corresponding peptide administered was ~0.5 μg per animal. Once sacrificed, the counts were determined in a 50 μL plasma sample from each animal. For each set of three animals at each time point, the counts were averaged, converted to % injected dose/ml plasma (ID %/mL), and then plotted to assess the rate of clearance (FIG. 19). Then this data was fit to either a 4 or 5 parameter equation to determine the biphasic half life of this molecule. The 4 parameter fit resulted in a $T_{1/2\alpha}$ of 2.55 minutes and a $T_{1/2\beta}$ of 64.66 minutes. The 5 parameter fit resulted in a $T_{1/2\alpha}$ of 2.13 minutes and a $T_{1/2\beta}$ of 23.26 minutes.

Figure 20:
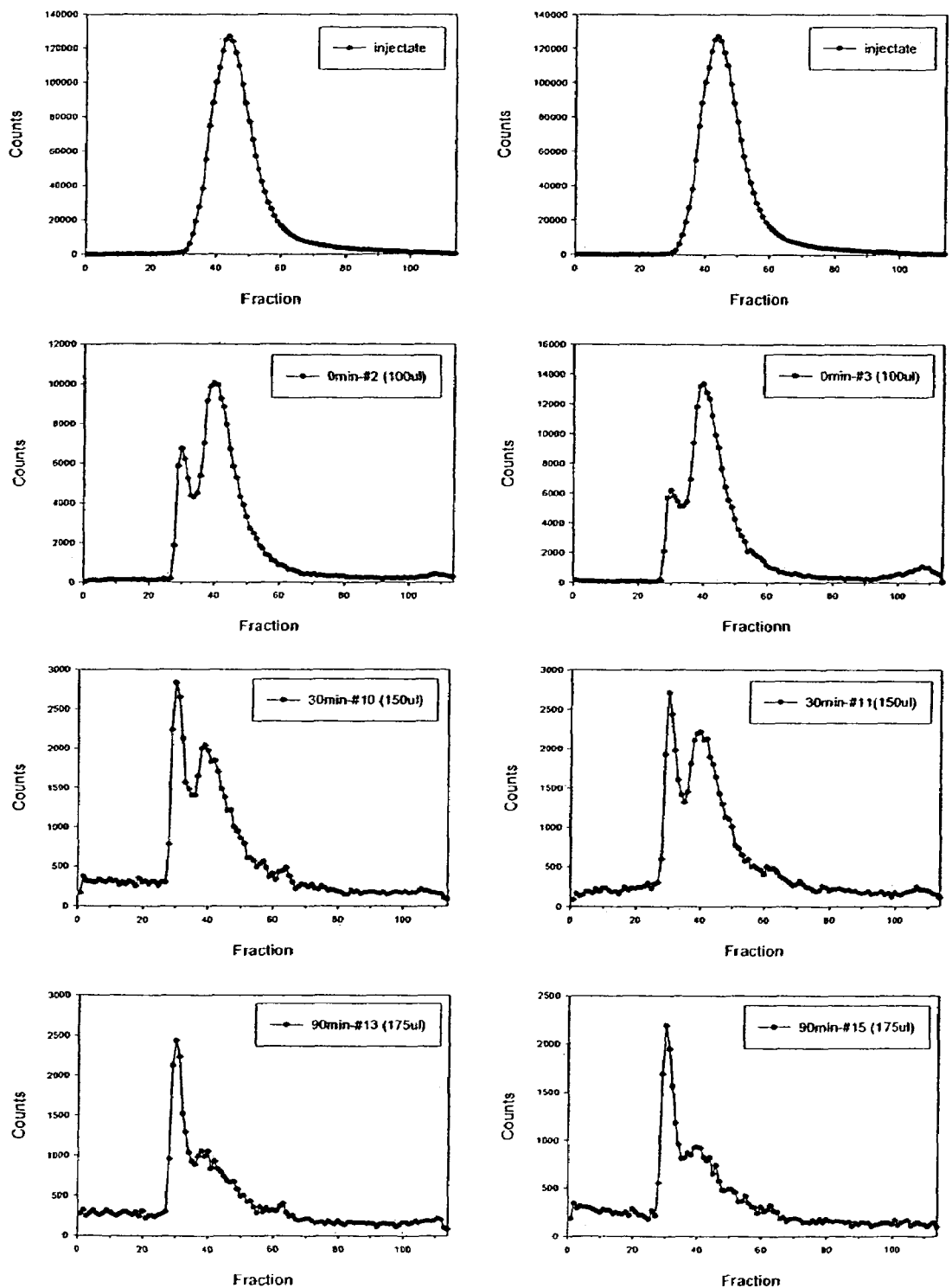
FIG. 20 shows SE-HPLC profiles of plasma from the Superdex peptide column. Top panel, sample injected; followed by 0 min, 30 min, and 90 min. The insert within each panel shows time point, animal number and volume injected for HPLC analysis.

Besides taking counts from the plasma samples, larger volumes of plasma were taken from mice sacrificed at the 0, 30, and 90 minute time points. These samples were injected onto a Superdex peptide column (Pharmacia) coupled to a radioactivity detector to assess the association of the peptide with serum proteins (FIG. 20). As shown, the labeled peptide does associate with higher MW proteins, which could explain its biphasic half life clearance behavior.

To help assess the potency of the peptide as an anti-angiogenesis inhibitor, D6 was tested in an endothelial cell proliferation assay using HUVECs and BrdU detection. Briefly, freshly isolated HUVECs (between p3–6) were cultured in RPMI+10% FCS+1% antibiotics+1% 1-glutamin+0.4% BBE (bovine brain extract) and seeded per well, 5000–10000/well in 100 μL. The cells were allowed to recover for 24 h prior to use. Then the cells were washed with PBS twice and treated for 48 h with anti-VEGF antibody (positive control) or peptides A, B and C (0.1 and 10 ug/mL) in RPMI+0.1% BSA+1% 1-glutamin. The following 6 variables were tested in 2 series (n=4):

Series I: w/o VEGF
Series II: w/VEGF (30 ng/mL)
1. Standard medium: RPMI+10% FCS+1% antibiotics+1% 1-glutamin+0.4% BBE
2. Negative control 1: RPMI (true starvation)
3. Negative control 2: RPMI+0.1% BSA+1% 1-glutamin
1. Positive control: anti-VEGF 10 μg/ml in RPMI+0.1% BSA+1% 1-glutamin
5. 0.1 μg/ml KDR peptides in RPMI+0.1% BSA+1% 1-glutamin
6. 10 μg/ml KDR peptides in RPMI+0.1% BSA+1% 1-glutamin Protocol:
1) cells are incubated for 48 hours under various conditions
2) 10 μL BrdU dilution (1:100 in EBM) is added to each well at 24 hours
3) incubate for another 24 hours (total 48 hrs)
4) aspirate the culture medium
5) add 100 μL FixDenat to each well, incubate at room temperature for 30 min.
6) Discard FixDenat solution
7) 100 μL antibody-solution (PBS 1% BSA and anti-BrdU PO) added to each well.
8) incubate at RT for 90 minutes.
9) wash 3 times with PBS, 200 μL/well, 5 min.
10) add substrate solution (TMB), incubate for 10–30 minutes
11) transfer all to a flexibel plate
12) stop the reaction by adding 2M $H_2SO_4$, 25 μL/well
13) read absorbance at 450 nm within 5 minutes after stopping the reaction.

Note: Background binding was determined by omitting the anti-BrdU antibody in 4 wells with control cells (cultured in complete medium; EBM+BulletKit) and by complete labeling of cells that was not exposed to BrdU.

Figure 21:
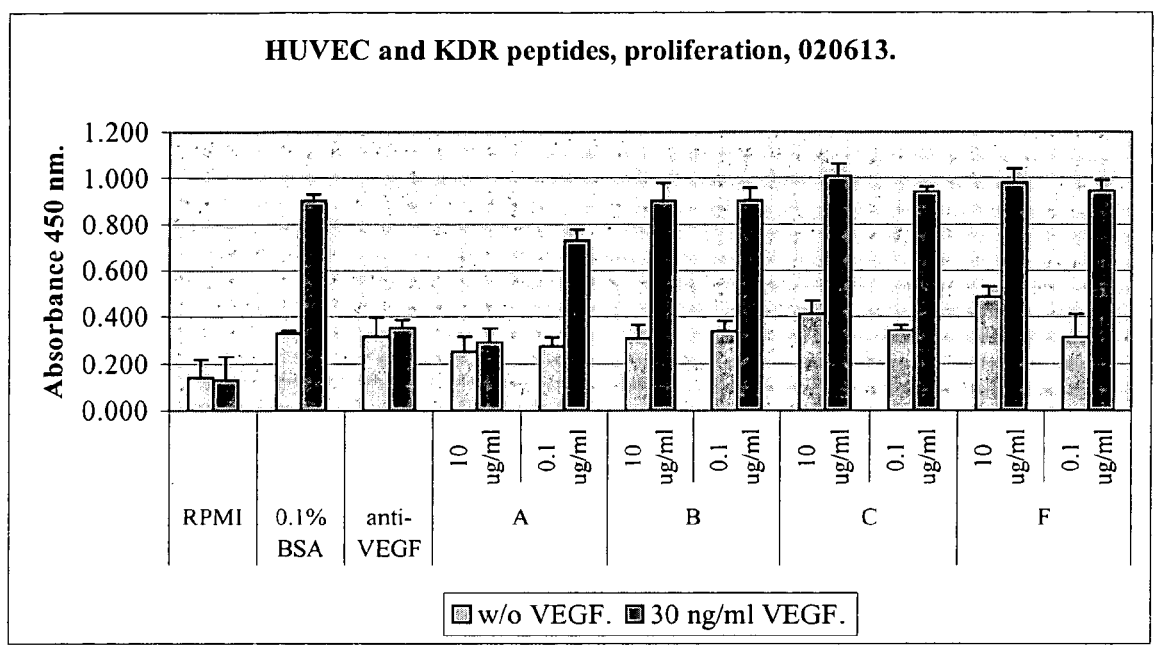
FIG. 21 is a graph showing the results of testing of KDR peptides in HUVEC proliferation assay. A represents D6; B represents P12-G; C represents PNC-1 (negative control); F, PNC-1 (negative control).

Of the two KDR binding constructs tested (D6 and P12-G (Ac-AGPTWC*EDDWYYC*WLFGT-GGGK-$NH_2$)) as shown in FIG. 21 (A, D6; B, P12-G; C, PNC-1; F, PNC-1), D6 completely inhibits HUVEC proliferation at 10 μg/mL in the presence of VEGF, similar to an anti-VEGF antibody (positive control). PNC-1 (Ac-AEGTGDLHCYFPWVC-SLDPGPEGGGK-OH) (SEQ ID NO: 29) was used as negative control. On the other hand, P12-G (one of the peptides that make up the heterodimer) does not inhibit proliferation this assay at the highest concentration tested (10 μg/mL). As a result, the heterodimer clearly shows an enhanced ability to compete with VEGF in comparison with P12-G alone.

EXAMPLE 16

BIAcore Analysis—Murine KDR-Fc Binding of Peptide Dimers D1 and D7

Using BIAcore, determine the binding constants of peptide dimers D1 (a heterodimer of P12-G and a truncated form of P6-D) and D7 (a heterodimer of P5-D and P6-D) for murine KDR-Fc.

Procedure

Three densities of recombinant murine KDR-Fc were cross-linked to the dextran surface of a CM5 sensor chip by the standard amine coupling procedure (0.5 mg/mL solution diluted 1:100 or 1:40 with 50 mM acetate, pH 6.0). Flow cell 1 was activated and then blocked to serve as a reference subtraction. Final immobilization levels achieved:
$R_L$ Fc 2 KDR-FC=2770
$R_L$ Fc 3 KDR-Fc=5085
$R_L$ Fc 4 KDR-Fc=9265

Experiments were performed in PBS buffer (5.5 mM phosphate, pH 7.65, 0.15 M NaCl)+0.005% P-20 (v/v)). P12-G, run as a control, was diluted to 125 nM in PBS. Serial dilutions were performed to produce 62.5, 31.3, 15.6, 7.8, and 3.9 nM solutions. D1 and D7 were diluted to 50nM in PBS and serial dilutions were performed to produce 25, 12.5, 6.25, 3.13, 1.56, 0.78, and 0.39 nM solutions. All samples were injected in duplicate. For association, peptides were injected at 30 μL/min for 3 minutes using the kinject program. Following a 10 minute dissociation, any remaining peptide was stripped from the rmKDR-Fc surface with a quickinject of 50 mM NaOH+1M NaCl for 12 s at 75 μL/min.

Figure 22:
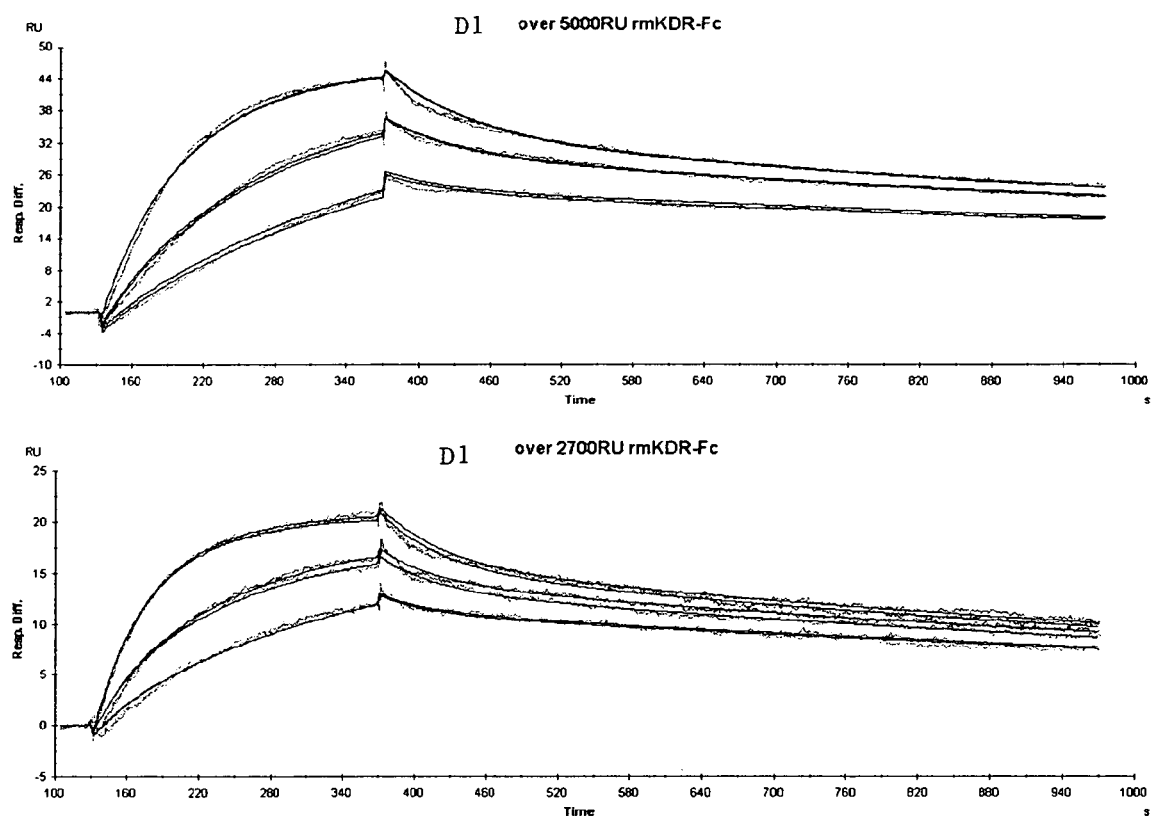
FIG. 22 shows the kinetic analysis of D1 (heterodimer of a truncated form of P6-D and P12-G) binding to murine KDR-Fc. All sensograms are fit to the bivalent analyte model.
Figure 23:
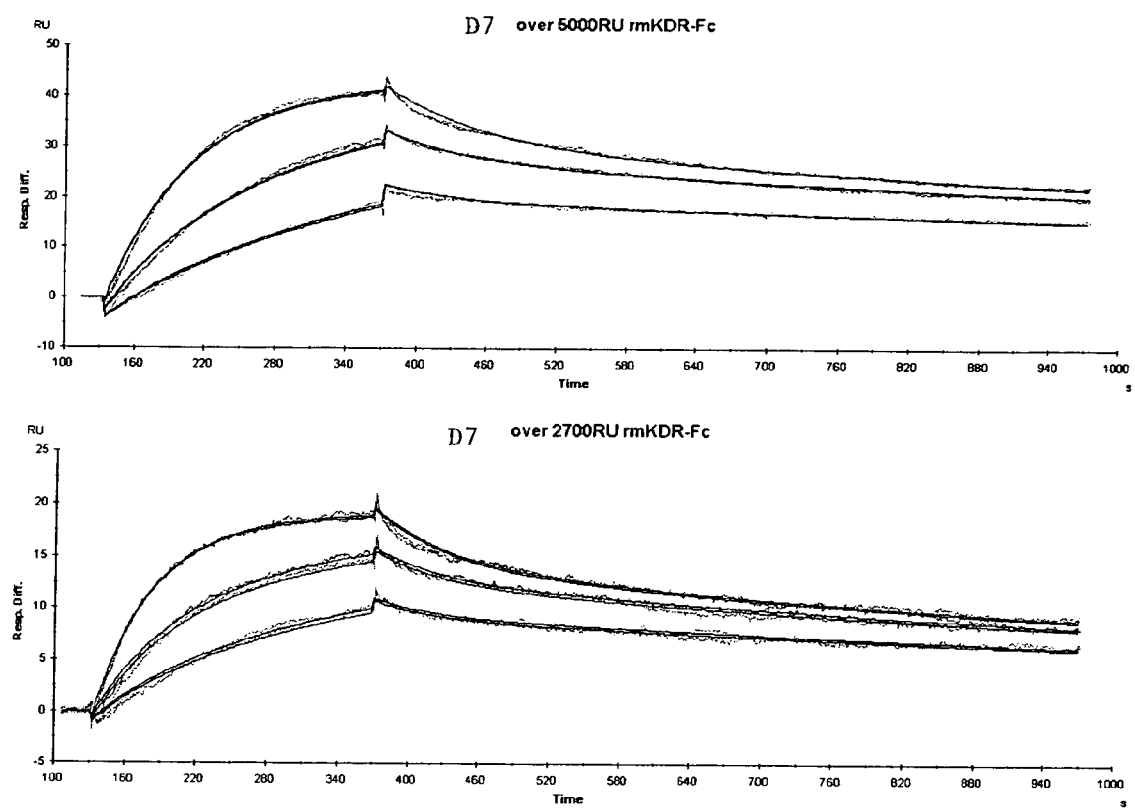
FIG. 23 shows the kinetic analysis of D7 (heterodimer of P5-D and P6-D) binding to murine KDR-Fc. All sensograms are fit to the bivalent analyte model.
Figure 24:
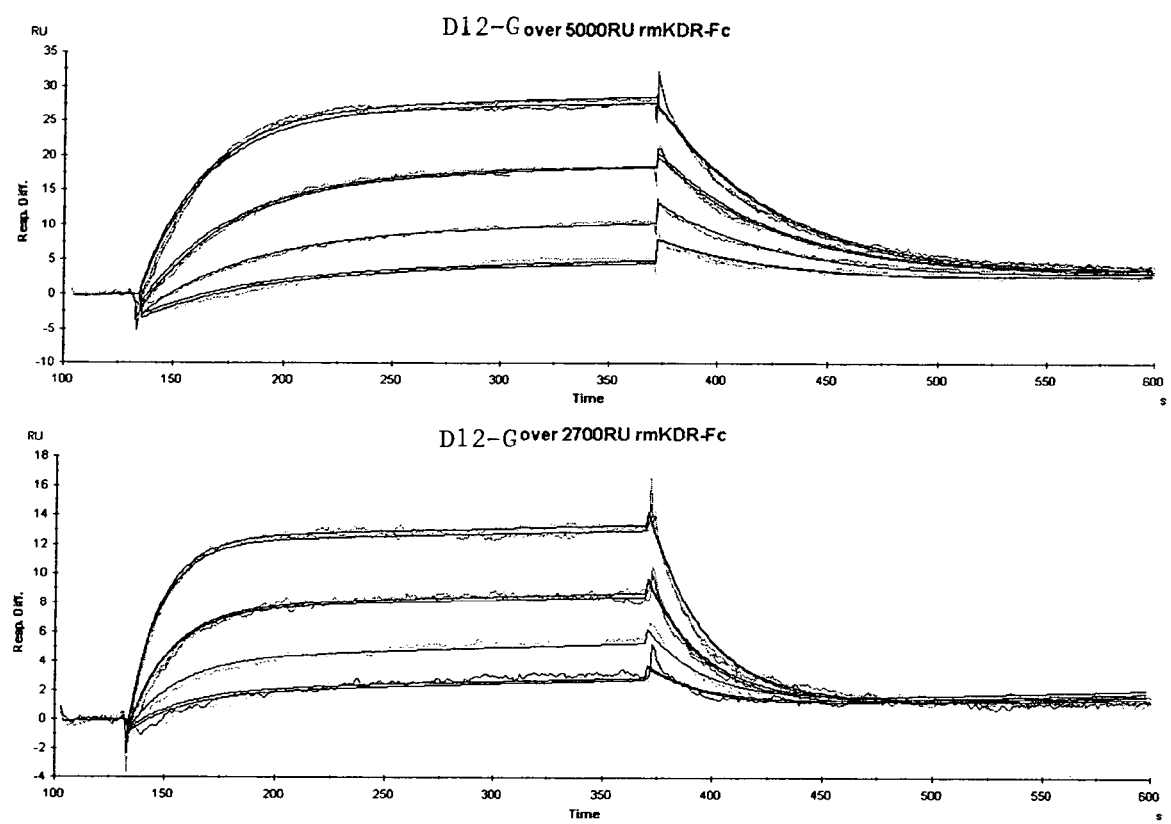
FIG. 24 shows kinetic analysis of fluorescein labeled P12-G binding to murine KDR-Fc. All sensograms are fit to the 1:1 Langmuir model.

Sensorgrams were analyzed using the simultaneous ka/kd fitting program in the BIAevaluation software 3.1. The Results are shown in Table 8 and FIGS. 22–24. The fact that about the same $K_{D2}$ constant was achieved for both heterodimers even when the density of receptor on the sensor chip was reduced by half is consistent with multimeric binding of the heterodimers to individual receptors rather than cross-link-type binding between receptors.

1.

EXAMPLE 17

Demonstration of the Distinction between Binding Affinity and Biological Potency through In Vitro Assays The following experiments showed that heteromultimers can display much greater biological potency than a monomeric peptide with similar binding affinity to the same target.

Protocol Experiment 1:

293H cells were transfected with the KDR cDNA or mock-transfected by standard techniques described in Example 6. The cells were incubated with $^{125}$I-VEGF in the presence or absence of PG-1 (Ac-ERVTTCWPGEYGGVE-CYSVAY-NH$_2$) (SEQ ID NO: 30) or D1 (at 300, 30, 3, and 0.3 nM). After washing the cells, the bound radioactivity was quantitated on a gamma counter. The percentage inhibition of VEGF binding was calculated using the formula [(Y1−Y2)×100/Y1], where Y1 is specific binding to KDR-transfected 293H cells in the absence peptides, and Y2 is specific binding to KDR-transfected 293H cells in the presence of peptide competitors. Specific binding to KDR-transfected 293H cells was calculated by subtracting the binding to mock-transfected 293H cells from the binding to KDR-transfected 293H cells.

Protocol Experiment 2:

Serum-starved HUVECs were placed, 100,000 cells per well, into the upper chambers of BD fibronectin-coated FluoroBlok 24-well insert plates. Basal medium, with or without VEGF (10 ng/mL) in the presence or absence of increasing concentrations of PG-1 or D1, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. VEGF-stimulated migration was derived by subtracting the basal migration measured in the absence of VEGF.

Figure 26:
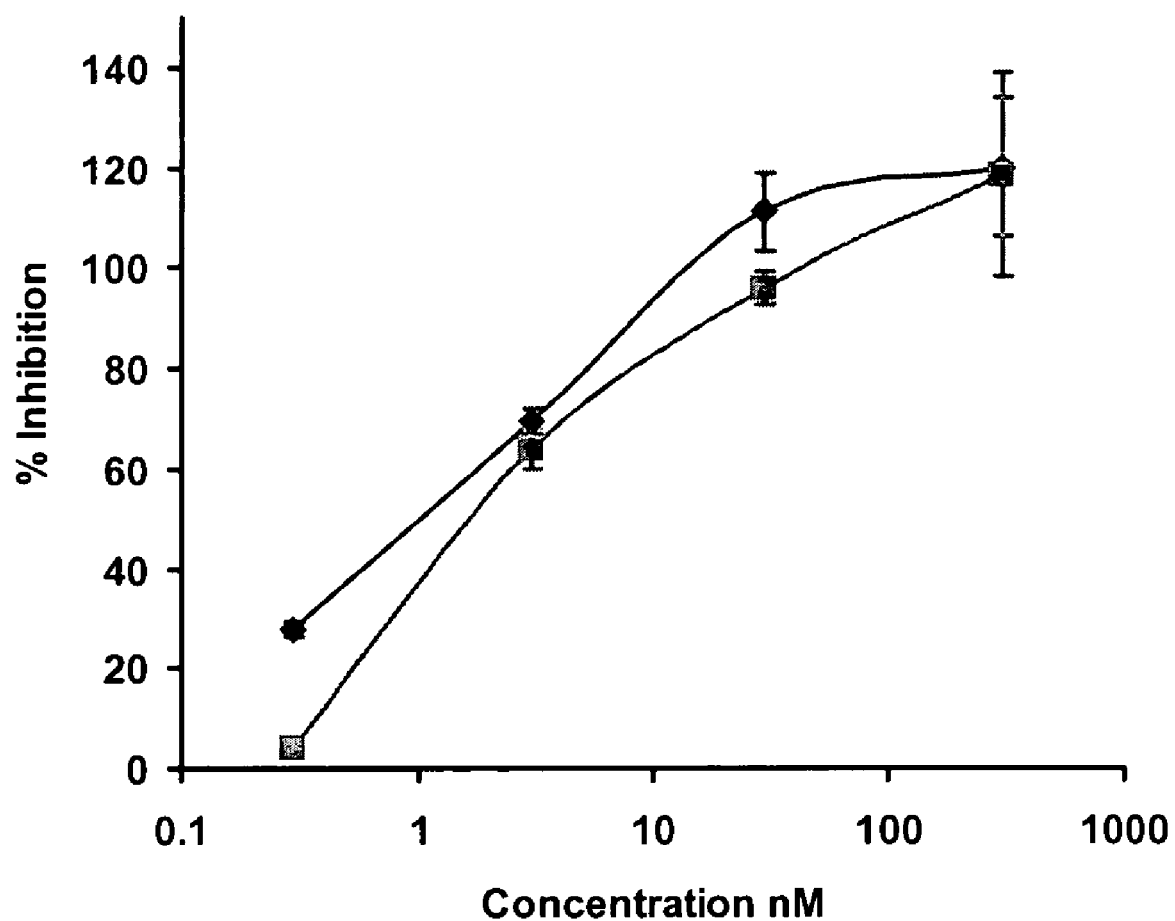
FIG. 26 is a graph depicting % inhibition ±s.d. of specific $^{125}$I-VEGF binding to KDR-transfected cells by PG-1 (squares) D1 (diamonds).
Figure 27:
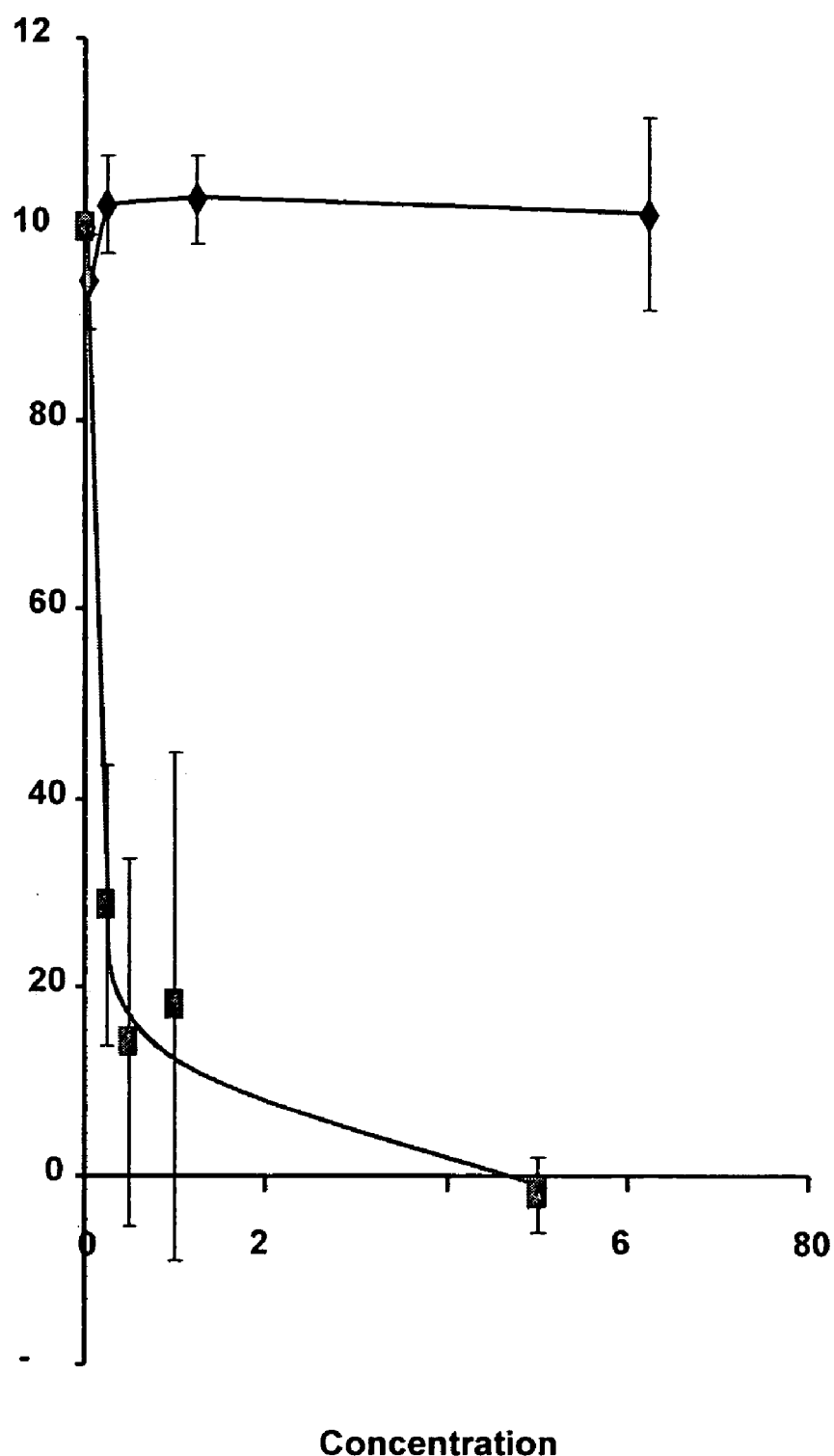
FIG. 27 is a graph depicting % maximum VEGF-stimulated migration ±s.d. of HUVEC cells in the presence of the indicated concentrations of PG-1 (diamonds) D1 (squares).

Results Experiment 1:

As shown in FIG. 26, PG-1 and D1 competed about equally well with $^{125}$I-VEGF for binding to KDR-transfected cells, indicating that they possess comparable binding affinities as well as a comparable ability to inhibit VEGF from binding to KDR.

Results Experiment 2:

In spite of the fact that both PG-1 and D1 potently block $^{125}$I-VEGF binding to KDR-expressing cells to the same degree (FIG. 26), the heterodimeric D1 was significantly more potent in blocking the biological effects of VEGF as demonstrated in an endothelial cell migration assay (FIG.

TABLE 8

Summary of Kinetic Parameters.

| | | ka1 (1/Ms) | kd1 (1/s) | ka2 (1/RUs) | kd2 (1/s) | KD1# (nM) | KD2‡(nM) | Chi²* |
|---|---|---|---|---|---|---|---|---|
| D1 | vs. 2700RU | 7.94E+05 | 0.0139 | 3.31E−04 | 5.96E−04 | 17.5 | 0.751 | 0.077 |
| | vs. 5000RU | 5.54E+05 | 8.88E−03 | 1.17E−04 | 4.57E−04 | 16.0 | 0.825 | 0.323 |
| D7 | vs. 2700RU | 7.59E+05 | 0.011 | 3.36E−04 | 6.44E−04 | 14.5 | 0.848 | 0.082 |
| | vs. 5000RU | 5.21E+05 | 7.39E−03 | 1.17E−04 | 4.68E−04 | 14.2 | 0.898 | 0.278 |
| Fluorescein | vs. 2700RU | 1.02E+06 | 0.037 | — | — | 36.4 | — | 0.073 |
| labeled P12-G | vs. 5000RU | 5.18E+05 | 0.0174 | — | — | 33.6 | — | 0.167 |

$K_{D1}$ is a calculated $K_D$ based on $kd_1/ka_1$
‡$K_{D2}$ is a calculated $K_D$ based on $kd_2/ka_1$ (i.e. avidity factor)
*The chi2 value is a standard statistical measure of the closeness of the fit. For good fitting to ideal data, chi2 is of the same order of magnitude as the instrument noise in RU (typically <2).

27) than the monomeric PG-1. At up to 62.5 nM, PG-1 had no effect on VEGF-stimulated migration whereas D1 completely blocked VEGF-stimulated migration at 50 nM. These data suggest that heteromultimeric binding can more effectively block the biological activity of a ligand than a monomer, even when the monomer has a comparable ability to inhibit ligand binding to its receptor.

EXAMPLE 18

Binding of Tc-Labeled Heterodimers of the Invention KDR-Transfected 293H Cells

In this Example, the ability of Tc-labeled D10 to bind KDR was assessed using KDR-transfected 293H cells. The results show that Tc-labeled D10 bound significantly better to KDR transfected 293H cells than to mock transfected 293H cells, and good binding was maintained in the presence of 40% mouse serum. In addition, a derivative of Tc-labeled D10 with its amino acid sequence scrambled, D18, was shown to possess no affinity for KDR-expressing cells, confirming the specificity of the D10 binding to those cells.

Synthesis of $^{99m}$Tc-Labeled Peptides

Preparation of $^{99m}$Tc-D10:

SnCl$_2$.2H$_2$O (20 mg) was dissolved in 1 mL of 1 N HCl, and 10 μL of this solution was added to 1 mL of a DTPA solution that was prepared by dissolving 10 mg of Ca Na$_2$ DTPA.2.5 H$_2$O (Fluka) in 1 mL of water. D10 (100 μg in 100 μL of 50% DMF) was mixed with 75 μL of 0.1 M, pH 9 phosphate buffer and 50 μL of $^{99m}$TcO$_4^-$ (2.4 to 5 mCi, Syncor), followed by 100 μL of the stannous Sn-DTPA solution. After 15 min at RT, the radiochemical purity (RCP) was 72%. The product was purified on a Supelco Discovery C16 amide column (4×250 mm, 5 um pore size) eluted at a flow rate of 0.7 mL/min using an aqueous/organic gradient of 0.1% TFA in water (A) and 0.085% TFA in acetonitrile (B). The following gradient was used: 30% B to 42% B in 36 min, ramp up to 70% B in 10 min. The compound, which eluted at a retention time of 32 min. was collected into 500 μL of 50 mM citrate buffer (pH 5.2) containing 0.2% HSA, and acetonitrile was removed using a Speed Vacuum (Savant). After purification, the compound had an RCP of >90%.

Preparation of $^{99m}$Tc-D18:

SnCl$_2$.2H$_2$O (20 mg) was dissolved in 1 mL of 1 N HCl, and 10 μL of this solution was added to 1 mL of a DTPA solution that was prepared by dissolving 10 mg of Ca Na$_2$ DTPA.2.5 H$_2$O (Fluka) in 1 mL of water. D18 (100 μg in 100 μL of 50% DMF) was mixed with 50 μL of 0.1 M, pH 9 phosphate buffer and 90 μL of $^{99m}$TcO$_4^-$ (14 mCi, Syncor), followed by 100 μL of the stannous Sn-DTPA solution. The reaction was warmed for 20 minutes at 37° C. The entire reaction was injected on a Vydac 218TP54 C18 column (4.6×250 mm, 5 um silica) and eluted at a flow rate of 1.5 mL/min using an aqueous/organic gradient of 0.1% TFA in water (A) and 0.085% TFA in acetonitrile (B). The following gradient was used: 32% to 39% B in 30 minutes, ramp up to 80% B in 2 min. The free ligand eluted at a retention time of 19 minutes. The complex, which eluted at 24 minutes, was collected into 500 μL of 50 mM citrate buffer (pH 5.3) containing 0.1% HSA and 1% Ascorbic Acid. Acetonitrile & excess TFA were removed using a Speed Vacuum (Savant) for 40 minutes. After purification, the compound had an RCP of 93%.

Transfection of 293H Cells 293H cells were transfected using the protocol described in Example 6. Transfection was done in black/clear 96-well plates (Becton Dickinson, cat. # 354640). The cells in one half of the plate (48 wells) were mock-transfected (with no DNA) and the cells in the other half of the plate were transfected with KDR cDNA. The cells were 80–90% confluent at the time of transfection and completely confluent the next day, at the time of the assay; otherwise the assay was aborted.

Preparation of Opti-MEMI Media with 0.1% HSA

Opti-MEMI was obtained from Invitrogen (cat. # 11058-021) and human serum albumin (HSA) was obtained from Sigma (cat. # A-3782). To prepare opti-MEMI media with 0.1% HSA, 0.1% w/v HSA was added to opti-MEMI, stirred at room temperature for 20 minutes, and then filter sterilized using 0.2 μM filter.

Preparation of Tc-Labeled Peptide Dilutions for the Assay

Stock solutions of Tc-labeled D10 and D18 were diluted in opti-MEMI with 0.1% HSA to provide solutions with final concentrations of 1.25, 2.5, 5.0, and 10 μCi/mL of each Tc-labeled heterodimer. A second set of dilutions was also prepared using a mixture of 40% mouse serum/60% opti-MEMI with 0.1% HSA as the diluent.

Assay to Detect the Binding of the Tc-Labeled Heterodimers

Cells were used 24 h after transfection, and to prepare the cells for the assay, they were washed 1× with 100 μL of room temperature opti-MEMI with 0.1% HSA. After washing, the opti-MEMI with 0.1% HSA was removed from the plate and replaced with 70 μL of 1.25, 2.5, 5.0, and 10 μCi/mL of Tc-labeled D10 or D18 (prepared as above with both diluent solutions). Each dilution was added to three separate wells of mock and KDR-transfected cells. After incubating at room temperature for 1 h, the plates were washed 5 times with 100 μL of cold binding buffer (opti-MEMI with 0.1% HSA). 100 μL of solubilizing solution (0.5 N NaOH) was added to each well and the plates were incubated at 37° C. for 10 minutes. The solubilizing solution in each well was mixed by pipeting up and down, and transferred to 1.2 mL tubes. Each well was washed once with 100 μL of solubilizing solution and the washes were added to the corresponding 1.2 mL tube. Each 1.2 mL tube was then transferred to a 15.7 mm×100 cm tube to be counted in an LKB Gamma Counter.

Binding of Tc-Labeled Heterodimers to KDR Transfected Cells

Figure 28:
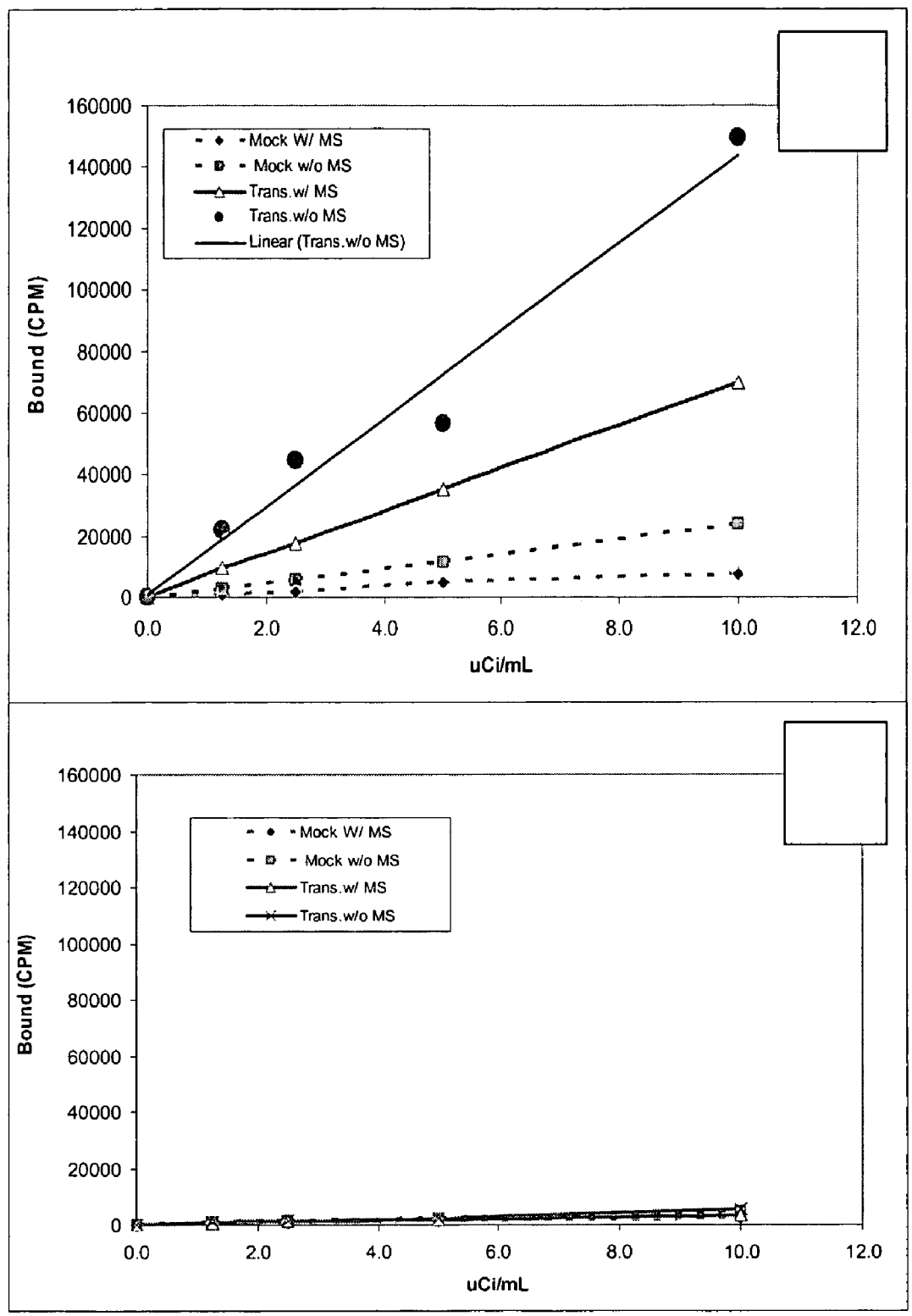
FIG. 28A is a graph depicting the binding of Tc-labeled D10 to KDR-transfected 293H cells as described in Example 18.
FIG. 28B is a graph depicting the lack of binding of Tc-labeled D 18 to KDR-transfected 293H cells as described in example 18. Mock =mock-transfected. Trans=KDR-transfected. MS=mouse serum.

The ability of Tc-labeled D10 and D18 to bind specifically to KDR was demonstrated using transiently transfected 293H cells. As shown in FIG. 28A, Tc-labeled D10 bound significantly better to KDR transfected 293H cells, as compared to mock-transfected 293H cells in both the presence and absence of 40% mouse serum, although there was some inhibition in the presence of serum. The total specific binding of this Tc-labeled heterodimer to KDR-expressing cells was much greater than that observed previously with a Tc-labeled monomeric peptide (Example 5). Tc-labeled D18, on the other hand, displayed no affinity for either mock-transfected or KDR-transfected 293H cells, confirming the specificity of D10 binding.

EXAMPLE 19

Binding of a Lu-Labeled Heterodimers to KDR-Transfected 293H Cells

In this Example, the ability of Lu-labeled D13 to bind KDR was assessed using KDR-transfected 293H cells. The results show that Lu-labeled D13 bound significantly better to KDR transfected 293H cells than to mock transfected 293H cells, and good binding was maintained in the presence of 40% mouse serum.

Synthesis of $^{177}$Lu-Labeled Peptide

Preparation of $^{177}$Lu-D13:

D13 (306 µg) was added to a 2-mL autosampler vial with a ~450 µL conical insert and dissolved in 0.01N NH$_4$OH (50 µL). To this was added 300 µL of 0.5M Ammonium Acetate containing stabilizers. A 6.8 µL aliquot of $^{177}$LuCl$_3$ in 0.05N HCl (39.3 mCi) was added, the vial was crimp-sealed, warmed for 15 min at 37° C., cooled for ~5 minutes, and 10 µL of 1% Na$_2$EDTA.2H$_2$O in H$_2$O was added. A 350 µL aliquot of the reaction mixture was injected onto a Supelco Discovery RP Amide C16 column (4 mm×250 mm×5 µm). The following HPLC conditions were used: Column temperature=37° C., Solvent A=H$_2$O containing 2 g/L NH$_4$OAc buffer, pH 7.0, Solvent B=80% ACN/20% H$_2$O, gradient 0.56/0.24 mL/min A/B at t=0 minutes to 0.47/0.33 mL/min A/B at t=30 minutes. The retention time for D13 was ~28 minutes; the retention time for $^{177}$Lu-D13 was ~29 minutes. The radioactive peak was collected into 1 mL of a buffer containing stabilizers, final pH=7.6 adjusted with Sodium Hydroxide. It was then spun down ~40 minutes using a Speed Vacuum (Savant) to remove ACN. The RCP of the isolated product was 86%.

Transfection of 293H Cells 293H cells were transfected using the protocol described in Example 6. Transfection was done in black/clear 96-well plates (Becton Dickinson, cat. # 354640). The cells in one half of the plate (48 wells) were mock-transfected (with no DNA) and the cells in the other half of the plate were transfected with KDR cDNA. The cells were 80–90% confluent at the time of transfection and completely confluent the next day, at the time of the assay; otherwise the assay was aborted.

Preparation of Opti-MEMI Media with 0.1% HSA

Opti-MEMI media with 0.1% HAS was prepared as in Example 18.

Preparation of Lu-Labeled Peptide Dilutions for the Assay

A stock solution of Lu-labeled D13 was diluted in opti-MEMI with 0.1% HSA to provide solutions with final concentrations of 1.25, 2.5, 5.0, and 10 µCi/mL of labeled heterodimer. A second set of dilutions was also prepared using a mixture of 40% mouse serum/60% opti-MEMI with 0.1% HSA as the diluent.

Assay to Detect the Binding of the Lu-Labeled Heterodimers

This was carried out as detailed in Example 18 except that Lu-labeled D13 was used in place of the Tc-labeled heterodimers.

Binding of Lu-Labeled Heterodimer to KDR Transfected Cells

Figure 29:
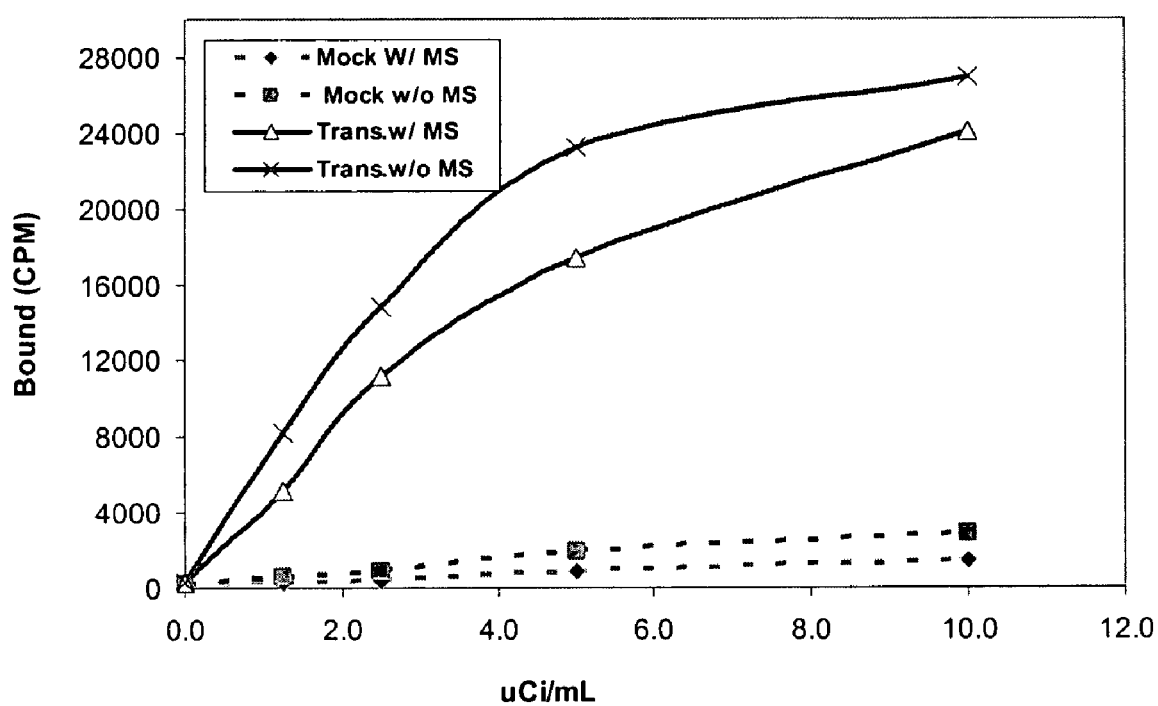
FIG. 29 is a graph depicting the binding of Lu-labeled D13 to KDR-transfected 293H cells as described in Example 19. Mock=mock-transfected. Trans=KDR-transfected. MS=mouse serum.

The ability of Lu-labeled D13 to bind specifically to KDR was demonstrated using transiently-transfected 293H cells. As shown in FIG. 29, Lu-labeled D13 bound significantly better to KDR transfected 293H cells, as compared to mock-transfected 293H cells in both the presence and absence of 40% mouse serum, although there was some binding inhibition in the presence of serum.

EXAMPLE 20

In Vitro Competition Experiments on KDR-Transfected Cells

Experiment A

The following experiment assessed the specificity of the binding of peptide-conjugated microbubbles to KDR-expressing cells.

Protocol:

293H cells were transfected with KDR cDNA. The transfected cells were incubated with a suspension of peptide-conjugated microbubbles in presence or absence of the corresponding free peptide (between 100 µM to 3 nM). Competition was also performed using a non-binding control peptide as a competing compound. At the end of the incubation, the transfected cells were rinsed three times in PBS and examined under a microscope. Binding of the conjugated bubbles was quantified and expressed as a percent of the surface covered by the targeted microbubbles.

Figure 30A:
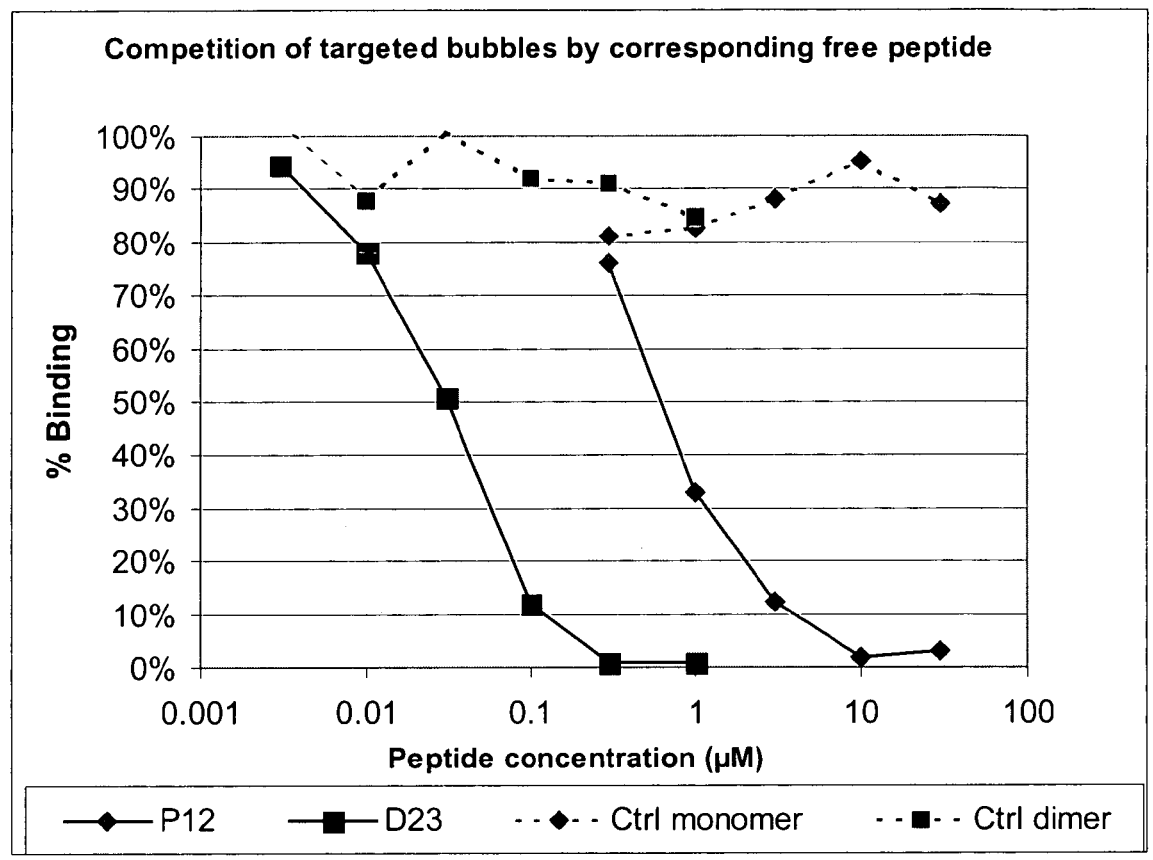
FIG. 30A is a graph illustrating the specificity of binding of peptide-conjugated microbubbles to KDR-expressing cells.

Results:

Microbubbles conjugated to a KDR-binding dimer, D23, or monomer, P12, were competed off by the corresponding free KDR-specific peptide whereas the presence of control peptide had no effect. Representative curves obtained by plotting the fraction of residual binding as a function of the competitor concentration are shown in FIG. 30A.

Experiment B

The following experiment compares the binding efficiency of monomers and dimers conjugated to microbubbles in the KDR-transfected cell assay.

Protocol:

293H cells were transfected with KDR cDNA. The transfected cells were incubated with a suspension of microbubbles conjugated to different peptides (monomers or dimers) in the presence or absence of increasing concentrations of free dimer (at 1000, 300, 100, 30, 10, 3, 1 nM). At the end of the incubation, the transfected cells were rinsed three times in PBS and examined under a microscope. Binding of the conjugated bubbles was quantified and expressed as a percentage of the surface covered by the targeted microbubbles.

Figure 30B:
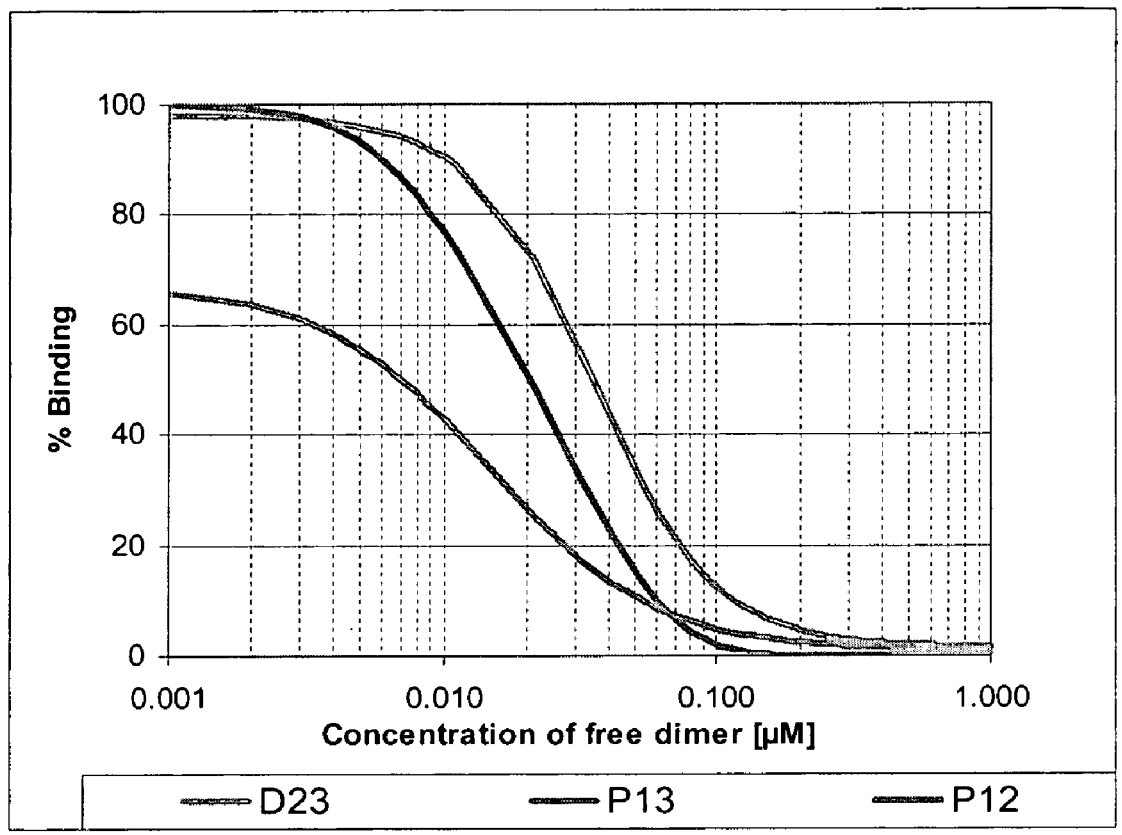
FIG. 30B is graph showing the binding efficiency of monomers and dimers conjugated to microbubbles on KDR-expressing cells.

Results:

Microbubbles conjugated to a KDR-specific dimer, D23, were more resistant to competition and less easily displaced by the corresponding free dimeric peptide than microbubbles conjugated to KDR-specific monomers P13 and P12. Examplary curves obtained by plotting the fraction of residual binding as a function of the competitor concentration are shown in FIG. 30B.

Experiment C

In Vitro Binding of Heteromultimers and Dimers Compared to Multimeric Monomers

The following experiment compares the binding efficiency of mixed monomers, dimers and monomers conjugated to microbubbles in the KDR-transfected cell assay.

Protocol:

Microbubbles were conjugated to either a dimer (D23) or one of two different peptide monomers (P6, P12). A fourth conjugation reaction was performed using equal quantities of each monomer and the same total peptide load (e.g. a "mixed monomer"). 293H cells were transfected with KDR cDNA. The transfected cells were incubated with the same number of targeted microbubble and in presence of 50% human serum. At the end of the incubation, the transfected cells were rinsed three times in PBS and examined under a microscope. Binding of the conjugated bubbles was quantified and expressed as percent of surface covered by the targeted microbubbles.

Figure 30C:
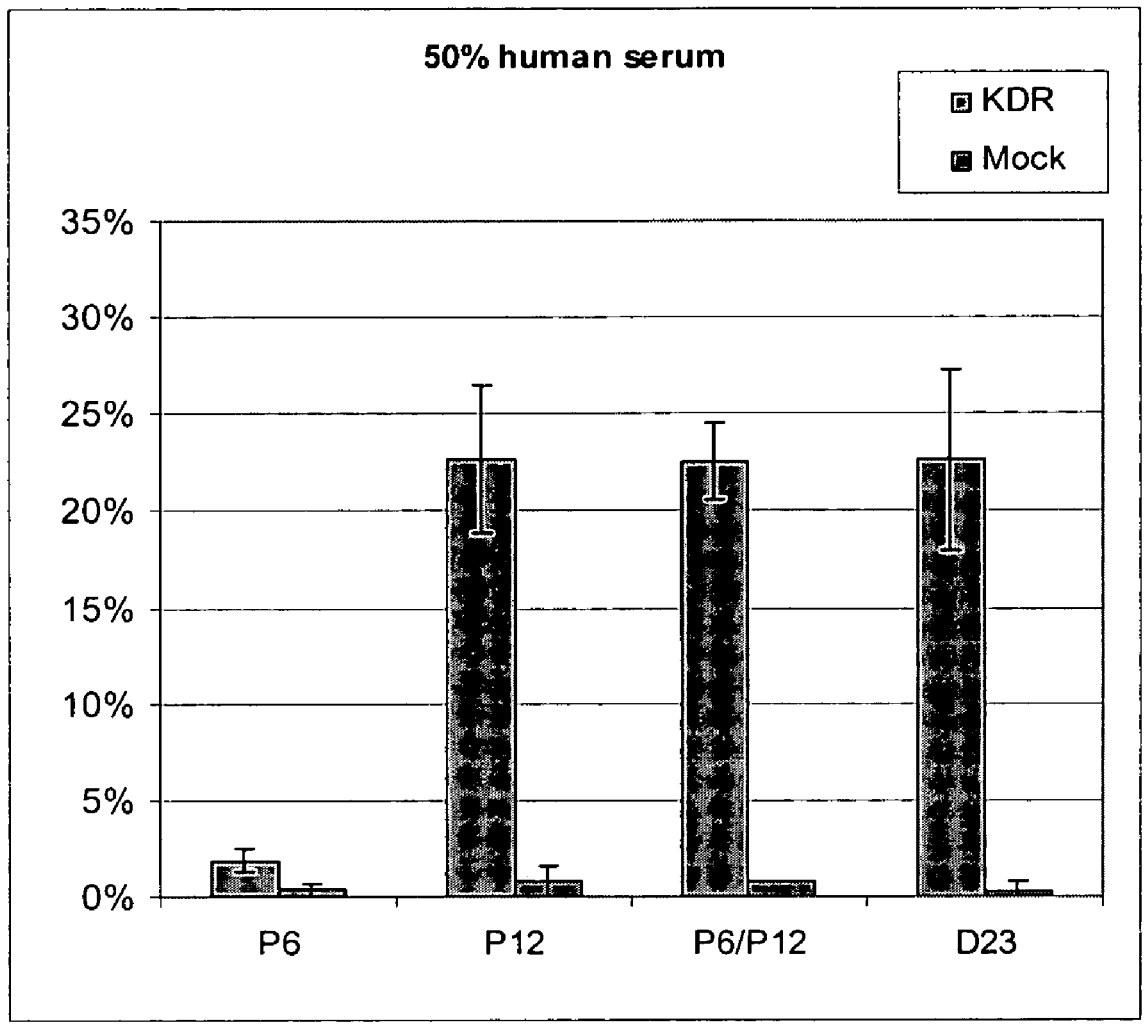
FIG. 30C is graph showing the binding efficiency of mixed monomers, dimers and monomers conjugated to microbubbles on KDR-expressing cells.

Results:

As shown in FIG. 30C, microbubbles conjugated with P6 bound poorly compared with microbubbles conjugated with P12 or dimer D23. Surprisingly, microbubbles conjugated to D23 bound equivalently to those conjugated to P12 although D23 has half the P12 load. Moreover, the "mixed monomer" conjugated microbubbles, which also have half the P12 load, bound as well as microbubbles conjugated with P12 or D23. These results show the increased binding capacity of heteromultimers.

EXAMPLE 21

Radiotherapy with a Lu-Labeled Heterodimers in Tumor-Bearing Mice.

In this Example, the ability of Lu-labeled D13 to inhibit the growth of PC3 cell tumors implanted in nude mice is demonstrated.

Synthesis of $^{177}$Lu-Labeled D13

$^{177}$Lu-labeled D13 was prepared as described in Example 19.

Animal Model

PC3 cells from ATCC, grown as recommended by the supplier, were injected subcutaneously between the shoulder blades of nude mice. When their tumors reached 100–400 mm$^3$, twelve mice were injected i.v. with 500 microcuries of Lu-labeled D13 and their growth monitored for an additional 18 days. Mice were sacrificed if they lost 20% or more of their body weight or their tumors exceeded 2000 mm3. Tumor growth in the treated mice was compared with the average tumor growth in 37 untreated nude mice implanted with PC3 tumors.

Results

Figure 31:
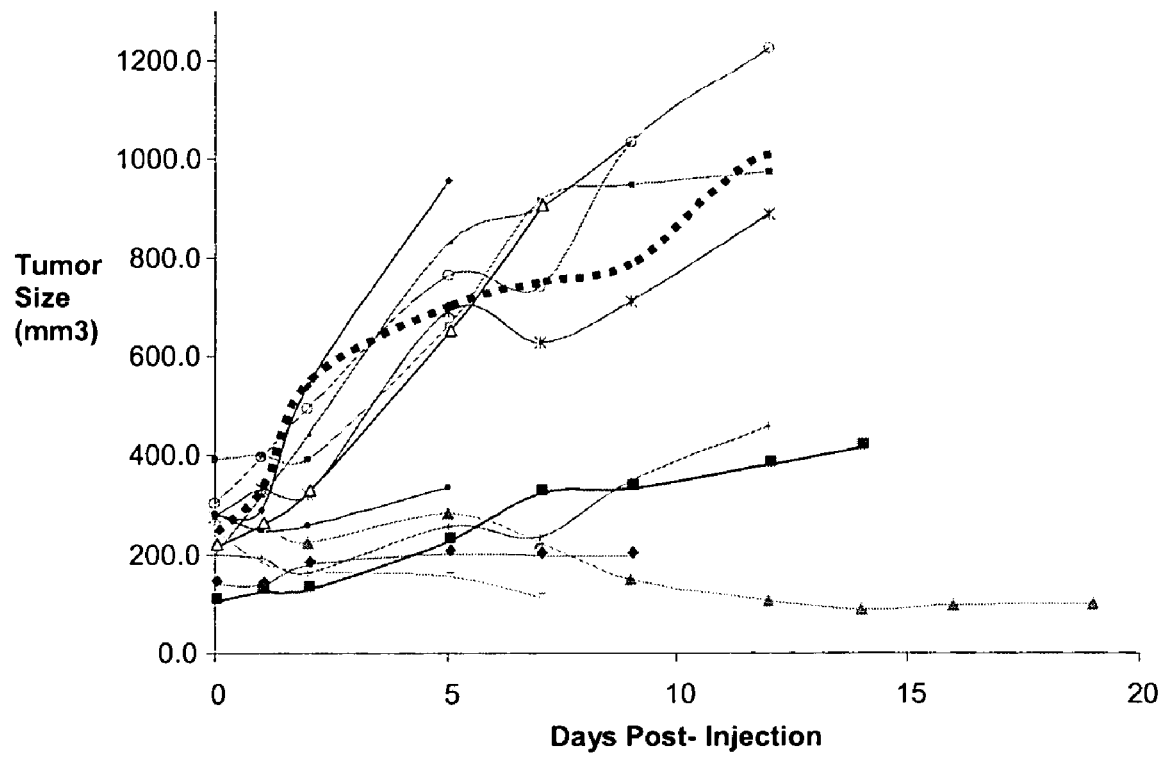
FIG. 31 is a graph summarizing the results of a radiotherapy study with D13 conducted in nude mice implanted with PC3 tumors. Each plotted line represents the growth over time for an individual tumor in a treated mouse, except for the heavy dashed line, which represents the average tumor growth in a set of untreated mice, as described in Example 21.

In 6 of the 12 treated mice in the study, the tumors experienced a significant or complete growth delay (FIG. 31) relative to untreated tumor mice, indicating that D13 was effective in slowing PC3 tumor growth under the conditions employed

EXAMPLE 22

Cell Based Assay for Binding of KDR/VEGF Complex Binders

In this experiment the ability of a KDR/VEGF complex-binding peptide to selectively bind to the KDR/VEGF complex is demonstrated.

Reagent Preparation

The reagents for this assay were prepared as described in Example 5 except where noted.

Preparation of Peptide-$^{125}$I-Streptavidin Complex Solution

Biotinylated peptides P30-XB, P31-XB, P32-XB and biotinylated non-binding control peptide were used to prepare 1.25 μM stock solutions in 50% DMSO. A 33.33 nM stock solution of $^{125}$I-streptavidin was purchased from Amersham. A stock solution of 13.33 nM I-125 streptavidin/100 nM VEGF was prepared by mixing 850 ml of I-125 streptavidin with 22 μl of 10 μM VEGF and 1275 μl of M199 media. Another stock solution was prepared in the same manner, but lacking VEGF. To prepare 13.33 nM peptide-$^{125}$I-streptavidin complex solution±VEGF, 500 μl of the $^{125}$-streptavidin (with & without VEGF) stock solutions (prepared in last step) were mixed with 24 μl of 1.25 μM peptide solution of P30-XB, P31-XB, P32-XB, or control peptide. The mixtures were incubated on a rotator at 4° C. for 60 minutes, followed by addition of 50 μl of soft release avidin-sepharose (50% slurry in ddH$_2$O) to remove excess peptides and another incubation for 30 minutes on a rotator at 4° C. Finally, the soft release avidin-sepharose was pelleted by centrifuging at 12,000 rpm for 5 minutes at room temperature, and the resulting supernatants were used for the assays.

TABLE 9

| | Biotinylated Peptides | |
|---|---|---|
| Reference Number | Structure or Sequence | SEQ ID NO: |
| P30 | AGPGPCKGYMPHQCWYMGTGGGK | 31 |
| P30-XB | Ac-AGPGPCKGYMPHQCWYMGTGGGK(Biotin-JJ)-NH$_2$ | |
| P31 | AGMPWCVEKDHWDCWWWGTGGGK | 32 |
| P31-XB | Ac-AGMPWCVEKDHWDCWWWGTGGGK(Biotin-JJ)-NH$_2$ | |
| P32 | AGYGPCKNMPPWMCWHEGTGGGK | 33 |
| P32-XB | Ac-AGYGPCKNMPPWMCWHEGTGGGK(Biotin-JJ)-NH$_2$ | |

Binding of Peptide/Neutravidin HRP to KDR-Transfected Cells

Figure 32:
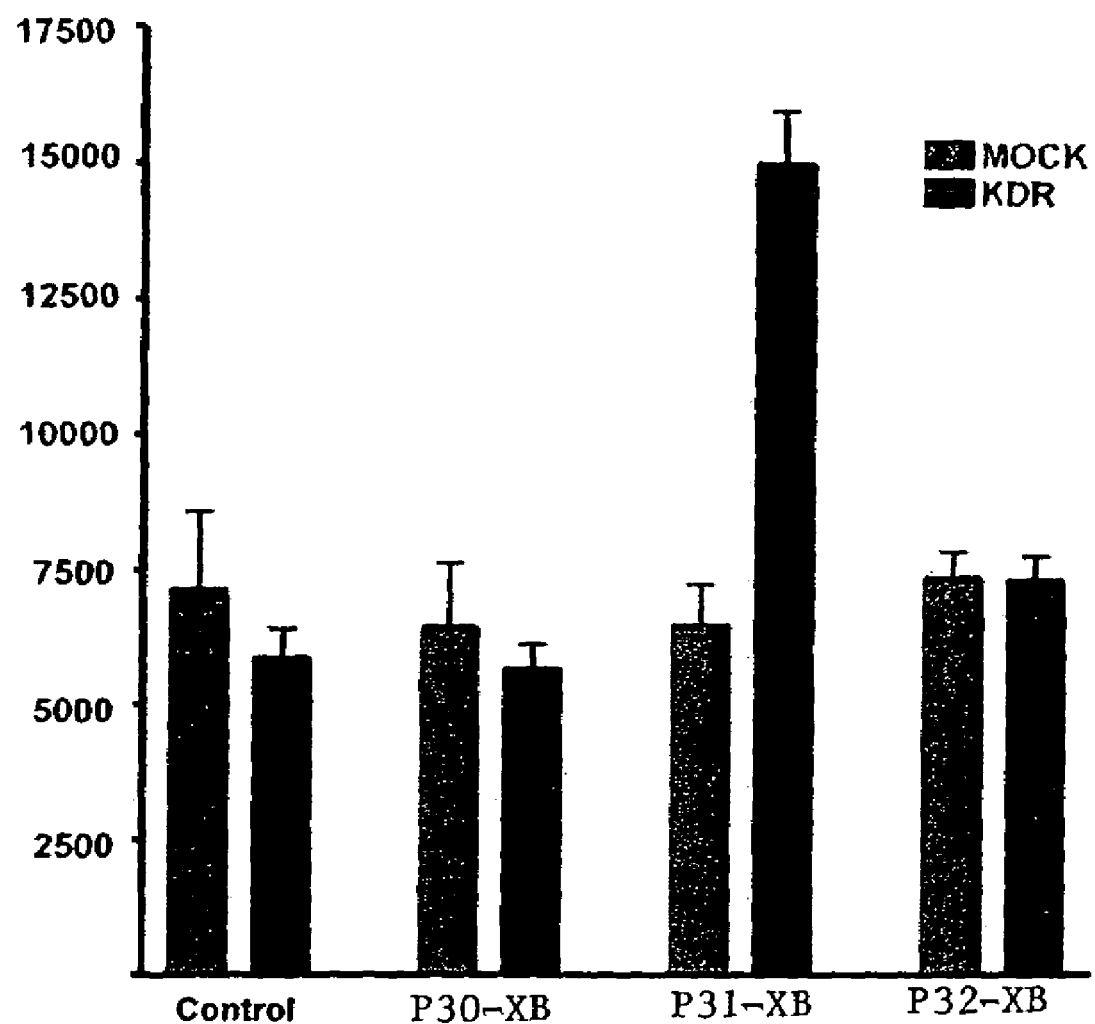
FIG. 32 is a graph showing the total binding of complexes of control peptide and the test peptides (P30-XB, P31-XB, P32-XB) with $^{125}$I-streptavidin (in the presence of VEGF) to mock-transfected and KDR-transfected cells. Only the complex containing P30-XB showed specific binding (KDR-mock).

In this assay, complexes of control peptide and the test peptides (P30-XB, P31-XB, P32-XB) with $^{125}$I-streptavidin in the presence or absence of VEGF (prepared as above) were tested for their ability to bind 293H cells that were transiently-transfected with KDR. The complex of P30-XB with $^{125}$I-streptavidin specifically bound to KDR-transfected 293H cells as compared to mock transfected cells in the presence of VEGF (FIG. 32A), but not when VEGF was omitted (FIG. 32B). P30-XB was also the best KDR/VEGF complex binder among the peptides tested using fluorescence polarization and SPR (BiaCore) assays. See Table 9, U.S. Ser. No. 60/360,851, U.S. Ser. No. 60/440,441, and copending U.S. Ser. No. 10/382,082, entitled "KDR and VEGF/KDR Binding Peptides and Their Use in Diagnosis and Therapy," filed on the same date as the instant application and incorporated by reference herein in its entirety. This example shows that peptide (P30-XB) can specifically bind to The KDR/VEGF complex present on the cell surface. Therefore, it may possibly be used in targeting the KDR/VEGF complex in vitro and in vivo for diagnostic or therapeutic purposes. Since the KDR/VEGF binding peptide only detects the functional and active KDR receptor and not all the KDR present on cell surface, it may be useful in detecting and/or treating active angiogenesis in tumors, metastasis, diabetic retinopathy, psoriasis, and arthropathies. Furthermore, these peptides, as well as other peptides which bind KDR/VEGF complex may advantageously be included in heteromultimers of the invention.

EXAMPLE 23

The following experiment assessed the ability of heterodimers D24 and D26 to block the VEGF-induced migration of HUVECs in culture and demonstrated that the added glycosylation and/or distinct spacer structure used in D26 enhanced its potency.

Protocol:

Serum-starved HUVECs were placed, 100,000 cells per well, into the upper chambers of BD fibronectin-coated FluoroBlok 24-well insert plates. Basal medium, with or without VEGF (10 ng/mL) in the presence or absence of D24 or D26, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. The VEGF-induced migration was calculated for each experimental condition by subtracting the amount of migration that occurred when only basal medium was added to the lower chamber of the wells.

Figure 33:
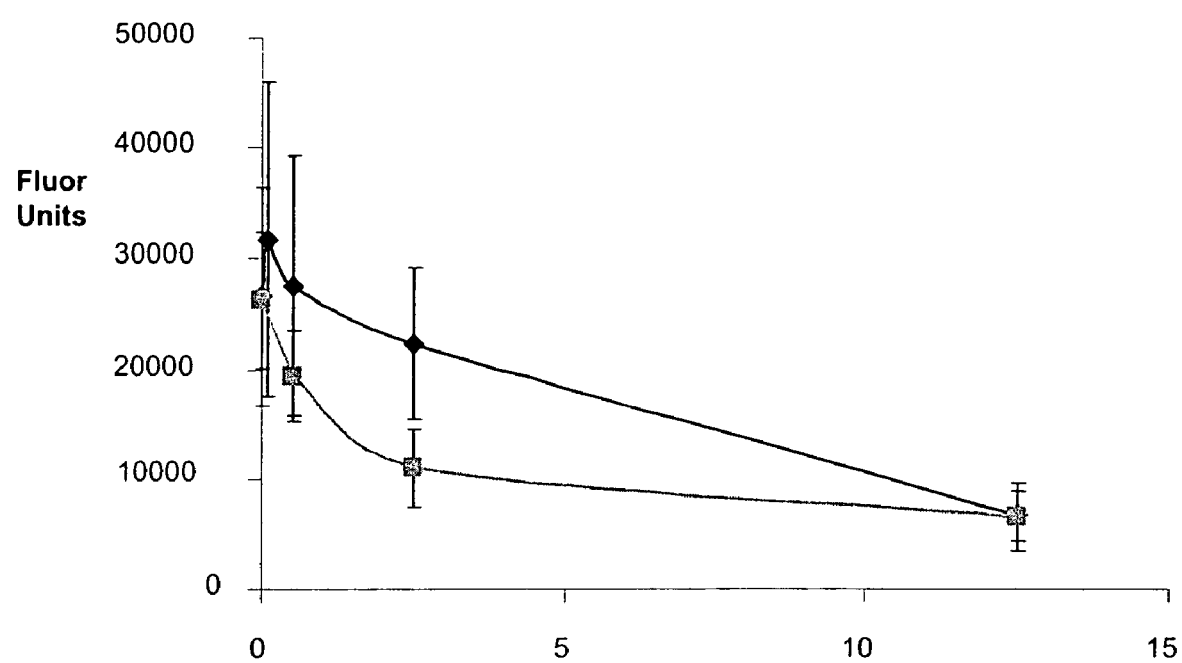
FIG. 33 is a graph showing that D26 (squares) with its glycosylation and modified spacer is able to block VEGF-stimulated migration even more potently than D24 (diamonds), which lacks those chemical modifications.

Results:

VEGF induced a large increase in endothelial cell migration in the assay, which was potently blocked by both D24 and D26 (FIG. 33). D26 was ten-fold more potent than D24 ($IC_{50}$ 0.5 nM and 5 nM respectively), indicating that the glycosylation of D26 and/or its distinct spacer properties has enhanced its ability to bind KDR and block the effects of VEGF.

EXAMPLE 24

The following experiment assessed the ability of TK-1 (structure provided below), a multimeric construct of the peptide TKPPR (which binds to NP-1, a VEGF receptor which enhances the effects of VEGF mediated by KDR), to enhance the inhibition of the VEGF-induced migration of HUVECs in culture produced by D6.

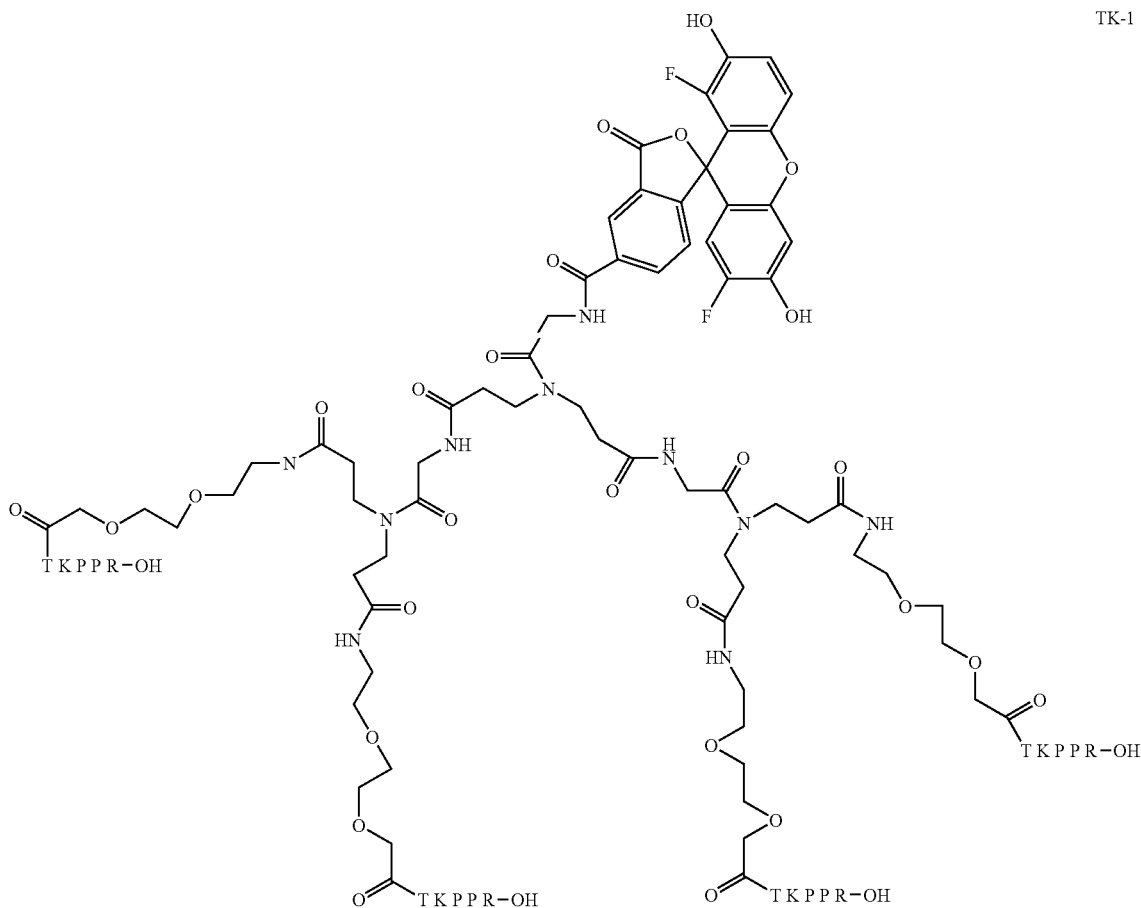

5CF-Gly-N{[CH₂CH₂C(=O)-Gly-N(CH₂CH₂C(=O)-Adoa-Thr-Lys-Pro-Pro-Arg-OH]₂}₂ where Adoa=3,6-dioxa-8-aminooctanoyl, 5CF=5-carboxyfluoresceinyl

Protocol:

Serum-starved HUVECs were placed, 100,000 cells per well, into the upper chambers of BD fibronectin-coated FluoroBlok 24-well insert plates. Basal medium, with or without VEGF (10 ng/mL) in the presence or absence of varying concentrations of D6, or varying concentrations of D6 in combination with a constant 100 nM TK-1 (synthesized as described in WO 01/91805 A2) was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. VEGF-induced migration was calculated for each experimental conditions by subtracting the amount of migration observed in the absence of VEGF.

Figure 34:
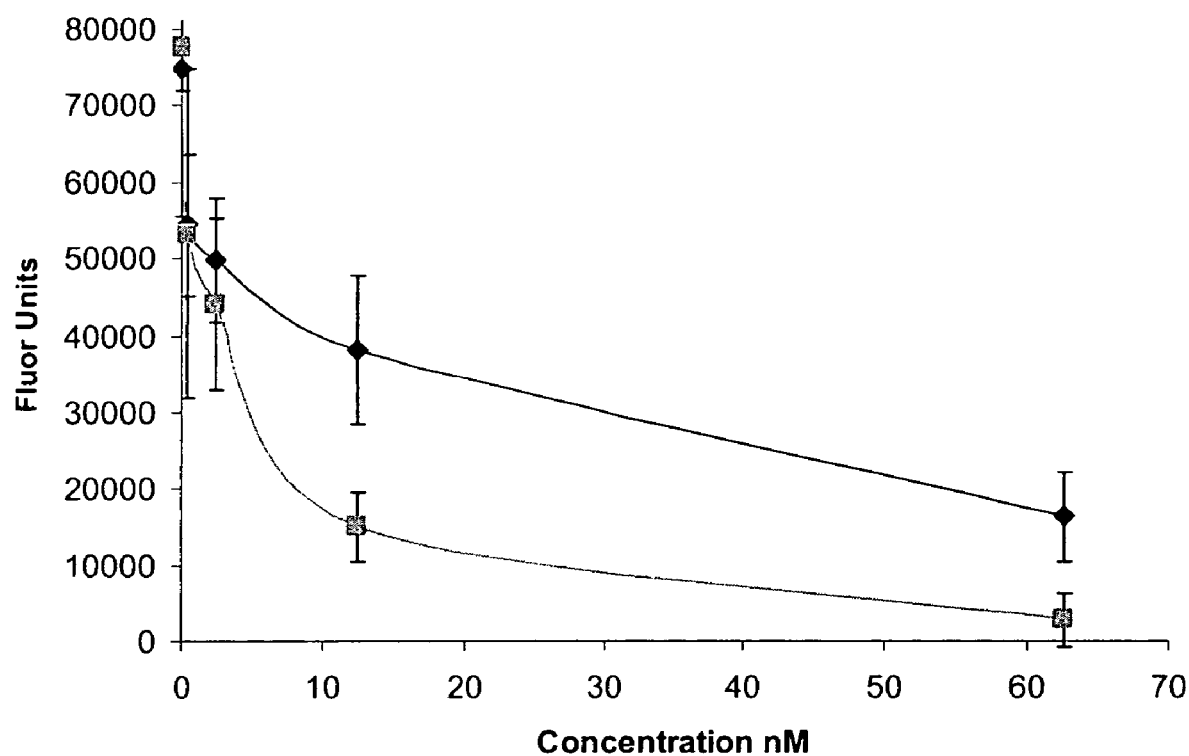
FIG. 34 is a graph showing that TK-1 enhances the potency of D6 in blocking the biological effects of VEGF in a migration assay with cultured HUVECs. Diamonds: D6 alone at the indicated concentrations. Squares: D6 at the indicated concentrations plus 100 nM TK-1 (constant).

Results:

VEGF induced a large increase in endothelial cell migration in the assay, which was potently blocked by D6 ($IC_{50}$ about 12.5 nM), but not by 100 nM TK-1 alone (FIG. 34). Surprisingly however, TK-1 was able to enhance the potency of D6 by about ten-fold when used in the assay simultaneously with D6 ($IC_{50}$ about 2.5 nM). This indicates that compounds containing the TKPPR sequence (or analogs) found in TK-1 can be used to enhance the potency of certain compounds such as D6 which compete with VEGF for binding to KDR. In addition, a heteromultimer containing the peptide sequences found in D6 (or similar) as well as the TKPPR sequence (or analogs), in one or more repetitions, would likely possess enhanced activity in this assay. (See U.S. Ser. No. 09/871,974 for details on the preparation of TKPPR constructs, which is herein incorporated by reference).

EXAMPLE 25

Identification of Fragments of P13-XB with KDR Binding Activity

The following experiment showed that fragments of P13-XB can maintain significant KDR binding activity.

Protocol:

293H cells were transfected with the KDR cDNA or mock-transfected by standard techniques described in Example 6. Streptavidin-HRP complexes containing P12-XB were prepared as in Example 6. Binding of the streptavidin-HRP complexes to the cells was carried out as in Example 6 with a complex concentration of 5.5 nM in the presence of 0 to 250 nM or 0 to 1000 nM of the following competing peptides: P13-XB, F1, F2, and F3. After determining the specific binding under each experimental condition, the $IC_{50}$ for each peptide was determined (where possible).

Results:

As shown in Table 9, F1, composed of just the Asp-Trp-Tyr-Tyr binding motif that is also shared with P12-XB along with the non-targeted Gly-Gly-Gly-Lys sequence that was added to most monomeric peptides synthesized based on phage display data, was the smallest fragment able to block P12-XB streptavidin-HRP complex binding with an $IC_{50}$ below one micromolar. Surprisingly, a larger fragment derived from P13-XB, F2, failed to significantly inhibit complex binding at one micromolar. However, when a solubilising motif, $(Gly-Arg-Gly)_3$ was added to the latter peptide to make F3, it was able to compete with the complex for binding with an $IC_{50}$ of 175 nM, confirming that certain fragments of P13-XB containing the Asp-Trp-Tyr-Tyr motif retain KDR-binding activity. These fragments (or other fragments of the binding polypeptides disclosed herein), which retain the ability to bind the target, may be utilized instead of the full-length peptide in heteromultimers of the invention.

TABLE 9

Fragments of P13-XB in a displacement assay competing with a complex composed of P12-XB and streptavidin-HRP for binding to KDR-expressing cells.

| Ref Number | Sequence/Structure | $IC_{50}$, nM | SEQ ID NO: |
|---|---|---|---|
| P13-XB | Ac-AQDWYYDEILSMADQLRHAFLSGG-GGGK-(Biotin-JJ-)-NH$_2$ | 93 | — |
| F1 | Ac-DWYYGGGK-NH$_2$ | 850 | 31 |
| F2 | Ac-AQDWYYDEIL-NH$_2$ | >1000 | 32 |
| F3 | Ac-AQDWYYDEILJGRGRGGRGG-NH$_2$ | 175 | 33 |

EXAMPLE 26

Heterodimers Targeting Two Epitopes on a Single Target Molecule Results in Superior Binding to a Homodimers that Binds One of the Two Epitopes on the Target Molecule.

The following experiment provides further evidence that heterodimeric constructs are superior to homodimers in their ability to block the biological effects of a peptide growth factor or cytokine.

Protocol:

Serum-starved HUVECs were placed, 100,000 cells per well, into the upper chambers of BD fibronectin-coated FluoroBlok 24-well insert plates. Basal medium, containing either nothing or VEGF in the presence or absence of increasing concentrations of homodimeric D8 or heterodimeric D17, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader.

Figure 35:
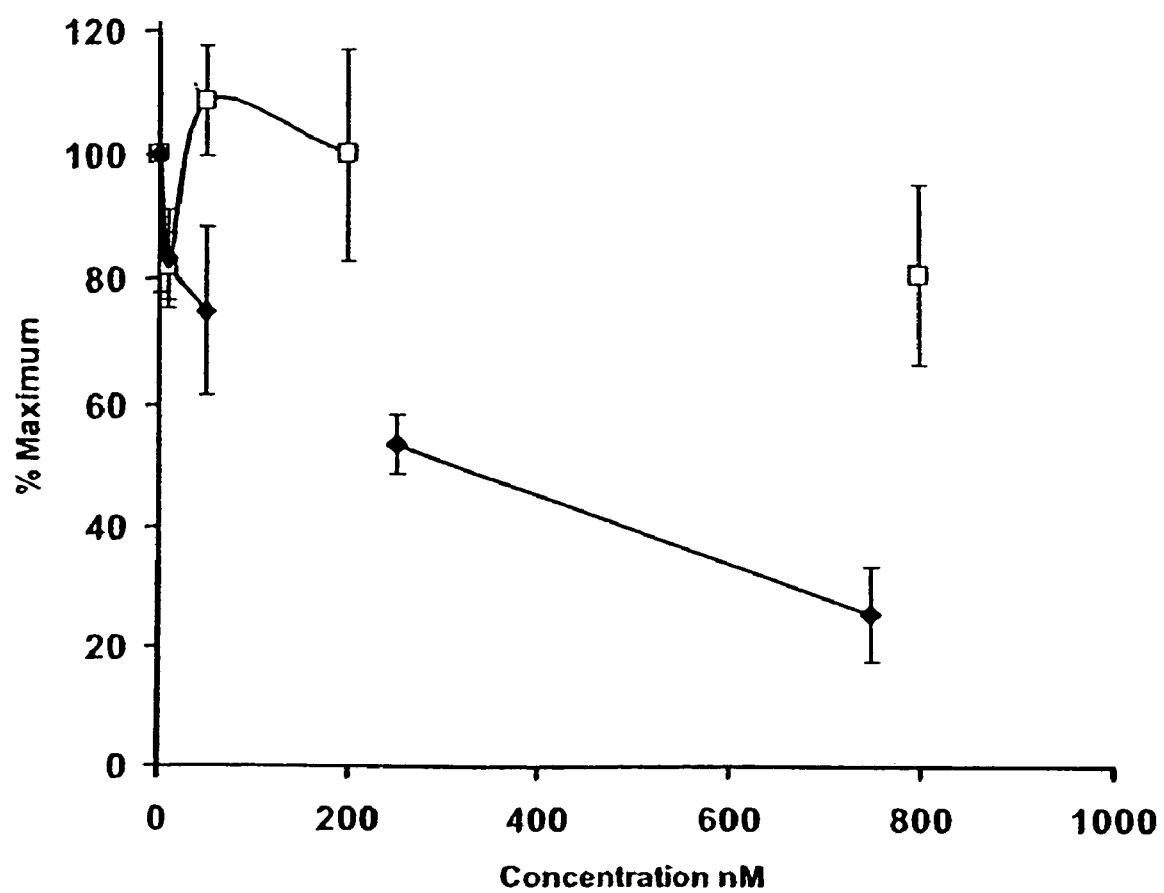
FIG. 35 is a graph showing that homodimeric D8 (squares) is less able than heterodimeric D17 (diamonds) to block the effects of VEGF in the migration assay as carried out in Example 26.

Results:

VEGF induced a large increase in endothelial cell migration in the assay, which was potently blocked by D17 but not D8 (FIG. 35). D17 blocked VEGF-induced migration with an $IC_{50}$ of about 250 nM while D8 had no significant effect on migration even at 800 nM. This is in spite of the fact that D8 used the full targeting sequence found inp 13-XB while D17 contained a truncated version of the P13-XB sequence (as seen in F3) with a lower affinity for KDR (as demonstrated in Example 24). Thus a heterodimer with the capability of binding to two separate epitopes on the same target molecule can be more effective at blocking ligand binding to the target molecule than a homodimer containing the same or even more potent targeting sequences.

EXAMPLE 27

Preparation of Cyclic Peptides in which the Disulfide Bond is Replaced by an Amide Bond Disulfide bond substitution analogs of P12-G (P12 with non-target GGGK sequence) where the Cys residues at position 6 and 13 are replaced by a pair of amino acids, one with a carboxy-bearing side-chain (either Glu or Asp) and the other with an amino-bearing side chain [(Lys or Dpr (2,3-diaminopropanoic acid)] were prepared. The cycle, encompassing the same sequence positions as those included in P12-G (made by formation of the disulfide bond) was made by condensation of the side-chain amino and side-chain acid moieties, resulting in a lactam ring which bridges the residues 6–13 as does the disulfide bond of P12-G.

TABLE 10

Examples of the substitutions made for Cys$^6$ and Cys$^{13}$ of P12-G in lactam analogs.
Lactam Analogs of P12

| Ref No. | Sequence or Structure | SEQ ID NO | Position 6 | Position 13 | Difference in Ring Size vs P12 |
|---|---|---|---|---|---|
| P12-G (parent seq) | AGPTWCEDDWYYCWLFGTGGGK | 29 | Cys | Cys | — |
| P33 | AGPTWEEDDWYYKWLFGTGGGK | 34 | Glu | Lys | — |
| P33-L | Ac-AGPTWEEDDWYYKWLFGTGGGK-NH$_2$ (6–13 lactam) | | Glu | Lys | 4 |
| P34 | AGPTWKEDDWYYEWLFGTGGGK | 35 | Lys | Glu | — |
| P34-L | Ac-AGPTWKEDDWYYEWLFGTGGGK-NH$_2$ (6–13 lactam) | | Lys | Glu | 4 |
| P35 | AGPTW-Dpr-EDDWYYDWLFGTGGGK-NH$_2$ | 36 | Dpr | Asp | — |
| P35-L | Ac-AGPTW-Dpr-EDDWYYDWLFGTGGGK-NH$_2$ (6–13 lactam) | | Dpr | Asp | 0 |
| P36 | AGPTWDEDDWYY-Dpr-WLFGTGGGK | 37 | Asp | Dpr | — |
| P36-L | Ac-AGPTWDEDDWYY-Dpr-WLFGTGGGK-NH$_2$ (6–13 lactam) | | Asp | Dpr | 0 |
| P37 | AGPTWDEDDWYYKWLFGTGGGK | 38 | Asp | Lys | — |
| P37-L | Ac-AGPTWDEDDWYYKWLFGTGGGK-NH$_2$ (6–13 lactam) | | Asp | Lys | 3 |

Representative Synthesis of Cyclic Lactam Peptides—P33-L

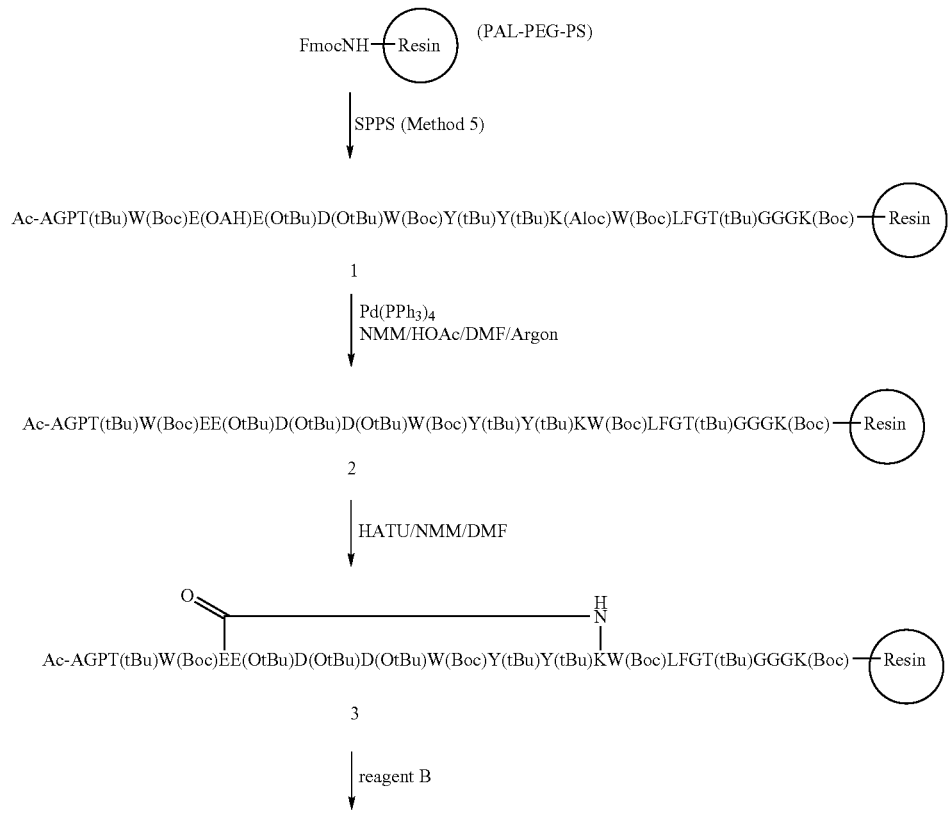

-continued

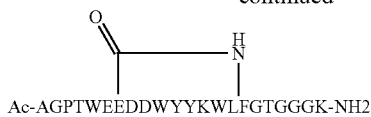
Ac-AGPTWEEDDWYYKWLFGTGGGK-NH2

4

Synthesis of Resin Bound Peptide 1

Synthesis of 1 was carried out using Method 5 on a 0.25 mmol scale. The peptide resin 1 was washed and dried for further derivatization manually.

Synthesis of 4 P33-L

To 1 (240 mg, 0.06 mmol) was added NMM (N-methyl morpholine)/HOAc/DMF 1/2/10 (v/v/v) (65 mL). Palladium tris-triphenylphosphine [Pd(PPh$_3$)$_4$, 554.4 mg, 0.48 mmol] was added and the resin was shaken for 20 h shielded from light. The resin was filtered and washed with a solution of sodium diethyldithiocarbamate (0.5 g)/DIEA (0.5 ml)/DMF (100 mL), and finally with DMF (3×70 mL). This treatment served to expose only the carboxy and amino groups of Glu6 and Lys 13 which are required for the lactam forming reaction. The on-resin cyclization of 2 was carried out using HATU (114 mg, 0.3 mmol), NMM (66 µL, 0.6 mmol) and DMF (10 mL) for 3 h. The completion of the cyclization was monitored by Kaiser test. The peptide was cleaved from the peptide resin 3 using reagent B for 4 h. The resin was filtered and the filtrate was evaporated to a paste. The crude peptide was precipitated in ether and washed twice with ether. The cyclic peptide was purified by preparative reverse phase linear gradient HPLC using a Waters-YMC C-18 column (250 mm×30 mm i.d.) with CH$_3$CN into H$_2$O (both with 0.1% TFA) as the eluent. Lyophilization of the product-containing fractions afforded 8 mg of (P33-L). P34-L, P35-L, P36-L and P37-L were prepared similarly.

Replacement of the Disulfide Bridge of P12-G while Retaining KDR-Binding Activity The following experiment demonstrated that the lactam P34-L, which replaced the chemically reactive disulfide bridge of P12-G maintained significant KDR binding activity.

Protocol:

293H cells were transfected with the KDR cDNA or mock-transfected by standard techniques described in Example 6. Streptavidin-HRP complexes containing P12-XB were prepared as in Example 6. Binding of the streptavidin-HRP complexes to the cells was carried out as in Example 6 with a complex concentration of 5.5 nM in the presence of 0 to 250 nM P12-G, or P34-L. After determining the specific binding under each experimental condition, the IC$_{50}$ for each peptide was determined.

Results:

As shown in Table 11, P34-L, containing a lactam disulfide bridge replacement, was still able to compete with P12-XB-streptavidin-HRP complexes for binding to KDR although some affinity was lost (IC$_{50}$ 108 nM versus 13 nM for P12-G). These lactam peptides (or similarly prepared lactam analogs of binding polypeptides disclosed herein) may be utilized instead of the disulfide bridge-containing peptides in heteromultimers of the invention.

TABLE 11

P12-G and P34-L (disulfide bridge replacement analog) in a displacement assay competing with a complex composed of P12-XB and streptavidin-HRP for binding to KDR-expressing cells.

| Fragment (Ref Number) | IC$_{50}$, nM |
|---|---|
| P12-G | 13 |
| P34-L | 108 |

EXAMPLE 28

Measurement of Binding of Peptide Dimers to cMet

Using a BIAcore machine, the binding constant was determined for the dimer D28 binding to immobilized cMet-Fc.

Procedure

Three densities of cMet-Fc (R&D Systems) were cross-linked to the dextran surface of a CM5 sensor chip by the standard amine coupling procedure (3 µM solution diluted 1:100, 1:50, or 1:20 with 50 mM acetate, pH 5.5). Flow cell 1 was activated and then blocked to serve as a reference subtraction.

Final Immobilization Levels Achieved:
R$_L$ Fc 2 cMet-Fc=2582
R$_L$ FC 3 cMet-Fc=5048
R$_L$ Fc 4 cMet-Fc=9721

Experiments were performed in PBST buffer (5.5 mM phosphate, pH 7.65, 0.15 M NaCl)+0.05% (v/v) Tween-20). Peptide dimers were dissolved in deionized H$_{20}$ to 1 mg/mL solutions. Dimers were diluted to 50 nM in PBS. Serial dilutions were performed to produce 25, 12.5, 6.25, and 3.125 nM solutions. All samples were injected in duplicate. For association, dimers were injected at 30 µL/minute for 3 minutes using the kinject program. Following a 10-minute dissociation, any remaining peptide was stripped from the cMet surface with two quickinjects of 4M MgCl$_2$ for 2 minutes at 50 µL/minute. Sensorgrams were analyzed using BIAevaluation software 3.1.

Kd value of 0.79 nM was obtained for D28 (heterodimer of P26-A and P27-X), which was significantly better than KD value of either heterodimer alone (see SEQ ID NO:369 (880 nM) and SEQ ID NO:370 (220 nM) as shown in the Table 8 of U.S. Ser. No. 60/451,588, entitled "Peptides that specifically bind HGF receptor (cMet) and uses thereof," filed on the same date as the instant application and incorporated by reference herein in its entirety.

EXAMPLE 29

In Vitro Cell Proliferation Assay

Figure 36:
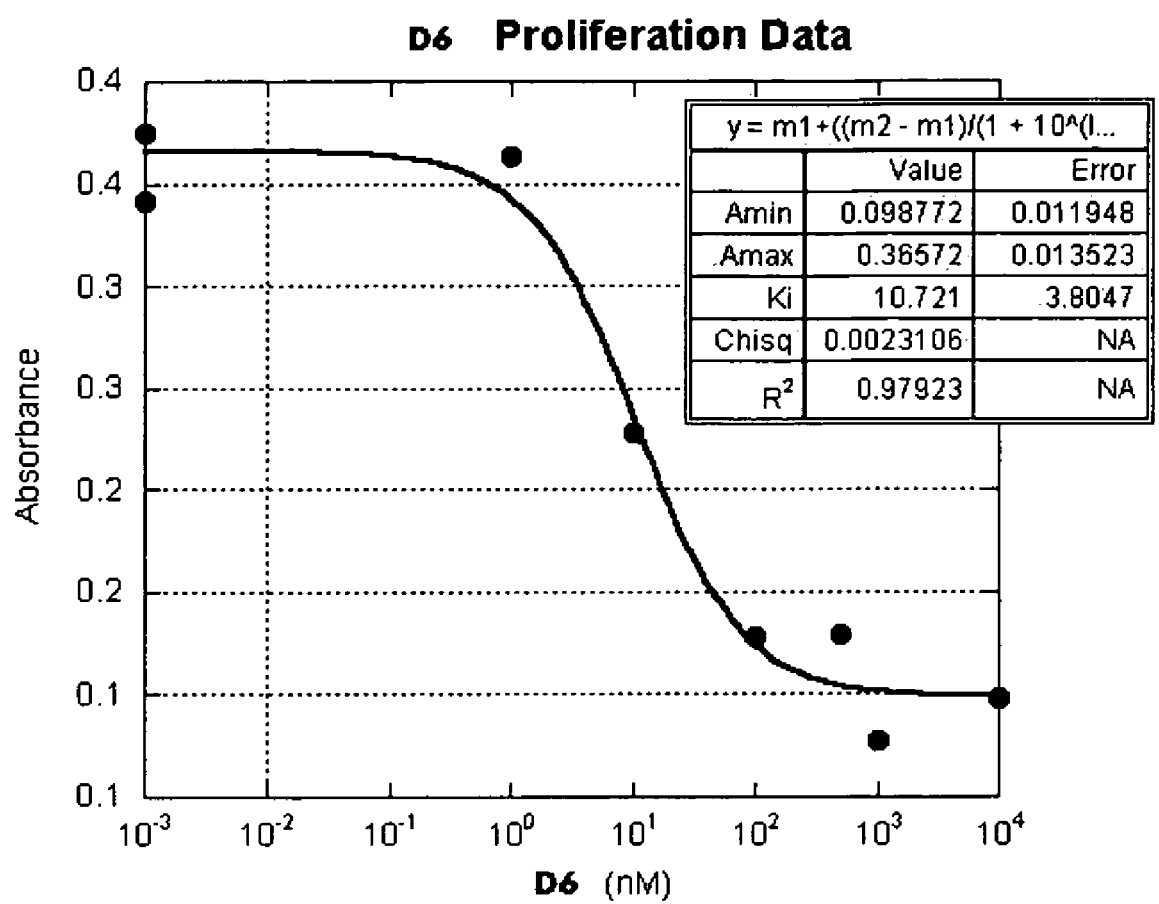
FIG. 36 is a graph showing cell proliferation data for D6 as described in Example 31 below.

Microvascular endothelial cells (MVECs, Cascade Biologics, Portland, Oreg.) were used to assess the in vitro efficacy of D6 and related analogues for their ability to inhibit VEGF-stimulated proliferation. MVECs (passage 2) were grown to 90% confluency, trypsinized and plated in gelatin-coated 96-well microtiter plates at a density of 4–8×10$^3$ cells/well. Sixteen to 24 hours after plating, the cells were washed one time (200 μL/well) with media devoid of fetal bovine serum but containing 0.1% bovine serum albumin (BSA). Fresh BSA-containing media was added to each well and the cells were incubated for an additional 24 hours. After this 24 hour period of starvation, fresh BSA-containing media with or without D6 or other test substances was added and the cells were incubated for an additional 48 hours at 37° C. The media was removed and fresh BSA-containing media was added with or without BrdU and the cells were incubated for an additional 24 hours prior to determining the level of incorporation exactly as described by the manufacturer (Oncogene Cat# QIA58). Results are shown in FIG. 36.

EXAMPLE 30

Blocking VEGF-Enhanced Peritoneal Vascular Permeability with a Heterodimeric Peptide.

In this Example, the ability of heterodimer D25 to inhibit the enhanced vascular permeability caused by VEGF injected into the peritoneum of nude mice is demonstrated.

Protocol

Male balb/c nu/nu mice were injected i.p. with 2 mL vehicle (1% bovine serum albumin in 95% saline/5% DMSO), vehicle+1.2 nM VEGF$_{165}$, or vehicle+1.2 nM VEGF$_{165}$+20 μM D25. Immediately after, the mice were injected with Evan's Blue Dye (0.5% in saline, 4 mL/kg) i.v. via their tail veins. After 60 min mice were sacrificed by CO$_2$ asphyxiation and the peritoneal fluid was retrieved. After centrifuging the samples briefly, the absorbance at 590 nm was measured for each.

Results

Figure 39:
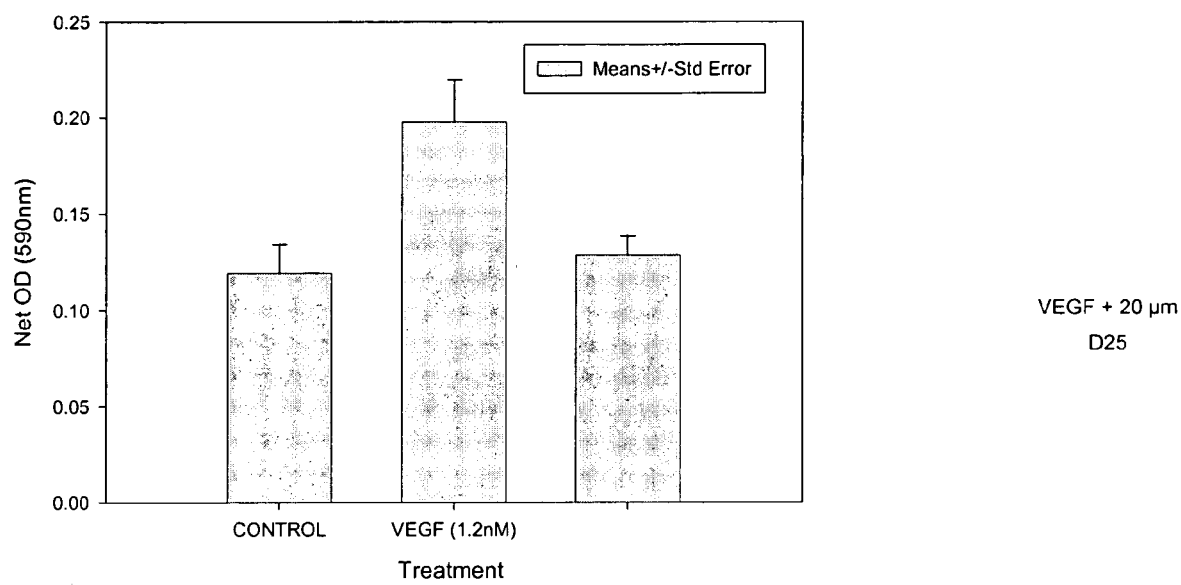
FIG. 39 is a graph showing that D25 blocks increased peritoneal vascular permeability induced by VEGF injected intraperitoneally.

As shown in FIG. 39, VEGF, when added to the fluid injected i.p., significantly increased the dye leakage into the peritoneum, and this increase was substantially blocked by including D25 with the VEGF.

EXAMPLE 31

In Vivo Inhibition of Tumor Growth.

Conditions are described providing methods for determining efficacy of three (3) concentrations for a test compound (dimer D6) suspected of having anti-angiogenic activity on SW-480 human colon carcinoma cells using an in vivo xenograft tumor model.

Athymic nude mice are acceptable hosts for the growth of allogenic and heterogenic cells. Nude mice are required in Points to Consider in the Characterization of Cell Lines used to Produce Biologicals (Points to Consider in the Characterization of Cell Lines used to Produce Biologicals, FDA 1993).

D6 is a synthetic heterodimeric peptide suspected of having anti-angiogenic activity. This peptide binds to the human VEGF receptor 2 (KDR) with high affinity and competes with VEGF binding. The following experiments confirms its anti-angiogenic activity.

SW-480 Human Carcinoma Cells

Colon carcinoma, SW-480, cells (ATCC) were cultured in Dulbecco's Modified Eagles Medium (DMEM) supplemented with 4 mM L-glutamine, 0.1 mM non-essential amino acids, 50 mg/mL Gentamicin, 250 mg/mL Fungizone and 10% heat inactivated fetal bovine serum at 37° C. in 95% air and 5% CO$_2$.

Exponentially growing cells were harvested, washed twice in phosphate buffered saline (PBS) to remove any traces of trypsin or serum. Cells were suspended in Hanks Balanced Salt Solution (HBSS) for injections.

Sterile phosphate buffered saline (BioWhittaker) was manufactured in accordance with cGMP regulations and was cell culture tested to assure compatibility; having a pH of 7.3–7.7 and an osmolarity of 271–287 mOsm/kg. PBS was the vehicle used to reconstitute Test Articles and for vehicle control injections.

Cisplatin (American Pharmaceutical Partners, Inc.; Los Angeles, Calif.) was prepared according to manufacture's specifications. Cisplatin was prepared in an aseptic fashion using a BL2 BioChem guard hood.

Test System

Species/Strain: *Mus musculus*, Crl:NU/NU-nuBR mice (nude mice)

Sex: Female

Age: 6–8 weeks at initiation of treatment

Weight Range: No weight requirement

Source: Animals were received from the Gnottobiotic Department at Charles River Laboratories, Wilmington, Mass.

Number: A total of 115 animals were received and injected for this study, with 90 mice used on study.

Method of Identification:

Mice were uniquely numbered using an ear tag system. Additionally, cages were marked with cage cards minimally identifying group number, animal number, study number and IACUC protocol number.

Randomization:

Animals were randomly assigned to treatment groups using Microsoft® Excel 97 SR-1 program.

Animal Care

Mice were fed gamma-irradiated rodent chow ad libitum. Tap water was sterilized and supplied via bottle and sipper tube ad libitum.

Animal Environment:

Animals were housed by groups in semi-rigid isolators. Mice were housed in flat bottom caging containing five to ten animals. Cages contained gamma-irradiated contact bedding. The number of mice in each cage may have been altered due to the behavior of the mice, changes were noted in the isolator inventory. The housing conforms to the recommendations set forth in the Guide for the Care and Use of Laboratory Animals, National Academy Press, Washington, D.C., 1996 and all subsequent revisions.

Environmental controls were set to maintain a temperature of 16–26° C. (70±8° F.) with a relative humidity of 30–70. A 12:12 hour light: dark cycle was maintained.

Acclimation:

Once animals were received, they were allowed to acclimate to the laboratory environment for 24-hours prior to the study start. Mice were observed for signs of disease, unusual food and/or water consumption or other general signs of poor condition. At the time of animal receipt, animals were clinically observed and appeared to be healthy.

Experimental Design:

Female athymic nude mice (Crl:NU/NU-nuBR) at 6–8 weeks of age were used in this study. A total of 115 mice were injected subcutaneously into the right lateral thorax with $5\times10^6$ SW-480, human colon carcinoma cells. When tumors reached a target window size of approximately 150±75 mg, 90 tumor-bearing mice were randomly selected and distributed into one of nine groups. Test compound and vehicle were administered intraperitoneally (IP), Cisplatin was administered intravenously (IV). Tumor measurements were recorded twice weekly using hand-held calipers. Mice were monitored daily for signs of toxicity and morbidity. At study termination, animals were euthanized by carbon dioxide overdose and necropsied for tissue collection.

A total of nine (9) groups were used in this study. Each group contained ten (10) tumor-bearing mice. Groups 1 and 2 contained untreated and vehicle treated negative control mice, respectively. Groups 3, 4, and 5 contained mice that received one of three different concentrations of the D6 heterodimer. Groups 6, 7, and 8 contained mice that received one of three different concentrations of a different anti-angiogenic peptide. Group 9 contained mice that received cisplatin, a standard chemotherapeutic compound as a positive control.

Dose levels for each group are provided in Table 12. Dosing began the same day that animals were randomly sorted into groups (Study Day 7). Each dose was removed from the dose vial using aseptic technique for each animal and the injection site was wiped with an alcohol swab prior to dose administration. Doses were administered with a 1.0 mL syringe and a 27-gauge×½" needle for each mouse.

TABLE 12

Study Treatment Groups

| Group | Test Compound | Concentration mg/kg | Number of Animals |
|---|---|---|---|
| 1 | Untreated | — | 10 |
| 2 | Vehicle | 0 | 10 |
| 3 | D6 | 0.05 | 10 |
| 4 | D6 | 0.5 | 10 |
| 5 | D6 | 5.0 | 10 |
| 9 | Cisplatin | 6.0 | 10 |

The Test compound- and vehicle-treated mice received daily intraperitoneal (IP) injections for 15 days. Cisplatin was administered every other workday for a total of five (5) doses via an intravenous route.

Clinical Observations of each animal were performed and recorded at least once daily for toxicity, morbidity and mortality. Morbidity included signs of illness such as, but not limited to, emaciation, dehydration, lethargy, hunched posture, unkempt appearance, dyspnea and urine or fecal staining.

Tumor Measurements:

In accordance with the protocol, tumor measurements were taken twice weekly throughout the study by measuring the length and width of tumors with calibrated calipers. Measurements occurred a minimum of 3–4 days apart, except when animals were euthanized and measurements were taken; this sometimes resulted in an interval of less than 3 days. Tumor weights were calculated using the following formula: $mg=(L\times W^2)/2$. Animals were euthanized either when mean tumor weight was ≧1000 mg per group over two (2) consecutive measurements, or if tumors became ulcerated, impaired the animal's ability to ambulate or obtain food and water.

Unscheduled Euthanasia and Unexpected Deaths:
1. Unscheduled Euthanasia:
None of the animals required unscheduled euthanasia while on study.
2. Unexpected Deaths:
None of the animals died while on study.

Necropsy:

1. Euthanasia and Necropsy Order:
All mice in groups 1, 2, 3, 4, and 5 (50 total) were submitted for necropsy when tumors reached a group mean target size of ≧1000 mg over two (2) consecutive measurements within a group. Animals were submitted for necropsy to the Charles River Laboratories Health Monitoring Laboratory (HM), Wilmington, Mass. All animals were euthanized on Study Day 22, short of received the full 28 day treatment regiment with Test Articles because mean tumor size was ≧1000 mg in Test Article Treated Groups 3–8. All animals were humanely euthanized by carbon dioxide ($CO_2$) inhalation.

Tissue Collection:
Tumors were dissected free of surrounding tissue and overlying skin. Additionally the kidneys were collected. Any abnormalities noted on the renal surfaces were noted.

Frozen blocks were made of tumors and kidneys for each animal. A representative section of the tissue (tumor, kidneys) was taken. Kidney sections included the cortex and medulla. Tissue sections were placed in the bottom of a labeled plastic-freezing mold. Tissue was embedded with OCT medium. Blocks were submerged into isopentane chilled with dry ice until frozen. Blocks were briefly examined for quality, and stored on dry ice.

Blocks were labeled with the animal number and a letter code corresponding to tissue (A=left kidney; B=right kidney; C=mass). Blocks from one animal were placed into a labeled bag.

Results:

A. In-Life Measurements and Observations:

1. Clinical Observations, Morbidity and Mortality Summary Statement:
All animals appeared healthy and were within normal limits throughout the study and the Test Compound (D6) did not show any signs of toxicity at the doses used in this study.

Animals were euthanized on Study Day 22. All mice, except Group 9 mice, were euthanized prior to completing Test compound administration, because mean tumor size was ≧1000 mg in Groups 1–8. Group 9, Cisplatin-treated animals were euthanized on Study Day 22 when mean tumor weight was 995 mg. No animals died while on study.

Mass Palpation Summary

Throughout the study palpable masses were detected in all mice, with tumors progressively growing for the duration of the study. As expected tumors in untreated and vehicle treated negative control mice (Groups 1 and 2) grew the fastest, reaching a mean tumor size of 1000 mg on or before Study Day 20. In addition, animals treated with Cisplatin (Group 9) developed tumors that grew the slowest reaching a mean tumor size of 995 mg at study termination (Day 22).

In general, except for Group 3 mice, all animals treated with Test compounds resulted in slower tumor growth. Animals in Group 3, which were treated with the low dose of D6 (0.05 mg/kg) had tumors that grew at approximately the same rate as the tumors in untreated and vehicle treated animals in Groups 1 and 2. Animals treated with higher doses of D6 (Groups 4 and 5) had tumors that grew slower; reaching a mean tumor size of 1000 mg on Study Day 21. When compared to control Groups 1 and 2 mice, Test compound treatment resulted in a delay of tumor growth of approximately 1 day.

Conclusions

Data from this study validate the model used because tumor-bearing mice in negative control Groups 1 and 2 and positive control Group 9 responded as expected.

Throughout the study palpable masses were observed in all groups. In addition, all animals were healthy and within normal limits throughout the study. Furthermore, the Test compound (D6) did not appear to adversely affect the animals. Therefore, these data would suggest that animals treated with D6 had tumors that grew slowly (approximately 1 day slower over the 22 day test period than controls). Also, since the Test compound did not show any significant toxic effects, higher concentrations of Test compound could also be used with potentially better tumor regression.

EXAMPLE 32

The following example describes the preparation of an ultrasound contrast agent conjugated to a KDR-binding heterodimer of the invention and the ability of the heterodimer conjugated contrast agent to localize to KDR-expressing cells in vitro and angiogenic tissue in vivo.

Preparation of Derivatized Microbubbles for Peptide Conjugation.

200 mg of DSPC (distearoylphosphatidylcholine), 275 mg of DPPG.Na (distearoylphosphatidylglycerol sodium salt) and 25 mg of N-MPB-PE were solubilized at 60° C. in 50 ml of Hexan/isopropanol (42/8). The solvent was evaporated under vacuum, and then PEG-4000 (35.046 g) was added to the lipids and the mixture was solubilized in 106.92 g of t-butyl alcohol at 60° C., in a water bath. The solution was filled in vials with 1.5 ml of solution. The samples were rapidly frozen at −45° C. and lyophilized. The air in the headspace was replaced with a mixture of $C_4F_{10}$/Air (50/50) and vials capped and crimped. The lyophilized samples were reconstituted with 10 ml saline solution (0.9%-NaCl) per vial, yielding a suspension of phospholipids stabilized microbubbles.

Peptide Conjugation

D23 (a dimeric construct of P6- and P12-derived sequences) was conjugated with a preparation of microbubbles as above described, according to the following methodology. The thioacetylated peptide (200% g) was dissolved in 20 μl DMSO and then diluted in 1 ml of Phosphate Buffer Saline (PBS). This solution was mixed to the N-MPB-functionalized microbubbles dispersed in 18 ml of PBS-EDTA 10 mM, pH 7.5 and 2 ml of deacetylation solution (50 mM sodium phosphate, 25 mM EDTA, 0.5 M hydroxylamine.HCl, pH 7.5) was added. The headspace was filled with $C_4F_{10}$/Air (50/50) and the mixture was incubated for 2.5 hours at room temperature under gentle agitation (rotating wheel), in the dark. Conjugated bubbles were washed by centrifugation. Similarly, the monomer peptides making up D23 were separately conjugated to two different microbubble preparations according to the methodology described above.

In Vitro Assay on Transfected Cells

The ability of phospholipid stabilized microbubbles conjugated to heteromultimeric constructs of the invention to bind to KDR-expressing cells was assessed using 293H cells transfected to expresss KDR.

Transfection of 293H Cells on Thermanox® Coverslips:

293H cells were transfected with KDR DNA as set forth in Example 6. The transfected cells were incubated with a suspension of peptide-conjugated microbubbles prepared as described above. For the incubation with the transfected cells a small plastic cap is filled with a suspension containing 1 to $3.10^8$ peptide-conjugated microbubbles and the cap covered with an inverted Thermanox® coverslip is placed so that the transfected cells are in contact with the conjugated microbubbles. After about 20 min at RT, the coverslip is lifted with tweezers, rinsed three times in PBS and examined under a microscope to assess binding of the conjugated microbubbles.

Determination of the % of Surface Covered by Microvesicles

Images were acquired with a digital camera DC300F (Leica) and the percent of surface covered by bound microbubbles in the imaged area was determined using the software QWin (Leica Microsystem AG, Basel, Switzerland). Table 13 shows the results of the binding affinity (expressed as coverage % of the imaged surface) of targeted microvesicles of the invention to KDR transfected cells, as compared to the binding of the same targeted microvesicles to Mock-transfected cells.

TABLE 13

Conjugated microbubbles prepared as described above

| Peptide code | % of covered surface | |
|---|---|---|
| | KDR | Mock |
| P6 Derivative | 3.5% | 0.9% |
| P12 Derivative | 16.8% | 1.0% |
| D23 (dimer) | 22.9% | 3.3% |
| D6 Deriv./ P12 Deriv. | 12.9% | 0.8% |

When the P-6 derived sequence and the P12-derived sequence are separately attached to phospholipid stabilized microbubbles as monomers the resulting preparations achieve binding of the bubbles to KDR transfected cells in vitro to a different extent (3.5% & 16.8%). When a preparation of phospholipid stabilized microbubbles resulting from the addition of equal quantities of each of these peptide monomers (but the same total peptide load) is tested in the same system 12.9% binding is achieved. Binding is a little more than the average of the two but as it is achieved with two sequences that bind to different sites on the target will be more resistant to competition at one or other of the sites on the target. However, for D23, the dimer, binding is increased to 22.9% (with the same peptide load). These results indicate that hetromultimers of the invention permit increased binding and increased resistance to competition.

In Vivo Animal Models

A known model of angiogenic tissue (the rat Mat B III model) was used to examine the ability of phospholipid stabilized microbubbles conjugated to a heteromultimer of the invention to localize to and provide images of angiogenic tissue.

Animals: Female Fisher 344 rat (Charles River Laboratories, France) weighing 120 to 160° g. were used for the MATBIII tumor implantation. Male OFA rats (Charles River Laboratories, France) weighing 100 to 150 g were used for Matrigel injection.

Anesthesia

Rats were anesthetized with an intramuscular injection (1 ml/kg) of Ketaminol®/xylazine (Veterinaria AG/Sigma) (50/10 mg/ml) mixture before implantation of Matrigel or MatBIII cells. For imaging experiments, animals were anesthetized with the same mixture, plus subcutaneous injection of 50% urethane (1 g/kg).

Rat MATBIII Tumor Model

A rat mammary adenocarcinoma, designated 13762 Mat B III, was obtained from ATCC (CRL-1666) and grown in McCoy's 5a medium+10% FCS. 1% glutamine and 1% pen/strep (Invitrogen cat# 15290-018). Cells in suspension were collected and washed in growth medium, counted, centrifuged and resuspended in PBS or growth medium at $1.10$ cells per ml. For tumor induction: $1 \times 10^6$ cells in 0.1 ml were injected into the mammary fat pad of anesthetized female Fisher 344 rat. Tumors usually grow to a diameter of 5–8 mm within 8 days.

In Vivo Ultrasound Imaging

Tumor imaging was performed using an ultrasound imaging system ATL HDI 5000 apparatus equipped with a L7-4 linear probe. B-mode pulse inversion at low acoustic power (MI=0.05) was used to follow accumulation of peptide conjugated-microbubbles on the KDR receptor expressed on the endothelium of neovessels. For the control experiments, an intravenous bolus of unconjugated microbubbles or microbubbles conjugated to non-specific peptide was injected. The linear probe was fixed on the skin directly on line with the implanted tumors and accumulation of targeted bubbles was followed during thirty minutes.

A perfusion of SonoVue® was administrated before injecting the test bubble suspension. This allows to evaluate the vascularization status and the video intensity obtained after SonoVue® injection is taken as an internal reference.

A baseline frame was recorded and then insonation was stopped during the injection of the microbubbles. At various time points after injection (1, 2, 5, 10, 15, 20, 25, 30 minutes) insonation was reactivated and 2 frames of one second were recorded on a videotape.

Video frames from tumor imaging experiments were captured and analysed with the video-capture and Image-Pro Plus 2.0 software respectively. The same rectangular Area of Interest (AOI) including the whole sectional area of the tumor was selected on images at different time points (1, 2, 5, 10, 15, 20, 25, 30 minutes). At each time point, the sum of the video pixel inside the AOI was calculated after the subtraction of the AOI baseline. Results are expressed as the percentage of the signal obtained with SonoVue®, which is taken as 100%. Similarly, a second AOI situated outside the tumor, and representing the freely circulating contrast agent, is also analyzed.

Figure 38:
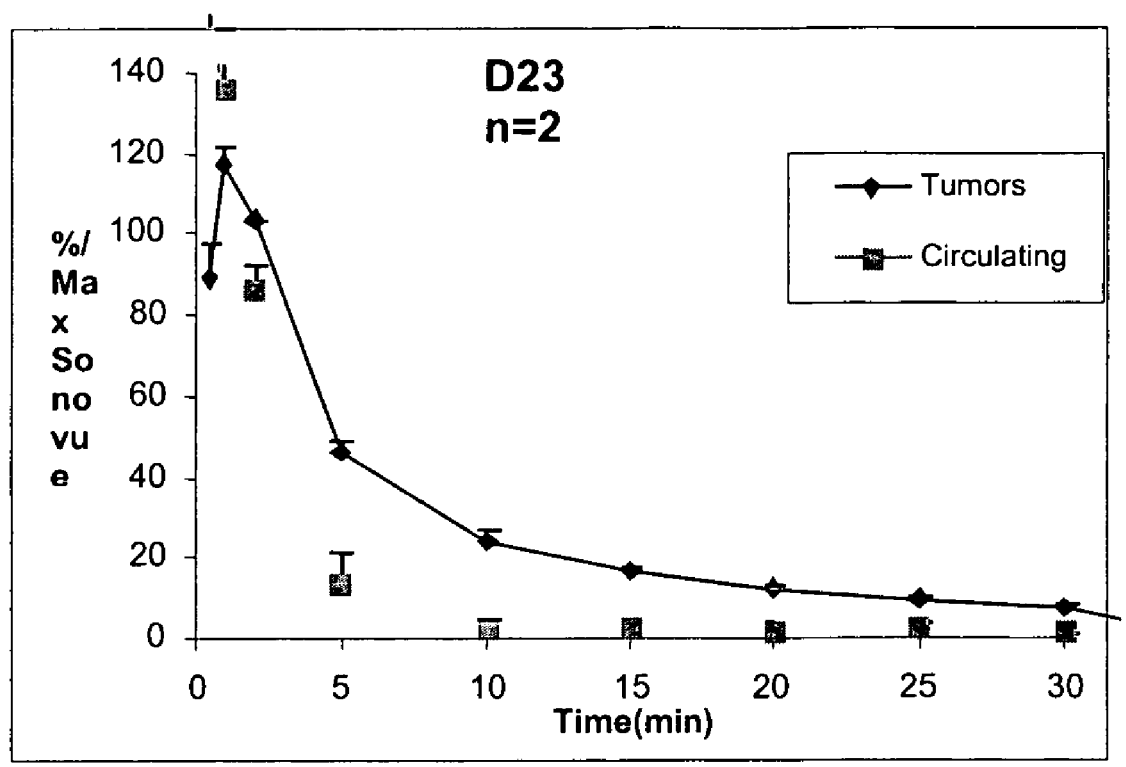
FIG. 38 is a graph showing uptake and retention of bubble contrast in the tumor up to 30 minutes post injection for suspensions of phospholipid stabilized microbubbles conjugated to a heteromultimeric construct (D23).

FIG. 38 shows uptake and retention of bubble contrast in the tumor up to 30 minutes post injection for suspensions of phospholipid stabilized microbubbles conjugated to a heteromultimeric construct of the invention prepared as described above (D23). In contrast, the same bubbles showed only transient (no more than 10 minutes) visualization/bubble contrast in the AOI situated outside the tumor site.

1. Other Embodiments

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are encompassed in the scope of the present invention.

All publications and patents mentioned in this specification are herein incorporated by reference.

What is claimed is:

1. A compound comprising a dimer having the following formula:

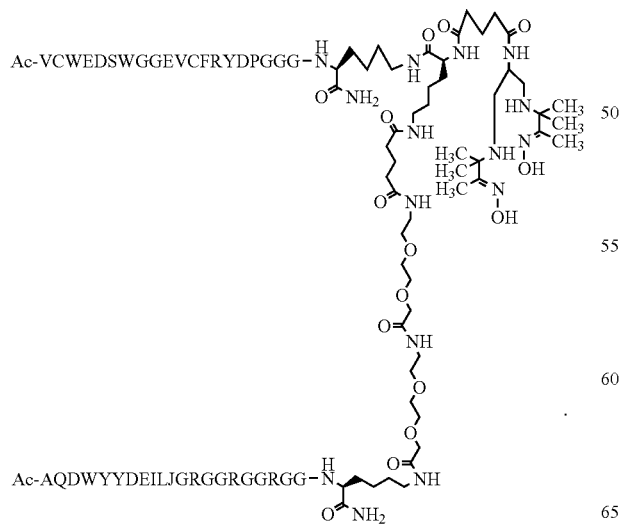

2. A compound comprising a dimer having the following formula:

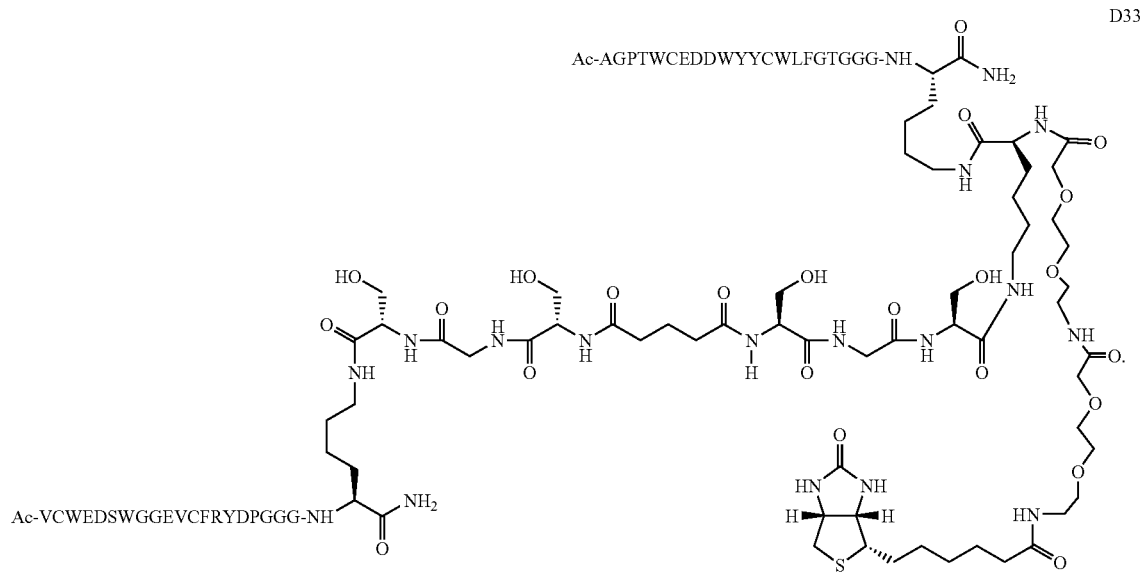

3. A diagnostic imaging agent comprising a compound of claim 1 or 2 conjugated to a microbubble or microballoon.

4. The imaging agent of claim 3, wherein said microbubble or microballoon comprises a phospholipid comprising the formula:

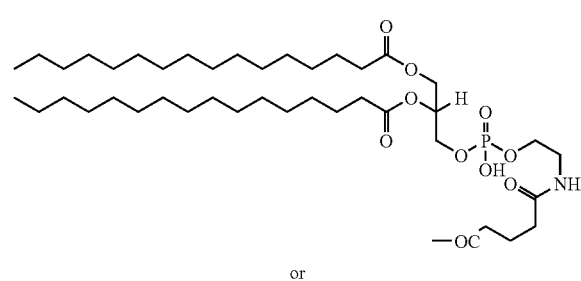

or

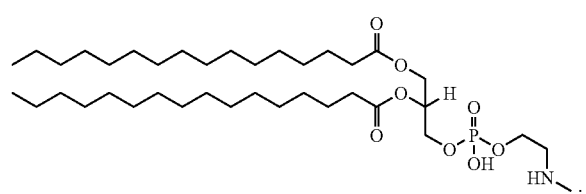

5. The imaging agent of claim 4, wherein said microbubble or microballoon comprises an biocompatible fluorinated gas selected from the group consisting of $SF_6$, freons, and perfluorocarbons.

6. A diagnostic imaging method comprising the steps of:
(a) administering to a patient a pharmaceutical preparation comprising a compound according to claim 1 or 2 conjugated to the detectable label; and
(b) imaging the compound after administration of the compound to the patient.

7. The method of claim 6, wherein the imaging step comprises magnetic resonance imaging, ultrasound imaging, optical imaging, sonoluminescence imaging, photoacoustic imaging, or nuclear imaging.

8. The method of claim 6, wherein the administering step comprises inhaling, transdermal absorbing, intramuscular injecting, subcutaneous injecting, intravenous injecting, or intraarterial injecting.

9. A method of treating a disease selected from the group consisting of tumors, cancers, rheumatoid arthritis, psoriasis, ocular diseases, atherosclerosis, scleroderma, hypertropic scars, intestinal adhesions, vascular adhesions, angiofibroma, trachoma, corneal graft neovascularization, ulcers, malaria, HIV, SIV, and Simian hemorrhagic fever virus, comprising the step of administering to a patient a pharmaceutical preparation comprising a compound of claim 1 or 2.

10. A method of treating a disease associated with angiogenesis selected from the group consisting of tumors, cancers, rheumatoid arthritis, psoriasis, ocular diseases, atherosclerosis, scleroderma, hypertropic scars, intestinal adhesions, vascular adhesions, angiofibroma, trachoma, corneal graft neovascularization, ulcers, malaria, HIV, SIV, and Simian hemorrhagic fever virus, comprising the step of administering to a patient a pharmaceutical preparation comprising a compound of claim 1 or 2.

11. A method of synthesizing a multimeric compound comprising at least two binding moieties having specificity for different binding sites on the same target, wherein the compound has the structure of D32:

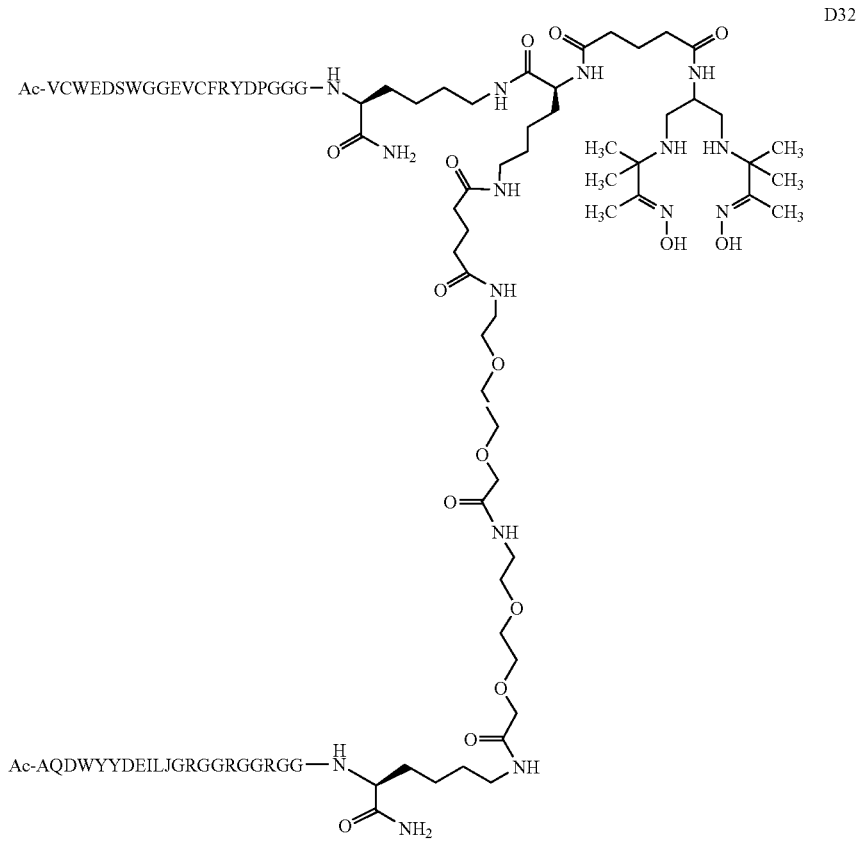

D32 comprising the following steps:
(a) Treating Ac-VCWEDSWGGEVCFRYDPGGGK [PnAO6-Glut-K]-NH₂ with Disuccinimidyl Glutarate/ DIEA/DMF;
(b) Adding Ac-AQDWYYDEIL-Adoa-GRGGRG-GRGGGK(Adoa-Adoa)-NH₂ to provide D32; and
(c) Purifying.

12. The compound of claim 1 or 2, further comprising at least one labeling group or therapeutic agent.

13. The compound of claim 12, wherein the labeling group or therapeutic agent comprises one or more paramagnetic metal ions or superparagametic particles, an ultrasound contrast agent, one or more photolabels, or one or more radionuclides.

14. The compound of claim 13, wherein the paramagnetic metal ion is selected from $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$, and $Eu^{2+}$.

15. The compound of claim 13, wherein the labeling group or therapeutic agent further comprises a chelator.

16. The compound of claim 15, further comprising gadolinium (III).

17. The compound of claim 15, wherein the chelator comprises DTPA, DOTA, EDTA, TETA, EHPG, HBED, NOTA, DOTMA, TETMA, PDTA, TTHA, LICAM, or MECAM.

18. The compound of claim 15, wherein the chelator comprises diethylenetriamine pentaacetic acid, tetraazacyclododecane triacetic acid, or a carboxymethyl-substituted derivative thereof.

19. The compound of claim 15, wherein the chelator is 1-substituted 1,4,7,-tricarboxymethyl 1,4,7,10 teraazacyclododecane triacetic acid (DO3A).

20. The compound of claim 13, where the radionuclide is $^{18}F$, $^{124}I$, $^{125}I$, $^{131}I$, $^{123}I$, $^{77}Br$, $^{76}Br$, $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$ or $^{199}Au$.

21. The compound of claim 20, further comprising a compound having a structure selected from the following:

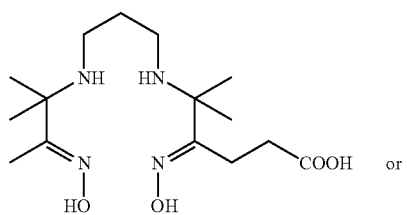

or

-continued

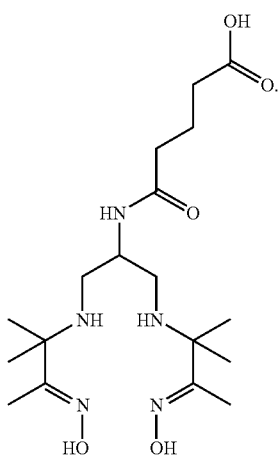

22. The compound of claim 20, further comprising a compound having a structure selected from the following:

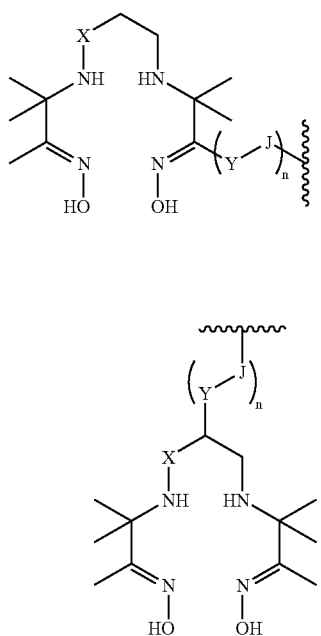

where X is CH$_2$ or O;

Y is C$_1$–C$_{10}$ branched or unbranched alkyl, aryl, aryloxy, arylamino, arylaminoacyl, or aralkyl comprising C$_1$–C$_{10}$ branched or unbranched alkyl groups, C$_1$–C$_{10}$ branched or unbranched hydroxy or polyhydroxyalkyl groups or polyalkoxyalkyl or polyhydroxy-polyalkoxyalkyl groups;

J is C(=O)—, OC(=O)—, SO$_2$—, NC(=O)—, NC(=S)—, N(Y), NC(=NCH$_3$)—, NC(=NH)—, N=N—, a homopolyamide or a heteropolyamine; and n is 1–100.

23. The compound of claim 20, further comprising a compound having the following structure:

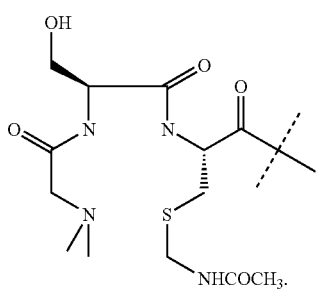

24. The compound of claim 21 or 22, further comprising $^{99m}$Tc, $^{186}$Re, or $^{188}$Re.

25. The compound of claim 23, further comprising $^{99m}$Tc.

26. The compound of claim 20, further comprising a compound having the following structure:

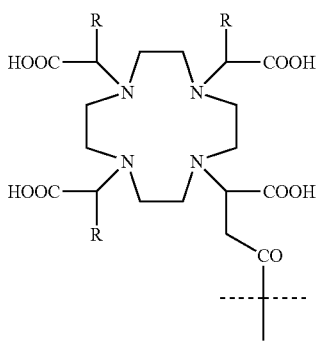

where R is an alkyl group.

27. The compound of claim 20, further comprising a compound having the following structure:

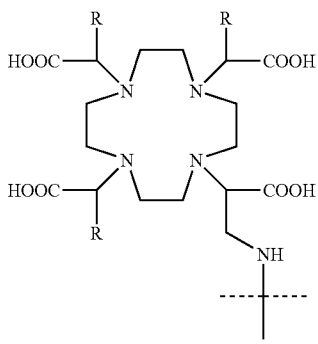

where R is an alkyl group.

28. The compound of claim 20, further comprising a compound having the following structure:

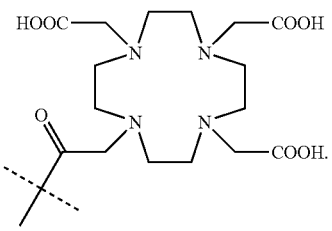

29. The compound of claim 26, 27 or 28, further comprising $^{177}$Lu, $^{90}$Y, $^{153}$Sm, $^{111}$In, or $^{166}$Ho.

30. The compound of claim 12, further comprising a linker between a binding moiety and the labeling group or therapeutic agent.

31. The compound of 30, wherein the linker comprises a substituted alkyl chain, an unsubstituted alkyl chain, a polyethylene glycol, an amino acid spacer, a sugar, an aliphatic spacer, an aromatic spacer, a lipid molecule, or combination thereof.

32. The compound of claim 12, wherein the therapeutic agent comprises a bioactive agent, a cytotoxic agent, a drug, a chemotherapeutic agent, or a radiotherapeutic agent.

33. A method of synthesizing a multimeric compound comprising at least two binding moieties having specificity for different binding sites on the same target, wherein the compound has the structure of D33:

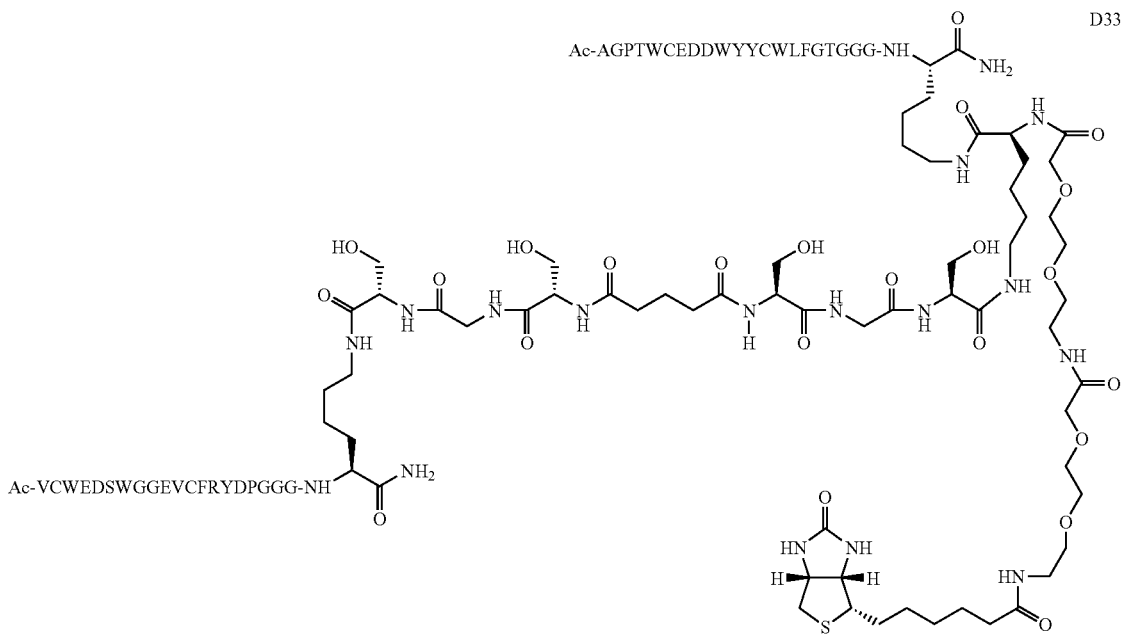

comprising the steps of:
(a) Treating Ac-VCWEDSWGGEVCFRYDPGGGK[(SGS)-NH$_2$ with Disuccinimidyl Glutarate/DIEA/DMF;
(b) Adding Ac-AGPTWCEDDWYYCWLFGTGGGK(SGS-(S)NH(CH$_2$)4—CH(Biotin-JJ-NH)—CO)—NH$_2$ to provide D33; and
(c) Purifying.

* * * * *

UNITED STATES PATENT AND TRADEMARK OFFICE
Certificate

Patent No. 7,261,876 B2                                                       Patented: August 28, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christophe Arbogast, Viuz-En-Sallaz (FR); Philippe Bussat, Feigers (FR); Hong Fan, Plainsboro, NJ (US); Karen E. Linder, Kingston, NJ (US); Edmund R. Marinelli, Tucson, AZ (US); Palaniappa Nanjappan, Princeton, NJ (US); Adrian Nunn, Lambertville, NJ (US); Radhakrishna Pillai, Cranbury, NJ (US); Sibylle Pochon, Troinex (CH); Kondareddiar Ramalingam, Dayton, NJ (US); Ajay Shrivastava, Princeton, NJ (US); Bo Song, Princeton, NJ (US); Rolf E. Swenson, Princeton, NJ (US); Mathew A. Von Wronski, Geneva (CH); Aaron Sato, Richmond, CA (US); Sharon Michele Walker, North Attleboro, MA (US); and Feng Yan, Grand-Lancy (CH).

Signed and Sealed this Twenty-eighth Day of February 2012.

*MICHAEL G. HARTLEY*
*Supervisory Patent Examiner*
*Art Unit 1618*
*Technology Center 1600*

UNITED STATES PATENT AND TRADEMARK OFFICE
CERTIFICATE OF CORRECTION

| | | |
|---|---|---|
| PATENT NO. | : 7,261,876 B2 | |
| APPLICATION NO. | : 10/661032 | |
| DATED | : August 28, 2007 | |
| INVENTOR(S) | : Christophe Arbogast et al. | |

It is certified that error appears in the above-identified patent and that said Letters Patent is hereby corrected as shown below:

Delete Drawing Sheet 8 of 59 and substitute therefore the attached Drawing Sheet 8 of 59.
FIG. 8(B) has been inserted.

Signed and Sealed this
Twenty-seventh Day of March, 2012

David J. Kappos
*Director of the United States Patent and Trademark Office*

(A)
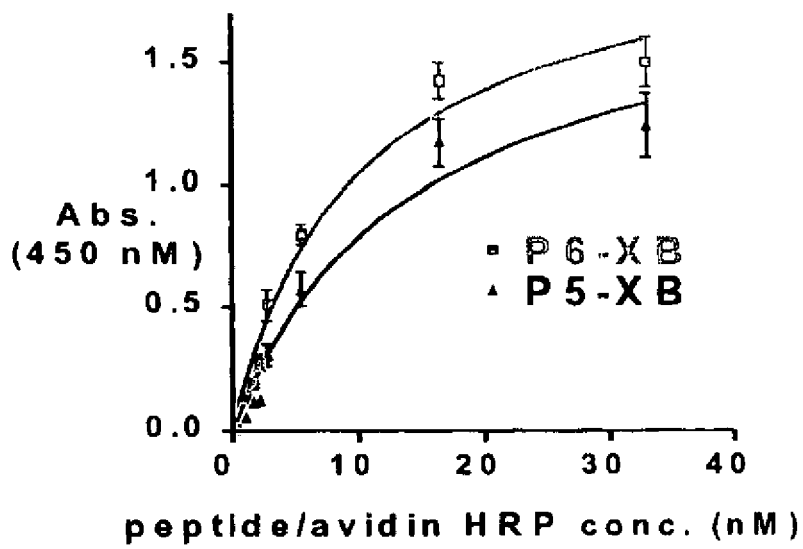
FIG. 8
(B)
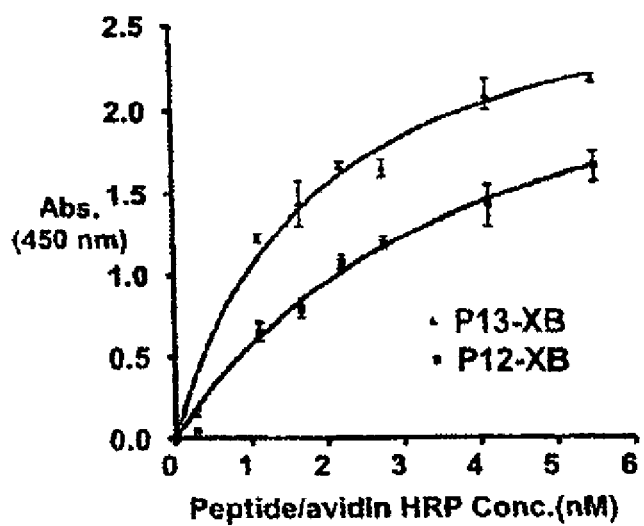

UNITED STATES PATENT AND TRADEMARK OFFICE
Certificate

Patent No. 7,261,876 B2

Patented: August 28, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christophe Arbogast, Viuz-En-Sallaz (FR); Philippe Bussat, Feigers (FR); Hong Fan, Plainsboro, NJ (US); Karen E. Linder, Kingston, NJ (US); Edmund R. Marinelli, Tucson, AZ (US); Palaniappa Nanjappan, Princeton, NJ (US); Adrian Nunn, Lambertville, NJ (US); Radhakrishna Pillai, Cranbury, NJ (US); Sibylle Pochon, Troinex (CH); Kondareddiar Ramalingam, Dayton, NJ (US); Ajay Shrivastava, Princeton, NJ (US); Bo Song, Princeton, NJ (US); Rolf E. Swenson, Princeton, NJ (US); Mathew A. Von Wronski, Geneva (CH); Aaron Sato, Richmond, CA (US); Sharon Michele Walker, North Attleboro, MA (US); Daniel T. Dransfield, Hanson, MA (US); Feng Yan, Grand-Lancy (CH).

Signed and Sealed this Twenty-sixth Day of March 2013.

MICHAEL G. HARTLEY
*Supervisory Patent Examiner*
Art Unit 1618
Technology Center 1600

SEQUENCE LISTING

```
<160> NUMBER OF SEQ ID NOS: 41

<210> SEQ ID NO 1
<211> LENGTH: 18
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 1

Ala Gly Trp Ile Glu Cys Tyr His Pro Asp Gly Ile Cys Tyr His Phe
1               5                   10                  15

Gly Thr

<210> SEQ ID NO 2
<211> LENGTH: 18
<212> TYPE: PRT
<213> ORGANISM: Artificial
<220> FEATURE:
<223> OTHER INFORMATION: Description of Artificial Sequnce:  KDR-binding
```

-continued

```
      peptides

<400> SEQUENCE: 2

Ala Gly Trp Leu Glu Cys Tyr Ala Glu Phe Gly His Cys Tyr Asn Phe
1               5                   10                  15

Gly Thr

<210> SEQ ID NO 3
<211> LENGTH: 18
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 3

Ala Gly Asp Ser Trp Cys Ser Thr Glu Tyr Thr Tyr Cys Glu Met Ile
1               5                   10                  15

Gly Thr

<210> SEQ ID NO 4
<211> LENGTH: 18
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 4

Ala Gly Pro Lys Trp Cys Glu Glu Asp Trp Tyr Tyr Cys Met Ile Thr
1               5                   10                  15

Gly Thr

<210> SEQ ID NO 5
<211> LENGTH: 21
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 5

Gly Asp Ser Arg Val Cys Trp Glu Asp Ser Trp Gly Gly Glu Val Cys
1               5                   10                  15

Phe Arg Tyr Asp Pro
            20

<210> SEQ ID NO 6
<211> LENGTH: 22
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 6

Gly Asp Trp Trp Glu Cys Lys Arg Glu Glu Tyr Arg Asn Thr Thr Trp
1               5                   10                  15

Cys Ala Trp Ala Asp Pro
            20

<210> SEQ ID NO 7
<211> LENGTH: 22
<212> TYPE: PRT
```

-continued

<213> ORGANISM: Artificial
<220> FEATURE:
<223> OTHER INFORMATION: Description of Artificial Sequnce: KDR-binding
peptides

<400> SEQUENCE: 7

Gly Asp Pro Asp Thr Cys Thr Met Trp Gly Asp Ser Gly Arg Trp Tyr
1 5 10 15

Cys Phe Pro Ala Asp Pro
20

<210> SEQ ID NO 8
<211> LENGTH: 24
<212> TYPE: PRT
<213> ORGANISM: Artificial
<220> FEATURE:
<223> OTHER INFORMATION: Description of Artificial Sequnce: KDR-binding
peptides

<400> SEQUENCE: 8

Ala Gln Glu Pro Glu Gly Tyr Ala Tyr Trp Glu Val Ile Thr Leu Tyr
1 5 10 15

His Glu Glu Asp Gly Asp Gly Gly
20

<210> SEQ ID NO 9
<211> LENGTH: 24
<212> TYPE: PRT
<213> ORGANISM: Artificial
<220> FEATURE:
<223> OTHER INFORMATION: Description of Artificial Sequnce: KDR-binding
peptides

<400> SEQUENCE: 9

Ala Gln Ala Phe Pro Arg Phe Gly Gly Asp Asp Tyr Trp Ile Gln Gln
1 5 10 15

Tyr Leu Arg Tyr Thr Asp Gly Gly
20

<210> SEQ ID NO 10
<211> LENGTH: 24
<212> TYPE: PRT
<213> ORGANISM: Artificial
<220> FEATURE:
<223> OTHER INFORMATION: Description of Artificial Sequnce: KDR-binding
peptides

<400> SEQUENCE: 10

Ala Gln Gly Asp Tyr Val Tyr Trp Glu Ile Ile Glu Leu Thr Gly Ala
1 5 10 15

Thr Asp His Thr Pro Pro Gly Gly
20

<210> SEQ ID NO 11
<211> LENGTH: 18
<212> TYPE: PRT
<213> ORGANISM: Artificial
<220> FEATURE:
<223> OTHER INFORMATION: Description of Artificial Sequnce: KDR-binding
peptides

<400> SEQUENCE: 11

Ala Gly Pro Thr Trp Cys Glu Asp Asp Trp Tyr Tyr Cys Trp Leu Phe
1 5 10 15

Gly Thr

-continued

```
<210> SEQ ID NO 12
<211> LENGTH: 24
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 12

Ala Gln Asp Trp Tyr Tyr Asp Glu Ile Leu Ser Met Ala Asp Gln Leu
1               5                   10                  15

Arg His Ala Phe Leu Ser Gly Gly
            20

<210> SEQ ID NO 13
<211> LENGTH: 24
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 13

Gly Ser Asp His His Cys Tyr Leu His Asn Gly Gln Trp Ile Cys Tyr
1               5                   10                  15

Pro Phe Ala Pro Gly Gly Gly Lys
            20

<210> SEQ ID NO 14
<211> LENGTH: 26
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 14

Gly Asp Tyr Pro Trp Cys His Glu Leu Ser Asp Ser Val Thr Arg Phe
1               5                   10                  15

Cys Val Pro Trp Asp Pro Gly Gly Gly Lys
            20                  25

<210> SEQ ID NO 15
<211> LENGTH: 26
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 15

Gly Asp Asp His Met Cys Arg Ser Pro Asp Tyr Gln Asp His Val Phe
1               5                   10                  15

Cys Met Tyr Trp Asp Pro Gly Gly Gly Lys
            20                  25

<210> SEQ ID NO 16
<211> LENGTH: 26
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 16
```

```
Gly Asp Pro Pro Leu Cys Tyr Phe Val Gly Thr Gln Glu Trp His His
1               5                   10                  15

Cys Asn Pro Phe Asp Pro Gly Gly Lys
            20                  25

<210> SEQ ID NO 17
<211> LENGTH: 26
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 17

Gly Asp Gly Ser Trp Cys Glu Met Arg Gln Asp Val Gly Lys Trp Asn
1               5                   10                  15

Cys Phe Ser Asp Asp Pro Gly Gly Gly Lys
            20                  25

<210> SEQ ID NO 18
<211> LENGTH: 26
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 18

Ala Gln Arg Gly Asp Tyr Gln Glu Gln Tyr Trp His Gln Gln Leu Val
1               5                   10                  15

Glu Gln Leu Lys Leu Leu Gly Gly Gly Lys
            20                  25

<210> SEQ ID NO 19
<211> LENGTH: 26
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 19

Gly Asp Asn Trp Glu Cys Gly Trp Ser Asn Met Phe Gln Lys Glu Phe
1               5                   10                  15

Cys Ala Arg Pro Asp Pro Gly Gly Gly Lys
            20                  25

<210> SEQ ID NO 20
<211> LENGTH: 23
<212> TYPE: PRT
<213> ORGANISM: Artificial
<220> FEATURE:
<223> OTHER INFORMATION: Description of Artificial Sequnce:  KDR-binding
      peptides
<220> FEATURE:
<221> NAME/KEY: MOD_RES
<222> LOCATION: (7)..(7)
<220> FEATURE:
<221> NAME/KEY: MOD_RES
<222> LOCATION: (7)..(7)
<223> OTHER INFORMATION: (4,4-dimethyl-2,6-dioxocyclohex-1-ylidene)-3-
      methylbutyl

<400> SEQUENCE: 20

Ala Gly Pro Gly Pro Cys Lys Gly Tyr Met Pro His Gln Cys Trp Tyr
1               5                   10                  15
```

```
Met Gly Thr Gly Gly Gly Lys
            20

<210> SEQ ID NO 21
<211> LENGTH: 23
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 21

Ala Gly Tyr Gly Pro Cys Ala Glu Met Ser Pro Trp Leu Cys Trp Tyr
1               5                   10                  15

Pro Gly Thr Gly Gly Gly Lys
            20

<210> SEQ ID NO 22
<211> LENGTH: 20
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 22

Ala Gln Asp Trp Tyr Tyr Glu Ile Leu Gly Arg Gly Arg Gly Gly
1               5                   10                  15

Arg Gly Gly Lys
            20

<210> SEQ ID NO 23
<211> LENGTH: 22
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 23

Ala Pro Gly Thr Trp Cys Asp Tyr Asp Trp Glu Tyr Cys Trp Leu Gly
1               5                   10                  15

Thr Phe Gly Gly Gly Lys
            20

<210> SEQ ID NO 24
<211> LENGTH: 25
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 24

Gly Val Asp Phe Arg Cys Glu Trp Ser Asp Trp Gly Glu Val Gly Cys
1               5                   10                  15

Arg Ser Pro Asp Tyr Gly Gly Gly Lys
            20                  25

<210> SEQ ID NO 25
<211> LENGTH: 24
<212> TYPE: PRT
<213> ORGANISM: Artificial
<220> FEATURE:
<223> OTHER INFORMATION: Description of Artificial Sequnce:  KDR-binding
``` peptides

<400> SEQUENCE: 25

Gly Ser Pro Glu Met Cys Met Met Phe Pro Phe Leu Tyr Pro Cys Asn
1               5                   10                  15

His His Ala Pro Gly Gly Gly Lys
            20

<210> SEQ ID NO 26
<211> LENGTH: 24
<212> TYPE: PRT
<213> ORGANISM: Artificial
<220> FEATURE:
<223> OTHER INFORMATION: Description of Artificial Sequnce: KDR-binding
      peptides

<400> SEQUENCE: 26

Gly Ser Phe Phe Pro Cys Trp Arg Ile Asp Arg Phe Gly Tyr Cys His
1               5                   10                  15

Ala Asn Ala Pro Gly Gly Gly Lys
            20

<210> SEQ ID NO 27
<211> LENGTH: 26
<212> TYPE: PRT
<213> ORGANISM: Artificial
<220> FEATURE:
<223> OTHER INFORMATION: Description of Artificial Sequnce: KDR-binding
      peptides

<400> SEQUENCE: 27

Ala Gln Glu Trp Glu Arg Glu Tyr Phe Val Asp Gly Phe Trp Gly Ser
1               5                   10                  15

Trp Phe Gly Ile Pro His Gly Gly Gly Lys
            20                  25

<210> SEQ ID NO 28
<211> LENGTH: 26
<212> TYPE: PRT
<213> ORGANISM: Artificial
<220> FEATURE:
<223> OTHER INFORMATION: Description of Artificial Sequnce: KDR-binding
      peptides

<400> SEQUENCE: 28

Gly Asp Tyr Ser Glu Cys Phe Phe Glu Pro Asp Ser Phe Glu Val Lys
1               5                   10                  15

Cys Tyr Asp Arg Asp Pro Gly Gly Gly Lys
            20                  25

<210> SEQ ID NO 29
<211> LENGTH: 22
<212> TYPE: PRT
<213> ORGANISM: Artificial
<220> FEATURE:
<223> OTHER INFORMATION: Description of Artificial Sequnce: KDR-binding
      peptides

<400> SEQUENCE: 29

Ala Gly Pro Thr Trp Cys Glu Asp Asp Trp Tyr Tyr Cys Trp Leu Phe
1               5                   10                  15

Gly Thr Gly Gly Gly Lys
            20

```
<210> SEQ ID NO 30
<211> LENGTH: 21
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 30

Glu Arg Val Thr Thr Cys Trp Pro Gly Glu Tyr Gly Gly Val Glu Cys
1               5                   10                  15

Tyr Ser Val Ala Tyr
            20

<210> SEQ ID NO 31
<211> LENGTH: 23
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 31

Ala Gly Pro Gly Pro Cys Lys Gly Tyr Met Pro His Gln Cys Trp Tyr
1               5                   10                  15

Met Gly Thr Gly Gly Gly Lys
            20

<210> SEQ ID NO 32
<211> LENGTH: 23
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 32

Ala Gly Met Pro Trp Cys Val Glu Lys Asp His Trp Asp Cys Trp Trp
1               5                   10                  15

Trp Gly Thr Gly Gly Gly Lys
            20

<210> SEQ ID NO 33
<211> LENGTH: 23
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 33

Ala Gly Tyr Gly Pro Cys Lys Asn Met Pro Pro Trp Met Cys Trp His
1               5                   10                  15

Glu Gly Thr Gly Gly Gly Lys
            20

<210> SEQ ID NO 34
<211> LENGTH: 8
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 34

Asp Trp Tyr Tyr Gly Gly Gly Lys
```

<210> SEQ ID NO 35
<211> LENGTH: 10
<212> TYPE: PRT
<213> ORGANISM: Artificial
<220> FEATURE:
<223> OTHER INFORMATION: Description of Artificial Sequnce: KDR-binding peptides

<400> SEQUENCE: 35

Ala Gln Asp Trp Tyr Tyr Asp Glu Ile Leu
1               5                   10

<210> SEQ ID NO 36
<211> LENGTH: 19
<212> TYPE: PRT
<213> ORGANISM: Artificial
<220> FEATURE:
<223> OTHER INFORMATION: Description of Artificial Sequnce: KDR-binding peptides

<400> SEQUENCE: 36

Ala Gln Asp Trp Tyr Tyr Asp Glu Ile Leu Gly Arg Gly Arg Gly Gly
1               5                   10                  15

Arg Gly Gly

<210> SEQ ID NO 37
<211> LENGTH: 22
<212> TYPE: PRT
<213> ORGANISM: Artificial
<220> FEATURE:
<223> OTHER INFORMATION: Description of Artificial Sequnce: KDR-binding peptides

<400> SEQUENCE: 37

Ala Gly Pro Thr Trp Glu Glu Asp Asp Trp Tyr Tyr Lys Trp Leu Phe
1               5                   10                  15

Gly Thr Gly Gly Gly Lys
            20

<210> SEQ ID NO 38
<211> LENGTH: 22
<212> TYPE: PRT
<213> ORGANISM: Artificial
<220> FEATURE:
<223> OTHER INFORMATION: Description of Artificial Sequnce: KDR-binding peptides

<400> SEQUENCE: 38

Ala Gly Pro Thr Trp Lys Glu Asp Asp Trp Tyr Tyr Glu Trp Leu Phe
1               5                   10                  15

Gly Thr Gly Gly Gly Lys
            20

<210> SEQ ID NO 39
<211> LENGTH: 21
<212> TYPE: PRT
<213> ORGANISM: Artificial
<220> FEATURE:
<223> OTHER INFORMATION: Description of Artificial Sequnce: KDR-binding peptides
<220> FEATURE:
<221> NAME/KEY: MOD_RES
<222> LOCATION: (5)..(5)
<223> OTHER INFORMATION: 2,3-diaminopropanoic acid

```
<400> SEQUENCE: 39

Ala Gly Pro Thr Trp Glu Asp Asp Trp Tyr Tyr Asp Trp Leu Phe Gly
1               5                   10                  15

Thr Gly Gly Gly Lys
            20

<210> SEQ ID NO 40
<211> LENGTH: 21
<212> TYPE: PRT
<213> ORGANISM: Artificial
<220> FEATURE:
<223> OTHER INFORMATION: Description of Artificial Sequnce:  KDR-binding
      peptides
<220> FEATURE:
<221> NAME/KEY: MOD_RES
<222> LOCATION: (12)..(12)
<223> OTHER INFORMATION: 2,3-diaminopropanoic acid

<400> SEQUENCE: 40

Ala Gly Pro Thr Trp Asp Glu Asp Asp Trp Tyr Tyr Trp Leu Phe Gly
1               5                   10                  15

Thr Gly Gly Gly Lys
            20

<210> SEQ ID NO 41
<211> LENGTH: 22
<212> TYPE: PRT
<213> ORGANISM: Artificial
<220> FEATURE:
<223> OTHER INFORMATION: Description of Artificial Sequnce:  KDR-binding
      peptides

<400> SEQUENCE: 41

Ala Gly Pro Thr Trp Asp Glu Asp Asp Trp Tyr Tyr Lys Trp Leu Phe
1               5                   10                  15

Gly Thr Gly Gly Gly Lys
            20
```